US010246691B2

(12) United States Patent
Sweeney et al.

(10) Patent No.: US 10,246,691 B2
(45) Date of Patent: Apr. 2, 2019

(54) VARIANTS OF POLYPEPTIDES HAVING CELLULOLYTIC ENHANCING ACTIVITY AND POLYNUCLEOTIDES ENCODING SAME

(75) Inventors: Matthew Sweeney, Sacramento, CA (US); Mark Wogulis, Davis, CA (US)

(73) Assignee: Novozymes, Inc., Davis, CA (US)

( * ) Notice: Subject to any disclaimer, the term of this patent is extended or adjusted under 35 U.S.C. 154(b) by 424 days.

(21) Appl. No.: 13/876,759

(22) PCT Filed: Sep. 29, 2011

(86) PCT No.: PCT/US2011/054034
§ 371 (c)(1), (2), (4) Date: May 9, 2013

(87) PCT Pub. No.: WO2012/044835
PCT Pub. Date: Apr. 5, 2012

(65) Prior Publication Data

US 2013/0219568 A1 Aug. 22, 2013

Related U.S. Application Data

(60) Provisional application No. 61/388,530, filed on Sep. 30, 2010.

(51) Int. Cl.

| | |
|---|---|
| ***C12N 9/18*** | (2006.01) |
| ***C12N 9/42*** | (2006.01) |
| ***D21C 5/00*** | (2006.01) |
| ***C12N 15/82*** | (2006.01) |

(52) U.S. Cl.
CPC ............. *C12N 9/18* (2013.01); *C12N 9/2437* (2013.01); *C12N 9/2445* (2013.01); *C12N 15/8257* (2013.01); *C12Y 302/01004* (2013.01); *C12Y 302/01021* (2013.01); *C12Y 302/01091* (2013.01); *D21C 5/005* (2013.01)

(58) Field of Classification Search
CPC .................. C12N 9/2402; C12N 9/2445–9/18
See application file for complete search history.

(56) References Cited

U.S. PATENT DOCUMENTS

| | | | | |
|---|---|---|---|---|
| 7,271,244 | B2 * | 9/2007 | Dotson | C07K 14/37 435/183 |
| 7,771,983 | B2 | 8/2010 | Spodsberg et al. | |
| 7,771,986 | B2 | 8/2010 | Ash et al. | |
| 8,541,651 | B2 * | 9/2013 | Woguls | 800/284 |
| 2010/0112672 | A1 | 5/2010 | Keasling et al. | |
| 2010/0143971 | A1 * | 6/2010 | Spodsberg et al. | 435/69.1 |
| 2010/0304437 | A1 * | 12/2010 | Garner et al. | 435/72 |

FOREIGN PATENT DOCUMENTS

| | | | |
|---|---|---|---|
| WO | 2005074647 | A2 | 8/2005 |
| WO | 2005074656 | A2 | 8/2005 |
| WO | 2006012904 | A1 | 2/2006 |
| WO | 2007089290 | A2 | 8/2007 |
| WO | 2008148131 | A1 | 12/2008 |
| WO | 2008151043 | A1 | 12/2008 |
| WO | 2009085859 | A2 | 7/2009 |
| WO | 2009085864 | A2 | 7/2009 |
| WO | 2009085868 | A1 | 7/2009 |
| WO | 2009085935 | A2 | 7/2009 |
| WO | 2010065830 | A1 | 6/2010 |

OTHER PUBLICATIONS

Guo et al (2004) Proc. Natl. Acad. Sci. USA vol. 101 pp. 9205-9210.*
Ngo et al. in the Protein Folding Problem and Tertiary Structure Prediction, 1994, Merz et al. (ed.), Birkhauser, Boston, MA, pp. 491-495.*
XP_022390804.1NCBI Reference Sequence: XP_752626.1 (Year: 2017) (Year: 2008).*
Langston et al (Applied and Environmentalmicrobiology, Oct. 2011, p. 7007-7015) (Year: 2011).*
Dimarogona et al (Bioresourse Technology 110 (2012) 480-487) (Year: 2012).*
Quinlan et al (PNAS,Sep. 13, 2011, 108(37) pp. 15079-15084) (Year: 2011).*
NCBI Reference Sequence: XP_752626.1 (Year: 2008).*
Harris et al (Biochemistry 2010, 49, 3305-3316) (Year: 2010).*
Fedorova et al, 2008—Uniprot Acess No. B6Q8F1.
Kaisha, 2011—Geneseq Acess No. AZF55171.
Nikolaj et al, 2005, Geneseq Acess No. AECO5922.
Pain et al, 2004—Uniprot Acess No. Q6MYM8.
Zhang et al, 2006, Biotechnol Adv 24,452-481.
Ren et al, 1980, Journal of Jilin Agricultura 3, 73-75—Abstract Only.
Si et al, 2002, Journal of Northwest Sei-Tech Univ. of Agri, and For 30(5), 69-73.

* cited by examiner

*Primary Examiner* — Lee A Visone
(74) *Attorney, Agent, or Firm* — Robert Starnes

(57) ABSTRACT

The present invention relates to variants of GH61 polypeptides having cellulolytic enhancing activity, wherein the variants comprise a substitution at one or more positions corresponding to positions 90, 131, 134, and 141 of the full-length polypeptide of SEQ ID NO: 2, and have cellulolytic enhancing activity. The present invention also relates to polynucleotides encoding the variants; nucleic acid constructs, vectors, and host cells comprising the polynucleotides; and methods of using the variants.

27 Claims, 5 Drawing Sheets

Specification includes a Sequence Listing.

VARIANTS OF POLYPEPTIDES HAVING CELLULOLYTIC ENHANCING ACTIVITY AND POLYNUCLEOTIDES ENCODING SAME

CROSS-REFERENCE TO RELATED APPLICATIONS

This application is a 35 U.S.C. 371 national application of PCT/US2011/054034 filed on Sep. 29, 2011, which claims priority or the benefit under 35 U.S.C. 119 of U.S. Provisional. Application Ser. No. 61/388,530 filed on Sep. 30, 2010, the contents of which are fully incorporated herein by reference.

STATEMENT AS TO RIGHTS TO INVENTIONS MADE UNDER FEDERALLY SPONSORED RESEARCH AND DEVELOPMENT

This invention was made with Government support under Cooperative Agreement DE-FC36-08GO18080 awarded by the Department of Energy. The government has certain rights in this invention.

REFERENCE TO A SEQUENCE LISTING

This application contains a Sequence Listing in computer readable form, which is incorporated herein by reference.

BACKGROUND OF THE INVENTION

Field of the Invention

The present invention relates to polypeptide having cellulolytic enhancing activity variants, polynucleotides encoding the variants, methods of producing the variants, and methods of using the variants.

Description of the Related Art

Cellulose is a polymer of the simple sugar glucose covalently linked by beta-1,4-bonds. Many microorganisms produce enzymes that hydrolyze beta-linked glucans. These enzymes include endoglucanases, cellobiohydrolases, and beta-glucosidases. Endoglucanases digest the cellulose polymer at random locations, opening it to attack by cellobiohydrolases. Cellobiohydrolases sequentially release molecules of cellobiose from the ends of the cellulose polymer. Cellobiose is a water-soluble beta-1,4-linked dimer of glucose. Beta-glucosidases hydrolyze cellobiose to glucose.

The conversion of lignocellulosic feedstocks into ethanol has the advantages of the ready availability of large amounts of feedstock, the desirability of avoiding burning or land filling the materials, and the cleanliness of the ethanol fuel. Wood, agricultural residues, herbaceous crops, and municipal solid wastes have been considered as feedstocks for ethanol production. These materials primarily consist of cellulose, hemicellulose, and lignin. Once the lignocellulose is converted to fermentable sugars, e.g., glucose, the fermentable sugars are easily fermented by yeast into ethanol.

WO 2005/074647, WO 2008/148131, WO 2011/035027 disclose isolated GH61 polypeptides having cellulolytic enhancing activity and the polynucleotides thereof from *Thielavia terrestris*. WO 2005/074656 and WO 2010/065830 disclose isolated GH61 polypeptides having cellulolytic enhancing activity and the polynucleotides thereof from *Thermoascus aurantiacus*. WO 2007/089290 discloses an isolated GH61 polypeptide having cellulolytic enhancing activity and the polynucleotide thereof from *Trichoderma reesei*. WO 2009/085935, WO 2009/085859, WO 2009/085864, and WO 2009/085868 disclose isolated GH61 polypeptides having cellulolytic enhancing activity and the polynucleotides thereof from *Myceliophthora thermophila*. WO 2010/138754 discloses isolated GH61 polypeptides having cellulolytic enhancing activity and the polynucleotides thereof from *Aspergillus fumigatus*. WO 2011/005867 discloses isolated GH61 polypeptides having cellulolytic enhancing activity and the polynucleotides thereof from *Penicillium pinophilum*. WO 2011/039319 discloses isolated GH61 polypeptides having cellulolytic enhancing activity and the polynucleotides thereof from *Thermoascus* sp. WO 2011/041397 discloses isolated GH61 polypeptides having cellulolytic enhancing activity and the polynucleotides thereof from *Penicillium* sp. WO 2011/041504 discloses isolated GH61 polypeptides having cellulolytic enhancing activity and the polynucleotides thereof from *Thermoascus crustaceous*. WO 2008/151043 discloses methods of increasing the activity of a GH61 polypeptide having cellulolytic enhancing activity by adding a soluble activating divalent metal cation to a composition comprising the polypeptide.

It would be advantageous in the art to improve the ability of polypeptides having cellulolytic enhancing activity to enhance enzymatic degradation of lignocellulosic feedstocks.

The present invention provides variants of a polypeptide having cellulolytic enhancing activity with improved properties.

SUMMARY OF THE INVENTION

The present invention relates to isolated variants, comprising a substitution at one or more (e.g., several) positions corresponding to positions 90, 131, 134, and 141 of the mature polypeptide of SEQ ID NO: 2, wherein the variants have cellulolytic enhancing activity.

The present invention also relates to isolated polynucleotides encoding the variants; nucleic acid constructs, vectors, and host cells comprising the polynucleotides; and methods of producing the variants.

The present invention also relates to methods for degrading or converting a cellulosic material, comprising: treating the cellulosic material with an enzyme composition in the presence of such a variant having cellulolytic enhancing activity.

The present invention also relates to methods for producing a fermentation product, comprising:

(a) saccharifying a cellulosic material with an enzyme composition in the presence of such a variant having cellulolytic enhancing activity;

(b) fermenting the saccharified cellulosic material with one or more (e.g., several) fermenting microorganisms to produce the fermentation product; and (c) recovering the fermentation product from the fermentation.

The present invention also relates to methods of fermenting a cellulosic material, comprising: fermenting the cellulosic material with one or more (e.g., several) fermenting microorganisms, wherein the cellulosic material is saccharified with an enzyme composition in the presence of such a variant having cellulolytic enhancing activity.

DEFINITIONS

Figure 1:
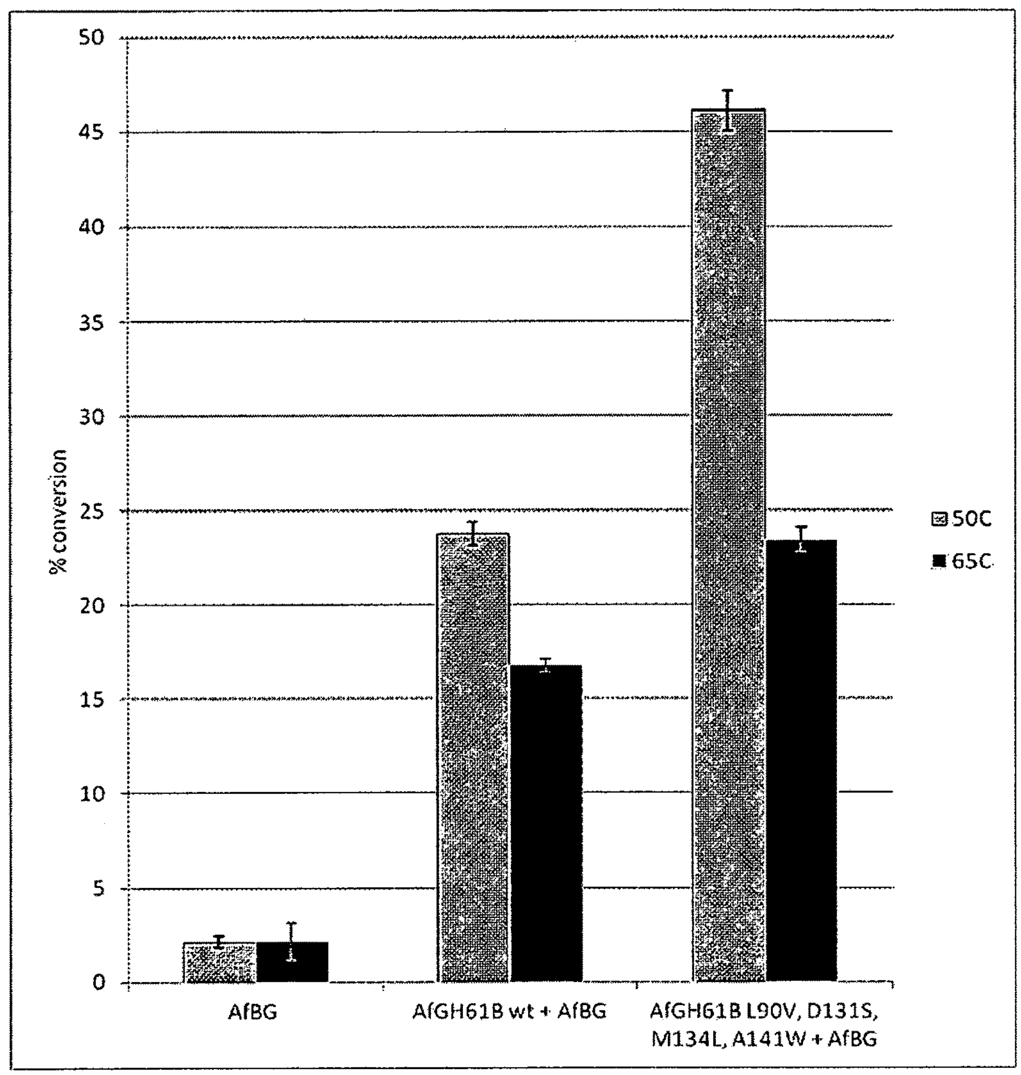
FIG. 1 shows the conversion of phosphoric acid swollen cellulose (0.5% w/w) by the combination of pyrogallol and *A. fumigatus* CEL3A beta-glucosidase; the combination of pyrogallol, *A. fumigatus* GH61B wild-type polypeptide, and *A. fumigatus* CEL3A beta-glucosidase; and the combination of pyrogallol, *A. fumigatus* GH61B variant L90V+D131S+M134L+A141W, and *A. fumigatus* CEL3A beta-glucosidase.

Acetylxylan esterase: The term "acetylxylan esterase" means a carboxylesterase (EC 3.1.1.72) that catalyzes the hydrolysis of acetyl groups from polymeric xylan, acetylated xylose, acetylated glucose, alpha-napthyl acetate, and p-nitrophenyl acetate. For purposes of the present invention, acetylxylan esterase activity is determined using 0.5 mM p-nitrophenylacetate as substrate in 50 mM sodium acetate pH 5.0 containing 0.01% TWEEN™ 20 (polyoxyethylene sorbitan monolaurate). One unit of acetylxylan esterase is defined as the amount of enzyme capable of releasing 1 μmole of p-nitrophenolate anion per minute at pH 5, 25° C.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Alpha-L-arabinofuranosidase: The term "alpha-L-arabinofuranosidase" means an alpha-L-arabinofuranoside arabinofuranohydrolase (EC 3.2.1.55) that catalyzes the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, polysaccharide alpha-L-arabinofuranosidase, alpha-L-arabinofuranoside hydrolase, L-arabinosidase, or alpha-L-arabinanase. For purposes of the present invention, alpha-L-arabinofuranosidase activity is determined using 5 mg of medium viscosity wheat arabinoxylan (Megazyme International Ireland, Ltd., Bray, Co. Wicklow, Ireland) per ml of 100 mM sodium acetate pH 5 in a total volume of 200 μl for 30 minutes at 40° C. followed by arabinose analysis by AMINEX® HPX-87H column chromatography (Bio-Rad Laboratories, Inc., Hercules, Calif., USA).

Alpha-glucuronidase: The term "alpha-glucuronidase" means an alpha-D-glucosiduronate glucuronohydrolase (EC 3.2.1.139) that catalyzes the hydrolysis of an alpha-D-glucuronoside to D-glucuronate and an alcohol. For purposes of the present invention, alpha-glucuronidase activity is determined according to de Vries, 1998, J. Bacteriol. 180: 243-249. One unit of alpha-glucuronidase equals the amount of enzyme capable of releasing 1 μmole of glucuronic or 4-O-methylglucuronic acid per minute at pH 5, 40° C.

Beta-glucosidase: The term "beta-glucosidase" means a beta-D-glucoside glucohydrolase (E.C. 3.2.1.21) that catalyzes the hydrolysis of terminal non-reducing beta-D-glucose residues with the release of beta-D-glucose. For purposes of the present invention, beta-glucosidase activity is determined using p-nitrophenyl-beta-D-glucopyranoside as substrate according to the procedure of Venturi et al., 2002, Extracellular beta-D-glucosidase from *Chaetomium thermophilum* var. *coprophilum*: production, purification and some biochemical properties, *J. Basic Microbiol.* 42: 55-66. One unit of beta-glucosidase is defined as 1.0 μmole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20.

Beta-xylosidase: The term "beta-xylosidase" means a beta-D-xyloside xylohydrolase (E.C. 3.2.1.37) that catalyzes the exo-hydrolysis of short beta (1→4)-xylooligosaccharides, to remove successive D-xylose residues from non-reducing termini. For purposes of the present invention, one unit of beta-xylosidase is defined as 1.0 μmole of p-nitrophenolate anion produced per minute at 40° C., pH 5 from 1 mM p-nitrophenyl-beta-D-xyloside as substrate in 100 mM sodium citrate containing 0.01% TWEEN® 20.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Cellobiohydrolase: The term "cellobiohydrolase" means a 1,4-beta-D-glucan cellobiohydrolase (E.C. 3.2.1.91) that catalyzes the hydrolysis of 1,4-beta-D-glucosidic linkages in cellulose, cellooligosaccharides, or any beta-1,4-linked glucose containing polymer, releasing cellobiose from the reducing or non-reducing ends of the chain (Teeri, 1997, Crystalline cellulose degradation: New insight into the function of cellobiohydrolases, *Trends in Biotechnology* 15: 160-167; Teeri et al., 1998, *Trichoderma reesei* cellobiohydrolases: why so efficient on crystalline cellulose?, *Biochem. Soc. Trans.* 26: 173-178). Cellobiohydrolase activity is determined according to the procedures described by Lever et al., 1972, *Anal. Biochem.* 47: 273-279; van Tilbeurgh et al., 1982, *FEBS Letters,* 149: 152-156; van Tilbeurgh and Claeyssens, 1985, *FEBS Letters,* 187: 283-288; and Tomme et al., 1988, *Eur. J. Biochem.* 170: 575-581. In the present invention, the Tomme et al. method can be used to determine cellobiohydrolase activity.

Cellulosic material: The term "cellulosic material" means any material containing cellulose. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material can be, but is not limited to, agricultural residue, herbaceous material (including energy crops), municipal solid waste, pulp and paper mill residue, waste paper, and wood (including forestry residue) (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In a preferred aspect, the cellulosic material is any biomass material. In another preferred aspect, the cellulosic material is lignocellulose, which comprises cellulose, hemicelluloses, and lignin.

In one aspect, the cellulosic material is agricultural residue. In another aspect, the cellulosic material is herbaceous material (including energy crops). In another aspect, the cellulosic material is municipal solid waste. In another aspect, the cellulosic material is pulp and paper mill residue. In another aspect, the cellulosic material is waste paper. In another aspect, the cellulosic material is wood (including forestry residue).

In another aspect, the cellulosic material is arundo. In another aspect, the cellulosic material is bagasse. In another aspect, the cellulosic material is bamboo. In another aspect, the cellulosic material is corn cob. In another aspect, the cellulosic material is corn fiber. In another aspect, the cellulosic material is corn stover. In another aspect, the cellulosic material is miscanthus. In another aspect, the cellulosic material is orange peel. In another aspect, the cellulosic material is rice straw. In another aspect, the cellulosic material is switchgrass. In another aspect, the cellulosic material is wheat straw.

In another aspect, the cellulosic material is aspen. In another aspect, the cellulosic material is eucalyptus. In another aspect, the cellulosic material is fir. In another aspect, the cellulosic material is pine. In another aspect, the cellulosic material is poplar. In another aspect, the cellulosic material is spruce. In another aspect, the cellulosic material is willow.

In another aspect, the cellulosic material is algal cellulose. In another aspect, the cellulosic material is bacterial cellulose. In another aspect, the cellulosic material is cotton linter. In another aspect, the cellulosic material is filter paper. In another aspect, the cellulosic material is microcrystalline cellulose. In another aspect, the cellulosic material is phosphoric-acid treated cellulose.

In another aspect, the cellulosic material is an aquatic biomass. As used herein the term "aquatic biomass" means biomass produced in an aquatic environment by a photosynthesis process. The aquatic biomass can be algae, emergent plants, floating-leaf plants, or submerged plants.

The cellulosic material may be used as is or may be subjected to pretreatment, using conventional methods known in the art, as described herein. In a preferred aspect, the cellulosic material is pretreated.

Cellulolytic enzyme or cellulase: The term "cellulolytic enzyme" or "cellulase" means one or more (e.g., several) enzymes that hydrolyze a cellulosic material. Such enzymes include endoglucanase(s), cellobiohydrolase(s), beta-glucosidase(s), or combinations thereof. The two basic approaches for measuring cellulolytic activity include: (1) measuring the total cellulolytic activity, and (2) measuring the individual cellulolytic activities (endoglucanases, cellobiohydrolases, and beta-glucosidases) as reviewed in Zhang et al., Outlook for cellulase improvement: Screening and selection strategies, 2006, *Biotechnology Advances* 24: 452-481. Total cellulolytic activity is usually measured using insoluble substrates, including Whatman No 1 filter paper, microcrystalline cellulose, bacterial cellulose, algal cellulose, cotton, pretreated lignocellulose, etc. The most common total cellulolytic activity assay is the filter paper assay using Whatman No 1 filter paper as the substrate. The assay was established by the International Union of Pure and Applied Chemistry (IUPAC) (Ghose, 1987, Measurement of cellulase activities, *Pure Appl. Chem.* 59: 257-68).

For purposes of the present invention, cellulolytic enzyme activity is determined by measuring the increase in hydrolysis of a cellulosic material by cellulolytic enzyme(s) under the following conditions: 1-50 mg of cellulolytic enzyme protein/g of cellulose in PCS (or other pretreated cellulosic material) for 3-7 days at a suitable temperature, e.g., 50° C., 55° C., or 60° C., compared to a control hydrolysis without addition of cellulolytic enzyme protein. Typical conditions are 1 ml reactions, washed or unwashed PCS, 5% insoluble solids, 50 mM sodium acetate pH 5, 1 mM $MnSO_4$, 50° C., 55° C., or 60° C., 72 hours, sugar analysis by AMINEX® HPX-87H column (Bio-Rad Laboratories, Inc., Hercules, Calif., USA).

Coding sequence: The term "coding sequence" means a polynucleotide, which directly specifies the amino acid sequence of a variant. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a variant of the present invention. Each control sequence may be native (i.e., from the same gene) or foreign (i.e., from a different gene) to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

Endoglucanase: The term "endoglucanase" means an endo-1,4-(1,3;1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). For purposes of the present invention, endoglucanase activity is determined using carboxymethyl cellulose (CMC) as substrate according to the procedure of Ghose, 1987, *Pure and Appl. Chem.* 59: 257-268, at pH 5, 40° C.

Expression: The term "expression" includes any step involved in the production of a variant including, but not limited to, transcription, post-transcriptional modification, translation, post-translational modification, and secretion.

Expression vector: The term "expression vector" means a linear or circular DNA molecule that comprises a polynucleotide encoding a variant and is operably linked to control sequences that provide for its expression.

Family 61 glycoside hydrolase: The term "Family 61 glycoside hydrolase" or "Family GH61" or "GH61" means a polypeptide falling into the glycoside hydrolase Family 61 according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696. The enzymes in this family were originally classified as a glycoside hydrolase family based on measurement of very weak endo-1,4-beta-D-glucanase activity in one family member. The structure and mode of action of these enzymes are non-canonical and they cannot be considered as bona fide glycosidases. However, they are kept in the CAZy classification on the basis of their capacity to enhance the breakdown of lignocellulose when used in conjunction with a cellulase or a mixture of cellulases.

Feruloyl esterase: The term "feruloyl esterase" means a 4-hydroxy-3-methoxycinnamoyl-sugar hydrolase (EC 3.1.1.73) that catalyzes the hydrolysis of 4-hydroxy-3-methoxycinnamoyl (feruloyl) groups from esterified sugar, which is usually arabinose in natural biomass substrates, to produce ferulate (4-hydroxy-3-methoxycinnamate). Feruloyl esterase is also known as ferulic acid esterase, hydroxycinnamoyl esterase, FAE-III, cinnamoyl ester hydrolase, FAEA, cinnAE, FAE-I, or FAE-II. For purposes of the present invention, feruloyl esterase activity is determined using 0.5 mM p-nitrophenylferulate as substrate in 50 mM sodium acetate pH 5.0. One unit of feruloyl esterase equals the amount of enzyme capable of releasing 1 μmole of p-nitrophenolate anion per minute at pH 5, 25° C.

Fragment: The term "fragment" means a polypeptide having one or more (e.g., several) amino acids absent from the amino and/or carboxyl terminus of a mature polypeptide; wherein the fragment has cellulolytic enhancing activity. In one aspect, a fragment contains at least 200 amino acid residues, e.g., at least 210 amino acid residues or at least 220 amino acid residues of the mature polypeptide of SEQ ID NO: 2.

Hemicellulolytic enzyme or hemicellulase: The term "hemicellulolytic enzyme" or "hemicellulase" means one or more (e.g., several) enzymes that hydrolyze a hemicellulosic material. See, for example, Shallom, D. and Shoham, Y. Microbial hemicellulases. *Current Opinion In Microbiology,* 2003, 6(3): 219-228). Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates of these enzymes, the hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, *Pure & Appl. Chem.* 59: 1739-1752, at a suitable temperature, e.g., 50° C., 55° C., or 60° C., and pH, e.g., 5.0 or 5.5.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Increased thermal activity: The term "increased thermal activity" means a higher or broader temperature-dependent activity profile of a variant compared to the temperature-dependent activity profile of the parent. The increased thermal activity of the variant enhances catalysis of a reaction at one or more (e.g., several) specific temperatures relative to the parent. A more thermoactive variant will lead to a decrease in the time required and/or a decrease in the enzyme concentration required for catalysis of the reaction. The increased thermal activity of the variant relative to the parent can be assessed, for example, under conditions of one or more (e.g., several) temperatures. For example, the one or more (e.g., several) temperatures can be any temperature in the range of 25° C. to 95° C., e.g., 25, 30, 35, 40, 45, 50, 55, 60, 65, 70, 75, 80, 85, 90, or 95° C. (or in between) at a pH in the range of 3 to 8, e.g., 3.0, 3.5, 4.0, 4.5, 5.0, 5.5, 6.0, 6.5, 7.0, 7.5, or 8.0, (or in between).

In one aspect, the thermal activity of the variant relative to the parent is determined at pH 3.0 and 40° C. In another aspect, the thermal activity of the variant relative to the parent is determined at pH 3.0 and 45° C. In another aspect, the thermal activity of the variant relative to the parent is determined at pH 3.0 and 50° C. In another aspect, the thermal activity of the variant relative to the parent is determined at pH 3.0 and 55° C. In another aspect, the thermal activity of the variant relative to the parent is determined at pH 3.0 and 60° C. In another aspect, the thermal activity of the variant relative to the parent is determined at pH 3.0 and 65° C. In another aspect, the thermal activity of the variant relative to the parent is determined at pH 3.0 and 70° C. In another aspect, the thermal activity of the variant relative to the parent is determined at pH 3.0 and 75° C. In another aspect, the thermal activity of the variant relative to the parent is determined at pH 3.0 and 80° C. In another aspect, the thermal activity of the variant relative to the parent is determined at pH 3.0 and 85° C. In another aspect, the thermal activity of the variant relative to the parent is determined at pH 3.0 and 90° C.

In another aspect, the thermal activity of the variant relative to the parent is determined at pH 3.5 and 40° C. In another aspect, the thermal activity of the variant relative to the parent is determined at pH 3.5 and 45° C. In another aspect, the thermal activity of the variant relative to the parent is determined at pH 3.5 and 50° C. In another aspect, the thermal activity of the variant relative to the parent is determined at pH 3.5 and 55° C. In another aspect, the thermal activity of the variant relative to the parent is determined at pH 3.5 and 60° C. In another aspect, the thermal activity of the variant relative to the parent is determined at pH 3.5 and 65° C. In another aspect, the thermal activity of the variant relative to the parent is determined at pH 3.5 and 70° C. In another aspect, the thermal activity of the variant relative to the parent is determined at pH 3.5 and 75° C. In another aspect, the thermal activity of the variant relative to the parent is determined at pH 3.5 and 80° C. In another aspect, the thermal activity of the variant relative to the parent is determined at pH 3.5 and 85° C. In another aspect, the thermal activity of the variant relative to the parent is determined at pH 3.5 and 90° C.

In another aspect, the thermal activity of the variant relative to the parent is determined at pH 4.0 and 40° C. In another aspect, the thermal activity of the variant relative to the parent is determined at pH 4.0 and 45° C. In another aspect, the thermal activity of the variant relative to the parent is determined at pH 4.0 and 50° C. In another aspect, the thermal activity of the variant relative to the parent is determined at pH 4.0 and 55° C. In another aspect, the thermal activity of the variant relative to the parent is determined at pH 4.0 and 60° C. In another aspect, the thermal activity of the variant relative to the parent is determined at pH 4.0 and 65° C. In another aspect, the thermal activity of the variant relative to the parent is determined at pH 4.0 and 70° C. In another aspect, the thermal activity of the variant relative to the parent is determined at pH 4.0 and 75° C. In another aspect, the thermal activity of the variant relative to the parent is determined at pH 4.0 and 80° C. In another aspect, the thermal activity of the variant relative to the parent is determined at pH 4.0 and 85° C. In another aspect, the thermal activity of the variant relative to the parent is determined at pH 4.0 and 90° C.

In another aspect, the thermal activity of the variant relative to the parent is determined at pH 4.5 and 40° C. In another aspect, the thermal activity of the variant relative to the parent is determined at pH 4.5 and 45° C. In another aspect, the thermal activity of the variant relative to the parent is determined at pH 4.5 and 50° C. In another aspect, the thermal activity of the variant relative to the parent is determined at pH 4.5 and 55° C. In another aspect, the thermal activity of the variant relative to the parent is determined at pH 4.5 and 60° C. In another aspect, the thermal activity of the variant relative to the parent is determined at pH 4.5 and 65° C. In another aspect, the thermal activity of the variant relative to the parent is determined at pH 4.5 and 70° C. In another aspect, the thermal activity of the variant relative to the parent is determined at pH 4.5 and 75° C. In another aspect, the thermal activity of the variant relative to the parent is determined at pH 4.5 and 80° C. In another aspect, the thermal activity of the variant relative to the parent is determined at pH 4.5 and 85° C. In another aspect, the thermal activity of the variant relative to the parent is determined at pH 4.5 and 90° C.

In another aspect, the thermal activity of the variant relative to the parent is determined at pH 5.0 and 40° C. In another aspect, the thermal activity of the variant relative to the parent is determined at pH 5.0 and 45° C. In another aspect, the thermal activity of the variant relative to the parent is determined at pH 5.0 and 50° C. In another aspect, the thermal activity of the variant relative to the parent is determined at pH 5.0 and 55° C. In another aspect, the thermal activity of the variant relative to the parent is determined at pH 5.0 and 60° C. In another aspect, the thermal activity of the variant relative to the parent is determined at pH 5.0 and 65° C. In another aspect, the thermal activity of the variant relative to the parent is determined at pH 5.0 and 70° C. In another aspect, the thermal activity of the variant relative to the parent is determined at pH 5.0 and 75° C. In another aspect, the thermal activity of the variant relative to the parent is determined at pH 5.0 and 80° C. In another aspect, the thermal activity of the variant relative to the parent is determined at pH 5.0 and 85° C. In another aspect, the thermal activity of the variant relative to the parent is determined at pH 5.0 and 90° C.

In another aspect, the thermal activity of the variant relative to the parent is determined at pH 5.5 and 40° C. In another aspect, the thermal activity of the variant relative to the parent is determined at pH 5.5 and 45° C. In another aspect, the thermal activity of the variant relative to the parent is determined at pH 5.5 and 50° C. In another aspect, the thermal activity of the variant relative to the parent is determined at pH 5.5 and 55° C. In another aspect, the thermal activity of the variant relative to the parent is determined at pH 5.5 and 60° C. In another aspect, the thermal activity of the variant relative to the parent is determined at pH 5.5 and 65° C. In another aspect, the thermal activity of the variant relative to the parent is determined at pH 5.5 and 70° C. In another aspect, the thermal activity of the variant relative to the parent is determined at pH 5.5 and 75° C. In another aspect, the thermal activity of the variant relative to the parent is determined at pH 5.5 and 80° C. In another aspect, the thermal activity of the variant relative to the parent is determined at pH 5.5 and 85° C. In another aspect, the thermal activity of the variant relative to the parent is determined at pH 5.5 and 90° C.

In another aspect, the thermal activity of the variant relative to the parent is determined at pH 6.0 and 40° C. In another aspect, the thermal activity of the variant relative to the parent is determined at pH 6.0 and 45° C. In another aspect, the thermal activity of the variant relative to the parent is determined at pH 6.0 and 50° C. In another aspect, the thermal activity of the variant relative to the parent is determined at pH 6.0 and 55° C. In another aspect, the thermal activity of the variant relative to the parent is determined at pH 6.0 and 60° C. In another aspect, the thermal activity of the variant relative to the parent is determined at pH 6.0 and 65° C. In another aspect, the thermal activity of the variant relative to the parent is determined at pH 6.0 and 70° C. In another aspect, the thermal activity of the variant relative to the parent is determined at pH 6.0 and 75° C. In another aspect, the thermal activity of the variant relative to the parent is determined at pH 6.0 and 80° C. In another aspect, the thermal activity of the variant relative to the parent is determined at pH 6.0 and 85° C. In another aspect, the thermal activity of the variant relative to the parent is determined at pH 6.0 and 90° C.

In another aspect, the thermal activity of the variant relative to the parent is determined at pH 6.5 and 40° C. In another aspect, the thermal activity of the variant relative to the parent is determined at pH 6.5 and 45° C. In another aspect, the thermal activity of the variant relative to the parent is determined at pH 6.5 and 50° C. In another aspect, the thermal activity of the variant relative to the parent is determined at pH 6.5 and 55° C. In another aspect, the thermal activity of the variant relative to the parent is determined at pH 6.5 and 60° C. In another aspect, the thermal activity of the variant relative to the parent is determined at pH 6.5 and 65° C. In another aspect, the thermal activity of the variant relative to the parent is determined at pH 6.5 and 70° C. In another aspect, the thermal activity of the variant relative to the parent is determined at pH 6.5 and 75° C. In another aspect, the thermal activity of the variant relative to the parent is determined at pH 6.5 and 80° C. In another aspect, the thermal activity of the variant relative to the parent is determined at pH 6.5 and 85° C. In another aspect, the thermal activity of the variant relative to the parent is determined at pH 6.5 and 90° C.

In another aspect, the thermal activity of the variant relative to the parent is determined at pH 7.0 and 40° C. In another aspect, the thermal activity of the variant relative to the parent is determined at pH 7.0 and 45° C. In another aspect, the thermal activity of the variant relative to the parent is determined at pH 7.0 and 50° C. In another aspect, the thermal activity of the variant relative to the parent is determined at pH 7.0 and 55° C. In another aspect, the thermal activity of the variant relative to the parent is determined at pH 7.0 and 60° C. In another aspect, the thermal activity of the variant relative to the parent is determined at pH 7.0 and 65° C. In another aspect, the thermal activity of the variant relative to the parent is determined at pH 7.0 and 70° C. In another aspect, the thermal activity of the variant relative to the parent is determined at pH 7.0 and 75° C. In another aspect, the thermal activity of the variant relative to the parent is determined at pH 7.0 and 80° C. In another aspect, the thermal activity of the variant relative to the parent is determined at pH 7.0 and 85° C. In another aspect, the thermal activity of the variant relative to the parent is determined at pH 7.0 and 90° C.

In another aspect, the thermal activity of the variant relative to the parent is determined at pH 7.5 and 40° C. In another aspect, the thermal activity of the variant relative to the parent is determined at pH 7.5 and 45° C. In another aspect, the thermal activity of the variant relative to the parent is determined at pH 7.5 and 50° C. In another aspect, the thermal activity of the variant relative to the parent is determined at pH 7.5 and 55° C. In another aspect, the thermal activity of the variant relative to the parent is determined at pH 7.5 and 60° C. In another aspect, the thermal activity of the variant relative to the parent is determined at pH 7.5 and 65° C. In another aspect, the thermal activity of the variant relative to the parent is determined at pH 7.5 and 70° C. In another aspect, the thermal activity of the variant relative to the parent is determined at pH 7.5 and 75° C. In another aspect, the thermal activity of the variant relative to the parent is determined at pH 7.5 and 80° C. In another aspect, the thermal activity of the variant relative to the parent is determined at pH 7.5 and 85° C. In another aspect, the thermal activity of the variant relative to the parent is determined at pH 7.5 and 90° C.

In another aspect, the thermal activity of the variant relative to the parent is determined at pH 8.0 and 40° C. In another aspect, the thermal activity of the variant relative to the parent is determined at pH 8.0 and 45° C. In another aspect, the thermal activity of the variant relative to the parent is determined at pH 8.0 and 50° C. In another aspect, the thermal activity of the variant relative to the parent is determined at pH 8.0 and 55° C. In another aspect, the thermal activity of the variant relative to the parent is determined at pH 8.0 and 60° C. In another aspect, the thermal activity of the variant relative to the parent is determined at pH 8.0 and 65° C. In another aspect, the thermal activity of the variant relative to the parent is determined at pH 8.0 and 70° C. In another aspect, the thermal activity of the variant relative to the parent is determined at pH 8.0 and 75° C. In another aspect, the thermal activity of the variant relative to the parent is determined at pH 8.0 and 80° C. In another aspect, the thermal activity of the variant relative to the parent is determined at pH 8.0 and 85° C. In another aspect, the thermal activity of the variant relative to the parent is determined at pH 8.0 and 90° C.

The increased thermal activity of the variant relative to the parent can be determined using any enzyme assay known in the art for GH61 polypeptides having cellulolytic enhancing activity. See for example, WO 2005/074647, WO 2008/148131 WO 2005/074656, WO 2010/065830, WO 2007/089290, WO 2009/085935, WO 2009/085859, WO 2009/085864, WO 2009/085868, and WO 2008/151043, which are incorporated herein by reference. Alternatively, the increased thermal activity of the variant relative to the parent can be determined using any application assay for the variant where the performance of the variant is compared to the parent. For example, the application assay described in Example 12 or 14 can be used.

In one aspect, the thermal activity of the variant is at least 1.01-fold, e.g., at least 1.05-fold, at least 1.1-fold, at least 1.5-fold, at least 1.8-fold, at least 2-fold, at least 5-fold, at least 10-fold, at least 15-fold, at least 20-fold, at least 25-fold, and at least 50-fold more thermally active than the parent.

A variant with increased thermal activity may or may not display increased thermostability relative to the parent. For example, a variant may have an improved thermal activity relative to the parent, but does not have increased thermostability.

Increased thermostability: The term "increased thermostability" means a higher retention of cellulolytic enhancing activity of a variant after a period of incubation at a temperature relative to the parent. The increased thermostability of the variant relative to the parent can be assessed, for example, under conditions of one or more (e.g., several) temperatures. For example, the one or more (e.g., several) temperatures can be any temperature in the range of 45° C. to 95° C., e.g., 45, 50, 55, 60, 65, 70, 75, 80, 85, or 95° C. (or in between) at a pH in the range of 3 to 8, e.g., 3.0, 3.5, 4.0, 4.5, 5.0, 5.5, 6.0, 6.5, 7.0, 7.5, or 8.0, (or in between) for a suitable period of incubation, e.g., 1 minute, 5 minutes, 10 minutes, 15 minutes, 30 minutes, 45 minutes, or 60 minutes, such that the variant retains residual activity.

In one aspect, the thermostability of the variant relative to the parent is determined at pH 3.0 and 50° C. In another aspect, the thermostability of the variant relative to the parent is determined at pH 3.0 and 55° C. In another aspect, the thermostability of the variant relative to the parent is determined at pH 3.0 and 60° C. In another aspect, the thermostability of the variant relative to the parent is determined at pH 3.0 and 65° C. In another aspect, the thermostability of the variant relative to the parent is determined at pH 3.0 and 70° C. In another aspect, the thermostability of the variant relative to the parent is determined at pH 3.0 and 75° C. In another aspect, the thermostability of the variant relative to the parent is determined at pH 3.0 and 80° C. In another aspect, the thermostability of the variant relative to the parent is determined at pH 3.0 and 85° C. In another aspect, the thermostability of the variant relative to the parent is determined at pH 3.0 and 90° C.

In another aspect, the thermostability of the variant relative to the parent is determined at pH 3.5 and 50° C. In another aspect, the thermostability of the variant relative to the parent is determined at pH 3.5 and 55° C. In another aspect, the thermostability of the variant relative to the parent is determined at pH 3.5 and 60° C. In another aspect, the thermostability of the variant relative to the parent is determined at pH 3.5 and 65° C. In another aspect, the thermostability of the variant relative to the parent is determined at pH 3.5 and 70° C. In another aspect, the thermostability of the variant relative to the parent is determined at pH 3.5 and 75° C. In another aspect, the thermostability of the variant relative to the parent is determined at pH 3.5 and 80° C. In another aspect, the thermostability of the variant relative to the parent is determined at pH 3.5 and 85° C. In another aspect, the thermostability of the variant relative to the parent is determined at pH 3.5 and 90° C.

In another aspect, the thermostability of the variant relative to the parent is determined at pH 4.0 and 50° C. In another aspect, the thermostability of the variant relative to the parent is determined at pH 4.0 and 55° C. In another aspect, the thermostability of the variant relative to the parent is determined at pH 4.0 and 60° C. In another aspect, the thermostability of the variant relative to the parent is determined at pH 4.0 and 65° C. In another aspect, the thermostability of the variant relative to the parent is determined at pH 4.0 and 70° C. In another aspect, the thermostability of the variant relative to the parent is determined at pH 4.0 and 75° C. In another aspect, the thermostability of the variant relative to the parent is determined at pH 4.0 and 80° C. In another aspect, the thermostability of the variant relative to the parent is determined at pH 4.0 and 85° C. In another aspect, the thermostability of the variant relative to the parent is determined at pH 4.0 and 90° C.

In another aspect, the thermostability of the variant relative to the parent is determined at pH 4.5 and 50° C. In another aspect, the thermostability of the variant relative to the parent is determined at pH 4.5 and 55° C. In another aspect, the thermostability of the variant relative to the parent is determined at pH 4.5 and 60° C. In another aspect, the thermostability of the variant relative to the parent is determined at pH 4.5 and 65° C. In another aspect, the thermostability of the variant relative to the parent is determined at pH 4.5 and 70° C. In another aspect, the thermostability of the variant relative to the parent is determined at pH 4.5 and 75° C. In another aspect, the thermostability of the variant relative to the parent is determined at pH 4.5 and 80° C. In another aspect, the thermostability of the variant relative to the parent is determined at pH 4.5 and 85° C. In another aspect, the thermostability of the variant relative to the parent is determined at pH 4.5 and 90° C.

In another aspect, the thermostability of the variant relative to the parent is determined at pH 5.0 and 50° C. In another aspect, the thermostability of the variant relative to the parent is determined at pH 5.0 and 55° C. In another aspect, the thermostability of the variant relative to the parent is determined at pH 5.0 and 60° C. In another aspect, the thermostability of the variant relative to the parent is determined at pH 5.0 and 65° C. In another aspect, the thermostability of the variant relative to the parent is determined at pH 5.0 and 70° C. In another aspect, the thermostability of the variant relative to the parent is determined at pH 5.0 and 75° C. In another aspect, the thermostability of the variant relative to the parent is determined at pH 5.0 and 80° C. In another aspect, the thermostability of the variant relative to the parent is determined at pH 5.0 and 85° C. In another aspect, the thermostability of the variant relative to the parent is determined at pH 5.0 and 90° C.

In another aspect, the thermostability of the variant relative to the parent is determined at pH 5.5 and 50° C. In another aspect, the thermostability of the variant relative to the parent is determined at pH 5.5 and 55° C. In another aspect, the thermostability of the variant relative to the parent is determined at pH 5.5 and 60° C. In another aspect, the thermostability of the variant relative to the parent is determined at pH 5.5 and 65° C. In another aspect, the thermostability of the variant relative to the parent is determined at pH 5.5 and 70° C. In another aspect, the thermostability of the variant relative to the parent is determined at pH 5.5 and 75° C. In another aspect, the thermostability of the variant relative to the parent is determined at pH 5.5 and 80° C. In another aspect, the thermostability of the variant relative to the parent is determined at pH 5.5 and 85° C. In another aspect, the thermostability of the variant relative to the parent is determined at pH 5.5 and 90° C.

In another aspect, the thermostability of the variant relative to the parent is determined at pH 6.0 and 50° C. In another aspect, the thermostability of the variant relative to the parent is determined at pH 6.0 and 55° C. In another aspect, the thermostability of the variant relative to the parent is determined at pH 6.0 and 60° C. In another aspect, the thermostability of the variant relative to the parent is determined at pH 6.0 and 65° C. In another aspect, the thermostability of the variant relative to the parent is determined at pH 6.0 and 70° C. In another aspect, the thermostability of the variant relative to the parent is determined at pH 6.0 and 75° C. In another aspect, the thermostability of the variant relative to the parent is determined at pH 6.0 and 80° C. In another aspect, the thermostability of the variant relative to the parent is determined at pH 6.0 and 85° C. In another aspect, the thermostability of the variant relative to the parent is determined at pH 6.0 and 90° C.

In another aspect, the thermostability of the variant relative to the parent is determined at pH 6.5 and 50° C. In another aspect, the thermostability of the variant relative to the parent is determined at pH 6.5 and 55° C. In another aspect, the thermostability of the variant relative to the parent is determined at pH 6.5 and 60° C. In another aspect, the thermostability of the variant relative to the parent is determined at pH 6.5 and 65° C. In another aspect, the thermostability of the variant relative to the parent is determined at pH 6.5 and 70° C. In another aspect, the thermostability of the variant relative to the parent is determined at pH 6.5 and 75° C. In another aspect, the thermostability of the variant relative to the parent is determined at pH 6.5 and 80° C. In another aspect, the thermostability of the variant relative to the parent is determined at pH 6.5 and 85° C. In another aspect, the thermostability of the variant relative to the parent is determined at pH 6.5 and 90° C.

In another aspect, the thermostability of the variant relative to the parent is determined at pH 7.0 and 50° C. In another aspect, the thermostability of the variant relative to the parent is determined at pH 7.0 and 55° C. In another aspect, the thermostability of the variant relative to the parent is determined at pH 7.0 and 60° C. In another aspect, the thermostability of the variant relative to the parent is determined at pH 7.0 and 65° C. In another aspect, the thermostability of the variant relative to the parent is determined at pH 7.0 and 70° C. In another aspect, the thermostability of the variant relative to the parent is determined at pH 7.0 and 75° C. In another aspect, the thermostability of the variant relative to the parent is determined at pH 7.0 and 80° C. In another aspect, the thermostability of the variant relative to the parent is determined at pH 7.0 and 85° C. In another aspect, the thermostability of the variant relative to the parent is determined at pH 7.0 and 90° C.

In another aspect, the thermostability of the variant relative to the parent is determined at pH 7.5 and 50° C. In another aspect, the thermostability of the variant relative to the parent is determined at pH 7.5 and 55° C. In another aspect, the thermostability of the variant relative to the parent is determined at pH 7.5 and 60° C. In another aspect, the thermostability of the variant relative to the parent is determined at pH 7.5 and 65° C. In another aspect, the thermostability of the variant relative to the parent is determined at pH 7.5 and 70° C. In another aspect, the thermostability of the variant relative to the parent is determined at pH 7.5 and 75° C. In another aspect, the thermostability of the variant relative to the parent is determined at pH 7.5 and 80° C. In another aspect, the thermostability of the variant relative to the parent is determined at pH 7.5 and 85° C. In another aspect, the thermostability of the variant relative to the parent is determined at pH 7.5 and 90° C.

In another aspect, the thermostability of the variant relative to the parent is determined at pH 8.0 and 50° C. In another aspect, the thermostability of the variant relative to the parent is determined at pH 8.0 and 55° C. In another aspect, the thermostability of the variant relative to the parent is determined at pH 8.0 and 60° C. In another aspect, the thermostability of the variant relative to the parent is determined at pH 8.0 and 65° C. In another aspect, the thermostability of the variant relative to the parent is determined at pH 8.0 and 70° C. In another aspect, the thermostability of the variant relative to the parent is determined at pH 8.0 and 75° C. In another aspect, the thermostability of the variant relative to the parent is determined at pH 8.0 and 80° C. In another aspect, the thermostability of the variant relative to the parent is determined at pH 8.0 and 85° C. In another aspect, the thermostability of the variant relative to the parent is determined at pH 8.0 and 90° C.

In each of the aspects above, the thermostability of the variant relative to the parent can be determined by incubating the variant and parent for 1 minute. In each of the aspects above, the thermostability of the variant relative to the parent can be determined by incubating the variant and parent for 5 minutes. In each of the aspects above, the thermostability of the variant relative to the parent can be determined by incubating the variant and parent for 10 minutes. In each of the aspects above, the thermostability of the variant relative to the parent can be determined by incubating the variant and parent for 15 minutes. In each of the aspects above, the thermostability of the variant relative to the parent can be determined by incubating the variant and parent for 30 minutes. In each of the aspects above, the thermostability of the variant relative to the parent can be determined by incubating the variant and parent for 45 minutes. In each of the aspects above, the thermostability of the variant relative to the parent can be determined by incubating the variant and parent for 60 minutes.

The increased thermostability of the variant relative to the parent can be determined by differential scanning calorimetry (DSC) using methods standard in the art (see, for example, Sturtevant, 1987, *Annual Review of Physical Chemistry* 38: 463-488). The increased thermostability of the variant relative to the parent can also be determined using any enzyme assay known in the art for GH61 polypeptides having cellulolytic enhancing activity. See for example, WO 2005/074647, WO 2008/148131 WO 2005/074656, WO 2010/065830, WO 2007/089290, WO 2009/085935, WO 2009/085859, WO 2009/085864, WO 2009/085868, and WO 2008/151043, which are incorporated herein by reference. Alternatively, the increased thermostability of the variant relative to the parent can be determined using any application assay for the variant where the performance of the variant is compared to the parent. For example, the application assay described in Example 12 or 14 can be used.

In one aspect, the thermostability of the variant having cellulolytic enhancing activity is at least 1.01-fold, e.g., at least 1.05-fold, at least 1.1-fold, at least 1.5-fold, at least 1.8-fold, at least 2-fold, at least 5-fold, at least 10-fold, at least 15-fold, at least 20-fold, at least 25-fold, and at least 50-fold more thermostable than the parent.

A variant with increased thermostability may or may not display increased thermal activity relative to the parent. For example, a variant may have an improved ability to refold following incubation at an elevated temperature relative to the parent, but does not have increased thermal activity.

Isolated: The term "isolated" means a substance in a form or environment which does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 22 to 250 of SEQ ID NO: 2 based on the SignalP program (Nielsen et al., 1997, *Protein Engineering* 10:1-6) that predicts amino acids 1 to 21 of SEQ ID NO: 2 are a signal peptide. It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having cellulolytic enhancing activity. In one aspect, the mature polypeptide coding sequence is nucleotides 64 to 859 of SEQ ID NO: 1 based on the SignalP program (Nielsen et al., 1997, supra) that predicts nucleotides 1 to 63 of SEQ ID NO: 1 encode a signal peptide. In another aspect, the mature polypeptide coding sequence is the cDNA sequence contained in nucleotides 64 to 859 of SEQ ID NO: 1.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

Mutant: The term "mutant" means a polynucleotide encoding a variant.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Parent or parent polypeptide having cellulolytic enhancing activity: The term "parent" or "parent polypeptide having cellulolytic enhancing activity" means a polypeptide having cellulolytic enhancing activity to which an alteration is made to produce the variants of the present invention. The parent may be a naturally occurring (wild-type) polypeptide or a variant thereof, or a fragment thereof.

Polypeptide having cellulolytic enhancing activity: The term "polypeptide having cellulolytic enhancing activity" means a GH61 polypeptide that catalyzes the enhancement of the hydrolysis of a cellulosic material by enzyme having cellulolytic activity. For purposes of the present invention, cellulolytic enhancing activity is determined by measuring the increase in reducing sugars or the increase of the total of cellobiose and glucose from the hydrolysis of a cellulosic material by cellulolytic enzyme under the following conditions: 1-50 mg of total protein/g of cellulose in PCS, wherein total protein is comprised of 50-99.5% w/w cellulolytic enzyme protein and 0.5-50% w/w protein of a polypeptide having cellulolytic enhancing activity for 1-7 days at a suitable temperature, e.g., 50° C., 55° C., or 60° C., and pH, e.g., 5.0 or 5.5, compared to a control hydrolysis with equal total protein loading without cellulolytic enhancing activity (1-50 mg of cellulolytic protein/g of cellulose in PCS). In a preferred aspect, a mixture of CELLUCLAST® 1.5L (Novozymes NS, Bagsvrd, Denmark) in the presence of 2-3% of total protein weight *Aspergillus oryzae* beta-glucosidase (recombinantly produced in *Aspergillus oryzae* according to WO 02/095014) or 2-3% of total protein weight *Aspergillus fumigatus* beta-glucosidase (recombinantly produced in *Aspergillus oryzae* as described in WO 2002/095014) of cellulase protein loading is used as the source of the cellulolytic activity.

The GH61 polypeptides having cellulolytic enhancing activity enhance the hydrolysis of a cellulosic material catalyzed by enzyme having cellulolytic activity by reducing the amount of cellulolytic enzyme required to reach the same degree of hydrolysis preferably at least 1.01-fold, e.g., at least 1.05-fold, at least 1.10-fold, at least 1.25-fold, at least 1.5-fold, at least 2-fold, at least 3-fold, at least 4-fold, at least 5-fold, at least 10-fold, or at least 20-fold.

Pretreated corn stover: The term "PCS" or "Pretreated Corn Stover" means a cellulosic material derived from corn stover by treatment with heat and dilute sulfuric acid, alkaline pretreatment, or neutral pretreatment.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0, 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

(Identical Residues×100)/(Length of Alignment–Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0, 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the –nobrief option) is used as the percent identity and is calculated as follows:

(Identical Deoxyribonucleotides×100)/(Length of Alignment–Total Number of Gaps in Alignment)

Subsequence: The term "subsequence" means a polynucleotide having one or more (e.g., several) nucleotides absent from the 5'- and/or 3'-end of a mature polypeptide coding sequence; wherein the subsequence encodes a fragment having cellulolytic enhancing activity. In one aspect, a subsequence contains at least 600 nucleotides, e.g., at least 630 nucleotides or at least 660 nucleotides of the mature polypeptide coding sequence of SEQ ID NO: 1.

Variant: The term "variant" means a polypeptide having cellulolytic enhancing activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position. The variants of the present invention have at least 20%, e.g., at least 40%, at least 50%, at least 60%, at least 70%, at least 80%, at least 90%, at least 95%, or at least 100% of the cellulolytic enhancing activity of the mature polypeptide of SEQ ID NO: 2.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

Xylan-containing material: The term "xylan-containing material" means any material comprising a plant cell wall polysaccharide containing a backbone of beta-(1-4)-linked xylose residues. Xylans of terrestrial plants are heteropolymers possessing a beta-(1-4)-D-xylopyranose backbone, which is branched by short carbohydrate chains. They comprise D-glucuronic acid or its 4-O-methyl ether, L-arabinose, and/or various oligosaccharides, composed of D-xylose, L-arabinose, D- or L-galactose, and D-glucose.

Xylan-type polysaccharides can be divided into homoxylans and heteroxylans, which include glucuronoxylans, (arabino)glucuronoxylans, (glucurono)arabinoxylans, arabinoxylans, and complex heteroxylans. See, for example, Ebringerova et al., 2005, *Adv. Polym. Sci.* 186: 1-67.

In the methods of the present invention, any material containing xylan may be used. In a preferred aspect, the xylan-containing material is lignocellulose.

Xylan degrading activity or xylanolytic activity: The term "xylan degrading activity" or "xylanolytic activity" means a biological activity that hydrolyzes xylan-containing material. The two basic approaches for measuring xylanolytic activity include: (1) measuring the total xylanolytic activity, and (2) measuring the individual xylanolytic activities (e.g., endoxylanases, beta-xylosidases, arabinofuranosidases, alpha-glucuronidases, acetylxylan esterases, feruloyl esterases, and alpha-glucuronyl esterases). Recent progress in assays of xylanolytic enzymes was summarized in several publications including Biely and Puchard, Recent progress in the assays of xylanolytic enzymes, 2006, *Journal of the Science of Food and Agriculture* 86(11): 1636-1647; Spanikova and Biely, 2006, Glucuronoyl esterase—Novel carbohydrate esterase produced by *Schizophyllum commune, FEBS Letters* 580(19): 4597-4601; Herrmann, Vrsanska, Jurickova, Hirsch, Biely, and Kubicek, 1997, The beta-D-xylosidase of *Trichoderma reesei* is a multifunctional beta-D-xylan xylohydrolase, *Biochemical Journal* 321: 375-381.

Total xylan degrading activity can be measured by determining the reducing sugars formed from various types of xylan, including, for example, oat spelt, beechwood, and larchwood xylans, or by photometric determination of dyed xylan fragments released from various covalently dyed xylans. The most common total xylanolytic activity assay is based on production of reducing sugars from polymeric 4-O-methyl glucuronoxylan as described in Bailey, Biely, Poutanen, 1992, Interlaboratory testing of methods for assay of xylanase activity, *Journal of Biotechnology* 23(3): 257-270. Xylanase activity can also be determined with 0.2% AZCL-arabinoxylan as substrate in 0.01% TRITON® X-100 (4-(1,1,3,3-tetramethylbutyl)phenyl-polyethylene glycol) and 200 mM sodium phosphate buffer pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6 buffer.

For purposes of the present invention, xylan degrading activity is determined by measuring the increase in hydrolysis of birchwood xylan (Sigma Chemical Co., Inc., St. Louis, Mo., USA) by xylan-degrading enzyme(s) under the following typical conditions: 1 ml reactions, 5 mg/ml substrate (total solids), 5 mg of xylanolytic protein/g of substrate, 50 mM sodium acetate pH 5, 50° C., 24 hours, sugar analysis using p-hydroxybenzoic acid hydrazide (PHBAH) assay as described by Lever, 1972, A new reaction for colorimetric determination of carbohydrates, *Anal. Biochem* 47: 273-279.

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. For purposes of the present invention, xylanase activity is determined with 0.2% AZCL-arabinoxylan as substrate in 0.01% TRITON® X-100 and 200 mM sodium phosphate buffer pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6 buffer.

Wild-type polypeptide: The term "wild-type polypeptide" means a polypeptide having cellulolytic enhancing activity expressed by a naturally occurring microorganism, such as a bacterium, yeast, or filamentous fungus found in nature.

DETAILED DESCRIPTION OF THE INVENTION

The present invention relates to isolated variants, comprising a substitution at one or more (e.g., several) positions corresponding to positions 90, 131, 134, and 141 of the mature polypeptide of SEQ ID NO: 2, wherein the variants have cellulolytic enhancing activity.

Conventions for Designation of Variants

For purposes of the present invention, the mature polypeptide disclosed in SEQ ID NO: 2 is used to determine the corresponding amino acid residue in another polypeptide having cellulolytic enhancing activity. The amino acid sequence of another polypeptide having cellulolytic enhancing activity is aligned with the mature polypeptide disclosed in SEQ ID NO: 2, and based on the alignment, the amino acid position number corresponding to any amino acid residue in the mature polypeptide disclosed in SEQ ID NO: 2 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix.

Identification of the corresponding amino acid residue in another polypeptide having cellulolytic enhancing activity can be determined by an alignment of multiple polypeptide sequences using several computer programs including, but not limited to, MUSCLE (multiple sequence comparison by log-expectation; version 3.5 or later; Edgar, 2004, *Nucleic Acids Research* 32: 1792-1797), MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 537: 39-64; Katoh and Toh, 2010, *Bioinformatics* 26: 1899-1900), and EMBOSS EMMA employing ClustalW (1.83 or later; Thompson et al., 1994, *Nucleic Acids Research* 22: 4673-4680), using their respective default parameters.

When the other polypeptide has diverged from the mature polypeptide of SEQ ID NO: 2 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example, the SCOP superfamilies of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Engineering* 11: 739-747), and implementation of these algorithms can additionally be utilized to query structure databases with a structure of interest in order to discover possible structural homologs (e.g., Holm and Park, 2000, *Bioinformatics* 16: 566-567).

In describing the variants of the present invention, the nomenclature described below is adapted for ease of reference. The accepted IUPAC single letter or three letter amino acid abbreviation is employed.

Substitutions.

For an amino acid substitution, the following nomenclature is used: Original amino acid, position, substituted amino acid. Accordingly, the substitution of threonine at position 226 with alanine is designated as “Thr226Ala” or “T226A”. Multiple mutations are separated by addition marks (“+”), e.g., “Gly205Arg+Ser411 Phe” or “G205R+S411F”, representing substitutions at positions 205 and 411 of glycine (G) with arginine (R) and serine (S) with phenylalanine (F), respectively.

Deletions.

For an amino acid deletion, the following nomenclature is used: Original amino acid, position, *. Accordingly, the deletion of glycine at position 195 is designated as “Gly195*” or “G195*”. Multiple deletions are separated by addition marks (“+”), e.g., “Gly195*+Ser411*” or “G195*+S411*”.

Insertions.

For an amino acid insertion, the following nomenclature is used: Original amino acid, position, original amino acid, inserted amino acid. Accordingly the insertion of lysine after glycine at position 195 is designated “Gly195GlyLys” or “G195GK”. An insertion of multiple amino acids is designated [Original amino acid, position, original amino acid, inserted amino acid #1, inserted amino acid #2; etc.]. For example, the insertion of lysine and alanine after glycine at position 195 is indicated as “Gly195GlyLysAla” or “G195GKA”.

In such cases the inserted amino acid residue(s) are numbered by the addition of lower case letters to the position number of the amino acid residue preceding the inserted amino acid residue(s). In the above example, the sequence would thus be:

| Parent: | Variant: |
|---|---|
| 195<br>G | 195 195a 195b<br>G - K - A |

Multiple Alterations.

Variants comprising multiple alterations are separated by addition marks (“+”), e.g., “Arg170Tyr+Gly195Glu” or “R170Y+G195E” representing a substitution of arginine and glycine at positions 170 and 195 with tyrosine and glutamic acid, respectively.

Different Alterations.

Where different alterations can be introduced at a position, the different alterations are separated by a comma, e.g., “Arg170Tyr,Glu” represents a substitution of arginine at position 170 with tyrosine or glutamic acid. Thus, “Tyr167Gly,Ala+Arg170Gly,Ala” designates the following variants: “Tyr167Gly+Arg170Gly”, “Tyr167Gly+Arg170Ala”, “Tyr167Ala+Arg170Gly”, and “Tyr167Ala+Arg170Ala”.

Variants

The present invention provides variants comprising a substitution at one or more (e.g., several) positions corresponding to positions 90, 131, 134, and 141 of the mature polypeptide of SEQ ID NO: 2, wherein the variants have cellulolytic enhancing activity.

In an embodiment, the variant has sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, to the amino acid sequence of the parent polypeptide having cellulolytic enhancing activity.

In another embodiment, the variant has at least 60%, e.g., at least 65%, at least 70%, at least 75%, at least 80%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, such as at least 96%, at least 97%, at least 98%, or at least 99%, but less than 100%, sequence identity to the mature polypeptide of SEQ ID NO: 2.

In one aspect, the number of substitutions in the variants of the present invention is 1-4, such as 1, 2, 3, or 4 substitutions.

In another aspect, a variant comprises a substitution at one or more (e.g., several) positions corresponding to positions 90, 131, 134, and 141. In another aspect, a variant comprises a substitution at two positions corresponding to any of positions 90, 131, 134, and 141. In another aspect, a variant comprises a substitution at three positions corresponding to any of positions 90, 131, 134, and 141. In another aspect, a variant comprises a substitution at each position corresponding to positions 90, 131, 134, and 141.

In another aspect, the variant comprises or consists of a substitution at a position corresponding to position 90. In another aspect, the amino acid at a position corresponding to position 90 is substituted with Ala, Arg, Asn, Asp, Cys, Gln, Glu, Gly, His, Ile, Leu, Lys, Met, Phe, Pro, Ser, Thr, Trp, Tyr, or Val, preferably with Val. In another aspect, the variant comprises or consists of the substitution L90V of the mature polypeptide of SEQ ID NO: 2.

In another aspect, the variant comprises or consists of a substitution at a position corresponding to position 131. In another aspect, the amino acid at a position corresponding to position 131 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ser. In another aspect, the variant comprises or consists of the substitution D131S of the mature polypeptide of SEQ ID NO: 2.

In another aspect, the variant comprises or consists of a substitution at a position corresponding to position 134. In another aspect, the amino acid at a position corresponding to position 134 is substituted with Ala, Arg, Asn, Asp, Cys, Gln, Glu, Gly, His, Ile, Leu, Lys, Met, Phe, Pro, Ser, Thr, Trp, Tyr, or Val, preferably with Leu. In another aspect, the variant comprises or consists of the substitution M134L of the mature polypeptide of SEQ ID NO: 2.

In another aspect, the variant comprises or consists of a substitution at a position corresponding to position 141. In another aspect, the amino acid at a position corresponding to position 141 is substituted with Ala, Arg, Asn, Asp, Cys, Gln, Glu, Gly, His, Ile, Leu, Lys, Met, Phe, Pro, Ser, Thr, Trp, Tyr, or Val, preferably with Trp. In another aspect, the variant comprises or consists of the substitution A141W of the mature polypeptide of SEQ ID NO: 2.

In another aspect, the variant comprises or consists of a substitution at positions corresponding to positions 90 and 131, such as those described above.

In another aspect, the variant comprises or consists of substitutions at positions corresponding to positions 90 and 134, such as those described above.

In another aspect, the variant comprises or consists of substitutions at positions corresponding to positions 90 and 141, such as those described above.

In another aspect, the variant comprises or consists of substitutions at positions corresponding to positions 131 and 134, such as those described above.

In another aspect, the variant comprises or consists of substitutions at positions corresponding to positions 131 and 141, such as those described above.

In another aspect, the variant comprises or consists of substitutions at positions corresponding to positions 134 and 141, such as those described above.

In another aspect, the variant comprises or consists of substitutions at positions corresponding to positions 90, 131, and 134, such as those described above.

In another aspect, the variant comprises or consists of substitutions at positions corresponding to positions 90, 131, and 141, such as those described above.

In another aspect, the variant comprises or consists of substitutions at positions corresponding to positions 90, 134, and 141, such as those described above.

In another aspect, the variant comprises or consists of substitutions at positions corresponding to positions 131, 134, and 141, such as those described above.

In another aspect, the variant comprises or consists of substitutions at positions corresponding to positions 90, 131, 134, and 141, such as those described above.

In another aspect, the variant comprises or consists of one or more (e.g., several) substitutions selected from the group consisting of L90V, D131S, M134L, and A141W.

In another aspect, the variant comprises or consists of the substitutions L90V+D131S of the mature polypeptide of SEQ ID NO: 2.

In another aspect, the variant comprises or consists of the substitutions L90V+M134L of the mature polypeptide of SEQ ID NO: 2.

In another aspect, the variant comprises or consists of the substitutions L90V+A141W of the mature polypeptide of SEQ ID NO: 2.

In another aspect, the variant comprises or consists of the substitutions D131S+M134L of the mature polypeptide of SEQ ID NO: 2.

In another aspect, the variant comprises or consists of the substitutions D131S+A141W of the mature polypeptide of SEQ ID NO: 2.

In another aspect, the variant comprises or consists of the substitutions M134L+A141W of the mature polypeptide of SEQ ID NO: 2.

In another aspect, the variant comprises or consists of the substitutions L90V+D131S+M134L of the mature polypeptide of SEQ ID NO: 2.

In another aspect, the variant comprises or consists of the substitutions L90V+D131S+A141W of the mature polypeptide of SEQ ID NO: 2.

In another aspect, the variant comprises or consists of the substitutions L90V+M134L+A141W of the mature polypeptide of SEQ ID NO: 2.

In another aspect, the variant comprises or consists of the substitutions D131S+M134L+A141W of the mature polypeptide of SEQ ID NO: 2.

In another aspect, the variant comprises or consists of the substitutions L90V+D131S+M134L+A141W of the mature polypeptide of SEQ ID NO: 2.

The variants of the present invention may further comprise an alteration, e.g., deletion, insertion, and/or substitution at one or more (e.g., several) other positions.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for polypeptide having cellulolytic enhancing activity to identify amino acid residues that are critical to the activity of the molecule. See also, Hilton et al., 1996, *J. Biol. Chem.* 271: 4699-4708. The active site of the polypeptide having cellulolytic enhancing activity or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

The variants may consist of 200 to 220 amino acids, e.g., 205 to 220, 210 to 220, and 215 to 220 amino acids.

In an embodiment, the variant has increased thermal activity.

In an embodiment, the variant has increased thermostability.

In an embodiment, the variant has increased thermal activity and increased thermostability.

Parent Polypeptides Having Cellulolytic Enhancing Activity

The parent polypeptide having cellulolytic enhancing activity may be (a) a polypeptide having at least 60% sequence identity to the mature polypeptide of SEQ ID NO: 2; (b) a polypeptide encoded by a polynucleotide that hybridizes under at least low stringency conditions with (i) the mature polypeptide coding sequence of SEQ ID NO: 1, (ii) the cDNA sequence thereof, or (iii) the full-length complement of (i) or (ii); or (c) a polypeptide encoded by a polynucleotide having at least 60% sequence identity to the mature polypeptide coding sequence of SEQ ID NO: 1 or the cDNA sequence thereof.

In one aspect, the parent has a sequence identity to the mature polypeptide of SEQ ID NO: 2 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have cellulolytic enhancing activity. In one aspect, the amino acid sequence of the parent differs by up to 10 amino acids, e.g., by 1, 2, 3, 4, 5, 6, 7, 8, 9, or 10 amino acids, from the mature polypeptide of SEQ ID NO: 2.

In another aspect, the parent comprises or consists of the amino acid sequence of SEQ ID NO: 2. In another aspect, the parent comprises or consists of the mature polypeptide of SEQ ID NO: 2. In another aspect, the parent comprises or consists of amino acids 22 to 250 of SEQ ID NO: 2.

In another aspect, the parent is a fragment of the mature polypeptide of SEQ ID NO: 2 containing at least 200 amino acid residues, e.g., at least 210 amino acid residues or at least 220 amino acid residues.

In another aspect, the parent is an allelic variant of the mature polypeptide of SEQ ID NO: 2.

In another aspect, the parent is encoded by a polynucleotide that hybridizes under very low stringency conditions, low stringency conditions, medium stringency conditions, medium-high stringency conditions, high stringency conditions, or very high stringency conditions with (i) the mature polypeptide coding sequence of SEQ ID NO: 1, (ii) the cDNA sequence thereof, or (iii) the full-length complement of (i) or (ii) (J. Sambrook, E. F. Fritsch, and T. Maniatis, 1989, *Molecular Cloning, A Laboratory Manual,* 2d edition, Cold Spring Harbor, N.Y.).

The polynucleotide of SEQ ID NO: 1 or a subsequence thereof, as well as the polypeptide of SEQ ID NO: 2 or a fragment thereof, may be used to design nucleic acid probes to identify and clone DNA encoding a parent from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a parent. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1 or a subsequence thereof, the carrier material is used in a Southern blot.

For purposes of the present invention, hybridization indicates that the polynucleotide hybridizes to a labeled nucleic acid probe corresponding to (i) SEQ ID NO: 1; (ii) the mature polypeptide coding sequence of SEQ ID NO: 1; (iii) the cDNA sequence thereof; (iv) the full-length complement thereof; or (v) a subsequence thereof; under very low to very high stringency conditions. Molecules to which the nucleic acid probe hybridizes under these conditions can be detected using, for example, X-ray film or any other detection means known in the art.

In one aspect, the nucleic acid probe is the mature polypeptide coding sequence of SEQ ID NO: 1 or the cDNA sequence thereof. In another aspect, the nucleic acid probe is nucleotides 64 to 859 of SEQ ID NO: 1 or the cDNA sequence thereof. In another aspect, the nucleic acid probe is a polynucleotide that encodes the polypeptide of SEQ ID NO: 2; the mature polypeptide thereof; or a fragment thereof. In another aspect, the nucleic acid probe is SEQ ID NO: 1 or the cDNA sequence thereof.

In another aspect, the parent is encoded by a polynucleotide having a sequence identity to the mature polypeptide coding sequence of SEQ ID NO: 1 or the cDNA sequence thereof of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, a at least 91%, at least 92%, at least 93%, at least 94%, at least 95%, at least 96%, at least 97%, at least 98%, at least 99%, or 100%, which encodes a polypeptide having cellulolytic enhancing activity. In one aspect, the mature polypeptide coding sequence is nucleotides 64 to 859 of SEQ ID NO: 1.

The parent may be a hybrid polypeptide in which a region of one polypeptide is fused at the N-terminus or the C-terminus of a region of another polypeptide.

The parent may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

The parent may be obtained from microorganisms of any genus. For purposes of the present invention, the term "obtained from" as used herein in connection with a given source shall mean that the parent encoded by a polynucleotide is produced by the source or by a strain in which the polynucleotide from the source has been inserted. In one aspect, the parent is secreted extracellularly.

The parent may be a bacterial polypeptide having cellulolytic enhancing activity. For example, the parent may be a Gram-positive bacterial polypeptide such as a *Bacillus, Clostridium, Enterococcus, Geobacillus, Lactobacillus, Lactococcus, Oceanobacillus, Staphylococcus, Streptococcus*, or *Streptomyces* polypeptide having cellulolytic enhancing activity, or a Gram-negative bacterial polypeptide such as a *Campylobacter, E. coli, Flavobacterium, Fusobacterium, Helicobacter, Ilyobacter, Neisseria, Pseudomonas, Salmonella*, or *Ureaplasma* polypeptide having cellulolytic enhancing activity.

In one aspect, the parent is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis* polypeptide having cellulolytic enhancing activity.

In another aspect, the parent is a *Streptococcus equisimilis, Streptococcus pyogenes, Streptococcus uberis*, or *Streptococcus equi* subsp. *Zooepidemicus* polypeptide having cellulolytic enhancing activity.

In another aspect, the parent is a *Streptomyces achromogenes, Streptomyces avermitilis, Streptomyces coelicolor, Streptomyces griseus*, or *Streptomyces lividans* polypeptide having cellulolytic enhancing activity.

The parent may be a fungal polypeptide having cellulolytic enhancing activity. For example, the parent may be a yeast polypeptide having cellulolytic enhancing activity such as a *Candida, Kluyveromyces, Pichia, Saccharomyces, Schizosaccharomyces*, or *Yarrowia* polypeptide having cellulolytic enhancing activity. For example, the parent may be a filamentous fungal polypeptide having cellulolytic enhancing activity such as an *Acremonium, Agaricus, Alternaria, Aspergillus, Aureobasidium, Botryospaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella*, or *Xylaria* polypeptide having cellulolytic enhancing activity.

In another aspect, the parent is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* polypeptide having cellulolytic enhancing activity.

In another aspect, the parent is an *Acremonium cellulolyticus, Aspergillus aculeatus, Aspergillus awamori, Aspergillus foetidus, Aspergillus fumigatus, Aspergillus japonicus, Aspergillus nidulans, Aspergillus niger, Aspergillus oryzae, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia setosa, Thielavia spededonium, Thielavia subthermophila, Thielavia terrestris, Trichoderma harzianum, Trichoderma koningii, Trichoderma longibrachiatum, Trichoderma reesei*, or *Trichoderma viride* polypeptide having cellulolytic enhancing activity.

In another aspect, the parent is an *Aspergillus fumigatus* polypeptide having cellulolytic enhancing activity, e.g., the polypeptide comprising the mature polypeptide of SEQ ID NO: 2.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The parent may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding a parent may then be obtained by similarly screening a genomic DNA or cDNA library of another microorganism or mixed DNA sample. Once a polynucleotide encoding a parent has been detected with the probe(s), the polynucleotide can be isolated or cloned by utilizing techniques that are known to those of ordinary skill in the art (see, e.g., Sambrook et al., 1989, supra).

Preparation of Variants

The present invention also relates to methods for obtaining a variant having cellulolytic enhancing activity, comprising: (a) introducing into a parent polypeptide having cellulolytic enhancing activity a substitution at one or more (e.g., several) positions corresponding to positions 90, 131, 134, and 141 of the mature polypeptide of SEQ ID NO: 2, wherein the variant has cellulolytic enhancing activity; and (b) recovering the variant.

The variants can be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more (e.g., several) mutations are introduced at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, *Proc. Natl. Acad. Sci. USA* 76: 4949-4955; and Barton et al., 1990, *Nucleic Acids Res.* 18: 7349-4966.

Site-directed mutagenesis can also be accomplished in vivo by methods known in the art. See, e.g., U.S. Patent Application Publication No. 2004/0171154; Storici et al., 2001, *Nature Biotechnol.* 19: 773-776; Kren et al., 1998, *Nat. Med.* 4: 285-290; and Calissano and Macino, 1996, *Fungal Genet. Newslett.* 43: 15-16.

Any site-directed mutagenesis procedure can be used in the present invention. There are many commercial kits available that can be used to prepare variants.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432: 1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204) and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

Polynucleotides

The present invention also relates to isolated polynucleotides encoding a variant of the present invention.

Nucleic Acid Constructs

The present invention also relates to nucleic acid constructs comprising a polynucleotide encoding a variant of the present invention operably linked to one or more control sequences that direct the expression of the coding sequence in a suitable host cell under conditions compatible with the control sequences.

The polynucleotide may be manipulated in a variety of ways to provide for expression of a variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide which is recognized by a host cell for expression of the polynucleotide. The promoter contains transcriptional control sequences that mediate the expression of the variant. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* ctyIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (VIIIa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans acetamidase, Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium* venenatum amyloglucosidase (WO 00/56900), *Fusarium* venenatum Daria (WO 00/56900), *Fusarium venenatum* Quinn (WO 00/56900), *Rhizomucor miehei lipase, Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus neutral* alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator sequence, which is recognized by a host cell to terminate transcription. The terminator sequence is operably linked to the 3'-terminus of the polynucleotide encoding the variant. Any terminator that is functional in the host cell may be used.

Preferred terminators for bacterial host cells are obtained from the genes for *Bacillus* clausii alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans acetamidase, Aspergillus nidulans* anthranilate synthase, *Aspergillus niger glucoamylase, Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae enolase, Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a variant of the present invention which increases expression of the variant.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader sequence is operably linked to the 5'-terminus of the polynucleotide encoding the variant. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the variant-encoding sequence and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a variant and directs the variant into the cell's secretory pathway. The 5'-end of the coding sequence of the polynucleotide may inherently contain a signal peptide coding sequence naturally linked in translation reading frame with the segment of the coding sequence that encodes the variant. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the variant. However, any signal peptide coding sequence that directs the expressed variant into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis subtilisin, Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993*, Microbiological Reviews* 57: 109-137.

Effective signal peptide coding sequences for filamentous fungal host cells are the signal peptide coding sequences obtained from the genes for *Aspergillus niger* neutral amylase, *Aspergillus niger glucoamylase, Aspergillus oryzae* TAKA amylase, *Humicola insolens cellulase, Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a variant. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of the variant and the signal peptide sequence is positioned next to the N-terminus of the propeptide sequence.

It may also be desirable to add regulatory sequences that regulate expression of the variant relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the variant would be operably linked to the regulatory sequence.

Expression Vectors

The present invention also relates to recombinant expression vectors comprising a polynucleotide encoding a variant of the present invention, a promoter, and transcriptional and translational stop signals. The various nucleotide and control sequences may be joined together to produce a recombinant expression vector that may include one or more (e.g., several) convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more (e.g., several) selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosyl-aminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is a hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the variant or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMR1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a variant. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide encoding a variant of the present invention operably linked to one or more (e.g., several) control sequences that direct the production of a variant of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the variant and the source of the parent.

The host cell may be any cell useful in the recombinant production of a variant, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell, including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell, including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell, including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397), or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804) or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., *In, Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, *Soc. App. Bacteriol. Symposium Series* No. 9, 1980).

The yeast host cell may be a *Candida, Hansenula, Kluyveromyces, Pichia, Saccharomyces, Schizosaccharomyces*, or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a variant, comprising: (a) cultivating a host cell of the present invention under conditions suitable for expression of the variant; and (b) recovering the variant.

The host cells are cultivated in a nutrient medium suitable for production of the variant using methods known in the art. For example, the cells may be cultivated by shake flask cultivation, or small-scale or large-scale fermentation (including continuous, batch, fed-batch, or solid state fermentations) in laboratory or industrial fermentors performed in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The variant may be detected using methods known in the art that are specific for the variants. These detection methods include, but are not limited to, use of specific antibodies, formation of an enzyme product, or disappearance of an enzyme substrate. For example, an enzyme assay may be used to determine the activity of the variant.

The variant may be recovered using methods known in the art. For example, the variant may be recovered from the nutrient medium by conventional procedures including, but not limited to, collection, centrifugation, filtration, extraction, spray-drying, evaporation, or precipitation. In one aspect, the whole fermentation broth is recovered.

The variant may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure variants.

Compositions

The present invention also relates to compositions comprising a variant of the present invention. Preferably, the compositions are enriched in such a variant. The term "enriched" indicates that the cellulolytic enhancing activity of the composition has been increased, e.g., with an enrichment factor of at least 1.1.

The compositions may comprise a variant of the present invention as the major enzymatic component, e.g., a mono-component composition. Alternatively, the compositions may comprise multiple enzymatic activities, such as one or more (several) enzymes selected from the group consisting of a cellulase, a polypeptide having cellulolytic enhancing activity, a hemicellulase, an esterase, an expansin, a laccase, a ligninolytic enzyme, a pectinase, a peroxidase, a protease, and a swollenin.

The compositions may be prepared in accordance with methods known in the art and may be in the form of a liquid or a dry composition. The compositions may be stabilized in accordance with methods known in the art.

The compositions may be a fermentation broth formulation or a cell composition, as described herein. Consequently, the present invention also relates to fermentation broth formulations and cell compositions comprising a variant of the present invention. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compostions may further comprise a preservative and/or anti-microbial (e.g., bacteriostatic) agent, including, but not limited to, sorbitol, sodium chloride, potassium sorbate, and others known in the art.

The cell-killed whole broth or composition may further comprise one or more enzyme activities such as cellobiohydrolase, endoglucanase, beta-glucosidase, endo-beta-1,3 (4)-glucanase, glucohydrolase, xyloglucanase, xylanase, xylosidase, arabinofuranosidase, alpha-glucuronidase, acetyl xylan esterase, mannanase, mannosidase, alpha-galactosidase, mannan acetyl esterase, galactanase, arabinanase, pectate lyase, pectinase lyase, pectate lyase, polygalacturonase, pectin acetyl esterase, pectin methyl esterase, beta-galactosidase, galactanase, arabinanase, alpha-arabinofuranosidase, rhamnogalacturonase, ferrulic acid esterases rhamnogalacturonan lyase, rhamnogalacturonan acetyl esterase, xylogalacturonosidase, xylogalacturonase, rhamnogalacturonan lyase, lignin peroxidases, manganese-dependent peroxidases, hybrid peroxidases, with combined properties of lignin peroxidases and manganese-dependent peroxidases, glucoamylase, amylase, protease, and laccase.

In some embodiments, the cell-killed whole broth or composition includes cellulolytic enzymes including, but not limited to, (i) endoglucanases (EG) or 1,4-D-glucan-4-glucanohydrolases (EC 3.2.1.4), (ii) exoglucanases, including 1,4-D-glucan glucanohydrolases (also known as cellodextnnases) (EC 3.2.1.74) and 1,4-D-glucan cellobiohydrolases (exo-cellobiohydrolases, CBH) (EC 3.2.1.91), and (iii) beta-glucosidase (BG) or beta-glucoside glucohydrolases (EC 3.2.1.21).

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis (e.g., expression of cellulase and/or glucosidase enzyme(s)). In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Examples are given below of preferred uses of the compositions of the present invention. The dosage of the composition and other conditions under which the composition is used may be determined on the basis of methods known in the art.

Uses

The present invention is also directed to the following methods for using the variants, or compositions thereof.

The present invention also relates to methods for degrading or converting a cellulosic material, comprising: treating the cellulosic material with an enzyme composition in the presence of a variant of the present invention. In one aspect, the methods further comprise recovering the degraded or converted cellulosic material. Soluble products of degradation or conversion of the cellulosic material can be separated from insoluble cellulosic material using any method well known in the art such as, for example, centrifugation, filtration, and/or gravity settling.

The present invention also relates to methods for producing a fermentation product, comprising: (a) saccharifying a cellulosic material with an enzyme composition in the presence of a variant of the present invention; (b) fermenting the saccharified cellulosic material with one or more (e.g., several) fermenting microorganisms to produce the fermentation product; and (c) recovering the fermentation product from the fermentation.

The present invention also relates to methods of fermenting a cellulosic material, comprising: fermenting the cellulosic material with one or more (e.g., several) fermenting microorganisms, wherein the cellulosic material is saccharified with an enzyme composition in the presence of a variant of the present invention. In one aspect, the fermenting of the cellulosic material produces a fermentation product. In another aspect, the methods further comprise recovering the fermentation product from the fermentation.

The methods of the present invention can be used to saccharify the cellulosic material to fermentable sugars and to convert the fermentable sugars to many useful fermentation products, e.g., fuel, potable ethanol, and/or platform chemicals (e.g., acids, alcohols, ketones, gases, and the like). The production of a desired fermentation product from the cellulosic material typically involves pretreatment, enzymatic hydrolysis (saccharification), and fermentation.

The processing of the cellulosic material according to the present invention can be accomplished using processes conventional in the art. Moreover, the methods of the present invention can be implemented using any conventional biomass processing apparatus configured to operate in accordance with the invention.

Hydrolysis (saccharification) and fermentation, separate or simultaneous, include, but are not limited to, separate hydrolysis and fermentation (SHF); simultaneous saccharification and fermentation (SSF); simultaneous saccharification and co-fermentation (SSCF); hybrid hydrolysis and fermentation (HHF); separate hydrolysis and co-fermentation (SHCF); hybrid hydrolysis and co-fermentation (HHCF); and direct microbial conversion (DMC), also sometimes called consolidated bioprocessing (CBP). SHF uses separate process steps to first enzymatically hydrolyze the cellulosic material to fermentable sugars, e.g., glucose, cellobiose, and pentose monomers, and then ferment the fermentable sugars to ethanol. In SSF, the enzymatic hydrolysis of the cellulosic material and the fermentation of sugars to ethanol are combined in one step (Philippidis, G. P., 1996, Cellulose bioconversion technology, in *Handbook on Bioethanol: Production and Utilization*, Wyman, C. E., ed., Taylor & Francis, Washington, D.C., 179-212). SSCF involves the co-fermentation of multiple sugars (Sheehan, J., and Himmel, M., 1999, Enzymes, energy and the environment: A strategic perspective on the U.S. Department of Energy's research and development activities for bioethanol, *Biotechnol. Prog.* 15: 817-827). HHF involves a separate hydrolysis step, and in addition a simultaneous saccharification and hydrolysis step, which can be carried out in the same reactor. The steps in an HHF process can be carried out at different temperatures, i.e., high temperature enzymatic saccharification followed by SSF at a lower temperature that the fermentation strain can tolerate. DMC combines all three processes (enzyme production, hydrolysis, and fermentation) in one or more (e.g., several) steps where the same organism is used to produce the enzymes for conversion of the cellulosic material to fermentable sugars and to convert the fermentable sugars into a final product (Lynd, L. R., Weimer, P. J., van Zyl, W. H., and Pretorius, I. S., 2002, *Microbial cellulose utilization: Fundamentals and biotechnology, Microbiol. Mol. Biol. Reviews* 66: 506-577). It is understood herein that any method known in the art comprising pretreatment, enzymatic hydrolysis (saccharification), fermentation, or a combination thereof, can be used in the practicing the methods of the present invention.

A conventional apparatus can include a fed-batch stirred reactor, a batch stirred reactor, a continuous flow stirred reactor with ultrafiltration, and/or a continuous plug-flow column reactor (Fernanda de Castilhos Corazza, Flávio Faria de Moraes, Gisella Maria Zanin and Ivo Neitzel, 2003, Optimal control in fed-batch reactor for the cellobiose hydrolysis, *Acta Scientiarum. Technology* 25: 33-38; Gusakov, A. V., and Sinitsyn, A. P., 1985, Kinetics of the enzymatic hydrolysis of cellulose: 1. A mathematical model for a batch reactor process, *Enz. Microb. Technol.* 7: 346-352), an attrition reactor (Ryu, S. K., and Lee, J. M., 1983, Bioconversion of waste cellulose by using an attrition bioreactor, *Biotechnol. Bioeng.* 25: 53-65), or a reactor with intensive stirring induced by an electromagnetic field (Gusakov, A. V., Sinitsyn, A. P., Davydkin, I. Y., Davydkin, V. Y., Protas, O. V., 1996, Enhancement of enzymatic cellulose hydrolysis using a novel type of bioreactor with intensive stirring induced by electromagnetic field, *Appl. Biochem. Biotechnol.* 56: 141-153). Additional reactor types include: fluidized bed, upflow blanket, immobilized, and extruder type reactors for hydrolysis and/or fermentation.

Pretreatment. In practicing the methods of the present invention, any pretreatment process known in the art can be used to disrupt plant cell wall components of the cellulosic material (Chandra et al., 2007, Substrate pretreatment: The key to effective enzymatic hydrolysis of lignocellulosics? *Adv. Biochem. Engin./Biotechnol.* 108: 67-93; Galbe and Zacchi, 2007, Pretreatment of lignocellulosic materials for efficient bioethanol production, *Adv. Biochem. Engin./Biotechnol.* 108: 41-65; Hendriks and Zeeman, 2009, Pretreatments to enhance the digestibility of lignocellulosic biomass, *Bioresource Technol.* 100: 10-18; Mosier et al., 2005, Features of promising technologies for pretreatment of lignocellulosic biomass, *Bioresource Technol.* 96: 673-686; Taherzadeh and Karimi, 2008, Pretreatment of lignocellulosic wastes to improve ethanol and biogas production: A review, *Int. J. of Mol. Sci.* 9: 1621-1651; Yang and Wyman, 2008, Pretreatment: the key to unlocking low-cost cellulosic ethanol, *Biofuels Bioproducts and Biorefining-Biofpr.* 2: 26-40).

The cellulosic material can also be subjected to particle size reduction, sieving, pre-soaking, wetting, washing, and/or conditioning prior to pretreatment using methods known in the art.

Conventional pretreatments include, but are not limited to, steam pretreatment (with or without explosion), dilute acid pretreatment, hot water pretreatment, alkaline pretreatment, lime pretreatment, wet oxidation, wet explosion, ammonia fiber explosion, organosolv pretreatment, and biological pretreatment. Additional pretreatments include ammonia percolation, ultrasound, electroporation, microwave, supercritical $CO_2$, supercritical $H_2O$, ozone, ionic liquid, and gamma irradiation pretreatments.

The cellulosic material can be pretreated before hydrolysis and/or fermentation. Pretreatment is preferably performed prior to the hydrolysis. Alternatively, the pretreatment can be carried out simultaneously with enzyme hydrolysis to release fermentable sugars, such as glucose, xylose, and/or cellobiose. In most cases the pretreatment step itself results in some conversion of biomass to fermentable sugars (even in absence of enzymes).

Steam Pretreatment. In steam pretreatment, the cellulosic material is heated to disrupt the plant cell wall components, including lignin, hemicellulose, and cellulose to make the cellulose and other fractions, e.g., hemicellulose, accessible to enzymes. The cellulosic material is passed to or through a reaction vessel where steam is injected to increase the temperature to the required temperature and pressure and is retained therein for the desired reaction time. Steam pretreatment is preferably performed at 140-250° C., e.g., 160-200° C. or 170-190° C., where the optimal temperature range depends on addition of a chemical catalyst. Residence time for the steam pretreatment is preferably 1-60 minutes, e.g., 1-30 minutes, 1-20 minutes, 3-12 minutes, or 4-10 minutes, where the optimal residence time depends on temperature range and addition of a chemical catalyst. Steam pretreatment allows for relatively high solids loadings, so that the cellulosic material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996, *Bioresource Technology* 855: 1-33; Galbe and Zacchi, 2002, *Appl. Microbiol. Biotechnol.* 59: 618-628; U.S. Patent Application No. 20020164730). During steam pretreatment, hemicellulose acetyl groups are cleaved and the resulting acid autocatalyzes partial hydrolysis of the hemicellulose to monosaccharides and oligosaccharides. Lignin is removed to only a limited extent.

Chemical Pretreatment The term "chemical treatment" refers to any chemical pretreatment that promotes the separation and/or release of cellulose, hemicellulose, and/or lignin. Such a pretreatment can convert crystalline cellulose to amorphous cellulose. Examples of suitable chemical pretreatment processes include, for example, dilute acid pretreatment, lime pretreatment, wet oxidation, ammonia fiber/freeze explosion (AFEX), ammonia percolation (APR), ionic liquid, and organosolv pretreatments.

A catalyst such as $H_2SO_4$ or $SO_2$ (typically 0.3 to 5% w/w) is often added prior to steam pretreatment, which decreases the time and temperature, increases the recovery, and improves enzymatic hydrolysis (Ballesteros et al., 2006, *Appl. Biochem. Biotechnol.* 129-132: 496-508; Varga et al., 2004, *Appl. Biochem. Biotechnol.* 113-116: 509-523; Sassner et al., 2006, *Enzyme Microb. Technol.* 39: 756-762). In dilute acid pretreatment, the cellulosic material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, counter-current reactors, or continuous counter-current shrinking bed reactors (Duff and Murray, 1996, supra; Schell et al., 2004, *Bioresource Technol.* 91: 179-188; Lee et al., 1999, *Adv. Biochem. Eng. Biotechnol.* 65: 93-115).

Several methods of pretreatment under alkaline conditions can also be used. These alkaline pretreatments include, but are not limited to, sodium hydroxide, lime, wet oxidation, ammonia percolation (APR), and ammonia fiber/freeze explosion (AFEX).

Lime pretreatment is performed with calcium oxide or calcium hydroxide at temperatures of 85-150° C. and residence times from 1 hour to several days (Wyman et al., 2005, *Bioresource Technol.* 96: 1959-1966; Mosier et al., 2005, *Bioresource Technol.* 96: 673-686). WO 2006/110891, WO 2006/110899, WO 2006/110900, and WO 2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, *Bioresource Technol.* 64: 139-151; Palonen et al., 2004, *Appl. Biochem. Biotechnol.* 117: 1-17; Varga et al., 2004, *Biotechnol. Bioeng.* 88: 567-574; Martin et al., 2006, *J. Chem. Technol. Biotechnol.* 81: 1669-1677). The pretreatment is performed preferably at 1-40% dry matter, e.g., 2-30% dry matter or 5-20% dry matter, and often the initial pH is increased by the addition of alkali such as sodium carbonate.

A modification of the wet oxidation pretreatment method, known as wet explosion (combination of wet oxidation and steam explosion) can handle dry matter up to 30%. In wet explosion, the oxidizing agent is introduced during pretreatment after a certain residence time. The pretreatment is then ended by flashing to atmospheric pressure (WO 2006/032282).

Ammonia fiber explosion (AFEX) involves treating the cellulosic material with liquid or gaseous ammonia at moderate temperatures such as 90-150° C. and high pressure such as 17-20 bar for 5-10 minutes, where the dry matter content can be as high as 60% (Gollapalli et al., 2002, *Appl. Biochem. Biotechnol.* 98: 23-35; Chundawat et al., 2007, *Biotechnol. Bioeng.* 96: 219-231; Alizadeh et al., 2005, *Appl. Biochem. Biotechnol.* 121: 1133-1141; Teymouri et al., 2005, *Bioresource Technol.* 96: 2014-2018). During AFEX pretreatment cellulose and hemicelluloses remain relatively intact. Lignin-carbohydrate complexes are cleaved.

Organosolv pretreatment delignifies the cellulosic material by extraction using aqueous ethanol (40-60% ethanol) at 160-200° C. for 30-60 minutes (Pan et al., 2005, *Biotechnol. Bioeng.* 90: 473-481; Pan et al., 2006, *Biotechnol. Bioeng.* 94: 851-861; Kurabi et al., 2005, *Appl. Biochem. Biotechnol.* 121: 219-230). Sulphuric acid is usually added as a catalyst. In organosolv pretreatment, the majority of hemicellulose and lignin is removed.

Other examples of suitable pretreatment methods are described by Schell et al., 2003, *Appl. Biochem. and Biotechnol. Vol.* 105-108, p. 69-85, and Mosier et al., 2005, *Bioresource Technology* 96: 673-686, and U.S. Published Application 2002/0164730.

In one aspect, the chemical pretreatment is preferably carried out as a dilute acid treatment, and more preferably as a continuous dilute acid treatment. The acid is typically sulfuric acid, but other acids can also be used, such as acetic acid, citric acid, nitric acid, phosphoric acid, tartaric acid, succinic acid, hydrogen chloride, or mixtures thereof. Mild acid treatment is conducted in the pH range of preferably 1-5, e.g., 1-4 or 1-2.5. In one aspect, the acid concentration is in the range from preferably 0.01 to 10 wt % acid, e.g., 0.05 to 5 wt % acid or 0.1 to 2 wt % acid. The acid is contacted with the cellulosic material and held at a temperature in the range of preferably 140-200° C., e.g., 165-190° C., for periods ranging from 1 to 60 minutes.

In another aspect, pretreatment takes place in an aqueous slurry. In preferred aspects, the cellulosic material is present during pretreatment in amounts preferably between 10-80 wt %, e.g., 20-70 wt % or 30-60 wt %, such as around 40 wt %. The pretreated cellulosic material can be unwashed or washed using any method known in the art, e.g., washed with water.

Mechanical Pretreatment or Physical Pretreatment: The term "mechanical pretreatment" or "physical pretreatment" refers to any pretreatment that promotes size reduction of particles. For example, such pretreatment can involve various types of grinding or milling (e.g., dry milling, wet milling, or vibratory ball milling).

The cellulosic material can be pretreated both physically (mechanically) and chemically. Mechanical or physical pretreatment can be coupled with steaming/steam explosion, hydrothermolysis, dilute or mild acid treatment, high temperature, high pressure treatment, irradiation (e.g., microwave irradiation), or combinations thereof. In one aspect, high pressure means pressure in the range of preferably about 100 to about 400 psi, e.g., about 150 to about 250 psi. In another aspect, high temperature means temperatures in the range of about 100 to about 300° C., e.g., about 140 to about 200° C. In a preferred aspect, mechanical or physical pretreatment is performed in a batch-process using a steam gun hydrolyzer system that uses high pressure and high temperature as defined above, e.g., a Sunds Hydrolyzer available from Sunds Defibrator AB, Sweden. The physical and chemical pretreatments can be carried out sequentially or simultaneously, as desired.

Accordingly, in a preferred aspect, the cellulosic material is subjected to physical (mechanical) or chemical pretreatment, or any combination thereof, to promote the separation and/or release of cellulose, hemicellulose, and/or lignin.

Biological Pretreatment: The term "biological pretreatment" refers to any biological pretreatment that promotes the separation and/or release of cellulose, hemicellulose, and/or lignin from the cellulosic material. Biological pretreatment techniques can involve applying lignin-solubilizing microorganisms and/or enzymes (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh and Singh, 1993, Physicochemical and biological treatments for enzymatic/microbial conversion of cellulosic biomass, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, D.C., chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson and Hahn-Hagerdal, 1996, Fermentation of lignocellulosic hydrolysates for ethanol production, *Enz. Microb. Tech.* 18: 312-331; and Vallander and Eriksson, 1990, Production of ethanol from lignocellulosic materials: State of the art, *Adv. Biochem. Eng./Biotechnol.* 42: 63-95).

Saccharification.

In the hydrolysis step, also known as saccharification, the cellulosic material, e.g., pretreated, is hydrolyzed to break down cellulose and/or hemicellulose to fermentable sugars, such as glucose, cellobiose, xylose, xylulose, arabinose, mannose, galactose, and/or soluble oligosaccharides. The hydrolysis is performed enzymatically by an enzyme composition in the presence of a variant of the present invention. The components of the compositions can be added simultaneously or sequentially.

Enzymatic hydrolysis is preferably carried out in a suitable aqueous environment under conditions that can be readily determined by one skilled in the art. In one aspect, hydrolysis is performed under conditions suitable for the activity of the enzyme components, i.e., optimal for the enzyme components. The hydrolysis can be carried out as a fed batch or continuous process where the cellulosic material is fed gradually to, for example, an enzyme containing hydrolysis solution.

The saccharification is generally performed in stirred-tank reactors or fermentors under controlled pH, temperature, and mixing conditions. Suitable process time, temperature and pH conditions can readily be determined by one skilled in the art. For example, the saccharification can last up to 200 hours, but is typically performed for preferably about 12 to about 120 hours, e.g., about 16 to about 72 hours or about 24 to about 48 hours. The temperature is in the range of preferably about 25° C. to about 70° C., e.g., about 30° C. to about 65° C., about 40° C. to about 60° C., or about 50° C. to about 55° C. The pH is in the range of preferably about 3 to about 8, e.g., about 3.5 to about 7, about 4 to about 6, or about 5.0 to about 5.5. The dry solids content is in the range of preferably about 5 to about 50 wt %, e.g., about 10 to about 40 wt % or about 20 to about 30 wt %.

The enzyme compositions can comprise any protein useful in degrading the cellulosic material.

In one aspect, the enzyme composition comprises or further comprises one or more (e.g., several) proteins selected from the group consisting of a cellulase, a polypeptide having cellulolytic enhancing activity, a hemicellulase, an esterase, an expansin, a laccase, a ligninolytic enzyme, a pectinase, a peroxidase, a protease, and a swollenin. In another aspect, the cellulase is preferably one or more (e.g., several) enzymes selected from the group consisting of an endoglucanase, a cellobiohydrolase, and a beta-glucosidase. In another aspect, the hemicellulase is preferably one or more (e.g., several) enzymes selected from the group consisting of an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase.

In another aspect, the enzyme composition comprises one or more (e.g., several) cellulolytic enzymes. In another aspect, the enzyme composition comprises or further comprises one or more (e.g., several) hemicellulolytic enzymes. In another aspect, the enzyme composition comprises one or more (e.g., several) cellulolytic enzymes and one or more (e.g., several) hemicellulolytic enzymes. In another aspect, the enzyme composition comprises one or more (e.g., several) enzymes selected from the group of cellulolytic enzymes and hemicellulolytic enzymes. In another aspect, the enzyme composition comprises an endoglucanase. In another aspect, the enzyme composition comprises a cellobiohydrolase. In another aspect, the enzyme composition comprises a beta-glucosidase. In another aspect, the enzyme composition comprises a polypeptide having cellulolytic enhancing activity. In another aspect, the enzyme composition comprises an endoglucanase and a polypeptide having cellulolytic enhancing activity. In another aspect, the enzyme composition comprises a cellobiohydrolase and a polypeptide having cellulolytic enhancing activity. In another aspect, the enzyme composition comprises a beta-glucosidase and a polypeptide having cellulolytic enhancing activity. In another aspect, the enzyme composition comprises an endoglucanase and a cellobiohydrolase. In another aspect, the enzyme composition comprises an endoglucanase and a beta-glucosidase. In another aspect, the enzyme composition comprises a cellobiohydrolase and a beta-glucosidase. In another aspect, the enzyme composition comprises an endoglucanase, a cellobiohydrolase, and a polypeptide having cellulolytic enhancing activity. In another aspect, the enzyme composition comprises an endoglucanase, a beta-glucosidase, and a polypeptide having cellulolytic enhancing activity. In another aspect, the enzyme composition comprises a cellobiohydrolase, a beta-glucosidase, and a polypeptide having cellulolytic enhancing activity. In another aspect, the enzyme composition comprises an endoglucanase, a cellobiohydrolase, and a beta-glucosidase. In another aspect, the enzyme composition comprises an endoglucanase, a cellobiohydrolase, a beta-glucosidase, and a polypeptide having cellulolytic enhancing activity.

In another aspect, the enzyme composition comprises an acetylmannan esterase. In another aspect, the enzyme composition comprises an acetylxylan esterase. In another aspect, the enzyme composition comprises an arabinanase (e.g., alpha-L-arabinanase). In another aspect, the enzyme composition comprises an arabinofuranosidase (e.g., alpha-L-arabinofuranosidase). In another aspect, the enzyme composition comprises a coumaric acid esterase. In another aspect, the enzyme composition comprises a feruloyl esterase. In another aspect, the enzyme composition comprises a galactosidase (e.g., alpha-galactosidase and/or beta-galactosidase). In another aspect, the enzyme composition comprises a glucuronidase (e.g., alpha-D-glucuronidase). In another aspect, the enzyme composition comprises a glucuronoyl esterase. In another aspect, the enzyme composition comprises a mannanase. In another aspect, the enzyme composition comprises a mannosidase (e.g., beta-mannosidase). In another aspect, the enzyme composition comprises a xylanase. In a preferred aspect, the xylanase is a Family 10 xylanase. In another aspect, the enzyme composition comprises a xylosidase (e.g., beta-xylosidase).

In another aspect, the enzyme composition comprises an esterase. In another aspect, the enzyme composition comprises an expansin. In another aspect, the enzyme composition comprises a laccase. In another aspect, the enzyme composition comprises a ligninolytic enzyme. In a preferred aspect, the ligninolytic enzyme is a manganese peroxidase. In another preferred aspect, the ligninolytic enzyme is a lignin peroxidase. In another preferred aspect, the ligninolytic enzyme is a $H_2O_2$-producing enzyme. In another aspect, the enzyme composition comprises a pectinase. In another aspect, the enzyme composition comprises a peroxidase. In another aspect, the enzyme composition comprises a protease. In another aspect, the enzyme composition comprises a swollenin.

In the methods of the present invention, the enzyme(s) can be added prior to or during saccharification, saccharification and fermentation, or fermentation.

One or more (e.g., several) components of the enzyme composition may be wild-type proteins, recombinant proteins, or a combination of wild-type proteins and recombinant proteins. For example, one or more (e.g., several) components may be native proteins of a cell, which is used as a host cell to express recombinantly one or more (e.g., several) other components of the enzyme composition. One or more (e.g., several) components of the enzyme composition may be produced as monocomponents, which are then combined to form the enzyme composition. The enzyme composition may be a combination of multicomponent and monocomponent protein preparations.

The enzymes used in the methods of the present invention may be in any form suitable for use, such as, for example, a fermentation broth formulation or a cell composition, a cell lysate with or without cellular debris, a semi-purified or purified enzyme preparation, or a host cell as a source of the enzymes. The enzyme composition may be a dry powder or granulate, a non-dusting granulate, a liquid, a stabilized liquid, or a stabilized protected enzyme. Liquid enzyme preparations may, for instance, be stabilized by adding stabilizers such as a sugar, a sugar alcohol or another polyol, and/or lactic acid or another organic acid according to established processes.

The optimum amounts of the enzymes and a variant of the present invention depend on several factors including, but not limited to, the mixture of cellulolytic and/or hemicellulolytic enzyme components, the cellulosic substrate, the concentration of cellulosic substrate, the pretreatment(s) of the cellulosic substrate, temperature, time, pH, and inclusion of fermenting organism (e.g., yeast for Simultaneous Saccharification and Fermentation).

In one aspect, an effective amount of cellulolytic or hemicellulolytic enzyme protein to cellulosic material is about 0.5 to about 50 mg, preferably at about 0.5 to about 40 mg, more preferably at about 0.5 to about 25 mg, more preferably at about 0.75 to about 20 mg, more preferably at about 0.75 to about 15 mg, even more preferably at about 0.5 to about 10 mg, and most preferably at about 2.5 to about 10 mg per g of cellulosic material.

In another aspect, an effective amount of a variant having cellulolytic enhancing activity to cellulosic material is about 0.01 to about 50.0 mg, preferably about 0.01 to about 40 mg, more preferably about 0.01 to about 30 mg, more preferably about 0.01 to about 20 mg, more preferably about 0.01 to about 10 mg, more preferably about 0.01 to about 5 mg, more preferably at about 0.025 to about 1.5 mg, more preferably at about 0.05 to about 1.25 mg, more preferably at about 0.075 to about 1.25 mg, more preferably at about 0.1 to about 1.25 mg, even more preferably at about 0.15 to about 1.25 mg, and most preferably at about 0.25 to about 1.0 mg per g of cellulosic material.

In another aspect, an effective amount of a variant having cellulolytic enhancing activity to cellulolytic enzyme protein is about 0.005 to about 1.0 g, preferably at about 0.01 to about 1.0 g, more preferably at about 0.15 to about 0.75 g, more preferably at about 0.15 to about 0.5 g, more preferably at about 0.1 to about 0.5 g, even more preferably at about 0.1 to about 0.5 g, and most preferably at about 0.05 to about 0.2 g per g of cellulolytic enzyme protein.

The polypeptides having cellulolytic enzyme activity or hemicellulolytic enzyme activity as well as other proteins/polypeptides useful in the degradation of the cellulosic material, e.g., GH61 polypeptides having cellulolytic enhancing activity (collectively hereinafter "polypeptides having enzyme activity") can be derived or obtained from any suitable origin, including, bacterial, fungal, yeast, plant, or mammalian origin. The term "obtained" also means herein that the enzyme may have been produced recombinantly in a host organism employing methods described herein, wherein the recombinantly produced enzyme is either native or foreign to the host organism or has a modified amino acid sequence, e.g., having one or more (e.g., several) amino acids that are deleted, inserted and/or substituted, i.e., a recombinantly produced enzyme that is a mutant and/or a fragment of a native amino acid sequence or an enzyme produced by nucleic acid shuffling processes known in the art. Encompassed within the meaning of a native enzyme are natural variants and within the meaning of a foreign enzyme are variants obtained recombinantly, such as by site-directed mutagenesis or shuffling.

A polypeptide having enzyme activity may be a bacterial polypeptide. For example, the polypeptide may be a gram positive bacterial polypeptide such as a *Bacillus, Streptococcus, Streptomyces, Staphylococcus, Enterococcus, Lactobacillus, Lactococcus, Clostridium, Geobacillus, Caldi-*

*cellulosiruptor, Acidothermus, Thermobifidia*, or *Oceanobacillus* polypeptide having enzyme activity, or a Gram negative bacterial polypeptide such as an *E. coli, Pseudomonas, Salmonella, Campylobacter, Helicobacter, Flavobacterium, Fusobacterium, Ilyobacter, Neisseria*, or *Ureaplasma* polypeptide having enzyme activity.

In one aspect, the polypeptide is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis* polypeptide having enzyme activity.

In another aspect, the polypeptide is a *Streptococcus equisimilis, Streptococcus pyogenes, Streptococcus uberis*, or *Streptococcus equi* subsp. *Zooepidemicus* polypeptide having enzyme activity.

In another aspect, the polypeptide is a *Streptomyces achromogenes, Streptomyces avermitilis, Streptomyces coelicolor, Streptomyces griseus*, or *Streptomyces lividans* polypeptide having enzyme activity.

The polypeptide having enzyme activity may also be a fungal polypeptide, and more preferably a yeast polypeptide such as a *Candida, Kluyveromyces, Pichia, Saccharomyces, Schizosaccharomyces*, or *Yarrowia* polypeptide having enzyme activity; or more preferably a filamentous fungal polypeptide such as an *Acremonium, Agaricus, Alternaria, Aspergillus, Aureobasidium, Botryospaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella*, or *Xylaria* polypeptide having enzyme activity.

In one aspect, the polypeptide is a *Saccharomyces carlsbergensis, Saccharomyces cerevisiae, Saccharomyces diastaticus, Saccharomyces douglasfi, Saccharomyces kluyveri, Saccharomyces norbensis*, or *Saccharomyces oviformis* polypeptide having enzyme activity.

In another aspect, the polypeptide is an *Acremonium cellulolyticus, Aspergillus aculeatus, Aspergillus awamori, Aspergillus fumigatus, Aspergillus foetidus, Aspergillus japonicus, Aspergillus nidulans, Aspergillus niger, Aspergillus oryzae, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Trichoderma harzianum, Trichoderma koningii, Trichoderma longibrachiatum, Trichoderma reesei, Trichoderma viride*, or *Trichophaea saccata* polypeptide having enzyme activity.

Chemically modified or protein engineered mutants of polypeptides having enzyme activity may also be used.

One or more (e.g., several) components of the enzyme composition may be a recombinant component, i.e., produced by cloning of a DNA sequence encoding the single component and subsequent cell transformed with the DNA sequence and expressed in a host (see, for example, WO 91/17243 and WO 91/17244). The host is preferably a heterologous host (enzyme is foreign to host), but the host may under certain conditions also be a homologous host (enzyme is native to host). Monocomponent cellulolytic proteins may also be prepared by purifying such a protein from a fermentation broth.

In one aspect, the one or more (e.g., several) cellulolytic enzymes comprise a commercial cellulolytic enzyme preparation. Examples of commercial cellulolytic enzyme preparations suitable for use in the present invention include, for example, CELLIC® CTec (Novozymes NS), CELLIC® CTec2 (Novozymes NS), CELLUCLAST™ (Novozymes NS), NOVOZYM™ 188 (Novozymes NS), CELLUZYME™ (Novozymes NS), CEREFLO™ (Novozymes NS), and ULTRAFLO™ (Novozymes NS), ACCELERASE™ (Genencor Int.), LAMINEX™ (Genencor Int.), SPEZYME™ CP (Genencor Int.), FILTRASE® NL (DSM); METHAPLUS® S/L 100 (DSM), ROHAMENT™ 7069 W (Röhm GmbH), FIBREZYME® LDI (Dyadic International, Inc.), FIBREZYME® LBR (Dyadic International, Inc.), or VISCOSTAR® 150L (Dyadic International, Inc.). The cellulase enzymes are added in amounts effective from about 0.001 to about 5.0 wt % of solids, e.g., about 0.025 to about 4.0 wt % of solids or about 0.005 to about 2.0 wt % of solids.

Examples of bacterial endoglucanases that can be used in the methods of the present invention, include, but are not limited to, an Acidothermus cellulolyticus endoglucanase (WO 91/05039; WO 93/15186; U.S. Pat. No. 5,275,944; WO 96/02551; U.S. Pat. No. 5,536,655, WO 00/70031, WO 05/093050); *Thermobifida fusca* endoglucanase III (WO 05/093050); and *Thermobifida fusca* endoglucanase V (WO 05/093050).

Examples of fungal endoglucanases that can be used in the present invention include, but are not limited to, a *Trichoderma reesei* endoglucanase I (Penttila et al., 1986, *Gene* 45: 253-263; *Trichoderma reesei* Cel7B endoglucanase I; GENBANK™ accession no. M15665; SEQ ID NO: 4); *Trichoderma reesei* endoglucanase II (Saloheimo, et al., 1988, *Gene* 63:11-22; *Trichoderma reesei* CeI5A endoglucanase II; GENBANK™ accession no. M19373; SEQ ID NO: 6); *Trichoderma reesei* endoglucanase III (Okada et al., 1988, *Appl. Environ. Microbiol.* 64: 555-563; GENBANK™ accession no. AB003694; SEQ ID NO: 8); *Trichoderma reesei* endoglucanase V (Saloheimo et al., 1994, *Molecular Microbiology* 13: 219-228; GENBANK™ accession no. Z33381; SEQ ID NO: 10); *Aspergillus aculeatus* endoglucanase (Ooi et al., 1990, *Nucleic Acids Research* 18: 5884); *Aspergillus kawachii* endoglucanase (Sakamoto et al., 1995, *Current Genetics* 27: 435-439); *Erwinia carotovara* endoglucanase (Saarilahti et al., 1990, *Gene* 90: 9-14); *Fusarium oxysporum* endoglucanase (GENBANK™ accession no. L29381); *Humicola grisea* var. *thermoidea* endoglucanase (GENBANK™ accession no. AB003107); Melanocarpus albomyces endoglucanase (GENBANK™ accession no.

MAL515703); *Neurospora crassa* endoglucanase (GENBANK™ accession no. XM_324477); *Humicola insolens* endoglucanase V (SEQ ID NO: 12); *Myceliophthora thermophila* CBS 117.65 endoglucanase (SEQ ID NO: 14); basidiomycete CBS 495.95 endoglucanase (SEQ ID NO: 16); basidiomycete CBS 494.95 endoglucanase (SEQ ID NO: 18); *Thielavia terrestris* NRRL 8126 CEL6B endoglucanase (SEQ ID NO: 20); *Thielavia terrestris* NRRL 8126 CEL6C endoglucanase (SEQ ID NO: 22); *Thielavia terrestris* NRRL 8126 CEL7C endoglucanase (SEQ ID NO: 24); *Thielavia terrestris* NRRL 8126 CEL7E endoglucanase (SEQ ID NO: 26); *Thielavia terrestris* NRRL 8126 CEL7F endoglucanase (SEQ ID NO: 28); *Cladorrhinum foecundissimum* ATCC 62373 CEL7A endoglucanase (SEQ ID NO: 30); and *Trichoderma reesei* strain No. VTT-D-80133 endoglucanase (SEQ ID NO: 32; GENBANK™ accession no. M15665). The endoglucanases of SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, and SEQ ID NO: 32, described above are encoded by the mature polypeptide coding sequence of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, and SEQ ID NO: 31, respectively.

Examples of cellobiohydrolases useful in the present invention include, but are not limited to, *Trichoderma reesei* cellobiohydrolase I (SEQ ID NO: 34); *Trichoderma reesei* cellobiohydrolase II (SEQ ID NO: 36); *Humicola insolens* cellobiohydrolase I (SEQ ID NO: 38); *Myceliophthora thermophila* cellobiohydrolase II (SEQ ID NO: 40 and SEQ ID NO: 42); *Thielavia terrestris* cellobiohydrolase II (CEL6A) (SEQ ID NO: 44); *Chaetomium thermophilum* cellobiohydrolase I (SEQ ID NO: 46); and *Chaetomium thermophilum* cellobiohydrolase II (SEQ ID NO: 48), *Aspergillus fumigatus* cellobiohydrolase I (SEQ ID NO: 50), and *Aspergillus fumigatus* cellobiohydrolase II (SEQ ID NO: 52). The cellobiohydrolases of SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, and SEQ ID NO: 52, described above are encoded by the mature polypeptide coding sequence of SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, and SEQ ID NO: 51, respectively.

Examples of beta-glucosidases useful in the present invention include, but are not limited to, *Aspergillus oryzae* beta-glucosidase (SEQ ID NO: 54); *Aspergillus fumigatus* beta-glucosidase (SEQ ID NO: 56); *Penicillium brasilianum* IBT 20888 beta-glucosidase (SEQ ID NO: 58); *Aspergillus niger* beta-glucosidase (SEQ ID NO: 60); and *Aspergillus aculeatus* beta-glucosidase (SEQ ID NO: 62). The beta-glucosidases of SEQ ID NO: 54, SEQ ID NO: 56, SEQ ID NO: 58, SEQ ID NO: 60, and SEQ ID NO: 61 described above are encoded by the mature polypeptide coding sequence of SEQ ID NO: 53, SEQ ID NO: 55, SEQ ID NO: 57, SEQ ID NO: 59, and SEQ ID NO: 61, respectively.

Examples of other beta-glucosidases useful in the present invention include a *Aspergillus oryzae* beta-glucosidase variant fusion protein of SEQ ID NO: 64 or the *Aspergillus oryzae* beta-glucosidase fusion protein of SEQ ID NO: 66. The beta-glucosidase fusion proteins of SEQ ID NO: 64 and SEQ ID NO: 66 are encoded by SEQ ID NO: 63 and SEQ ID NO: 65, respectively.

The *Aspergillus oryzae* beta-glucosidase can be obtained according to WO 2002/095014. The *Aspergillus fumigatus* beta-glucosidase can be obtained according to WO 2005/047499. The *Penicillium brasilianum* beta-glucosidase can be obtained according to WO 2007/019442. The *Aspergillus niger* beta-glucosidase can be obtained according to Dan et al., 2000, *J. Biol. Chem.* 275: 4973-4980. The *Aspergillus aculeatus* beta-glucosidase can be obtained according to Kawaguchi et al., 1996, *Gene* 173: 287-288.

Other useful endoglucanases, cellobiohydrolases, and beta-glucosidases are disclosed in numerous Glycosyl Hydrolase families using the classification according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696.

Other cellulolytic enzymes that may be used in the present invention are described in WO 98/13465, WO 98/015619, WO 98/015633, WO 99/06574, WO 99/10481, WO 99/025847, WO 99/031255, WO 2002/101078, WO 2003/027306, WO 2003/052054, WO 2003/052055, WO 2003/052056, WO 2003/052057, WO 2003/052118, WO 2004/016760, WO 2004/043980, WO 2004/048592, WO 2005/001065, WO 2005/028636, WO 2005/093050, WO 2005/093073, WO 2006/074005, WO 2006/117432, WO 2007/071818, WO 2007/071820, WO 2008/008070, WO 2008/008793, U.S. Pat. No. 5,457,046, U.S. Pat. No. 5,648,263, and U.S. Pat. No. 5,686,593.

In one aspect, the polypeptide having cellulolytic enhancing activity is used in the presence of a soluble activating divalent metal cation according to WO 2008/151043, e.g., manganese sulfate.

In another aspect, the polypeptide having cellulolytic enhancing activity is used in the presence of a dioxy compound, a bicylic compound, a heterocyclic compound, a nitrogen-containing compound, a quinone compound, a sulfur-containing compound, or a liquor obtained from a pretreated cellulosic material such as pretreated corn stover (PCS).

The dioxy compound may include any suitable compound containing two or more oxygen atoms. In some aspects, the dioxy compounds contain a substituted aryl moiety as described herein. The dioxy compounds may comprise one or more (e.g., several) hydroxyl and/or hydroxyl derivatives, but also include substituted aryl moieties lacking hydroxyl and hydroxyl derivatives. Non-limiting examples of the dioxy compounds include pyrocatechol or catechol; caffeic acid; 3,4-dihydroxybenzoic acid; 4-tert-butyl-5-methoxy-1,2-benzenediol; pyrogallol; gallic acid; methyl-3,4,5-trihydroxybenzoate; 2,3,4-trihydroxybenzophenone; 2,6-dimethoxyphenol; sinapinic acid; 3,5-dihydroxybenzoic acid; 4-chloro-1,2-benzenediol; 4-nitro-1,2-benzenediol; tannic acid; ethyl gallate; methyl glycolate; dihydroxyfumaric acid; 2-butyne-1,4-diol; (croconic acid; 1,3-propanediol; tartaric acid; 2,4-pentanediol; 3-ethyoxy-1,2-propanediol; 2,4,4'-trihydroxybenzophenone; cis-2-butene-1,4-diol; 3,4-dihydroxy-3-cyclobutene-1,2-dione; dihydroxyacetone; acrolein acetal; methyl-4-hydroxybenzoate; 4-hydroxybenzoic acid; and methyl-3,5-dimethoxy-4-hydroxybenzoate; or a salt or solvate thereof.

The bicyclic compound may include any suitable substituted fused ring system as described herein. The compounds may comprise one or more (e.g., several) additional rings, and are not limited to a specific number of rings unless otherwise stated. In one aspect, the bicyclic compound is a flavonoid. In another aspect, the bicyclic compound is an optionally substituted isoflavonoid. In another aspect, the bicyclic compound is an optionally substituted flavylium ion, such as an optionally substituted anthocyanidin or optionally substituted anthocyanin, or derivative thereof. Non-limiting examples of thebicyclic compounds include epicatechin; quercetin; myricetin; taxifolin; kaempferol; morin; acacetin; naringenin; isorhamnetin; apigenin; cyanidin; cyanin; kuromanin; keracyanin; or a salt or solvate thereof.

The heterocyclic compound may be any suitable compound, such as an optionally substituted aromatic or non-aromatic ring comprising a heteroatom, as described herein. In one aspect, the heterocyclic is a compound comprising an optionally substituted heterocycloalkyl moiety or an optionally substituted heteroaryl moiety. In another aspect, the optionally substituted heterocycloalkyl moiety or optionally substituted heteroaryl moiety is an optionally substituted 5-membered heterocycloalkyl or an optionally substituted 5-membered heteroaryl moiety. In another aspect, the optionally substituted heterocycloalkyl or optionally substituted heteroaryl moiety is an optionally substituted moiety selected from pyrazolyl, furanyl, imidazolyl, isoxazolyl, oxadiazolyl, oxazolyl, pyrrolyl, pyridyl, pyrimidyl, pyridazinyl, thiazolyl, triazolyl, thienyl, dihydrothienopyrazolyl, thianaphthenyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, isoindolyl, acridinyl, benzoisazolyl, dimethylhydantoin, pyrazinyl, tetrahydrofuranyl, pyrrolinyl, pyrrolidinyl, morpholinyl, indolyl, diazepinyl, azepinyl, thiepinyl, piperidinyl, and oxepinyl. In another aspect, the optionally substituted heterocycloalkyl moiety or optionally substituted heteroaryl moiety is an optionally substituted furanyl. Non-limiting examples of the heterocyclic compounds include (1,2-dihydroxyethyl)-3,4-dihydroxyfuran-2(5H)-one; 4-hydroxy-5-methyl-3-furanone; 5-hydroxy-2(5H)-furanone; [1,2-dihydroxyethyl]furan-2,3,4(5H)-trione; α-hydroxy-γ-butyrolactone; ribonic γ-lactone; aldohexuronicaldohexuronic acid γ-lactone; gluconic acid δ-lactone; 4-hydroxycoumarin; dihydrobenzofuran; 5-(hydroxymethyl) furfural; furoin; 2(5H)-furanone; 5,6-dihydro-2H-pyran-2-one; and 5,6-dihydro-4-hydroxy-6-methyl-2H-pyran-2-one; or a salt or solvate thereof.

The nitrogen-containing compound may be any suitable compound with one or more nitrogen atoms. In one aspect, the nitrogen-containing compound comprises an amine, imine, hydroxylamine, or nitroxide moiety. Non-limiting examples of thenitrogen-containing compounds include acetone oxime; violuric acid; pyridine-2-aldoxime; 2-aminophenol; 1,2-benzenediamine; 2,2,6,6-tetramethyl-1-piperidinyloxy; 5,6,7,8-tetrahydrobiopterin; 6,7-dimethyl-5,6,7,8-tetrahydropterine; and maleamic acid; or a salt or solvate thereof.

The quinone compound may be any suitable compound comprising a quinone moiety as described herein. Non-limiting examples of the quinone compounds include 1,4-benzoquinone; 1,4-naphthoquinone; 2-hydroxy-1,4-naphthoquinone; 2,3-dimethoxy-5-methyl-1,4-benzoquinone or coenzyme $Q_0$; 2,3,5,6-tetramethyl-1,4-benzoquinone or duroquinone; 1,4-dihydroxyanthraquinone; 3-hydroxy-1-methyl-5,6-indolinedione or adrenochrome; 4-tert-butyl-5-methoxy-1,2-benzoquinone; pyrroloquinoline quinone; or a salt or solvate thereof.

The sulfur-containing compound may be any suitable compound comprising one or more sulfur atoms. In one aspect, the sulfur-containing comprises a moiety selected from thionyl, thioether, sulfinyl, sulfonyl, sulfamide, sulfonamide, sulfonic acid, and sulfonic ester. Non-limiting examples of the sulfur-containing compounds include ethanethiol; 2-propanethiol; 2-propene-1-thiol; 2-mercaptoethanesulfonic acid; benzenethiol; benzene-1,2-dithiol; cysteine; methionine; glutathione; cystine; or a salt or solvate thereof.

In one aspect, an effective amount of such a compound described above to cellulosic material as a molar ratio to glucosyl units of cellulose is about $10^{-6}$ to about 10, e.g., about $10^{-6}$ to about 7.5, about $10^{-6}$ to about 5, about $10^{-6}$ to about 2.5, about $10^{-6}$ to about 1, about $10^{-6}$ to about 1, about $10^{-6}$ to about $10^{-1}$, about $10^{-4}$ to about $10^{-1}$, about $10^{-3}$ to about $10^{-1}$, or about $10^{-3}$ to about $10^{-2}$. In another aspect, an effective amount of such a compound described above is about 0.1 μM to about 1 M, e.g., about 0.5 μM to about 0.75 M, about 0.75 μM to about 0.5 M, about 1 μM to about 0.25 M, about 1 μM to about 0.1 M, about 5 μM to about 50 mM, about 10 μM to about 25 mM, about 50 μM to about 25 mM, about 10 μM to about 10 mM, about 5 μM to about 5 mM, or about 0.1 mM to about 1 mM.

The term "liquor" means the solution phase, either aqueous, organic, or a combination thereof, arising from treatment of a lignocellulose and/or hemicellulose material in a slurry, or monosaccharides thereof, e.g., xylose, arabinose, mannose, etc., under conditions as described herein, and the soluble contents thereof. A liquor for cellulolytic enhancement of a GH61 polypeptide can be produced by treating a lignocellulose or hemicellulose material (or feedstock) by applying heat and/or pressure, optionally in the presence of a catalyst, e.g., acid, optionally in the presence of an organic solvent, and optionally in combination with physical disruption of the material, and then separating the solution from the residual solids. Such conditions determine the degree of cellulolytic enhancement obtainable through the combination of liquor and a GH61 polypeptide during hydrolysis of a cellulosic substrate by a cellulase preparation. The liquor can be separated from the treated material using a method standard in the art, such as filtration, sedimentation, or centrifugation.

In one aspect, an effective amount of the liquor to cellulose is about $10^{-6}$ to about 10 g per g of cellulose, e.g., about $10^{-6}$ to about 7.5 g, about $10^{-6}$ to about 5, about $10^{-6}$ to about 2.5 g, about $10^{-6}$ to about 1 g, about $10^{-5}$ to about 1 g, about $10^{-5}$ to about $10^{-1}$ g, about $10^{-4}$ to about $10^{-1}$ g, about $10^{-3}$ to about $10^{-1}$ g, or about $10^{-3}$ to about $10^{-2}$ g per g of cellulose.

In one aspect, the one or more (e.g., several) hemicellulolytic enzymes comprise a commercial hemicellulolytic enzyme preparation. Examples of commercial hemicellulolytic enzyme preparations suitable for use in the present invention include, for example, SHEARZYME™ (Novozymes NS), CELLIC® HTec (Novozymes NS), CELLIC® HTec2 (Novozymes NS), VISCOZYME® (Novozymes NS), ULTRAFLO® (Novozymes NS), PULPZYME® HC (Novozymes NS), MULTIFECT® Xylanase (Genencor), ACCELLERASE® XY (Genencor), ACCELLERASE® XC (Genencor), ECOPULP® TX-200A (AB Enzymes), HSP 6000 Xylanase (DSM), DEPOL™ 333P (Biocatalysts Limit, Wales, UK), DEPOL™ 740L. (Biocatalysts Limit, Wales, UK), and DEPOL™ 762P (Biocatalysts Limit, Wales, UK).

Examples of xylanases useful in the methods of the present invention include, but are not limited to, xylanases from *Aspergillus* aculeatus (GeneSeqP:AAR63790; WO 94/21785), *Aspergillus fumigatus* (WO 2006/078256; xyl 3 SEQ ID NO: 67 [DNA sequence] and SEQ ID NO: 68 [deduced amino acid sequence]), *Penicillium pinophilum*

(WO 2011/041405), *Penicillium* sp. (WO 2010/126772), *Thielavia terrestris* NRRL 8126 (WO 2009/079210), and *Trichophaea saccata* GH10 (WO 2011/057083).

Examples of beta-xylosidases useful in the methods of the present invention include, but are not limited to, *Trichoderma reesei* beta-xylosidase (UniProtKB/TrEMBL accession number Q92458; SEQ ID NO: 69 [DNA sequence] and SEQ ID NO: 70 [deduced amino acid sequence]), *Talaromyces emersonii* (SwissProt accession number Q8×212), and *Neurospora crassa* (SwissProt accession number Q7SOW4).

Examples of acetylxylan esterases useful in the methods of the present invention include, but are not limited to, acetylxylan esterases from *Aspergillus aculeatus* (WO 2010/108918), *Chaetomium globosum* (Uniprot accession number Q2GWX4), *Chaetomium gracile* (GeneSeqP accession number AAB82124), *Humicola insolens* DSM 1800 (WO 2009/073709), *Hypocrea jecorina* (WO 2005/001036), *Myceliophtera thermophila* (WO 2010/014880), *Neurospora crassa* (UniProt accession number q7s259), *Phaeosphaeria nodorum* (Uniprot accession number QOUHJ1), and *Thielavia terrestris* NRRL 8126 (WO 2009/042846).

Examples of feruloyl esterases (ferulic acid esterases) useful in the methods of the present invention include, but are not limited to, feruloyl esterases form *Humicola insolens* DSM 1800 (WO 2009/076122), *Neosartorya fischeri* (UniProt Accession number A1D9T4), *Neurospora crassa* (UniProt accession number Q9HGR3), *Penicillium aurantiogriseum* (WO 2009/127729), and *Thielavia terrestris* (WO 2010/053838 and WO 2010/065448).

Examples of arabinofuranosidases useful in the methods of the present invention include, but are not limited to, arabinofuranosidases from *Aspergillus niger* (GeneSeqP accession number AAR94170), *Humicola insolens* DSM 1800 (WO 2006/114094 and WO 2009/073383), and *M. giganteus* (WO 2006/114094).

Examples of alpha-glucuronidases useful in the methods of the present invention include, but are not limited to, alpha-glucuronidases from *Aspergillus clavatus* (UniProt accession number alcc12), *Aspergillus fumigatus* (SwissProt accession number Q4WW45), *Aspergillus niger* (Uniprot accession number Q96WX9), *Aspergillus terreus* (SwissProt accession number QOCJP9), *Humicola insolens* (WO 2010/014706), *Penicillium aurantiogriseum* (WO 2009/068565), *Talaromyces emersonii* (UniProt accession number Q8×211), and *Trichoderma reesei* (Uniprot accession number Q99024).

The polypeptides having enzyme activity used in the methods of the present invention may be produced by fermentation of the above-noted microbial strains on a nutrient medium containing suitable carbon and nitrogen sources and inorganic salts, using procedures known in the art (see, e.g., Bennett, J. W. and LaSure, L. (eds.), *More Gene Manipulations in Fungi*, Academic Press, CA, 1991). Suitable media are available from commercial suppliers or may be prepared according to published compositions (e.g., in catalogues of the American Type Culture Collection). Temperature ranges and other conditions suitable for growth and enzyme production are known in the art (see, e.g., Bailey, J. E., and Ollis, D. F., *Biochemical Engineering Fundamentals*, McGraw-Hill Book Company, NY, 1986).

The fermentation can be any method of cultivation of a cell resulting in the expression or isolation of an enzyme or protein. Fermentation may, therefore, be understood as comprising shake flask cultivation, or small- or large-scale fermentation (including continuous, batch, fed-batch, or solid state fermentations) in laboratory or industrial fermentors performed in a suitable medium and under conditions allowing the enzyme to be expressed or isolated. The resulting enzymes produced by the methods described above may be recovered from the fermentation medium and purified by conventional procedures.

Fermentation.

The fermentable sugars obtained from the hydrolyzed cellulosic material can be fermented by one or more (e.g., several) fermenting microorganisms capable of fermenting the sugars directly or indirectly into a desired fermentation product. "Fermentation" or "fermentation process" refers to any fermentation process or any process comprising a fermentation step. Fermentation processes also include fermentation processes used in the consumable alcohol industry (e.g., beer and wine), dairy industry (e.g., fermented dairy products), leather industry, and tobacco industry. The fermentation conditions depend on the desired fermentation product and fermenting organism and can easily be determined by one skilled in the art.

In the fermentation step, sugars, released from the cellulosic material as a result of the pretreatment and enzymatic hydrolysis steps, are fermented to a product, e.g., ethanol, by a fermenting organism, such as yeast. Hydrolysis (saccharification) and fermentation can be separate or simultaneous, as described herein.

Any suitable hydrolyzed cellulosic material can be used in the fermentation step in practicing the present invention. The material is generally selected based on the desired fermentation product, i.e., the substance to be obtained from the fermentation, and the process employed, as is well known in the art.

The term "fermentation medium" is understood herein to refer to a medium before the fermenting microorganism(s) is(are) added, such as, a medium resulting from a saccharification process, as well as a medium used in a simultaneous saccharification and fermentation process (SSF).

"Fermenting microorganism" refers to any microorganism, including bacterial and fungal organisms, suitable for use in a desired fermentation process to produce a fermentation product. The fermenting organism can be hexose and/or pentose fermenting organisms, or a combination thereof. Both hexose and pentose fermenting organisms are well known in the art. Suitable fermenting microorganisms are able to ferment, i.e., convert, sugars, such as glucose, xylose, xylulose, arabinose, maltose, mannose, galactose, and/or oligosaccharides, directly or indirectly into the desired fermentation product. Examples of bacterial and fungal fermenting organisms producing ethanol are described by Lin et al., 2006, *Appl. Microbiol. Biotechnol.* 69: 627-642.

Examples of fermenting microorganisms that can ferment hexose sugars include bacterial and fungal organisms, such as yeast. Preferred yeast includes strains of *Candida*, *Kluyveromyces*, and *Saccharomyces*, e.g., *Candida sonorensis*, *Kluyveromyces marxianus*, and *Saccharomyces cerevisiae*.

Examples of fermenting organisms that can ferment pentose sugars in their native state include bacterial and fungal organisms, such as some yeast. Preferred xylose fermenting yeast include strains of *Candida*, preferably *C. sheatae* or *C. sonorensis*; and strains of *Pichia*, preferably *P. stipitis*, such as *P. stipitis* CBS 5773. Preferred pentose fermenting yeast include strains of *Pachysolen*, preferably *P. tannophilus*. Organisms not capable of fermenting pentose sugars, such as xylose and arabinose, may be genetically modified to do so by methods known in the art.

Examples of bacteria that can efficiently ferment hexose and pentose to ethanol include, for example, *Bacillus coagulans, Clostridium acetobutylicum, Clostridium thermocellum, Clostridium phytofermentans, Geobacillus* sp., *Thermoanaerobacter saccharolyticum*, and *Zymomonas mobilis* (Philippidis, 1996, supra).

Other fermenting organisms include strains of *Bacillus*, such as *Bacillus coagulans; Candida*, such as *C. sonorensis, C. methanosorbosa, C. diddensiae, C. parapsilosis, C. naedodendra, C. blankii, C. entomophilia, C. brassicae, C. pseudotropicalis, C. boidinii, C. utilis*, and *C. scehatae; Clostridium*, such as *C. acetobutylicum, C. thermocellum*, and *C. phytofermentans; E. coli*, especially *E. coli* strains that have been genetically modified to improve the yield of ethanol; *Geobacillus* sp.; *Hansenula*, such as *Hansenula anomala; Klebsiella*, such as *K. oxytoca; Kluyveromyces*, such as *K. marxianus, K. lactis, K. thermotolerans*, and *K. fragilis; Schizosaccharomyces*, such as *S. pombe; Thermoanaerobacter*, such as *Thermoanaerobacter saccharolyticum*; and *Zymomonas*, such as *Zymomonas mobilis.*

In a preferred aspect, the yeast is a *Bretannomyces*. In a more preferred aspect, the yeast is *Bretannomyces clausenii*. In another preferred aspect, the yeast is a *Candida*. In another more preferred aspect, the yeast is *Candida sonorensis*. In another more preferred aspect, the yeast is *Candida boidinii*. In another more preferred aspect, the yeast is *Candida blankii*. In another more preferred aspect, the yeast is *Candida brassicae*. In another more preferred aspect, the yeast is *Candida diddensii*. In another more preferred aspect, the yeast is *Candida entomophilla*. In another more preferred aspect, the yeast is *Candida pseudotropicalis*. In another more preferred aspect, the yeast is *Candida scehatae*. In another more preferred aspect, the yeast is *Candida utilis*. In another preferred aspect, the yeast is a *Clavispora*. In another more preferred aspect, the yeast is *Clavispora lusitaniae*. In another more preferred aspect, the yeast is *Clavispora opuntiae*. In another preferred aspect, the yeast is a *Kluyveromyces*. In another more preferred aspect, the yeast is *Kluyveromyces fragilis*. In another more preferred aspect, the yeast is *Kluyveromyces marxianus*. In another more preferred aspect, the yeast is *Kluyveromyces thermotolerans*. In another preferred aspect, the yeast is a *Pachysolen*. In another more preferred aspect, the yeast is *Pachysolen tannophilus*. In another preferred aspect, the yeast is a *Pichia*. In another more preferred aspect, the yeast is a *Pichia stipitis*. In another preferred aspect, the yeast is a *Saccharomyces* spp. In a more preferred aspect, the yeast is *Saccharomyces cerevisiae*. In another more preferred aspect, the yeast is *Saccharomyces distaticus*. In another more preferred aspect, the yeast is *Saccharomyces uvarum.*

In a preferred aspect, the bacterium is a *Bacillus*. In a more preferred aspect, the bacterium is *Bacillus coagulans*. In another preferred aspect, the bacterium is a *Clostridium*. In another more preferred aspect, the bacterium is *Clostridium acetobutylicum*. In another more preferred aspect, the bacterium is *Clostridium phytofermentans*. In another more preferred aspect, the bacterium is *Clostridium thermocellum*. In another more preferred aspect, the bacterium is *Geobacilus* sp. In another more preferred aspect, the bacterium is a *Thermoanaerobacter*. In another more preferred aspect, the bacterium is *Thermoanaerobacter saccharolyticum*. In another preferred aspect, the bacterium is a *Zymomonas*. In another more preferred aspect, the bacterium is *Zymomonas mobilis.*

Commercially available yeast suitable for ethanol production include, e.g., BIOFERM™ AFT and XR (NABC—North American Bioproducts Corporation, GA, USA), ETHANOL RED™ yeast (Fermentis/Lesaffre, USA), FALI™ (Fleischmann's Yeast, USA), FERMIOL™ (DSM Specialties), GERT STRAND™ (Gert Strand AB, Sweden), and SUPERSTART™ and THERMOSACC™ fresh yeast (Ethanol Technology, Wis., USA).

In a preferred aspect, the fermenting microorganism has been genetically modified to provide the ability to ferment pentose sugars, such as xylose utilizing, arabinose utilizing, and xylose and arabinose co-utilizing microorganisms.

The cloning of heterologous genes into various fermenting microorganisms has led to the construction of organisms capable of converting hexoses and pentoses to ethanol (co-fermentation) (Chen and Ho, 1993, Cloning and improving the expression of *Pichia stipitis* xylose reductase gene in *Saccharomyces cerevisiae, Appl. Biochem. Biotechnol.* 39-40: 135-147; Ho et al., 1998, Genetically engineered *Saccharomyces* yeast capable of effectively cofermenting glucose and xylose, *Appl. Environ. Microbiol.* 64: 1852-1859; Kotter and Ciriacy, 1993, Xylose fermentation by *Saccharomyces cerevisiae, Appl. Microbiol. Biotechnol.* 38: 776-783; Walfridsson et al., 1995, Xylose-metabolizing *Saccharomyces cerevisiae* strains overexpressing the TKL1 and TAL1 genes encoding the pentose phosphate pathway enzymes transketolase and transaldolase, *Appl. Environ. Microbiol.* 61: 4184-4190; Kuyper et al., 2004, Minimal metabolic engineering of *Saccharomyces cerevisiae* for efficient anaerobic xylose fermentation: a proof of principle, *FEMS Yeast Research* 4: 655-664; Beall et al., 1991, Parametric studies of ethanol production from xylose and other sugars by recombinant *Escherichia coli, Biotech. Bioeng.* 38: 296-303; Ingram et al., 1998, Metabolic engineering of bacteria for ethanol production, *Biotechnol. Bioeng.* 58: 204-214; Zhang et al., 1995, Metabolic engineering of a pentose metabolism pathway in ethanologenic *Zymomonas mobilis, Science* 267: 240-243; Deanda et al., 1996, Development of an arabinose-fermenting *Zymomonas mobilis* strain by metabolic pathway engineering, *Appl. Environ. Microbiol.* 62: 4465-4470; WO 2003/062430, xylose isomerase).

In a preferred aspect, the genetically modified fermenting microorganism is *Candida sonorensis*. In another preferred aspect, the genetically modified fermenting microorganism is *Escherichia coli*. In another preferred aspect, the genetically modified fermenting microorganism is *Klebsiella oxytoca*. In another preferred aspect, the genetically modified fermenting microorganism is *Kluyveromyces marxianus*. In another preferred aspect, the genetically modified fermenting microorganism is *Saccharomyces cerevisiae*. In another preferred aspect, the genetically modified fermenting microorganism is *Zymomonas mobilis.*

It is well known in the art that the organisms described above can also be used to produce other substances, as described herein.

The fermenting microorganism is typically added to the degraded cellulosic material or hydrolysate and the fermentation is performed for about 8 to about 96 hours, e.g., about 24 to about 60 hours. The temperature is typically between about 26° C. to about 60° C., e.g., about 32° C. or 50° C., and about pH 3 to about pH 8, e.g., pH 4-5, 6, or 7.

In one aspect, the yeast and/or another microorganism are applied to the degraded cellulosic material and the fermentation is performed for about 12 to about 96 hours, such as typically 24-60 hours. In another aspect, the temperature is preferably between about 20° C. to about 60° C., e.g., about 25° C. to about 50° C., about 32° C. to about 50° C., or about 32° C. to about 50° C., and the pH is generally from about pH 3 to about pH 7, e.g., about pH 4 to about pH 7. However, some fermenting organisms, e.g., bacteria, have higher fermentation temperature optima. Yeast or another microorganism is preferably applied in amounts of approximately $10^5$ to $10^{12}$, preferably from approximately $10^7$ to $10^{10}$, especially approximately $2\times10^8$ viable cell count per ml of fermentation broth. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

For ethanol production, following the fermentation the fermented slurry is distilled to extract the ethanol. The ethanol obtained according to the methods of the invention can be used as, e.g., fuel ethanol, drinking ethanol, i.e., potable neutral spirits, or industrial ethanol.

A fermentation stimulator can be used in combination with any of the methods described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation Products:

A fermentation product can be any substance derived from the fermentation. The fermentation product can be, without limitation, an alcohol (e.g., arabinitol, n-butanol, isobutanol, ethanol, glycerol, methanol, ethylene glycol, 1,3-propanediol [propylene glycol], butanediol, glycerin, sorbitol, and xylitol); an alkane (e.g., pentane, hexane, heptane, octane, nonane, decane, undecane, and dodecane), a cycloalkane (e.g., cyclopentane, cyclohexane, cycloheptane, and cyclooctane), an alkene (e.g. pentene, hexene, heptene, and octene); an amino acid (e.g., aspartic acid, glutamic acid, glycine, lysine, serine, and threonine); a gas (e.g., methane, hydrogen ($H_2$), carbon dioxide ($CO_2$), and carbon monoxide (CO)); isoprene; a ketone (e.g., acetone); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); and polyketide. The fermentation product can also be protein as a high value product.

In a preferred aspect, the fermentation product is an alcohol. It will be understood that the term "alcohol" encompasses a substance that contains one or more hydroxyl moieties. In a more preferred aspect, the alcohol is n-butanol. In another more preferred aspect, the alcohol is isobutanol. In another more preferred aspect, the alcohol is ethanol. In another more preferred aspect, the alcohol is methanol. In another more preferred aspect, the alcohol is arabinitol. In another more preferred aspect, the alcohol is butanediol. In another more preferred aspect, the alcohol is ethylene glycol. In another more preferred aspect, the alcohol is glycerin. In another more preferred aspect, the alcohol is glycerol. In another more preferred aspect, the alcohol is 1,3-propanediol. In another more preferred aspect, the alcohol is sorbitol. In another more preferred aspect, the alcohol is xylitol. See, for example, Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Silveira, M. M., and Jonas, R., 2002, The biotechnological production of sorbitol, *Appl. Microbiol. Biotechnol.* 59: 400-408; Nigam, P., and Singh, D., 1995, Processes for fermentative production of xylitol—a sugar substitute, *Process Biochemistry* 30 (2): 117-124; Ezeji, T. C., Qureshi, N. and Blaschek, H. P., 2003, Production of acetone, butanol and ethanol by *Clostridium beijerinckii* BA101 and in situ recovery by gas stripping, *World Journal of Microbiology and Biotechnology* 19 (6): 595-603.

In another preferred aspect, the fermentation product is an alkane. The alkane can be an unbranched or a branched alkane. In another more preferred aspect, the alkane is pentane. In another more preferred aspect, the alkane is hexane. In another more preferred aspect, the alkane is heptane. In another more preferred aspect, the alkane is octane. In another more preferred aspect, the alkane is nonane. In another more preferred aspect, the alkane is decane. In another more preferred aspect, the alkane is undecane. In another more preferred aspect, the alkane is dodecane.

In another preferred aspect, the fermentation product is a cycloalkane. In another more preferred aspect, the cycloalkane is cyclopentane. In another more preferred aspect, the cycloalkane is cyclohexane. In another more preferred aspect, the cycloalkane is cycloheptane. In another more preferred aspect, the cycloalkane is cyclooctane.

In another preferred aspect, the fermentation product is an alkene. The alkene can be an unbranched or a branched alkene. In another more preferred aspect, the alkene is pentene. In another more preferred aspect, the alkene is hexene. In another more preferred aspect, the alkene is heptene. In another more preferred aspect, the alkene is octene.

In another preferred aspect, the fermentation product is an amino acid. In another more preferred aspect, the organic acid is aspartic acid. In another more preferred aspect, the amino acid is glutamic acid. In another more preferred aspect, the amino acid is glycine.

In another more preferred aspect, the amino acid is lysine. In another more preferred aspect, the amino acid is serine. In another more preferred aspect, the amino acid is threonine. See, for example, Richard, A., and Margaritis, A., 2004, Empirical modeling of batch fermentation kinetics for poly (glutamic acid) production and other microbial biopolymers, *Biotechnology and Bioengineering* 87 (4): 501-515.

In another preferred aspect, the fermentation product is a gas. In another more preferred aspect, the gas is methane. In another more preferred aspect, the gas is $H_2$. In another more preferred aspect, the gas is $CO_2$. In another more preferred aspect, the gas is CO. See, for example, Kataoka, N., A. Miya, and K. Kiriyama, 1997, Studies on hydrogen production by continuous culture system of hydrogen-producing anaerobic bacteria, *Water Science and Technology* 36 (6-7): 41-47; and Gunaseelan V. N. in *Biomass and Bioenergy*, Vol. 13 (1-2), pp. 83-114, 1997, Anaerobic digestion of biomass for methane production: A review.

In another preferred aspect, the fermentation product is isoprene.

In another preferred aspect, the fermentation product is a ketone. It will be understood that the term "ketone" encompasses a substance that contains one or more ketone moieties. In another more preferred aspect, the ketone is acetone. See, for example, Qureshi and Blaschek, 2003, supra.

In another preferred aspect, the fermentation product is an organic acid. In another more preferred aspect, the organic acid is acetic acid. In another more preferred aspect, the organic acid is acetonic acid. In another more preferred aspect, the organic acid is adipic acid. In another more preferred aspect, the organic acid is ascorbic acid. In another more preferred aspect, the organic acid is citric acid. In another more preferred aspect, the organic acid is 2,5-diketo-D-gluconic acid. In another more preferred aspect, the organic acid is formic acid. In another more preferred aspect, the organic acid is fumaric acid. In another more preferred aspect, the organic acid is glucaric acid. In another more preferred aspect, the organic acid is gluconic acid. In another more preferred aspect, the organic acid is glucuronic acid. In another more preferred aspect, the organic acid is glutaric acid. In another preferred aspect, the organic acid is 3-hydroxypropionic acid. In another more preferred aspect, the organic acid is itaconic acid. In another more preferred aspect, the organic acid is lactic acid. In another more preferred aspect, the organic acid is malic acid. In another more preferred aspect, the organic acid is malonic acid. In another more preferred aspect, the organic acid is oxalic acid. In another more preferred aspect, the organic acid is propionic acid. In another more preferred aspect, the organic acid is succinic acid. In another more preferred aspect, the organic acid is xylonic acid. See, for example, Chen, R., and Lee, Y. Y., 1997, Membrane-mediated extractive fermentation for lactic acid production from cellulosic biomass, *Appl. Biochem. Biotechnol.* 63-65: 435-448.

In another preferred aspect, the fermentation product is polyketide.

Recovery.

The fermentation product(s) can be optionally recovered from the fermentation medium using any method known in the art including, but not limited to, chromatography, electrophoretic procedures, differential solubility, distillation, or extraction. For example, alcohol is separated from the fermented cellulosic material and purified by conventional methods of distillation. Ethanol with a purity of up to about 96 vol. % can be obtained, which can be used as, for example, fuel ethanol, drinking ethanol, i.e., potable neutral spirits, or industrial ethanol.

Detergent Compositions

The variant polypeptides having cellulolytic enhancing activity of the present invention may be added to and thus become a component of a detergent composition.

The detergent composition of the present invention may be formulated, for example, as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the present invention provides a detergent additive comprising a variant polypeptide of the invention. The detergent additive as well as the detergent composition may comprise one or more (e.g., several) enzymes such as a protease, lipase, cutinase, an amylase, carbohydrase, cellulase, pectinase, mannanase, arabinase, galactanase, xylanase, oxidase, e.g., a laccase, and/or peroxidase.

In general the properties of the selected enzyme(s) should be compatible with the selected detergent, (i.e., pH-optimum, compatibility with other enzymatic and non-enzymatic ingredients, etc.), and the enzyme(s) should be present in effective amounts.

Cellulases:

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. No. 4,435,307, U.S. Pat. No. 5,648,263, U.S. Pat. No. 5,691,178, U.S. Pat. No. 5,776,757 and WO 89/09259.

Especially suitable cellulases are the alkaline or neutral cellulases having color care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and PCT/DK98/00299.

Commercially available cellulases include CELLUZYME™, and CAREZYME™ (Novozymes NS), CLAZINASE™, and PURADAX HA™ (Genencor International Inc.), and KAC-500(B)™ (Kao Corporation).

Proteases:

Suitable proteases include those of animal, vegetable or microbial origin. Microbial origin is preferred. Chemically modified or protein engineered mutants are included. The protease may be a serine protease or a metalloprotease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g., of porcine or bovine origin) and the *Fusarium* protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235, and 274.

Preferred commercially available protease enzymes include ALCALASE™ SAVINASE™, PRIMASET™, DURALASE™, ESPERASE™, and KANNASE™ (Novozymes NS), MAXATASE™, MAXACAL™, MAXAPEM™, PROPERASE™, PURAFECTT™, PURAFECT OXP™, FN2™, and FN3™ (Genencor International Inc.).

Lipases:

Suitable lipases include those of bacterial or fungal origin. Chemically modified or protein engineered mutants are included. Examples of useful lipases include lipases from *Humicola* (synonym *Thermomyces*), e.g., from *H. lanuginosa* (*T. lanuginosus*) as described in EP 258 068 and EP 305 216 or from *H. insolens* as described in WO 96/13580, a *Pseudomonas lipase*, e.g., from *P. alcaligenes* or *P. pseudoalcaligenes* (EP 218 272), *P. cepacia* (EP 331 376), *P. stutzeri* (GB 1,372,034), *P. fluorescens, Pseudomonas* sp. strain SD 705 (WO 95/06720 and WO 96/27002), *P. wisconsinensis* (WO 96/12012), a *Bacillus lipase*, e.g., from *B.*

*subtilis* (Dartois et al., 1993, *Biochemica et Biophysica Acta*, 1131: 253-360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include LIPOLASE™ and LIPOLASE ULTRA™ (Novozymes NS).

Amylases:

Suitable amylases (a and/or (3) include those of bacterial or fungal origin. Chemically modified or protein engineered mutants are included. Amylases include, for example, α-amylases obtained from *Bacillus*, e.g., a special strain of *Bacillus licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are DURAMYL™, TERMAMYL™, FUNGAMYL™ and BAN™ (Novozymes NS), RAPIDASE™ and PURASTAR™ (from Genencor International Inc.).

Peroxidases/Oxidases:

Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257.

Commercially available peroxidases include GUARDZYME™ (Novozymes NS).

The detergent enzyme(s) may be included in a detergent composition by adding separate additives containing one or more (e.g., several) enzymes, or by adding a combined additive comprising all of these enzymes. A detergent additive of the invention, i.e., a separate additive or a combined additive, can be formulated, for example, as a granulate, liquid, slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the invention may be in any convenient form, e.g., a bar, a tablet, a powder, a granule, a paste or a liquid. A liquid detergent may be aqueous, typically containing up to 70% water and 0-30% organic solvent, or non-aqueous.

The detergent composition comprises one or more (e.g., several) surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid, or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates, or layered silicates (e.g., SKS-6 from Hoechst).

The detergent may comprise one or more (e.g., several) polymers. Examples are carboxymethylcellulose, poly(vinylpyrrolidone), poly (ethylene glycol), poly(vinyl alcohol), poly(vinylpyridine-N-oxide), poly(vinylimidazole), polycarboxylates such as polyacrylates, maleic/acrylic acid copolymers, and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine or nonanoyloxybenzenesulfonate. Alternatively, the bleaching system may comprise peroxyacids of, for example, the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, for example, WO 92/19709 and WO 92/19708.

The detergent may also contain other conventional detergent ingredients such as, e.g., fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

In the detergent compositions, any enzyme may be added in an amount corresponding to 0.01-100 mg of enzyme protein per liter of wash liquor, preferably 0.05-5 mg of enzyme protein per liter of wash liquor, in particular 0.1-1 mg of enzyme protein per liter of wash liquor.

In the detergent compositions, a variant polypeptide of the present invention having cellulolytic enhancing activity may be added in an amount corresponding to 0.001-100 mg of protein, preferably 0.005-50 mg of protein, more preferably 0.01-25 mg of protein, even more preferably 0.05-10 mg of protein, most preferably 0.05-5 mg of protein, and even most preferably 0.01-1 mg of protein per liter of wash liquor.

A variant polypeptide of the present invention having cellulolytic enhancing activity may also be incorporated in the detergent formulations disclosed in WO 97/07202, which is hereby incorporated by reference.

Plants

The present invention also relates to plants, e.g., a transgenic plant, plant part, or plant cell, comprising a polynucleotide of the present invention so as to express and produce the variant in recoverable quantities. The variant may be recovered from the plant or plant part. Alternatively, the plant or plant part containing the variant may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, *Poa*), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats.

Also included within the scope of the present invention are the progeny of such plants, plant parts, and plant cells.

The transgenic plant or plant cell expressing a variant may be constructed in accordance with methods known in the art. In short, the plant or plant cell is constructed by incorporating one or more (e.g., several) expression constructs encoding a variant into the plant host genome or chloroplast genome and propagating the resulting modified plant or plant cell into a transgenic plant or plant cell.

The expression construct is conveniently a nucleic acid construct that comprises a polynucleotide encoding a variant operably linked with appropriate regulatory sequences required for expression of the polynucleotide in the plant or plant part of choice. Furthermore, the expression construct may comprise a selectable marker useful for identifying plant cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the variant is desired to be expressed. For instance, the expression of the gene encoding a variant may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiol.* 86: 506.

For constitutive expression, the 35S-CaMV, the maize ubiquitin 1, and the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the *chlorella* virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may inducible by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a variant in the plant. For instance, the promoter enhancer element may be an intron that is placed between the promoter and the polynucleotide encoding a variant. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Mol. Biol.* 19: 15-38) and can also be used for transforming monocots, although other transformation methods are often used for these plants. Presently, the method of choice for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21: 415-428. Additional transformation methods for use in accordance with the present disclosure include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct prepared according to the present invention, transgenic plants may be made by crossing a plant having the construct to a second plant lacking the construct. For example, a construct encoding a variant can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention, or a portion of a DNA construct prepared in accordance with the present invention. Crossing results in the introduction of a transgene into a plant line by cross pollinating a starting line with a donor plant line. Non-limiting examples of such steps are further articulated in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a variant of the present invention comprising: (a) cultivating a transgenic plant or a plant cell comprising a polynucleotide encoding the variant under conditions conducive for production of the variant; and (b) recovering the variant.

The present invention is further described by the following examples that should not be construed as limiting the scope of the invention.

EXAMPLES

Media

2×YT plates were composed of 10 g of tryptone, 5 g of yeast extract, 5 g of sodium chloride, 15 g of Bacto Agar, and deionized water to 1 liter.

PDA plates were composed of 39 g of potato dextrose agar and deionized water to 1 liter.

MDU2BP medium was composed of 45 g of maltose, 1 g of $MgSO_4.7H_2O$, 1 g of NaCl, 2 g of $K_2HSO_4$, 12 g of $KH_2PO_4$, 2 g of urea, 500 μl of AMG trace metals solution, and deionized water to 1 liter; the pH was adjusted to 5.0 and then filter sterilized with a 0.22 μm filtering unit.

AMG trace metals solution was composed of 14.3 g of $ZnSO_4.7H_2O$, 2.5 g of $CuSO_4.5H_2O$, 0.5 g of $NiCl_2.6H_2O$, 13.8 g of $FeSO_4.H_2O$, 8.5 g of $MnSO_4.7H_2O$, 3 g of citric acid, and deionized water to 1 liter.

M410 medium was composed of 50 g of maltose, 50 g of glucose, 2 g of $MgSO_4.7H_2O$, 2 g of $KH_2PO_4$, 4 g of citric acid anhydrous powder, 8 g of yeast extract, 2 g of urea, 0.5 g of AMG trace metals solution, 0.5 g of $CaCl_2$, and deionized water to 1 liter (pH 6.0).

LB medium was composed of 10 g of Bacto-tryptone. 5 g of yeast extract, 10 g of sodium chloride, and deionized water to 1 liter.

LB plates were composed of 10 g of Bacto-tryptone. 5 g of yeast extract, 10 g of sodium chloride, 15 g of Bacto-agar, and deionized water to 1 liter.

YPG medium was composed of 4 g of yeast extract, 1 g of $K_2HPO_4$, 0.5 g of $MgSO_4$, 15.0 g of glucose, and deionized water to 1 liter (pH 6.0).

YPM medium was composed of 1% yeast extract, 2% peptone, and 2% maltodextrin.

SC agar plates were composed of 20 g of agar per liter of SC-URA medium.

SC-URA medium with galactose was composed of 100 ml of 10× Basal salts, 25 ml of 20% casamino acids without vitamins, 10 ml of 1% tryptophan, 4 ml of 5% threonine (filter sterilized, added after autoclaving), and 100 ml of 20% glucose or 100 ml of 20% galactose (filter sterilized, added after autoclaving), and deionized water to 1 liter.

10× Basal salts solution was composed of 75 g of yeast nitrogen base, 113 g of succinic acid, 68 g of NaOH, and deionized water to 1 liter.

YP medium was composed of 10 g of yeast extract, 20 g of Bacto peptone, and deionized water to 1 liter.

COVE salt solution was composed of 26 g of KCl, 26 g of $MgSO_4.7H_2O$, 76 g of $KH_2PO_4$, 50 ml of COVE trace metals solution, and deionized water to 1 liter.

COVE trace metals solution was composed of 0.04 g of $NaB_4O_7.10H_2O$, 0.4 g of $CuSO_4.5H_2O$, 1.2 g of $FeSO_4.7H_2O$, 0.7 g of $MnSO_4.H_2O$, 0.8 g of $Na_2MoO_2.2H_2O$, 10 g of $ZnSO_4.7H_2O$, and deionized water to 1 liter.

COVE plates were composed of 342.3 g of sucrose, 20 ml of COVE salt solution, 10 ml of 1 M acetamide, 10 ml of 1.5 M CsCl, 25 g of Noble agar (Difco), and deionized water to 1 liter.

COVE2 plates were composed of 30 g of sucrose, 20 ml of COVE salt solution, 10 ml of 1 M acetamide, 25 g of Noble agar (Difco), and deionized water to 1 liter.

*Trichoderma* trace metals solution was composed of 216 g of $FeCl_3.6H_2O$, 58 g of $ZnSO_4.7H_2O$, 27 g of $MnSO_4.H_2O$, 10 g of $CuSO_4.5H_2O$, 2.4 g of $H_3BO_3$, 336 g of citric acid, and deionized water to 1 liter.

CIM medium was composed of 20 g of cellulose, 10 g of corn steep solids, 1.45 g of $(NH_4)_2SO_4$, 2.08 g of $KH_2PO_4$, 0.28 g of $CaCl_2$, 0.42 g of $MgSO_4.7H_2O$, 0.42 ml of *Trichoderma* trace metals solution, 1-2 drops of antifoam, and deionized water to 1 liter; pH adjusted to 6.0.

Example 1: Preparation of *Aspergillus fumigatus* GH61B Polypeptide Having Cellulolytic Enhancing Activity A tblastn search (Altschul et al., 1997, *Nucleic Acids Res.* 25: 3389-3402) of the *A. fumigatus* partial genome sequence (The Institute for Genomic Research, Rockville, Md., USA) was performed using as query several known GH61 polypeptides including GH61A polypeptide from *Thermoascus aurantiacus* (GeneSeqP Accession Number AEC05922). Several genes were identified as putative Family GH61 homologs based upon a high degree of similarity to the query sequences at the amino acid level. One genomic region of approximately 850 bp with greater than 70% sequence identity to the *Thermoascus aurantiacus* GH61A polypeptide sequence at the amino acid level was chosen for further study.

*A. fumigatus* NN051616 was grown and harvested as described in U.S. Pat. No. 7,244,605. Frozen mycelia were ground, by mortar and pestle, to a fine powder and genomic DNA was isolated using a DNEASY® Plant Maxi Kit (QIAGEN Inc., Valencia, Calif., USA) according to manufacturer's instructions.

Two synthetic oligonucleotide primers shown below were designed to PCR amplify the *A. fumigatus* Family GH61B polypeptide gene from the genomic DNA. An IN-FUSION® Cloning Kit (BD Biosciences, Palo Alto, Calif., USA) was used to clone the fragment directly into the expression vector pAlLo2 (WO 2004/099228), without the need for restriction digestion and ligation.

```
Forward primer:
                                        (SEQ ID NO: 71)
5'-ACTGGATTTACCATGACTTTGTCCAAGATCACTTCCA-3'

Reverse primer:
                                        (SEQ ID NO: 72)
5'-TCACCTCTAGTTAATTAAGCGTTGAACAGTGCAGGACCAG-3'
```

Bold letters represent coding sequence. The remaining sequence is homologous to the insertion sites of pAlLo2.

Fifty picomoles of each of the primers above were used in a PCR reaction composed of 204 ng of *A. fumigatus* genomic DNA, 1×Pfx Amplification Buffer (Invitrogen Corp., Carlsbad, Calif., USA), 1.5 μl of a 10 mM blend of dATP, dTTP, dGTP, and dCTP, 2.5 units of PLATINUM® Pfx DNA polymerase (Invitrogen Corp., Carlsbad, Calif., USA), and 1 μl of 50 mM $MgSO_4$ in a final volume of 50 μl. The amplification was performed using an EPPENDORF® MASTERCYCLER® 5333 epgradient S (Eppendorf Scientific, Inc., Westbury, N.Y., USA) programmed for 1 cycle at 94° C. for 3 minutes; and 30 cycles each at 94° C. for 30 seconds, 56° C. for 30 seconds, and 72° C. for 1 minutes. The heat block was then held at 72° C. for 15 minutes followed by a 4° C. soak cycle.

The reaction products were isolated by 1.0% agarose gel electrophoresis using 40 mM Tris base-20 mM sodium acetate-1 mM disodium EDTA (TAE) buffer where an approximately 850 bp product band was excised from the gel and purified using a MINELUTE® Gel Extraction Kit (QIAGEN Inc., Valencia, Calif., USA) according to the manufacturer's instructions.

The fragment was then cloned into pAlLo2 using an IN-FUSION® Cloning Kit. The vector was digested with Nco I and Pac I. The fragment was purified by gel electrophoresis as above and a QIAQUICK® Gel Purification Kit (QIAGEN Inc., Valencia, Calif., USA). The gene fragment and the digested vector were combined together in a reaction resulting in the expression plasmid pAG43 in which transcription of the Family GH61B polypeptide gene was under the control of the NA2-tpi promoter. The NA2-tpi promoter is a modified promoter from the *Aspergillus niger* neutral alpha-amylase gene in which the untranslated leader has been replaced by an untranslated leader from the *Aspergillus nidulans* triose phosphate isomerase gene. The recombination reaction (20 μl) was composed of 1×IN-FUSION® Buffer (BD Biosciences, Palo Alto, Calif., USA), 1×BSA (BD Biosciences, Palo Alto, Calif., USA), 1 μl of IN-FUSION® enzyme (diluted 1:10) (BD Biosciences, Palo Alto, Calif., USA), 166 ng of pAlLo2 digested with Nco I and Pac I, and 110 ng of the *A. fumigatus* GH61B polypeptide purified PCR product. The reaction was incubated at 37° C. for 15 minutes followed by 15 minutes at 50° C. The reaction was diluted with 40 μl of a 10 mM Tris-0.1 M EDTA buffer and 2.5 μl of the diluted reaction were used to transform *E. coli* XL10 SOLOPACK® Gold competent cells (Stratagene, La Jolla, Calif., USA). An *E. coli* transformant containing AG43 (GH61B protein gene) was identified by restriction enzyme digestion and plasmid DNA was prepared using a BIOROBOT® 9600 (QIAGEN Inc., Valencia, Calif., USA).

DNA sequencing of the 862 bp PCR fragment was performed with an Applied Biosystems Model 377 XL Automated DNA Sequencer (Applied Biosystems, Carlsbad, Calif., USA) using dye-terminator chemistry (Giesecke et al., 1992, *Journal of Virology Methods* 38: 47-60) and primer walking strategy. The following vector specific primers were used for sequencing

```
pAllo2 5 Seq:
                                        (SEQ ID NO: 73)
5'-TGTCCCTTGTCGATGCG 3'

pAllo2 3 Seq:
                                        (SEQ ID NO: 74)
5'-CACATGACTTGGCTTCC 3'
```

Nucleotide sequence data were scrutinized for quality and all sequences were compared to each other with assistance of PHRED/PHRAP software (University of Washington, Seattle, Wash., USA).

A gene model for the *A. fumigatus* sequence was constructed based on similarity of the encoded protein to the *Thermoascus aurantiacus* GH61A polypeptide (GeneSeqP Accession Number AEC05922). The nucleotide sequence and deduced amino acid sequence of the *A. fumigatus* GH61B polypeptide gene are shown in SEQ ID NO: 1 and SEQ ID NO: 2, respectively. The genomic fragment encodes a polypeptide of 250 amino acids, interrupted by 2 introns of 53 and 56 bp. The % G+C content of the gene and the mature coding sequence are 53.9% and 57%, respectively. Using the SignalP software program (Nielsen et al., 1997, *Protein Engineering* 10:1-6), a signal peptide of 21 residues was predicted. The predicted mature protein contains 229 amino acids with a predicted molecular mass of 23.39 kDa.

*Aspergillus oryzae* JaL355 protoplasts were prepared according to the method of Christensen et al., 1988, *Bio/Technology* 6: 1419-1422. Six μg of pAG43 were used to transform *Aspergillus oryzae* JaL355. Twenty-six transformants were isolated to individual PDA plates.

Confluent PDA plates of 24 transformants were each washed with 5 ml of 0.01% TWEEN®20 and the spores were each collected. Eight μl of each spore stock were added to 1 ml of TPG, YPM, and M410 media separately in 24 well plates and incubated at 34° C. After 3 days of incubation, 7.5 μl of supernatant from four transformants were analyzed using a CRITERION® stain-free, 8-16% gradient SDS-PAGE gel (Bio-Rad Laboratories, Inc., Hercules, Calif., USA) according to the manufacturer's instructions. Based on this gel, M410 medium was chosen as the best medium.

Five days after incubation, 7.5 μl of supernatant from each M410 culture were analyzed using a CRITERION@ stain-free, 8-16% gradient SDS-PAGE gel. SDS-PAGE profiles of the cultures showed that several transformants had a new major band of approximately 25 kDa.

A confluent plate of one transformant (grown on a PDA plate) was washed with 5 ml of 0.01% TWEEN® 20 and inoculated into four 500 ml Erlenmeyer flasks containing 100 ml of M410 medium to generate broth for characterization of the enzyme. The flasks were harvested on day 5 (300 ml), filtered using a 0.22 μm EXPRESS™ Plus Membrane (Millipore, Bedford, Mass., USA), and stored at 4° C.

The filtered shake flask broth containing the recombinantly produced *A. fumigatus* GH61B polypeptide having cellulolytic enhancing activity was first concentrated by a tangential flow concentrator (Pall Filtron, Northborough, Mass., USA) equipped with a 10 kDa polyethersulfone membrane (Pall Filtron, Northborough, Mass., USA), buffer exchanged into 20 mM Tris-HCl pH 8.0, and then purified using a HIGHLOAD™ 26/60 SUPERDEX™ 75 gel filtration column (GE Healthcare, Piscataway, N.J., USA) with a 750 ml isocratic gradient in 150 mM NaCl, 20 mM Tris-HCl pH 8.0. Fractions were collected and pooled based on SDS-PAGE analysis. Protein concentration was determined using a Microplate BCA™ Protein Assay Kit (Thermo Fisher Scientific Inc., Rockford, Ill., USA) in which bovine serum albumin was used as a protein standard.

Example 2: Construction of *Aspergillus fumigatus* GH61B Variant L90V+D131S+M134L+A141W A variant of the wild-type *A. fumigatus* GH61B polypeptide having cellulolytic enhancing activity was constructed with the substitutions L90V, D131S, M134L, and A141W. The wild-type *A. fumigatus* GH61B backbone from plasmid pAG43 (Example 2) was used as starting template upon which substitutions were introduced in several separate steps, generating intermediates until the following plasmid with the final target amino acid substitutions was obtained: pTH230 (L90V+D131S+M134L+A141W). A QUIKCHANGE® XL Site-Directed Mutagenesis Kit (Stratagene, La Jolla, Calif., USA) was used to generate the mutations via PCR mediated reactions in which synthetic oligonucleotide primer pairs, as shown in Table 1, designed with the target changes were used to incorporate the desired substitutions.

Variant plasmid pTH228 was generated using the reverse and forward primer pair 68339 and 68340 and pAG43 as the starting template. Variant plasmid pTH229 was generated using the reverse and forward primer pair 68638 and 68639 and variant plasmid pTH228 as the starting template. Variant plasmid pTH230 was generated using the reverse and forward primer pair 68640 and 68641 and variant plasmid pTH229 as the starting template.

TABLE 1

| Amino acid changes | Primer ID | Sequence | Plasmid name |
|---|---|---|---|
| L90V | 68339 | GGCTAACATAGCATAGGTGATTACTTACCTCGCTCC (SEQ ID NO: 75) | pTH228 |
| | 68340 | GGAGCGAGGTAAGTAATCACCTATGCTATGTTAGCC (SEQ ID NO: 76) | |
| D131S, M134L | 68638 | CCTGGTGTTTGGGCTTCCGATGAACTGATCGCCAACAACAACACG (SEQ ID NO: 77) | pTH229 |
| | 68639 | CGTGTTGTTGTTGGCGATCAGTTCATCGGAAGCCCAAACACCAGG (SEQ ID NO: 78) | |
| A141W | 68640 | GCCAACAACAACACGTGGACAGTGACCATTCCTGC (SEQ ID NO: 79) | pTH230 |
| | 68641 | GCAGGAATGGTCACTGTCCACGTGTTGTTGTTGGC (SEQ ID NO: 80) | |

The resulting mutant plasmid DNAs were prepared using a BIOROBOT® 9600 and sequenced using a 3130×1 Genetic Analyzer (Applied Biosystems, Carlsbad, Calif., USA).

Example 3: Expression of the *Aspergillus fumigatus* GH61B Variant L90V+D131S+M134L+A141W in *Aspergillus oryzae* JaL250

*Aspergillus oryzae* JaL250 (WO 99/61651) protoplasts were prepared according to the method of Christensen et al., 1988, *Bio/Technology* 6: 1419-1422, and transformed with 5 μg of pTH230 (or pAllo2 as a control). The transformation yielded about 20-25 transformants. The transformants were then spore purified to individual selective PDA plates and then grown in 24 well culture plates containing 1 ml of MDU2BP medium and incubated at 34° C. stationary for 5 days. Broth samples were harvested at day 5 and analyzed by 8-16% Tris-glycine SDS-PAGE (Bio-Rad Laboratories, Inc., Hercules, Calif., USA). Once the cultures from each spore purified transformant were confluent and had sporulated, spore stocks were made by applying 5 ml of sterile filtered 0.01% TWEEN® 80 (diluted with glass distilled water) onto the center of each PDA plate and using a sterile spreader to scrape the spores into solution. Spore stocks from the highest producing transformants for each batch identified by SDS-PAGE as having darker bands at the predicted molecular weight of 26 kDa were used to inoculate a 2 liter shake flask containing 300 ml of MDU2BP medium. Shake flasks were incubated for 5 days at 34° C. with agitation at 220 rpm. After the incubation, the broths were sterile filtered using a 0.22 μm polyethersulfone membrane (Millipore, Bedford, Mass., USA) for purification. The *A. oryzae* strain identified from SDS-PAGE analysis of the shake flask broths with the strongest band at 26 kDa was designated TH169 (*A. fumigatus* GH61B variant L90V+D131S+M134L+A141W).

Example 4: Purification of the *Aspergillus fumigatus* GH61B Variant L90V+D131S+M134L+A141W The recombinantly produced *Aspergillus fumigatus* GH61B variant L90V+D131S+M134L+A141W was first concentrated by a tangential flow concentrator (Pall Filtron, Northborough, Mass., USA) equipped with a 10 kDa polyethersulfone membrane (Pall Filtron, Northborough, Mass., USA), buffer exchanged into 20 mM Tris-HCl pH 8.0, and then purified using a (self-packed) 75 ml Q-SEPHAROSE® High Performance column (GE Healthcare, Piscataway, N.J., USA) with a 800 ml 0-600 mM NaCl linear gradient in 20 mM Tris-HCl pH 8.0. Fractions were collected and pooled based on SDS-PAGE analysis. Protein concentration was determined using a Microplate BCA™ Protein Assay Kit in which bovine serum albumin was used as a protein standard.

Example 5: Preparation of *Trichoderma reesei* CEL5A Endoglucanase II

The *Trichoderma reesei* Family GH5A endoglucanase II gene (SEQ ID NO: 5 [DNA sequence] and SEQ ID NO: 6 [deduced amino acid sequence]) was cloned into an *Aspergillus oryzae* expression vector as described below.

Two synthetic oligonucleotide primers, shown below, were designed to PCR amplify the endoglucanase II gene from *T. reesei* RutC30 genomic DNA. Genomic DNA was isolated using a DNEASY® Plant Maxi Kit. An IN-FUSION™ PCR Cloning Kit was used to clone the fragment directly into pAlLo2 (WO 2004/099228).

```
Forward primer:
                                    (SEQ ID NO: 81)
5'-ACTGGATTTACCATGAACAAGTCCGTGGCTCCATTGCT-3'

Reverse primer:
                                    (SEQ ID NO: 82)
5'-TCACCTCTAGTTAATTAACTACTTTCTTGCGAGACACG-3'
```

Bold letters represent coding sequence. The remaining sequence contains sequence identity compared with the insertion sites of pAlLo2 (WO 2004/099228).

Fifty picomoles of each of the primers above were used in a PCR reaction composed of 200 ng of *T. reesei* genomic DNA, 1×Pfx Amplification Buffer, 6 μl of a 10 mM blend of dATP, dTTP, dGTP, and dCTP, 2.5 units of PLATINUM® Pfx DNA polymerase, and 1 μl of 50 mM $MgSO_4$ in a final volume of 50 μl. The amplification reaction was incubated in an EPPENDORF® MASTERCYCLER® 5333 (Eppendorf Scientific, Inc., Westbury, N.Y., USA) programmed for 1 cycle at 98° C. for 2 minutes; and 35 cycles each at 94° C. for 30 seconds, 61° C. for 30 seconds, and 68° C. for 1.5 minutes. After the 35 cycles, the reaction was incubated at 68° C. for 10 minutes and then cooled at 10° C. A 1.5 kb PCR reaction product was isolated on a 0.8% GTG® agarose gel (Cambrex Bioproducts, Rutherford, N.J., USA) using TAE buffer and 0.1 μg of ethidium bromide per ml. The DNA band was visualized with the aid of a DARK-READER™ (Clare Chemical Research, Dolores, Colo., USA). The 1.5 kb DNA band was excised with a disposable razor blade and purified using an ULTRAFREE® DA spin cup (Millipore, Billerica, Mass., USA) according to the manufacturer's instructions.

Plasmid pAlLo2 was linearized by digestion with Nco I and Pac I. The plasmid fragment was purified by gel electrophoresis and ultrafiltration as described above. Cloning of the purified PCR fragment into the linearized and purified pAlLo2 vector was performed using an IN-FUSION™ PCR Cloning Kit. The reaction (20 μl) contained 1×IN-FUSION™ Buffer, 1×BSA, 1 μl of IN-FUSION™ enzyme (diluted 1:10), 100 ng of pAlLo2 digested with Nco I and Pac I, and 100 ng of the *T. reesei* CEL5A endoglucanase II PCR product. The reaction was incubated at room temperature for 30 minutes. A 2 μl sample of the reaction was used to transform *E. coli* XL10 SOLOPACK® Gold competent cells according to the manufacturer's instructions. After a recovery period, two 100 μl aliquots from the transformation reaction were plated onto 150 mm 2×YT plates supplemented with 100 μg of ampicillin per ml. The plates were incubated overnight at 37° C. A set of 3 putative recombinant clones was recovered from the selection plates and plasmid DNA was prepared from each one using a BIOROBOT® 9600. Clones were analyzed by Pci I/Bsp LU111 restriction digestion. One clone with the expected restriction digestion pattern was then sequenced to confirm that there were no mutations in the cloned insert. Clone #3 was selected and designated pAlLo27.

*Aspergillus oryzae* JaL250 (WO 99/61651) protoplasts were prepared according to the method of Christensen et al., 1988, supra, and transformed with 5 μg of pAlLo27 (or pAlLo2 as a control). The transformation yielded about 50 transformants. Eleven transformants were isolated to individual PDA plates and incubated for five days at 34° C.

Confluent spore plates were washed with 3 ml of 0.01% TWEEN® 80 and the spore suspension was used to inoculate 25 ml of MDU2BP medium in 125 ml glass shake flasks. Transformant cultures were incubated at 34° C. with constant shaking at 200 rpm. At day five post-inoculation, cultures were centrifuged at 6000×g and their supernatants collected. Five microliters of each supernatant were mixed with an equal volume of 2× loading buffer (10% beta-mercaptoethanol) and loaded onto a 1.5 mm 8%-16% Tris-Glycine SDS-PAGE gel and stained with SIMPLYBLUE™ SafeStain (Invitrogen Corp., Carlsbad, Calif., USA). SDS-PAGE profiles of the culture broths showed that ten out of eleven transformants produced a new protein band of approximately 45 kDa. Transformant number 1, designated *Aspergillus oryzae* JaL250AlLo27, was cultivated in a fermentor.

Shake flask medium was composed of 50 g of sucrose, 10 g of $KH_2PO_4$, 0.5 g of $CaCl_2$, 2 g of $MgSO_4.7H_2O$, 2 g of $K_250_4$, 2 g of urea, 10 g of yeast extract, 2 g of citric acid, 0.5 ml of trace metals solution, and deionized water to 1 liter. The trace metals solution was composed of 13.8 g of $FeSO_4.7H_2O$, 14.3 g of $ZnSO_4.7H_2O$, 8.5 g of $MnSO_4.H_2O$, 2.5 g of $CuSO_4.5H_2O$, 3 g of citric acid, and deionized water to 1 liter.

One hundred ml of shake flask medium were added to a 500 ml shake flask. The shake flask was inoculated with two plugs of *A. oryzae* JaL250AlLo27 from a PDA plate and incubated at 34° C. on an orbital shaker at 200 rpm for 24 hours. Fifty ml of the shake flask broth were used to inoculate a 3 liter fermentation vessel.

Fermentation batch medium was composed of 10 g of yeast extract, 24 g of sucrose, 5 g of $(NH_4)_2SO_4$, 2 g of $KH_2PO_4$, 0.5 g of $CaCl_2.2H_2O$, 2 g of $MgSO_4.7H_2O$, 1 g of citric acid, 2 g of $K_2SO_4$, 0.5 ml of anti-foam, 0.5 ml of trace metals solution, and deionized water to 1 liter. The trace metals solution was composed of 13.8 g of $FeSO_4.7H_2O$, 14.3 g of $ZnSO_4.7H_2O$, 8.5 g of $MnSO_4.H_2O$, 2.5 g of $CuSO_4.5H_2O$, 3 g of citric acid, and deionized water to 1 liter. Fermentation feed medium was composed of maltose.

A total of 1.8 liters of the fermentation batch medium was added to an Applikon Biotechnology three liter glass jacketed fermentor (Applikon Biotechnology, Inc., Foster City, Calif., USA). Fermentation feed medium was dosed at a rate of 0 to 4.4 g/l/hr for a period of 185 hours. The fermentation vessel was maintained at a temperature of 34° C. and pH was controlled using an Applikon 1030 control system Applikon Biotechnology, Inc., Foster City, Calif., USA) to a set-point of 6.1+/−0.1. Air was added to the vessel at a rate of 1 vvm and the broth was agitated by Rushton impeller rotating at 1100 to 1300 rpm. At the end of the fermentation, whole broth was harvested from the vessel and centrifuged at 3000×g to remove the biomass. The supernatant was sterile filtered using a 0.22 μm EXPRESS™ Plus Membrane, and stored at 4° C.

The supernatant was desalted and buffer-exchanged into 20 mM Tris-HCl pH 8.0 using a 400 ml SEPHADEX™ G25 desalting column (GE Healthcare, Piscataway, N.J., USA) according to the manufacturer's instructions. Desalted *Trichoderma reesei* CEL5A endoglucanase II was loaded onto a MONOQ™ HR 16/10 ion exchange column (GE Healthcare, Piscataway, N.J., USA) and eluted with a 300 ml linear 0-300 mM NaCl gradient in 20 mM Tris-HCl pH 8 with collection of 10 ml fractions. Fractions were pooled based on SDS-PAGE analysis. Protein concentration was determined using a Microplate BCA™ Protein Assay Kit in which bovine serum albumin was used as a protein standard.

Example 6: Preparation of *Aspergillus fumigatus* GH3A Beta-Glucosidase

An *A. fumigatus* GH3A beta-glucosidase (SEQ ID NO: 55 [DNA sequence] and SEQ ID NO: 56 [deduced amino acid sequence]) was prepared according to U.S. Pat. No. 7,244,605. Protein concentration was determined using a Microplate BCA™ Protein Assay Kit in which bovine serum albumin was used as a protein standard.

Example 7: Preparation of *Aspergillus fumigatus* NN055679 Cel7A Cellobiohydrolase I A tfasty search (Pearson et al., 1997, *Genomics* 46:24-36) of the *A. fumigatus* partial genome sequence (The Institute for Genomic Research, Rockville, Md., USA) was performed using as query a Ce17 cellobiohydrolase protein sequence from *Trichoderma reesei* (Accession No. P00725). Several genes were identified as putative Family GH7 homologs based upon a high degree of similarity to the query sequence at the amino acid level. One genomic region with significant sequence identity to the query sequence was chosen for further study, and the corresponding gene was named ce17A.

Two synthetic oligonucleotide primers shown below were designed to PCR amplify the *A. fumigatus* NN055679 ce17A cellobiohydrolase I gene (SEQ ID NO: 49 [DNA sequence] and SEQ ID NO: 50 [deduced amino acid sequence]) from genomic DNA of *A. fumigatus* prepared as described in WO 2005/047499.

```
Forward primer:
                                  (SEQ ID NO: 83)
5'-gggcATGCTGGCCTCCACCTTCTCC-3'

Reverse primer:
                                  (SEQ ID NO: 84)
5'-gggttaattaaCTACAGGCACTGAGAGTAA-3'
```

Upper case letters represent the coding sequence. The remainder of the sequence provides restriction endonuclease sites for Sph I and Pac I in the forward and reverse sequences, respectively. Using these primers, the *A. fumigatus* cel7A gene was amplified using standard PCR methods and the reaction product isolated by 1% agarose gel electrophoresis using TAE buffer and purified using a QIAQUICK® Gel Extraction Kit (QIAGEN Inc., Valencia, Calif., USA) according to the manufacturer's instructions.

The fragment was digested with Sph I and Pac I and ligated into the expression vector pAlLo2 also digested with Sph I and Pac I according to standard procedures. The ligation products were transformed into *E. coli* XL10 SOLOPACK® Gold competent cells according to the manufacturer's instructions. An *E. coli* transformant containing a plasmid of the correct size was detected by restriction digestion and plasmid DNA was prepared using a BIOROBOT® 9600. DNA sequencing of the insert from this plasmid was performed with a Perkin-Elmer Applied Biosystems Model 377 XL Automated DNA Sequencer (Perkin-Elmer/Applied Biosystems, Inc., Foster City, Calif., USA) using dye-terminator chemistry (Giesecke et al., 1992, supra) and primer walking strategy. Nucleotide sequence data were scrutinized for quality and all sequences were compared to each other with assistance of PHRED/PHRAP software (University of Washington, Seattle, Wash., USA). The nucleotide sequence was shown to match the genomic sequence determined by TIGR (SEQ ID NO: 49 [DNA sequence] and SEQ ID NO: 50 [deduced amino acid sequence]). The resulting plasmid was named pEJG93.

*Aspergillus oryzae* JaL250 protoplasts were prepared according to the method of Christensen et al., 1988, supra, and transformed with 5 μg of pEJG93 (as well as pAlLo2 as a vector control). The transformation yielded about 100 transformants. Ten transformants were isolated to individual PDA plates.

Confluent PDA plates of five of the ten transformants were washed with 5 ml of 0.01% TWEEN® 20 and inoculated separately into 25 ml of MDU2BP medium in 125 ml glass shake flasks and incubated at 34° C., 250 rpm. Five days after incubation, 0.5 μl of supernatant from each culture was analyzed using 8-16% Tris-Glycine SDS-PAGE gels (Invitrogen Corp., Carlsbad, Calif., USA) according to the manufacturer's instructions. SDS-PAGE profiles of the cultures showed that one of the transformants had a major band of approximately 70 kDa. This transformant was named *A. oryzae* JaL250EJG93.

One hundred ml of shake flask medium (Example 5) were added to a 500 ml shake flask. The shake flask was inoculated with two plugs of *A. oryzae* JaL250EJG93 from a PDA plate and incubated at 34° C. on an orbital shaker at 200 rpm for 24 hours. Fifty ml of the shake flask broth was used to inoculate a 3 liter fermentation vessel.

A total of 1.8 liters of the fermentation batch medium (Example 5) was added to an Applikon Biotechnology three liter glass jacketed fermentor. Fermentation feed medium (Example 5) was dosed at a rate of 0 to 4.4 g/l/hr for a period of 185 hours. The fermentation vessel was maintained at a temperature of 34° C. and pH was controlled using an Applikon 1030 control system to a set-point of 6.1+/−0.1. Air was added to the vessel at a rate of 1 vvm and the broth was agitated by Rushton impeller rotating at 1100 to 1300 rpm. At the end of the fermentation, whole broth was harvested from the vessel and centrifuged at 3000×g to remove the biomass. The supernatant was sterile filtered using a 0.22 μm EXPRESS™ Plus Membrane, and stored at 4° C.

Filtered broth was concentrated and buffer exchanged using a tangential flow concentrator (Pall Filtron, Northborough, Mass., USA) equipped with a 10 kDa polyethersulfone membrane (Pall Filtron, Northborough, Mass., USA) with 20 mM Tris-HCl pH 8., and then purified using a (self-packed) 75 ml Q-SEPHAROSE® High Performance column (with a 750 ml 0-600 mM NaCl linear gradient in 20 mM Tris-HCl pH 8.0 with collection of 10 ml fractions. Fractions pooled based on SDS-PAGE analysis. Protein concentration was determined using a Microplate BCA™ Protein Assay Kit in which bovine serum albumin was used as a protein standard.

Example 8: Preparation of *Aspergillus fumigatus* CeI6A Cellobiohydrolase II

*A. fumigatus* NN055679 cellobiohydrolase II (CBHII) (SEQ ID NO: 51 [DNA sequence] and SEQ ID NO: 52 [deduced amino acid sequence]) was prepared according to the following procedure.

Two synthetic oligonucleotide primers, shown below, were designed to PCR amplify the full-length open reading frame of the *A. fumigatus* Family 6A glycosyl hydrolase from genomic DNA. A TOPO® Cloning Kit (Invitrogen Corp., Carlsbad, Calif., USA) was used to clone the PCR product. An IN-FUSION™ Cloning Kit was used to clone the fragment into pAlLo2.

```
Forward primer:
                                    (SEQ ID NO: 85)
5'-ACTGGATTTACCATGAAGCACCTTGCATCTTCCATCG-3'

Reverse primer:
                                    (SEQ ID NO: 86)
5'-TCACCTCTAGTTAATTAAAAGGACGGGTTAGCGT-3'
```

Bold letters represent coding sequence. The remaining sequence contains sequence identity compared with the insertion sites of pAlLo2.

Fifty picomoles of each of the primers above were used in a PCR reaction composed of 500 ng of *A. fumigatus* genomic DNA, 1× ThermoPol Taq reaction buffer (New England Biolabs, Ipswich, Mass., USA), 6 µl of a 10 mM blend of dATP, dTTP, dGTP, and dCTP, 0.1 unit of Taq DNA polymerase (New England Biolabs, Ipswich, Mass., USA), in a final volume of 50 µl. An EPPENDORF® MASTERCYCLER® 5333 was used to amplify the fragment programmed for 1 cycle at 98° C. for 2 minutes; and 35 cycles each at 96° C. for 30 seconds, 61° C. for 30 seconds, and 72° C. for 2 minutes. After the 35 cycles, the reaction was incubated at 72° C. for 10 minutes and then cooled at 10° C. until further processed. To remove the A-tails produced by Taq DNA polymerase the reaction was incubated for 10 minutes at 68° C. in the presence of 1 unit of Pfx DNA polymerase (Invitrogen Corp., Carlsbad, Calif., USA).

A 1.3 kb PCR reaction product was isolated on a 0.8% GTG-agarose gel (Cambrex Bioproducts, East Rutherford, N.J., USA) using TAE buffer and 0.1 µg of ethidium bromide per ml. The DNA band was visualized with the aid of a DARK READER™ (Clare Chemical Research, Dolores, Colo., USA) to avoid UV-induced mutations. The 1.3 kb DNA band was excised with a disposable razor blade and purified with an ULTRAFREE® DA spin cup according to the manufacturer's instructions.

The purified 1.3 kb PCR product was cloned into pCR®4Blunt-TOPO® (Invitrogen Corp., Carlsbad, Calif., USA). Two microliters of the purified PCR product were mixed with 1 µl of a 2 M sodium chloride solution and 1 µl of the pCR®4Blunt-TOPO® vector. The reaction was incubated at room temperature for 15 minutes and then 2 µl of the reaction were used to transform *E. coli* TOP10 competent cells (Invitrogen Corp., Carlsbad, Calif., USA) according to the manufacturer's instructions. Two aliquots of 100 microliters each of the transformation reaction were spreaded onto two 150 mm 2×YT plates supplemented with 100 µg of ampicillin per ml and incubated overnight at 37° C.

Eight recombinant colonies were used to inoculate liquid cultures containing 3 ml of LB medium supplemented with 100 µg of ampicillin per ml. Plasmid DNA was prepared from these cultures using a BIOROBOT® 9600. Clones were analyzed by restriction digest. Plasmid DNA from each clone was digested with Eco RI and analyzed by agarose gel electrophoresis as above. Six out of eight clones had the expected restriction digestion pattern and clones 2, 4, 5, 6, 7 and 8 were sequenced to confirm that there were no mutations in the cloned insert. Sequence analysis of their 5-prime and 3-prime ends indicated that clones 2, 6 and 7 had the correct sequence. These three clones were selected for re-cloning into pAlLo2. One microliter aliquot of each clone was mixed with 17 µl of 1:10 diluted 0.1 mM EDTA-10 mM Tris pH 7.4 and 1 µl of this mix was used to re-amplify the *A. fumigatus* glycosyl hydrolase 6A coding region.

Fifty picomoles of each of the primers above were used in a PCR reaction composed of 1 µl of the diluted mix of clones 2, 6 and 7, 1×Pfx Amplification Buffer, 6 µl of a 10 mM blend of dATP, dTTP, dGTP, and dCTP, 2.5 units of PLATINUM® Pfx DNA polymerase, 1 µl of 50 mM $MgSO_4$, in a final volume of 50 µl. An EPPENDORF® MASTERCYCLER® 5333 was used to amplify the fragment programmed for 1 cycle at 98° C. for 2 minutes; and 35 cycles each at 94° C. for 30 seconds, 61° C. for 30 seconds, and 68° C. for 1.5 minutes. After the 35 cycles, the reaction was incubated at 68° C. for 10 minutes and then cooled at 10° C. until further processed. A 1.3 kb PCR reaction product was isolated on a 0.8% GTG-agarose gel using TAE buffer and 0.1 µg of ethidium bromide per ml. The DNA band was visualized with the aid of a DARKREADER™ Transilluminator to avoid UV-induced mutations. The 1.3 kb DNA band was excised from the gel with a disposable razor blade and purified with an ULTRAFREE® DA spin cup according to the manufacturer's instructions.

The vector pAlLo2 was linearized by digestion with Nco I and Pac I. The fragment was purified by gel electrophoresis and ultrafiltration as described above. Cloning of the purified PCR fragment into the linearized and purified pAlLo2 vector was performed with an IN-FUSION™ Cloning Kit. The reaction (20 µl) was composed of 1×IN-FUSION™ Buffer, 1×BSA, 1 µl of IN-FUSION™ enzyme (diluted 1:10), 100 ng of pAlLo2 digested with Nco I and Pac I, and 50 ng of the *A. fumigatus* GH6A purified PCR product. The reaction was incubated at room temperature for 30 minutes. A 2 µl sample of the reaction was used to transform transform *E. coli* TOP10 competent cells according to the manufacturer's instructions. After the recovery period, two 100 µl aliquots from the transformation reaction were plated onto 150 mm 2×YT plates supplemented with 100 µg of ampicillin per ml. The plates were incubated overnight at 37° C. A set of eight putative recombinant clones was selected at random from the selection plates and plasmid DNA was prepared from each one using a BIOROBOT® 9600. Clones were analyzed by Pst I restriction digest. Seven out of eight clones had the expected restriction digestion pattern. Clones 1. 2 and 3 were then sequenced to confirm that there were no mutations in the cloned insert. Clone #2 was selected and designated pAlLo33.

*Aspergillus oryzae* JaL355 protoplasts were prepared according to the method of Christensen et al., 1988, supra, and transformed with 5 μg of pAlLo33 (as well as pAlLo2 as a vector control). The transformation yielded about 100 transformants. Ten transformants were isolated to individual PDA plates.

Confluent PDA plates of five of the ten transformants were washed with 5 ml of 0.01% TWEEN® 20 and inoculated separately into 25 ml of MDU2BP medium in 125 ml glass shake flasks and incubated at 34° C., 250 rpm. Five days after incubation, 0.5 μl of supernatant from each culture was analyzed using 8-16% Tris-Glycine SDS-PAGE gels (Invitrogen Corp., Carlsbad, Calif., USA) according to the manufacturer's instructions. SDS-PAGE profiles of the cultures showed that one of the transformants had a major band of approximately 70 kDa. This transformant was named *A. oryzae* JaL355 AlLo33.

One hundred ml of shake flask medium (Example 5) was added to a 500 ml shake flask. The shake flask was inoculated with two plugs of *A. oryzae* Ja1355 ALIo33 from a PDA plate and incubated at 34° C. on an orbital shaker at 200 rpm for 24 hours. Fifty ml of the shake flask broth was used to inoculate a 3 liter fermentation vessel.

A total of 1.8 liters of the fermentation batch medium (Example 5) was added to an Applikon Biotechnology three liter glass jacketed fermentor. Fermentation feed medium (Example 5) was dosed at a rate of 0 to 4.4 g/l/hr for a period of 185 hours. The fermentation vessel was maintained at a temperature of 34° C. and pH was controlled using an Applikon 1030 control system to a set-point of 6.1+/−0.1. Air was added to the vessel at a rate of 1 vvm and the broth was agitated by Rushton impeller rotating at 1100 to 1300 rpm. At the end of the fermentation, whole broth was harvested from the vessel and centrifuged at 3000×g to remove the biomass. The supernatant was sterile filtered using a 0.22 μm EXPRESS™ Plus Membrane, and stored at 4° C.

The broth was filtered using a 0.7 μm glass filter GF/F (Whatman, Piscataway, N.J., USA) and then using a 0.22 μm EXPRESS™ Plus Membrane. The filtered broth was concentrated and buffer exchanged using a tangential flow concentrator (Pall Filtron, Northborough, Mass., USA) equipped with a 10 kDa polyethersulfone membrane (Pall Filtron, Northborough, Mass., USA) with 20 mM Tris-HCl pH 8.0.

Desalted broth was loaded onto on a MONOQ™ HR 16/10 ion exchange column and eluted with a 300 ml linear 0-300 mM NaCl gradient in 20 mM Tris-HCl pH 8 with collection of 10 ml fractions. Fractions pooled based on SDS-PAGE analysis. Pooled fractions were adjusted to 1.2 M $(NH_4)_2 50_4$ in 20 mM Tris, pH 8.0 and then applied to a 75 ml self-poured PHENYL SEPHAROSE™ FAST-FLOW® HIGH-SUB® column (GE Healthcare, Piscataway, N.J., USA) and eluted with a 750 ml linear 1.2-0 M $(NH_4)_2 50_4$ gradient in 20 mM Tris-HCl pH 8 with collection of 10 ml fractions. Fractions pooled based on SDS-PAGE were concentrated using a VIVASPIN® 10 kDa MWCO centrifugal concentrator (GE Healthcare, Piscataway, N.J., USA). Concetrated material was then further purified using a HIGHLOAD™ 26/60 Superdex 75 gel filtration column with a 200 ml isoscratic gradient in 150 mM NaCl, 20 mM Tris-HCl pH 8.0. Fractions were collected and pooled based on SDS-PAGE and concentrated using concentrated using VIVASPIN® 10 kDa MWCO centrifugal concentrators. Protein concentration was determined using a Microplate BCA™ Protein Assay Kit in which bovine serum albumin was used as a protein standard.

Example 9: Preparation of *Aspergillus fumigatus* GH10 Xylanase

*Aspergillus fumigatus* $NNO_{55679}$ GH10 xylanase (xyn3; SEQ ID NO: 67 [DNA sequence] and SEQ ID NO: 68 [deduced amino acid sequence]) was prepared recombinantly according to WO 2006/078256 using *Aspergillus oryzae* BECh2 as a host.

The filtered broth was desalted and buffer-exchanged using a tangential flow concentrator (Pall Filtron, Northborough, Mass., USA) equipped with a 10 kDa polyethersulfone membrane (Pall Filtron, Northborough, Mass., USA) with 25 mM Tris-HCl pH 8.5. Desalted material was applied to 400 ml (hand-poured) Q-SEPHAROSE™ Fast-FIow™ column (GE Healthcare, Piscataway, N.J., USA), washed with 400 ml 25 mM Tris pH 8.5, and eluted with a 1400 ml linear gradient of 0-600 mM NaCl in 25 mM Tris pH 8.5 with collection of 10 ml fractions. Fractions were pooled based on SDS-PAGE, and adjusted to 1.5 M $(NH_4)_2SO_4$, 20 mM Tris pH 8.0 and applied to a 75 ml self-poured PHENYL SEPHAROSE™ FAST-FLOW® HIGH-SUB® column, washed with 75 ml 20 mM Tris-HCl pH 8.0, and eluted with a 1500 ml linear 1.5-0 M $(NH_4)_2 50_4$ gradient in 20 mM Tris-HCl pH 8 with collection of 10 ml fractions. Fractions were pooled based on SDS-PAGE analysis and concentrated using a 300 ml stirred cell concentration device (Millipore, Bedford, Mass., USA) equipped with a 10 kDa MWCO membrane and desalted into 20 mM Tris-HCl pH 8.0, 150 mM NaCl. Protein concentration was determined using a Microplate BCA™ Protein Assay Kit with bovine serum albumin as a protein standard.

Example 10: Preparation of *Trichoderma reesei* RutC30 GH3 Beta-Xylosidase

A *Trichoderma reesei* RutC30 beta-xylosidase gene (SEQ ID NO: 69 [DNA sequence] and SEQ ID NO: 70 [deduced amino acid sequence]) was isolated by screening a Lambda ZAP®-CMR XR Library prepared from *T. reesei* RutC30 genomic DNA using a Lambda ZAP®-CMR XR Library Construction Kit (Stratagene, La Jolla, Calif., USA) according to the manufacturer's instructions. *T. reesei* RutC30 genomic DNA was prepared using standard methods. A DNA segment encoding 2300 bp of the *T. reesei* beta-xylosidase was amplified using the PCR primers shown below.

```
Forward Primer:
                                    (SEQ ID NO: 87)
5'-gtgaataacgcagctcttctcg-3'

Reverse Primer:
                                    (SEQ ID NO: 88)
5'-ccttaattaattatgcgtcaggtgt-3'
```

Primer 994768 was designed to amplify from the first base after the beta-xylosidase start site and primer 994769 was designed with a Pac I site at the 5' end.

Fifty picomoles of each of the primers above were used in a PCR reaction composed of 50 ng of plasmid DNA from the lamda zap library, 1 μl of a 10 mM blend of dATP, dTTP, dGTP, and dCTP, 5 μl of 10× PLATINUM® Pfx DNA Polymerase Buffer, and 1 unit of PLATINUM® Pfx DNA polymerase, in a final volume of 50 μl. An EPPENDORF®

MASTERCYCLER® 5333 was used to amplify the DNA fragment programmed for 1 cycle at 95° C. for 3 minutes; and 30 cycles each at 94° C. for 45 seconds, 55° C. for 60 seconds, and 72° C. for 1 minute 30 seconds. After the 30 cycles, the reaction was incubated at 72° C. for 10 minutes and then cooled to 4° C. until further processing.

A 2.3 kb PCR product was purified by 1% agarose gel electrophoresis using TAE buffer, excised from the gel, and purified using a QIAQUICK® Gel Extraction Kit. The 2.3 kb PCR product was then digested with Pac I to facilitate insertion into pAlLo1 (WO 2004/099228).

The pAlLo1 vector was digested with Nco I and then filled in using T4 DNA polymerase (Roche Applied Science, Nutley, N.J., USA) according to manufacturer's instructions. A second enzyme, Pac I, was then used to digest the 5' end of pAlLo1 and the reaction was purified by agarose gel electrophoresis as described above to isolate a 6.9 kb vector fragment.

The 2.3 kb beta-xylosidase fragment was then ligated to the 6.9 kb vector fragment and transformed into *E. coli* XL1-Blue Subcloning Competent Cells (Invitrogen Corp., Carlsbad, Calif., USA) according to manufacturer's instructions. Transformants were screened using restriction digestion analysis in order to identify those with the correct insert. A new expression vector, pSaMe$_{04}$, was confirmed by sequencing using an ABI 3700 DNA Analyzer (Applied Biosystems, Foster City, Calif., USA) and dye terminator chemistry (Giesecke et al., 1992, supra).

Two synthetic oligonucleotide primers shown below were designed to PCR amplify the *Trichoderma reesei* beta-xylosidase gene from pSaMe04 to construct a *Trichoderma* expression vector. An IN-FUSION™ Cloning Kit was used to clone the fragment directly into the expression vector pMJ09 (WO 2005/056772), without the need for restriction digestion and ligation.

```
TrBXYL-F (ID 064491):
                                        (SEQ ID NO: 89)
5'-CGGACTGCGCACCATGGTGAATAACGCAGCTCT-3'

TrBXYL-R (ID 064492):
                                        (SEQ ID NO: 90)
5'-TCGCCACGGAGCTTATTATGCGTCAGGTGTAGCAT-3'
```

Bold letters represent coding sequence. The remaining sequence is homologous to the insertion sites of pMJ09.

Fifty picomoles of each of the primers above were used in a PCR reaction composed of 50 ng of pSaMe04, 1 μl of a 10 mM blend of dATP, dTTP, dGTP, and dCTP, 5 μl of 10× ACCUTAQ™ DNA Polymerase Buffer (Sigma-Aldrich, St. Louis, Mo., USA), and 5 units of ACCUTAQ™ DNA polymerase (Sigma-Aldrich, St. Louis, Mo., USA), in a final volume of 50 μl. An EPPENDORF® MASTERCYCLER® 5333 was used to amplify the DNA fragment programmed for 1 cycle at 95° C. for 3 minutes; and 30 cycles each at 94° C. for 45 seconds, 55° C. for 60 seconds, and 72° C. for 1 minute 30 seconds. After the 30 cycles, the reaction was incubated at 72° C. for 10 minutes and then cooled to 4° C. until further processing.

The reaction products were isolated by 1.0% agarose gel electrophoresis using TAE buffer where a 1.2 kb product band was excised from the gel and purified using a QIAQUICK® Gel Extraction Kit according to the manufacturer's instructions.

The 1.2 kb fragment was then cloned into pMJ09 using an IN-FUSION™ Cloning Kit. The vector was digested with Nco I and Pac I and purified by agarose gel electrophoresis as described above. The gene fragment and the digested vector were ligated together in a reaction resulting in the expression plasmid pSaMe-TrBXYL in which transcription of the beta-xylosidase gene was under the control of the *T. reesei* cbhl gene promoter. The ligation reaction (50 μl) was composed of 1×IN-FUSION™ Buffer, 1×BSA, 1 μl of IN-FUSION™ enzyme (diluted 1:10), 100 ng of pMJ09 digested with Nco I and Pac I, and 100 ng of the *T. reesei* beta-xylosidase purified PCR product. The reaction was incubated at room temperature for 30 minutes. One μl of the reaction was used to transform *E. coli* XL10 SOLOPACK® Gold competent cells. An *E. coli* transformant containing pSaMe-TrBXYL was detected by restriction enzyme digestion and plasmid DNA was prepared using a BIOROBOT® 9600. DNA sequencing of the *T. reesei* beta-xylosidase gene from pSaMe-TrBXYL was performed using dye-terminator chemistry (Giesecke et al., 1992, supra) and primer walking strategy.

Plasmid pSaMe-AaXYL was constructed to comprise the *Trichoderma reesei* cellobiohydrolase I gene promoter and terminator and the *Aspergillus* aculeatus GH10 xylanase coding sequence.

Cloning of the *A. aculeatus* xylanase followed the overall expression cloning protocol as outlined in H. Dalbøge et al., 1994, *Mol. Gen. Genet.* 243: 253-260.

RNA was isolated from *A. aculeatus* CBS 101.43 mycelium. Poly(A)$^+$ RNA was isolated from total RNA by chromatography on oligo(dT)-cellulose. Double-stranded cDNA was synthesized as described by Maniatis et al. (Molecular cloning: a laboratory manual. Cold Spring Harbor Laboratory Press, 1982). After synthesis the cDNA was treated with mung bean nuclease, blunt-ended with T4 DNA polymerase, and ligated to non-palindromic Bst XI adaptors (Invitrogen Corp., Carlsbad, Calif., USA). The cDNA was size fractionated by 1% agarose gel electrophoresis using TAE buffer where fragments ranging from 600 bp to 4000 bp were used in the library construction. The DNA was ligated into Bst XI-digested pYES 2.0 (Invitrogen Corp., Carlsbad, Calif., USA) between the GAL1 promoter and the iso-1-cytochrome c terminator and transformed into *Escherichia coli* MC1061 cells (Stratagene, La Jolla, Calif., USA). The library was plated onto LB plates and incubated overnight at 37° C. The colonies were scraped from the plates and resuspended in LB medium supplemented with 100 μg of ampicillin per ml. Plasmid DNA was isolated using a Plasmid Midi Kit (QIAGEN Inc., Valencia, Calif., USA). The purified plasmid DNA was pooled.

The purified plasmid DNA mixture was transformed into *Saccharomyces cerevisiae* W3124 cells (MATa; ura 3-52; leu 2-3, 112; his 3-D200; pep 4-1137; prcI::HIS3; prbI::LEU2; cir+; van den Hazel et al., 1992, *Eur. J. Biochem.* 207: 277-283). Cultivation, transformation and media were as described by Guthrie et al., 1991, *Meth. Enzymol.* Vol 194, Academic Press. The transformed cells were plated onto synthetic complete agar containing 2% glucose for 3 days at 30° C. After 3 days the colonies were replica plated to SC agar plates with 2% galactose and incubated for 4 days at 30° C. Xylanase expressing colonies were identified using a 1% agarose overlay with 0.1% AZCL-birch-xylan at pH 4.5 (Dalbøge, 2006, *FEMS Microbiology Reviews* 21: 29-42). Colonies expressing xylanase activity were surrounded by a blue zone. Plasmid DNA, rescued from the positive colonies, contained a DNA insert of approximately 1.3 kb. Sequencing of the isolated gene fragment revealed a 1218 bp open reading frame encoding a polypeptide with a theoretical molecular weight of 43.0 kDa. The cDNA fragment was subcloned into the *Aspergillus* expression vector pHD464 (Dalbøge and Heldt-Hansen, 1994, *Mol. Gen. Genet.* 243, 253-260) digested with Bam HI and Xho I by digesting the clone with Bam HI and Xho I and isolating the 1.2 kb cDNA insert (Christgau et al., 1996, *Biochem. J.* 319: 705-712) to generate piasmid pA2×2.

The *A. aculeatus* GH10 xylanase coding sequence was PCR amplified using plasmid pA2×2 as template and primers 153505 and 153506 shown below using standard methods to yield an approximately 1.2 kb fragment. The 1.2 kb fragment was digested with Bam HI and Xho I (introduced in the PCR primers) and cloned into vector pCaHj527 (WO 2004/099228). The resulting plasmid was designated pMT2155 in which the cDNA was under transcriptional control of the neutral amylase II (NA2) promoter from *A. niger* and the AMG terminator from *A. niger*.

```
Primer 153505:
                                        (SEQ ID NO: 91)
5'-TCTTGGATCCACCATGGTCGGACTGCTTTCAATCACC-3'

Primer 153506:
                                        (SEQ ID NO: 92)
5'-TTAACTCGAGTCACAGACACTGCGAGTAATAGTC-3'
```

Two synthetic oligonucleotide primers shown below were designed to PCR amplify the *A. aculeatus* GH10 gene from plasmid pMT2155 and introduce flanking regions for insertion into expression vector pMJ09 (WO 2005/056772). Bold letters represent coding sequence and the remaining sequence is homologous to the insertion sites of pMJ09.

Forward Primer:
(SEQ ID NO: 93)
5'-cggactgcgcaccatggtcggactgctttcaat-3'

Reverse Primer:
(SEQ ID NO: 94)
5'-tcgccacggagcttatcacagacactgcgagtaat-3'

Fifty picomoles of each of the primers above were used in a PCR reaction consisting of 50 ng of pMT2155, 1 μl of a 10 mM blend of dATP, dTTP, dGTP, and dCTP, 5 μl of 10× ACCUTAQ™ DNA Polymerase Buffer, and 5 units of ACCUTAQ™ DNA polymerase, in a final volume of 50 μl. An EPPENDORF® MASTERCYCLER® 5333 was used to amplify the DNA fragment programmed for 1 cycle at 95° C. for 3 minutes; and 30 cycles each at 94° C. for 45 seconds, 55° C. for 60 seconds, and 72° C. for 1 minute 30 seconds. After the 30 cycles, the reaction was incubated at 72° C. for 10 minutes and then cooled to 4° C. until further processing.

The reaction products were isolated by 1% agarose gel electrophoresis using TAE buffer where a 1.2 kb product band was excised from the gel and purified using a QIAquick Gel Extraction Kit according to the manufacturer's instructions.

The fragment was then cloned into pMJ09 using an IN-FUSION™ Cloning Kit. The vector was digested with Nco I and Pac I and purified by agarose gel electrophoresis as described above. The 1.2 kb gene fragment and the digested vector were ligated together in a reaction resulting in the expression plasmid pSaMe-AaXYL in which transcription of the Family GH10 gene was under the control of the *T. reesei* cbhl promoter. The ligation reaction (50 ul) was composed of 1× IN-FUSION™ Buffer, 1×BSA, 1 μl of IN-FUSION™ enzyme (diluted 1:10), 100 ng of pAlLo2 digested with Nco I and Pac I, and 100 ng of the *A. aculeatus* GH10 xylanase purified PCR product. The reaction was incubated at room temperature for 30 minutes. One μl of the reaction was used to transform *E. coli* XL10 SOLOPACK® Gold competent cells according to the manufacturer. An *E. coli* transformant containing pSaMe-AaGH10 was detected by restriction enzyme digestion and plasmid DNA was prepared using a BIOROBOT® 9600. DNA sequencing of the *A. aculeatus* GH10 gene from pSaMe-AaXYL was performed using dye-terminator chemistry (Giesecke et al., 1992, supra) and primer walking strategy.

Plasmids pSaMe-AaXYL encoding the *A. aculeatus* GH10 endoglucanase and pSaMe-TrBXYL encoding the *T. reesei* beta-xylosidase were co-transformed into *Trichoderma reesei* RutC30 by PEG-mediated transformation (Penttila et al., 1987, *Gene* 61 155-164) to generate *T. reesei* strain SaMe-BXX13. Each plasmid contained the *A. nidulans* amdS gene to enable transformants to grow on acetamide as the sole nitrogen source.

*T. reesei* RutC30 was cultivated at 27° C. and 90 rpm in 25 ml of YP medium supplemented with 2% (w/v) glucose and 10 mM uridine for 17 hours. Mycelia were collected by filtration using a Vacuum Driven Disposable Filtration System (Millipore, Bedford, Mass., USA) and washed twice with deionized water and twice with 1.2 M sorbitol. Protoplasts were generated by suspending the washed mycelia in 20 ml of 1.2 M sorbitol containing 15 mg of GLUCANEX™ (Novozymes NS, Bagsvaerd, Denmark) per ml and 0.36 units of chitinase (Sigma Chemical Co., St. Louis, Mo., USA) per ml and incubating for 15-25 minutes at 34° C. with gentle shaking at 90 rpm. Protoplasts were collected by centrifuging for 7 minutes at 400×g and washed twice with cold 1.2 M sorbitol. The protoplasts were counted using a haemacytometer and re-suspended in STC to a final concentration of $1\times10^8$ protoplasts per ml. Excess protoplasts were stored in a Cryo 1° C. Freezing Container (Nalgene, Rochester, N.Y., USA) at −80° C.

Approximately 4 μg of plasmids pSaMe-AaXYL and pSaMe-TRBXYL were digested with Pme I and added to 100 μl of protoplast solution and mixed gently, followed by 250 μl of 10 mM $CaCl_2$-10 mM Tris-HCl pH 7.5-60% PEG 4000, mixed, and incubated at room temperature for 30 minutes. STC (3 ml) was then added and mixed and the transformation solution was plated onto COVE plates using *Aspergillus nidulans* amdS selection. The plates were incubated at 28° C. for 5-7 days. Transformants were subcultured onto COVE2 plates and grown at 28° C.

Over 40 transformants were subcultured onto fresh plates containing acetamide and allowed to sporulate for 7 days at 28° C.

The *Trichoderma reesei* transformants were cultivated in 125 ml baffled shake flasks containing 25 ml of CIM medium at pH 6.0 by inoculating spores of the transformants and incubating at 28° C. and 200 rpm for 7 days. *Trichoderma reesei* RutC30 was run as a control. Culture broth samples were removed at day 5. One ml of each culture broth was centrifuged at 15,700×g for 5 minutes in a microcentrifuge and the supernatants transferred to new tubes.

SDS-PAGE was performed using CRITERION® Tris-HCl (5% resolving) gels with a CRITERION® System (Bio-Rad Laboratories, Inc., Hercules, Calif., USA). Five μl of day 7 supernatants (see above) were suspended in 2× concentration of Laemmli Sample Buffer (Bio-Rad Laboratories, Inc., Hercules, Calif., USA) and boiled in the presence of 5% beta-mercaptoethanol for 3 minutes. The supernatant samples were loaded onto a polyacrylamide gel and subjected to electrophoresis with 1× Tris/Glycine/SDS as running buffer (Bio-Rad Laboratories, Inc., Hercules, Calif., USA). The resulting gel was stained with BIO-SAFE™ Coomassie Stain. The transformant showing the highest expression of both the *A. aculeatus* GH10 xylanase and the *T. reesei* beta-xylosidase based on the protein gel was designated *T. reesei* SaMe-BXX13.

*Trichoderma reesei* SaMe-BXX13 was cultivated in 500 ml baffled shake flasks containing 250 ml of CIM medium at pH 6.0 inoculated with spores of *T. reesei* SaMe-BXX13. Shake flasks were incubated at 28° C. at 200 rpm for five days. The culture broth was then filtered using an 0.22 μm EXPRESS™ Plus Membrane.

The filtered broth was concentrated and buffer exchanged using a tangential a tangential flow concentrator (Pall Filtron, Northborough, Mass., USA) equipped with a 10 kDa polyethersulfone membrane (Pall Filtron, Northborough, Mass., USA) to pH 4.0 with acetic acid. Sample was loaded onto a SP SEPHAROSE® column (GE Healthcare, Piscataway, N.J., USA) equilibrated in 50 mM sodium acetate pH 4.0, eluting bound proteins with a gradient of 0-1000 mM sodium chloride. Fractions were buffer exchanged into 20 mM sodium phosphate pH 7.0 using a tangential flow concentrator and applied to a PHENYL SUPEROSE™ HR 16/10 column (GE Healthcare, Piscataway, N.J., USA) equilibrated with 1.5 M $(NH_4)_2 50_4$-20 mM sodium phosphate pH 7.0. Bound proteins were eluted with a linear gradient over 20 column volumes from 1.5 to 0 M $(NH_4)_2 50_4$ in 20 mM Tris-HCl pH 7.0. The protein fractions were buffer exchanged into 20 mM TEA HCl pH 7.5 using a tangential flow concentrator. Sample was applied to a MONOQ™ HR 16/10 ion exchange column, equilibrated in 20 mM TEA HCl pH 7.5, eluting bound proteins with a gradient from 0-300 mM sodium chloride. Buffer of final protein fractions was 20 mM TEA-100 mM sodium chloride pH 7.5. Protein concentration was determined using a Microplate BCA™ Protein Assay Kit in which bovine serum albumin was used as a protein standard.

Example 11: Preparation of Phosphoric Acid Swollen Cellulose

Phosphoric acid swollen cellulose (PASC) was prepared from AVICEL® PH101 (FMC, Philadelphia, Pa., USA) using the prortocol described by Zhang et al., 2006, *Biomacromolecules* 7: 644-648.

Example 12: Phosphoric Acid Swollen Cellulose (PASC) Hydrolysis Assay

A 1.0% slurry of PASC prepared as described in Example 11 was thoroughly resuspended by shaking, and quickly transferred to a 100 ml beaker and stirred rapidly with a magnetic stirrer. Five hundred μl aliquots of the 1.0% PASC slurry were pipetted into wells of a 2.0 ml 96-deepwell plate (Axygen, Union City, Calif., USA) using a 1000 μl micropipette with a wide aperture tip (end of tip cut off about 2 mm from the base). One hundred μl of 10 mM $MnSO_4$-500 mM sodium acetate pH 5 were then added to each well. Two hundred μl of either deionized water or a 1.0% pyrogallol (w/w) (Sigma Chemical Co., Inc., St. Louis, Mo., USA) solution were added to each well. Enzyme mixtures were prepared and then added simultaneously to all wells in a volume of 200 μl, for a total of 1 ml in each reaction. The plate was then sealed using an ALPS 300™ plate heat sealer (Abgene, Epsom, United Kingdom), mixed thoroughly, and incubated at either 50° C. or 65° C. for approximately 3 days. All experiments reported were performed in triplicate.

Primary analysis of the hydrolysis reactions was performed using an AGILENT® 1100 HPLC (Agilent Technologies, Inc., Santa Clara, Calif., USA) with CHEMSTATION® software (Agilent Technologies, Inc., Santa Clara, Calif., USA) equipped with an AMINEX™ HPX-87H column (Bio-Rad Laboratories, Inc., Hercules, Calif., USA). After approximately 4 days, the deep-well plate was removed from the incubator and chilled overnight to 4° C. The plate was then mixed well by inversion and briefly centrifuged at 52×g in a SORVALL® RT7 centrifuge for 10 seconds. Samples were then mixed by pipetting, and 200 μl from each well were transferred to a MULTISCREEN® HV (Millipore, Bedford, Mass., USA) centrifuge filter plate assembly. The centrifuge filter plate assembly was centrifuged at 2000 rpm in a SORVALL® RT7 centrifuge for 20 minutes. The filtrates were transferred to a 96 well autosampler plate and diluted 1:1 with 5 mM $H_2SO_4$, sealed with silicon sealing mat, and inserted into an HPLC injector module (set to 4° C.) for injection of 20 μl onto a CATION H™ guard column connected to a 4.6×250 mm AMINEX® HPX-87H column followed by elution with 0.05% w/w benzoic acid in 5 mM $H_2SO_4$. Sugars were detected by refractive index detection with quantification by integration compared to purified sugar standards.

All HPLC data processing was performed using MICROSOFT EXCEL™ software (Microsoft, Richland, Wash., USA). Measured glucose concentrations were adjusted for the appropriate dilution factor. In this assay only glucose was measured since beta-glucosidase was at high levels in all samples but the controls. Percent relative conversion was calculated using the following Equation:

% conversion=[sample glucose concentration]/[glucose concentration in a limit digest]×100

In order to calculate % conversion, a 100% conversion point was set based on a cellulase control of 100 mg of *Trichoderma reesei* cellulase per gram cellulose (CELLUCLAST PLUS™, Novozymes NS, Bagsvaerd, Denmark), and all values were divided by this number and then multiplied by 100. Triplicate data points were averaged and standard deviation was calculated.

Example 13: Effect of the Addition of *Aspergillus fumigatus* GH61B Variant L90V+D131S+M134L+A141W on the Conversion of Phosphoric Acid Swollen Cellulose by *Aspergillus fumigatus* Beta-Glucosidase in the Presence of Pyrogallol at 50° C. and 65° C.

*A. fumigatus* GH61B wild-type polypeptide and *A. fumigatus* GH61B variant L90V+D131S+M134L+A141W were evaluated for their ability to enhance the hydrolysis of phosphoric acid swollen cellulose by *A. fumigatus* CEL3A beta-glucosidase in the presence of pyrogallol. The phosphoric acid swollen cellulose hydrolysis assay was performed as described in Example 12.

The conversion of phosphoric acid swollen cellulose (0.5% w/w) by the combination of pyrogallol (0.2% w/w) and *A. fumigatus* CEL3A beta-glucosidase (5 mg protein per g cellulose); the combination of (0.2% w/w) pyrogallol, *A. fumigatus* GH61B wild-type polypeptide (10 mg protein per g cellulose), and *A. fumigatus* CEL3A beta-glucosidase (5 mg protein per g cellulose); and the combination of pyrogallol (0.2% w/w), *A. fumigatus* GH61B variant L90V+D131S+M134L+A141W (10 mg protein per g cellulose), and *A. fumigatus* CEL3A beta-glucosidase (5 mg protein per g cellulose) was determined according to the assay described in Example 12. Data were collected and analyzed, as described in Example 12, after 72 hours of incubation at either 50° C. or 65° C. The results are shown in FIG. 1.

The combination of pyrogallol (0.2% w/w) and *A. fumigatus* CEL3A beta-glucosidase (5 mg protein per g cellulose) resulted in conversion of phosphoric acid swollen cellulose of 2.1±0.3% and 2.2±1.0% at 50° C. and 65° C., respectively. Addition of *A. fumigatus* GH61B wild-type polypeptide (10 mg protein per g cellulose) to the combination of pyrogallol (0.2% w/w) and *A. fumigatus* CEL3A beta-glucosidase (5 mg protein per g cellulose) resulted in the conversion of phosphoric acid swollen cellulose of 23.8±0.6% and 16.8±0.4% at 50° C. and 65° C., respectively. Addition of *A. fumigatus* GH61B variant L90V+D131S+M134L+A141W (10 mg protein per g cellulose) to the combination of pyrogallol (0.2% w/w) and *A. fumigatus* CEL3A beta-glucosidase (5 mg protein per g cellulose) resulted in the conversion of phosphoric acid swollen cellulose of 46.1±1.1% and 23.4±0.7% at 50° C. and 65° C., respectively.

Example 14: Pretreated Corn Stover Hydrolysis Assay

Corn stover was pretreated at the U.S. Department of Energy National Renewable Energy Laboratory (NREL) using 1.4 wt % sulfuric acid at 165° C. and 107 psi for 8 minutes. The water-insoluble solids in the pretreated corn stover (PCS) contained approximately 59% cellulose, 5% hemicellulose and 28% lignin. Cellulose and hemicellulose were determined by a two-stage sulfuric acid hydrolysis with subsequent analysis of sugars by high performance liquid chromatography using NREL Standard Analytical Procedure #002. Lignin was determined gravimetrically after hydrolyzing the cellulose and hemicellulose fractions with sulfuric acid using NREL Standard Analytical Procedure #003.

The hydrolysis of PCS was conducted using 2.2 ml deep-well plates (Axygen, Union City, Calif., USA) in a total reaction volume of 1.0 ml. The hydrolysis was performed with 50 mg of PCS per ml of 50 mM sodium acetate pH 5.0 buffer containing 1 mM manganese sulfate and various protein loadings of the cellulase composition (expressed as mg protein per gram of cellulose). Enzyme mixtures were prepared and then added simultaneously to all wells in a volume of 100 μl, for a final volume of 1 ml in each reaction. The plate was then sealed using an ALPS-300™ plate heat sealer, mixed thoroughly, and incubated at 50° C., 55° C., 60° C., and/or 65° C. for 72 hours. All experiments were performed in triplicate.

Following hydrolysis, samples were filtered using a 0.45 μm MULTISCREEN® 96-well filter plate (Millipore, Bedford, Mass., USA) and filtrates analyzed for sugar content as described below. When not used immediately, filtered sugary aliquots were frozen at −20° C. The sugar concentrations of samples diluted in 0.005 M $H_2SO_4$ were measured using a 4.6×250 mm AMINEX® HPX-87H column by elution with 0.05% w/w benzoic acid-0.005 M $H_2SO_4$ at a flow rate of 0.6 ml per minute at 65° C., and quantitation by integration of glucose and cellobiose signal from refractive index detection (CHEMSTATION®, AGILENT® 1100 HPLC, Agilent Technologies, Santa Clara, Calif., USA) calibrated by pure sugar samples. The resultant equivalents were used to calculate the percentage of cellulose conversion for each reaction.

All HPLC data processing was performed using MICROSOFT EXCEL™ software. Measured sugar concentrations were adjusted for the appropriate dilution factor. Glucose and cellobiose were measured individually. However, to calculate total conversion the glucose and cellobiose values were combined. Cellobiose concentration was multiplied by 1.053 in order to convert to glucose equivalents and added to the glucose concentration. The degree of cellulose conversion was calculated using the following equation:

% A conversion=[sample glucose concentration]/[glucose concentration in a limit digest]×100

In order to calculate % conversion, a 100% conversion point was set based on a cellulase control of 100 mg of the cellulase composition per gram cellulose (CELLUCLAST PLUS™, Novozymes NS, Bagsvaerd, Denmark), and all values were divided by this number and then multiplied by 100. Triplicate data points were averaged and standard deviation was calculated.

Example 15: Effect of the Addition of *Aspergillus fumigatus* GH61B Variant L90V+D131S+M134L+A141W on Conversion of PCS by a *Trichoderma reesei* Cellulase Composition and *Aspergillus fumigatus* CEL3A Beta-Glucosidase at 50° C. and 55° C.

A cellulase composition from *Trichoderma reesei* strain 981-O-8 (D4) was prepared according to the fermentation protocol described below. *T. reesei* strain 981-O-8 (D4) is a mutagenized strain of *Trichoderma reesei* RutC30 (ATCC 56765; Montenecourt and Eveleigh, 1979, *Adv. Chem. Ser.* 181: 289-301). The cellulase composition is similar to CELLUCLAST (Novozymes NS, Bagsvaerd, Denmark). The cellulase composition was supplemented with *A. fumigatus* beta-glucosidase. The cellulase composition supplemented with *A. fumigatus* beta-glucosidase is designated in the Examples as "*Trichoderma reesei* cellulase composition".

Shake flask medium was composed of 20 g of dextrose, 10 g of corn steep solids, 1.45 g of $(NH_4)_2SO_4$, 2.08 g of $KH_2PO_4$, 0.36 g of $CaCl_2$, 0.42 g of $MgSO_4.7H_2O$, 0.42 ml of trace metals solution, and deionized water to 1 liter. Trace metals solution was composed of 216 g of $FeCl_3.6H_2O$, 58 g of $ZnSO_4.7H_2O$, 27 g of $MnSO_4.H_2O$, 10 g of $CuSO_4.5H_2O$, 2.4 g of $H_3B0_3$, 336 g of citric acid, and deionized water to 1 liter.

One hundred ml of shake flask medium was added to a 500 ml shake flask. The shake flask was inoculated with two plugs from a solid plate culture and incubated at 28° C. on an orbital shaker at 200 rpm for 48 hours. Fifty ml of the shake flask broth was used to inoculate a 2 liter fermentation vessel.

Fermentation batch medium was composed of 30 g of cellulose, 4 g of dextrose, 10 g of corn steep solids, 3.8 g of $(NH_4)_250_4$, 2.8 g of $KH_2PO_4$, 2.64 g of $CaCl_2$, 1.63 g of $MgSO_4.7H_2O$, 1.8 ml of anti-foam, 0.66 ml of trace metals solution, and deionized water to 1 liter. Trace metals solution was composed of 216 g of $FeCl_3.6H_2O$, 58 g of $ZnSO_4.7H_2O$, 27 g of $MnSO_4.H_2O$, 10 g of $CuSO_4.5H_2O$, 2.4 g of $H_3BO_3$, 336 g of citric acid.$H_2O$, and deionized water to 1 liter. Fermentation feed medium was composed of dextrose.

A total of 1.8 liters of the fermentation batch medium was added to an Applikon Biotechnology three liter glass jacketed fermentor. Fermentation feed medium was dosed at a rate of 0 to 4 g/l/hr for a period of 185 hours. The fermentation vessel was maintained at a temperature of 28° C. and pH was controlled using an Applikon 1030 control system to a set-point of 4.5+/−0.1. Air was added to the vessel at a rate of 1 vvm and the broth was agitated by Rushton impeller rotating at 1100 to 1300 rpm. At the end of the fermentation, whole broth was harvested from the vessel and centrifuged at 3000×g to remove the biomass. The supernatant was sterile filtered and stored at 5 to 10° C.

*A. fumigatus* GH61B wild-type polypeptide and *A. fumigatus* GH61B variant L90V+D131S+M134L+A141W were evaluated for their ability to enhance the hydrolysis of PCS by the combination of the *T. reesei* cellulase composition and *A. fumigatus* CEL3A beta-glucosidase at either 50° C. or 55° C. The PCS hydrolysis assay was performed as described in Example 14.

Figure 2A:
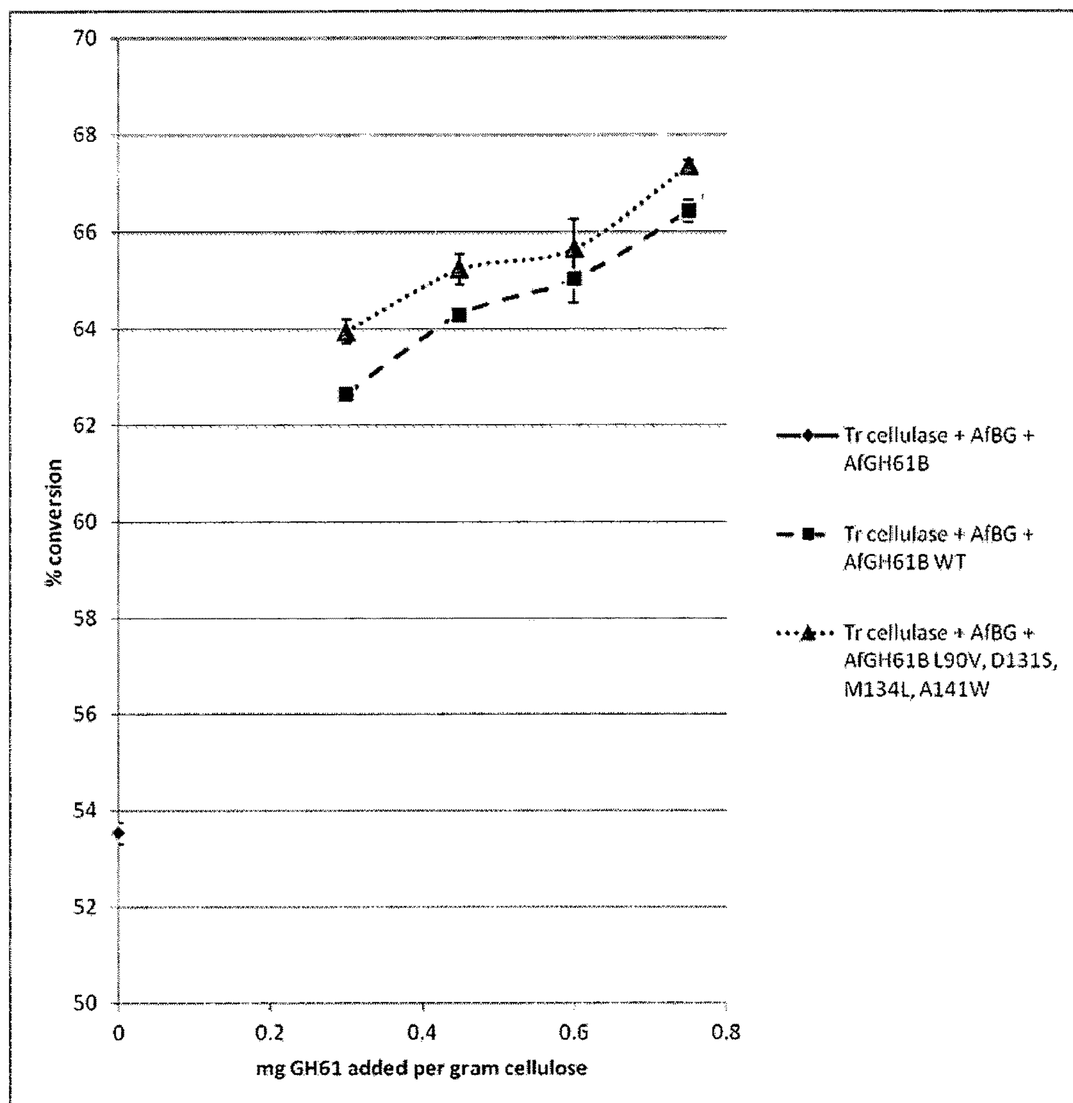
FIGS. 2A and 2B show the effect of the *A. fumigatus* GH61B wild-type polypeptide and *A. fumigatus* GH61B variant L90V+D131S+M134L+A141W on the conversion of pretreated corn stover (PCS) by by the combination of a *Trichoderma reesei* cellulase composition and *A. fumigatus* CEL3A beta-glucosidase at either 50° C. or 55° C.
Figure 2B:
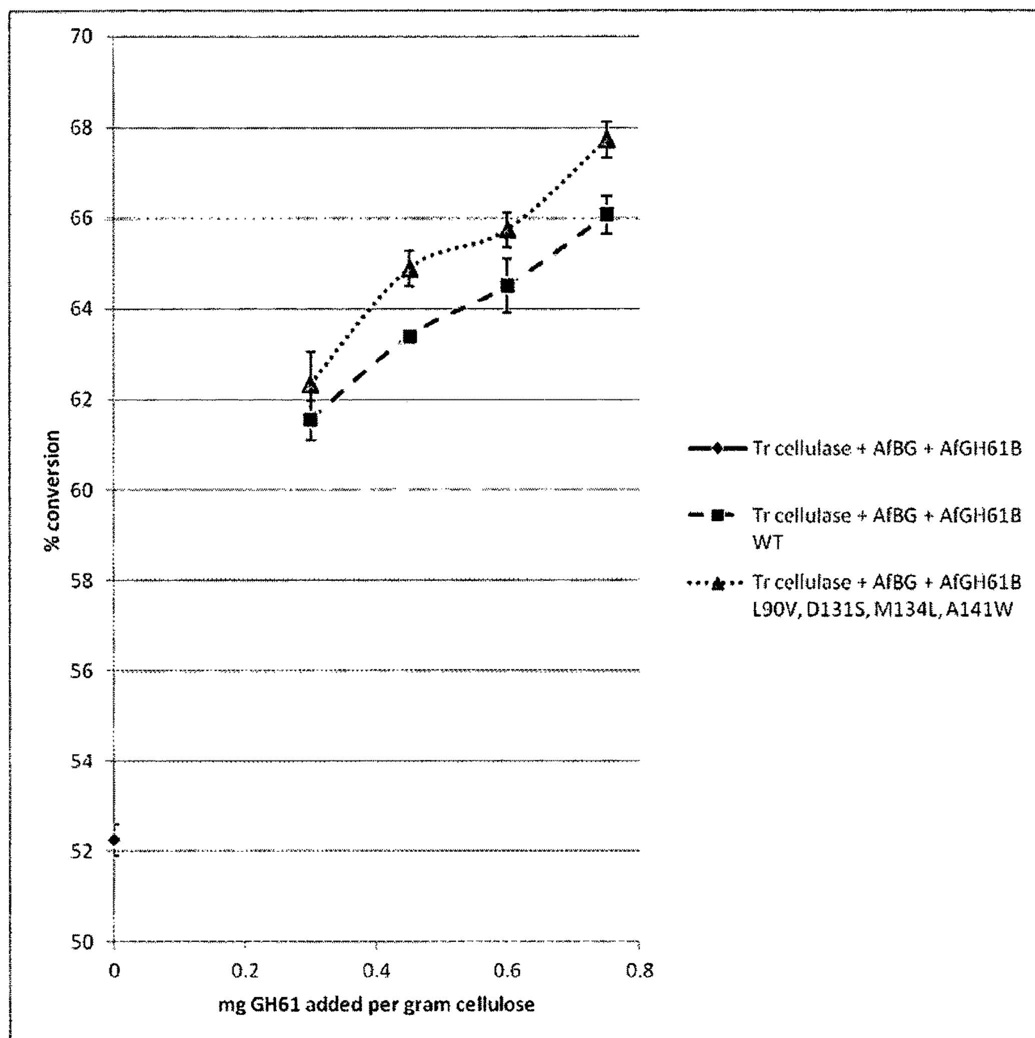

The conversion of PCS by the combination of the *T. reesei* cellulase composition (2.7 mg protein per gram cellulose) and *A. fumigatus* CEL3A beta-glucosidase (0.3 mg protein per g cellulose); the combination of the *T. reesei* cellulase composition (2.7 mg protein per gram cellulose), *A. fumigatus* GH61B wild-type polypeptide (0.3 mg protein per g cellulose), and *A. fumigatus* CEL3A beta-glucosidase (0.3 mg protein per g cellulose); the combination of the *T. reesei* cellulase composition (2.7 mg protein per gram cellulose), *A. fumigatus* GH61B wild-type polypeptide (0.45 mg protein per g cellulose), and *A. fumigatus* CEL3A beta-glucosidase (0.3 mg protein per g cellulose); the combination of the *T. reesei* cellulase composition (2.7 mg protein per gram cellulose), *A. fumigatus* GH61B wild-type polypeptide (0.6 mg protein per g cellulose), and *A. fumigatus* CEL3A beta-glucosidase (0.3 mg protein per g cellulose); the combination of the *T. reesei* cellulase composition (2.7 mg protein per gram cellulose), *A. fumigatus* GH61B wild-type polypeptide (0.75 mg protein per g cellulose), and *A. fumigatus* CEL3A beta-glucosidase (0.3 mg protein per g cellulose); the combination of the *T. reesei* cellulase composition (2.7 mg protein per gram cellulose), *A. fumigatus* GH61B variant L90V+D131S+M134L+A141W ((0.3 mg protein per g cellulose), and *A. fumigatus* CEL3A beta-glucosidase (0.3 mg protein per g cellulose); the combination of the *T. reesei* cellulase composition (2.7 mg protein per gram cellulose), *A. fumigatus* GH61B variant L90V+D131S+M134L+A141W (0.45 mg protein per g cellulose), and *A. fumigatus* CEL3A beta-glucosidase (0.3 mg protein per g cellulose); the combination of the *T. reesei* cellulase composition (2.7 mg protein per gram cellulose), *A. fumigatus* GH61B variant L90V+D131S+M134L+A141W (0.6 mg protein per g cellulose), and *A. fumigatus* CEL3A beta-glucosidase (0.3 mg protein per g cellulose); and the combination of the *T. reesei* cellulase composition (2.7 mg protein per gram cellulose), *A. fumigatus* GH61B variant L90V+D131S+M134L+A141W (0.75 mg protein per g cellulose), and *A. fumigatus* CEL3A beta-glucosidase (0.3 mg protein per g cellulose) was assayed as described in Example 14. Data were collected and analyzed, as described in Example 14, after 72 hours of incubation at either 50° C. or 55° C. Results for 50° C. and 55° C. are shown in FIGS. 2A and 2B, respectively.

The combination of the *T. reesei* cellulase composition (2.7 mg protein per gram cellulose) and *A. fumigatus* CEL3A beta-glucosidase (0.3 mg protein per g cellulose) resulted in conversion of PCS of 53.5±0.2% and 52.2±0.3% at 50° C. and 55° C., respectively.

The combination of the *T. reesei* cellulase composition (2.7 mg protein per gram cellulose), *A. fumigatus* GH61B wild-type polypeptide (0.3 mg protein per g cellulose), and *A. fumigatus* CEL3A beta-glucosidase (0.3 mg protein per g cellulose) resulted in conversion of PCS of 62.6±0.1% and 61.5±0.4% at 50° C. and 55° C., respectively. The combination of the *T. reesei* cellulase composition (2.7 mg protein per gram cellulose), *A. fumigatus* GH61B wild-type polypeptide (0.45 mg protein per g cellulose), and *A. fumigatus* CEL3A beta-glucosidase (0.3 mg protein per g cellulose) resulted in conversion of PCS of 64.3±0.1% and 63.4±0.1% at 50° C. and 55° C., respectively.

The combination of the *T. reesei* cellulase composition (2.7 mg protein per gram cellulose), *A. fumigatus* GH61B wild-type polypeptide (0.6 mg protein per g cellulose), and *A. fumigatus* CEL3A beta-glucosidase (0.3 mg protein per g cellulose) resulted in conversion of PCS of 65.0±0.5% and 64.5±0.6% at 50° C. and 55° C., respectively. The combination of the *T. reesei* cellulase composition (2.7 mg protein per gram cellulose), *A. fumigatus* GH61B wild-type polypeptide (0.75 mg protein per g cellulose), and *A. fumigatus* CEL3A beta-glucosidase (0.3 mg protein per g cellulose) resulted in conversion of PCS of 66.4±0.2% and 66.1±0.4% at 50° C. and 55° C., respectively.

The combination of the *T. reesei* cellulase composition (2.7 mg protein per gram cellulose), *A. fumigatus* GH61B variant L90V+D131S+M134L+A141W (0.3 mg protein per g cellulose), and *A. fumigatus* CEL3A beta-glucosidase (0.3 mg protein per g cellulose) resulted in conversion of PCS of 63.9±0.2% and 62.4±0.7% at 50° C. and 55° C., respectively. The combination of the *T. reesei* cellulase composition (2.7 mg protein per gram cellulose), *A. fumigatus* GH61B variant L90V+D131S+M134L+A141W (0.45 mg protein per g cellulose), and *A. fumigatus* CEL3A beta-glucosidase (0.3 mg protein per g cellulose) resulted in conversion of PCS of 65.2±0.3% and 64.9±0.4% at 50° C. and 55° C., respectively. The combination of the *T. reesei* cellulase composition (2.7 mg protein per gram cellulose), *A. fumigatus* GH61B variant L90V+D131S+M134L+A141W (0.6 mg protein per g cellulose), and *A. fumigatus* CEL3A beta-glucosidase (0.3 mg protein per g cellulose) resulted in conversion of PCS of 65.7±0.6% and 65.7±0.4% at 50° C. and 55° C., respectively. The combination of the *T. reesei* cellulase composition (2.7 mg protein per gram cellulose), *A. fumigatus* GH61B variant L90V+D131S+M134L+A141W (0.75 mg protein per g cellulose), and *A. fumigatus* CEL3A beta-glucosidase (0.3 mg protein per g cellulose) resulted in conversion of PCS of 67.4±0.1% and 67.7±0.4% at 50° C. and 55° C., respectively.

Example 16: Effect of the Addition of *Aspergillus fumigatus* GH61B Variant L90V+D131S+M134L+A141W on the Conversion of PCS by a High-Temperature Cellulase Composition at 50° C., 55° C., 60° C., and 65° C.

A mixture of cellulase enzymes, designated "high temperature cellulase composition", was prepared by mixing prepared enzyme components in the following ratios (of total protein): 43.5% *Aspergillus fumigatus* cellobiohydrolase I, 29.4% *Aspergillus fumigatus* cellobiohydrolase II, 5.9% *Aspergillus fumigatus* beta-glucosidase, 5.9% *Aspergillus fumigatus* GH10 xylanase 3, 3.5% *Trichoderma reesei* beta-xylosidase, and 11.8% *Trichoderma reesei* CELSA endoglucanase II. The composition when loaded in assay at 3 mg total protein per gram cellulose had the following enzyme loadings per gram cellulose: 1.31 mg *A. fumigatus* cellobiohydrolase I per gram cellulose, 0.88 mg *A. fumigatus* cellobiohydrolase II per gram cellulose, 0.18 mg *A. fumigatus* beta-glucosidase per gram cellulose, 0.18 mg *A. fumigatus* GH10 xylanase 3 per gram cellulose, 0.11 mg *T. reesei* beta-xylosidase per gram cellulose, and 0.35 mg *T. reesei* CEL5A endoglucanase II per gram cellulose.

*A. fumigatus* GH61B wild-type polypeptide and *A. fumigatus* GH61B variant L90V+D131S+M134L+A141W were evaluated for their ability to enhance the hydrolysis of PCS by the high temperature cellulase composition at 50° C., 55° C., 60° C., or 65° C. The pretreated corn stover hydrolysis assay was performed as described in Example 14.

Figure 3A:
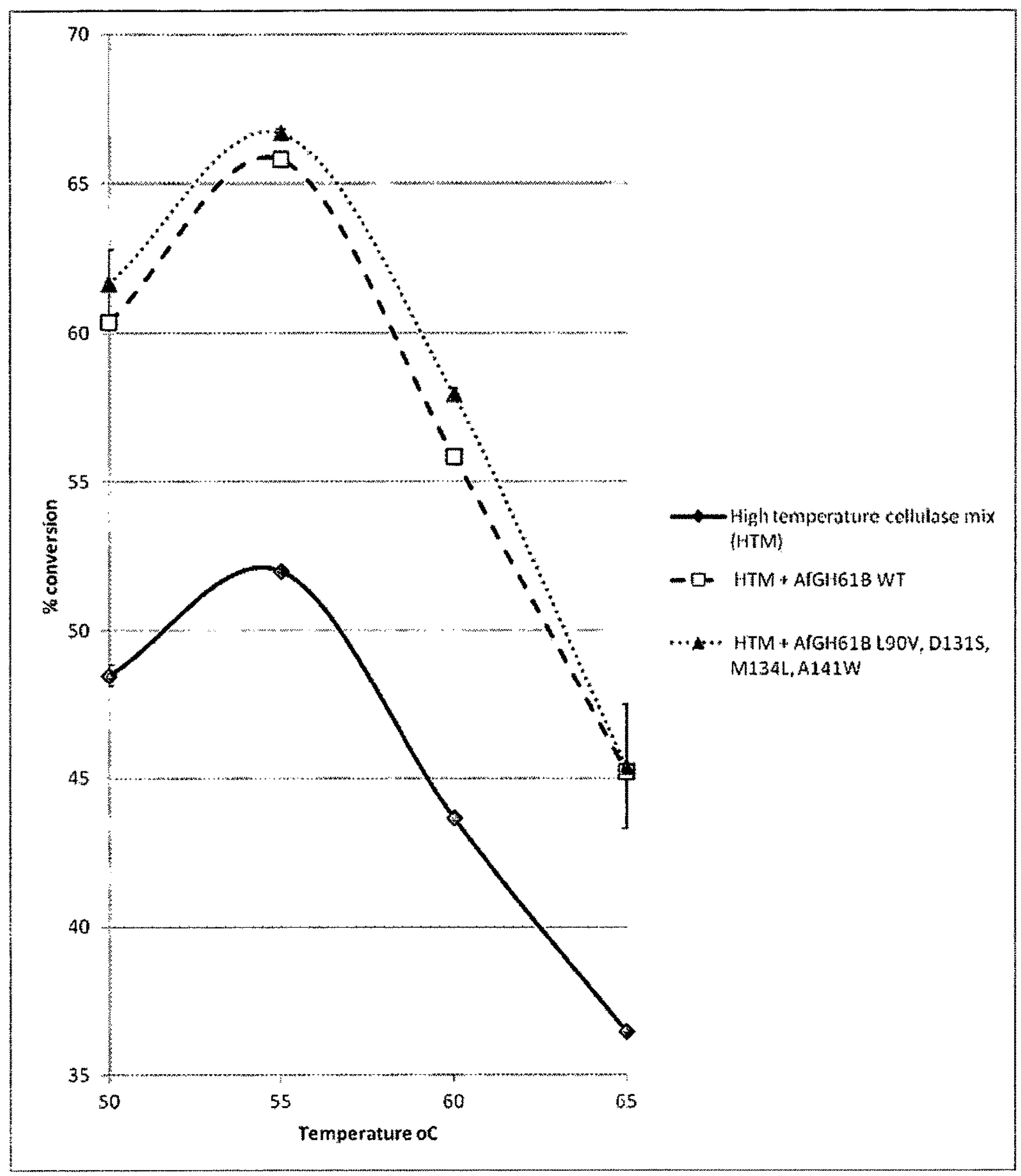
FIGS. 3A (0.45 mg/g GH61) and 3B (0.75 mg/g GH61) show the effect of the *A. fumigatus* GH61B wild-type polypeptide and *A. fumigatus* GH61B variant L90V+D131S+M134L+A141W on the conversion of PCS by by the combination of a high temperature cellulase composition and *A. fumigatus* CEL3A beta-glucosidase at 50° C., 55° C., 60° C., or 65° C.
Figure 3B:
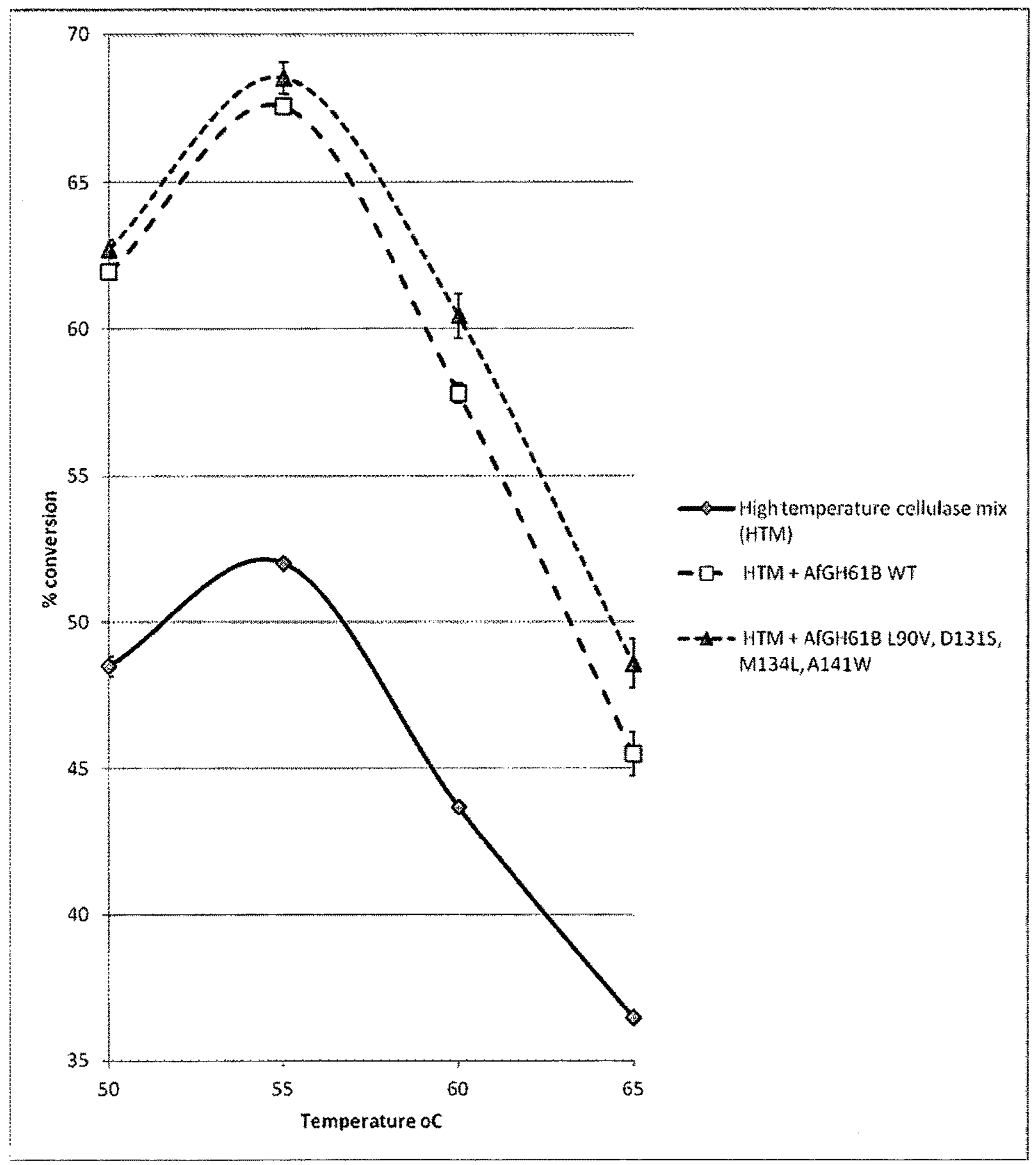

The conversion of pretreated corn stover by the high temperature cellulase composition (3 mg protein per g cellulose); the combination of the high temperature cellulase composition (3 mg protein per g cellulose) and *A. fumigatus* GH61B wild-type polypeptide (0.45 mg protein per g cellulose); the combination of the high temperature cellulase composition (3 mg protein per g cellulose) and *A. fumigatus* GH61B wild-type polypeptide (0.75 mg protein per g cellulose); the combination of the high temperature cellulase composition (3 mg protein per g cellulose) and *A. fumigatus* GH61B variant L90V+D131S+M134L+A141W (0.45 mg protein per g cellulose); and the combination of the high temperature cellulase composition (3 mg protein per g cellulose) and *A. fumigatus* GH61B variant L90V+D131S+M134L+A141W (0.75 mg protein per g cellulose) was assayed as described in Example 14. Data were collected and analyzed, as described in Example 14, after 72 hours of incubation at 50° C., 55° C., 60° C., or 65° C. Results for 0.45 mg addition of GH61 polypeptide per gram cellulose and 0.75 mg addition of GH61 polypeptide per gram cellulose are shown in FIGS. 3A and 3B, respectively.

The high temperature cellulase composition (3 mg protein per g cellulose) resulted in conversion of pretreated corn stover of 48.5±0.3%, 52.0±0.1%, 43.7±0.2%, and 36.4±0.1% at 50° C., 55° C., 60° C., or 65° C., respectively.

The combination of the high temperature cellulase composition (3 mg protein per g cellulose) and *A. fumigatus* GH61B wild-type polypeptide (0.45 mg protein per g cellulose) resulted in conversion of pretreated corn stover of 60.4±0.2%, 65.8±0.1%, 55.8±0.1%, and 45.2±0.2% at 50° C., 55° C., 60° C., or 65° C., respectively. The combination of the high temperature cellulase composition (3 mg protein per g cellulose) and *A. fumigatus* GH61B wild-type polypeptide (0.75 mg protein per g cellulose) resulted in conversion of pretreated corn stover of 61.9±0.1%, 67.6±0.2%, 57.8±0.3%, and 45.5±0.7% at 50° C., 55° C., 60° C., or 65° C., respectively.

The combination of the high temperature cellulase composition (3 mg protein per g cellulose) and *A. fumigatus* GH61B variant L90V+D131S+M134L+A141W (0.45 mg protein per g cellulose) resulted in conversion of pretreated corn stover of 61.7±1.1%, 66.7±0.1%, 57.9±0.2%, and 45.4±2.1% at 50° C., 55° C., 60° C., or 65° C., respectively. The combination of the high temperature cellulase composition (3 mg protein per g cellulose) and *A. fumigatus* GH61B variant L90V+D131S+M134L+A141W (0.75 mg protein per g cellulose) resulted in conversion of pretreated corn stover of 62.7±0.3%, 68.5±0.5%, 60.4±0.8%, and 48.6±0.8% at 50° C., 55° C., 60° C., or 65° C., respectively.

The present invention is further described by the following numbered paragraphs:

[1] A variant, comprising a substitution at one or more positions corresponding to positions 90, 131, 134, and 141 of the mature polypeptide of SEQ ID NO: 2, wherein the variant has cellulolytic enhancing activity.

[2] The variant of paragraph 1, which is a variant of a parent polypeptide having cellulolytic enhancing activity selected from the group consisting of: (a) a polypeptide having at least 60% sequence identity to the mature polypeptide of SEQ ID NO: 2; (b) a polypeptide encoded by a polynucleotide that hybridizes under at least low stringency conditions with (i) the mature polypeptide coding sequence of SEQ ID NO: 1, (ii) the cDNA sequence thereof, or (iii) the full-length complement of (i) or (ii); (c) a polypeptide encoded by a polynucleotide having at least 60% sequence identity to the mature polypeptide coding sequence of SEQ ID NO: 1 or the cDNA sequence thereof; and (d) a fragment of the mature polypeptide of SEQ ID NO: 2, which has cellulolytic enhancing activity.

[3] The variant of paragraph 2, wherein the parent polypeptide having cellulolytic enhancing activity has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 2.

[4] The variant of paragraph 2, wherein the parent polypeptide having cellulolytic enhancing activity is encoded by a polynucleotide that hybridizes under low stringency conditions, medium stringency conditions, medium-high stringency conditions, high stringency conditions, or very high stringency conditions with (i) the mature polypeptide coding sequence of SEQ ID NO: 1, (ii) the cDNA sequence thereof, or (iii) the full-length complement of (i) or (ii).

[5] The variant of paragraph 2, wherein the parent polypeptide having cellulolytic enhancing activity is encoded by a polynucleotide having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 1 or the cDNA sequence thereof.

[6] The variant of paragraph 2, wherein the parent polypeptide having cellulolytic enhancing activity comprises or consists of the mature polypeptide of SEQ ID NO: 2.

[7] The variant of paragraph 2, wherein the parent polypeptide having cellulolytic enhancing activity is a fragment of the mature polypeptide of SEQ ID NO: 2, wherein the fragment has cellulolytic enhancing activity.

[8] The variant of paragraph 2, which has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to the amino acid sequence of the parent polypeptide having cellulolytic enhancing activity.

[9] The variant of any of paragraphs 1-8, which has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the mature polypeptide of SEQ ID NO: 2.

[10] The variant of any of paragraphs 1-9, wherein the variant consists of 200 to 220 amino acids, e.g., 205 to 220, 210 to 220, and 215 to 220 amino acids.

[11] The variant of any of paragraphs 1-10, wherein the number of substitutions is 1-4, e.g., such as 1, 2, 3, or 4 substitutions.

[12] The variant of any of paragraphs 1-11, which comprises a substitution at a position corresponding to position 90.

[13] The variant of paragraph 12, wherein the substitution is Val.

[14] The variant of any of paragraphs 1-13, which comprises a substitution at a position corresponding to position 131.

[15] The variant of paragraph 14, wherein the substitution is Ser.

[16] The variant of any of paragraphs 1-15, which comprises a substitution at a position corresponding to position 134.

[17] The variant of paragraph 16, wherein the substitution is Leu.

[18] The variant of any of paragraphs 1-17, which comprises a substitution at a position corresponding to position 141.

[19] The variant of paragraph 18, wherein the substitution is Trp.

[20] The variant of any of paragraphs 1-19, which comprises a substitution at two positions corresponding to any of positions 90, 131, 134, and 141.

[21] The variant of any of paragraphs 1-19, which comprises a substitution at three positions corresponding to any of positions 90, 131, 134, and 141.

[22] The variant of any of paragraphs 1-19, which comprises a substitution at each position corresponding to positions 90, 131, 134, and 141.

[23] The variant of any of paragraphs 1-22, which comprises or consists of one or more substitutions selected from the group consisting of L90V, D131S, M134L, and A141W.

[24] The variant of any of paragraphs 1-22, which comprises or consists of the substitutions L90V+D131S of the mature polypeptide of SEQ ID NO: 2.

[25] The variant of any of paragraphs 1-22, which comprises or consists of the substitutions L90V+M134L of the mature polypeptide of SEQ ID NO: 2.

[26] The variant of any of paragraphs 1-22, which comprises or consists of the substitutions L90V+A141W of the mature polypeptide of SEQ ID NO: 2.

[27] The variant of any of paragraphs 1-22, which comprises or consists of the substitutions D131S+M134L of the mature polypeptide of SEQ ID NO: 2.

[28] The variant of any of paragraphs 1-22, which comprises or consists of the substitutions D131S+A141W of the mature polypeptide of SEQ ID NO: 2.

[29] The variant of any of paragraphs 1-22, which comprises or consists of the substitutions M134L+A141W of the mature polypeptide of SEQ ID NO: 2.

[30] The variant of any of paragraphs 1-22, which comprises or consists of the substitutions L90V+D131S+M134L of the mature polypeptide of SEQ ID NO: 2.

[31] The variant of any of paragraphs 1-22, which comprises or consists of the substitutions L90V+D131S+A141W of the mature polypeptide of SEQ ID NO: 2.

[32] The variant of any of paragraphs 1-22, which comprises or consists of the substitutions L90V+M134L+A141W of the mature polypeptide of SEQ ID NO: 2.

[33] The variant of any of paragraphs 1-22, which comprises or consists of the substitutions D131S+M134L+A141W of the mature polypeptide of SEQ ID NO: 2.

[34] The variant of any of paragraphs 1-22, which comprises or consists of the substitutions L90V+D131S+M134L+A141W of the mature polypeptide of SEQ ID NO: 2.

[35] An isolated polynucleotide encoding the variant of any of paragraphs 1-34.

[36] A nucleic acid construct comprising the polynucleotide of paragraph 35.

[37] An expression vector comprising the polynucleotide of paragraph 35.

[38] A host cell comprising the polynucleotide of paragraph 35.

[39] A method of producing a variant, comprising: (a) cultivating the host cell of paragraph 38 under conditions suitable for the expression of the variant; and (b) recovering the variant.

[40] A transgenic plant, plant part or plant cell transformed with the polynucleotide of paragraph 35.

[41] A method of producing the variant of any of paragraphs 1-34, comprising: (a) cultivating a transgenic plant or a plant cell comprising a polynucleotide encoding the variant under conditions conducive for production of the variant; and (b) recovering the variant.

[42] A method for obtaining a variant, comprising introducing into a parent polypeptide a substitution at one or more positions corresponding to positions 90, 131, 134, and 141 of the mature polypeptide of SEQ ID NO: 2, wherein the variant has cellulolytic enhancing activity; and recovering the variant.

[43] A method for degrading or converting a cellulosic material, comprising: treating the cellulosic material with an enzyme composition in the presence of the variant of any of paragraphs 1-34.

[44] The method of paragraph 43, wherein the cellulosic material is pretreated.

[45] The method of paragraph 43 or 44, further comprising recovering the degraded cellulosic material.

[46] The method of any of paragraphs 43-45, wherein the enzyme composition comprises one or more enzymes selected from the group consisting of a cellulase, a polypeptide having cellulolytic enhancing activity, a hemicellulase, an expansin, an esterase, a laccase, a ligninolytic enzyme, a pectinase, a peroxidase, a protease, and a swollenin.

[47] The method of paragraph 46, wherein the cellulase is one or more enzymes selected from the group consisting of an endoglucanase, a cellobiohydrolase, and a beta-glucosidase.

[48] The method of paragraph 46, wherein the hemicellulase is one or more enzymes selected from the group consisting of a xylanase, an acetylxylan esterase, a feruloyl esterase, an arabinofuranosidase, a xylosidase, and a glucuronidase.

[49] The method of any of paragraphs 43-48, wherein the degraded cellulosic material is a sugar.

[50] The method of paragraph 49, wherein the sugar is selected from the group consisting of glucose, xylose, mannose, galactose, and arabinose.

[51] A method for producing a fermentation product, comprising: (a) saccharifying a cellulosic material with an enzyme composition in the presence of the variant of any of paragraphs 1-34; (b) fermenting the saccharified cellulosic material with one or more fermenting microorganisms to produce the fermentation product; and (c) recovering the fermentation product from the fermentation.

[52] The method of paragraph 51, wherein the cellulosic material is pretreated.

[53] The method of paragraph 51 or 52, wherein the enzyme composition comprises one or more enzymes selected from the group consisting of a cellulase, a polypeptide having cellulolytic enhancing activity, a hemicellulase, an expansin, an esterase, a laccase, a ligninolytic enzyme, a pectinase, a peroxidase, a protease, and a swollenin.

[54] The method of paragraph 53, wherein the cellulase is one or more enzymes selected from the group consisting of an endoglucanase, a cellobiohydrolase, and a beta-glucosidase.

[55] The method of paragraph 53, wherein the hemicellulase is one or more enzymes selected from the group consisting of a xylanase, an acetylxylan esterase, a feruloyl esterase, an arabinofuranosidase, a xylosidase, and a glucuronidase.

[56] The method of any of paragraphs 51-55, wherein steps (a) and (b) are performed simultaneously in a simultaneous saccharification and fermentation.

[57] The method of any of paragraphs 51-56, wherein the fermentation product is an alcohol, an organic acid, a ketone, an amino acid, or a gas.

[58] A method of fermenting a cellulosic material, comprising: fermenting the cellulosic material with one or more fermenting microorganisms, wherein the cellulosic material is saccharified with an enzyme composition in the presence of the variant of any of paragraphs 1-34.

[59] The method of paragraph 58, wherein the cellulosic material is pretreated before saccharification.

[60] The method of paragraph 58 or 59, wherein the enzyme composition comprises one or more enzymes selected from the group consisting of a cellulase, a polypeptide having cellulolytic enhancing activity, a hemicellulase, an expansin, an esterase, a laccase, a ligninolytic enzyme, a pectinase, a peroxidase, a protease, and a swollenin.

[61] The method of paragraph 60, wherein the cellulase is one or more enzymes selected from the group consisting of an endoglucanase, a cellobiohydrolase, and a beta-glucosidase.

[62] The method of paragraph 60, wherein the hemicellulase is one or more enzymes selected from the group consisting of a xylanase, an acetylxylan esterase, a feruloyl esterase, an arabinofuranosidase, a xylosidase, and a glucuronidase.

[63] The method of any of paragraphs 58-62, wherein the fermenting of the cellulosic material produces a fermentation product.

[64] The method of paragraph 63, further comprising recovering the fermentation product from the fermentation.

[65] The method of any of paragraphs 63 or 64, wherein the fermentation product is an alcohol, an organic acid, a ketone, an amino acid, or a gas.

[66] A detergent composition comprising the variant of any of paragraphs 1-34 and a surfactant.

[67] A whole broth formulation or cell culture composition comprising the variant of any of paragraphs 1-34.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. A variant of a parent GH61 polypeptide having cellulolytic enhancing activity, comprising a substitution at one or more positions corresponding to positions 90, 131, 134, and 141 of the full-length polypeptide of SEQ ID NO: 2, wherein the substitution at a position corresponding to position 90 is with Val, the substitution at a position corresponding to position 131 is with Ser, the substitution at a position corresponding to position 134 is with Leu, and the substitution at a position corresponding to position 141 is with Trp, wherein the variant has cellulolytic enhancing activity and increased thermal activity and/or increased thermostability, and wherein the variant has
at least 95% sequence identity to the mature polypeptide of SEQ ID NO: 2.

2. The variant of claim 1, which comprises one or more substitutions selected from the group consisting of L90V, D131S, M134L, and A141W.

3. The variant of claim 1, which comprises the substitutions L90V+D131S+M134L+A141W of the mature polypeptide of SEQ ID NO: 2.

4. An isolated polynucleotide encoding the variant of claim 1.

5. An isolated recombinant host cell transformed with the polynucleotide of claim 4.

6. A method of producing a variant, comprising:
(a) cultivating the recombinant host cell of claim 5 under conditions suitable for the expression of the variant; and
(b) recovering the variant.

7. A transgenic plant, plant part or plant cell transformed with the polynucleotide of claim 4.

8. A method of producing the variant of claim 1, comprising:
(a) cultivating a transgenic plant or a plant cell comprising a polynucleotide encoding the variant under conditions conducive for production of the variant; and
(b) recovering the variant.

9. A method for obtaining a variant of a parent GH61 polypeptide having cellulolytic enhancing activity, comprising introducing into the parent GH61 polypeptide a substitution at one or more positions corresponding to positions 90, 131, 134, and 141 of the full-length polypeptide of SEQ ID NO: 2, wherein the substitution at a position corresponding to position 90 is with Val, the substitution at a position corresponding to position 131 is with Ser, the substitution at a position corresponding to position 134 is with Leu, and the substitution at a position corresponding to position 141 is with Trp, wherein the variant has cellulolytic enhancing activity and increased thermal activity and/or increased thermostability, and wherein the variant has
at least 95% sequence identity to the mature polypeptide of SEQ ID NO: 2.

10. A method for degrading a cellulosic material, comprising: treating the cellulosic material with an enzyme composition comprising the variant of claim 1.

11. The method of claim 10, further comprising recovering the degraded cellulosic material.

12. A method for producing a fermentation product, comprising:
(a) saccharifying a cellulosic material with an enzyme composition comprising the variant of claim 1;
(b) fermenting the saccharified cellulosic material with one or more fermenting microorganisms to produce the fermentation product; and
(c) recovering the fermentation product from the fermentation.

13. A method of fermenting a cellulosic material, comprising: fermenting the cellulosic material with one or more fermenting microorganisms, wherein the cellulosic material is saccharified with an enzyme composition comprising the variant of claim 1.

14. The method of claim 13, wherein the fermenting of the cellulosic material produces a fermentation product.

15. The method of claim 14, further comprising recovering the fermentation product from the fermentation.

16. A detergent composition comprising the variant of claim 1 and a surfactant.

17. A whole broth formulation or cell culture composition comprising the variant of claim 1.

18. The variant of claim 1, wherein the variant has at least 96% sequence identity to the mature polypeptide of SEQ ID NO: 2.

19. The variant of claim 1, wherein the variant has at least 97% sequence identity to the mature polypeptide of SEQ ID NO: 2.

20. The variant of claim 1, which comprises a substitution at two positions corresponding to any of positions 90, 131, 134, and 141.

21. The variant of claim 1, which comprises a substitution at three positions corresponding to any of positions 90, 131, 134, and 141.

22. The variant of claim 1, which comprises a substitution at each position corresponding to positions 90, 131, 134, and 141.

23. The method of claim 10, wherein the enzyme composition further comprises one or more enzymes selected from the group consisting of a cellulase, a polypeptide having cellulolytic enhancing activity, a hemicellulase, an expansin, an esterase, a laccase, a ligninolytic enzyme, a pectinase, a peroxidase, a protease, and a swollenin.

24. The method of claim 12, wherein the enzyme composition further comprises one or more enzymes selected from the group consisting of a cellulase, a polypeptide having cellulolytic enhancing activity, a hemicellulase, an expansin, an esterase, a laccase, a ligninolytic enzyme, a pectinase, a peroxidase, a protease, and a swollenin.

25. The method of claim 13, wherein the enzyme composition further comprises one or more enzymes selected from the group consisting of a cellulase, a polypeptide having cellulolytic enhancing activity, a hemicellulase, an expansin, an esterase, a laccase, a ligninolytic enzyme, a pectinase, a peroxidase, a protease, and a swollenin.

26. The variant of claim 1, wherein the variant has at least 98% sequence identity to the mature polypeptide of SEQ ID NO: 2.

27. The variant of claim 1, wherein the variant has at least 99% sequence identity to the mature polypeptide of SEQ ID NO: 2.

* * * * *

SEQUENCE LISTING

```
<160> NUMBER OF SEQ ID NOS: 94

<210> SEQ ID NO 1
<211> LENGTH: 862
<212> TYPE: DNA
<213> ORGANISM: Aspergillus fumigatus

<400> SEQUENCE: 1

atgactttgt ccaagatcac ttccattgct ggccttctgg cctcagcgtc tctcgtggct      60

ggccacggct ttgtttctgg cattgttgct gatgggaaat agtatgtgct tgaaccacac     120

aaatgacagc tgcaacagct aacttctatt ccagttacgg agggtacctt gttaaccaat     180

acccctacat gagcaaccct cccgacacca ttgcctggtc caccaccgcc accgacctcg     240

gctttgtgga cggcaccggc taccagtctc cggatattat ctgccacaga gacgcaaaga     300

atggcaagtt gaccgcaacc gttgcagccg gttcacagat cgaattccag tggacgacgt     360

ggccagagtc tcaccatgga ccggtacgac gccgaagaga agagaacata ttgtgaccag     420

ataggctaac atagcatagt tgattactta cctcgctcca tgcaacggcg actgtgccac     480

cgtggacaag accaccctga agtttgtcaa gatcgccgct caaggcttga tcgacggctc     540

caacccacct ggtgtttggg ctgatgatga aatgatcgcc aacaacaaca cggccacagt     600

gaccattcct gcctcctatg cccccggaaa ctacgtcctt cgccacgaga tcatcgccct     660

tcactctgcg ggtaacctga acggcgcgca gaactacccc cagtgtttca acatccaaat     720

caccggtggc ggcagtgctc agggatctgg caccgctggc acgtccctgt acaagaatac     780

tgatcctggc atcaagtttg acatctactc ggatctgagc ggtggatacc ctattcctgg     840
```

```
tcctgcactg ttcaacgctt aa                                          862


<210> SEQ ID NO 2
<211> LENGTH: 250
<212> TYPE: PRT
<213> ORGANISM: Aspergillus fumigatus
<220> FEATURE:
<221> NAME/KEY: SIGNAL
<222> LOCATION: (1)..(21)
<220> FEATURE:
<221> NAME/KEY: mat_peptide
<222> LOCATION: (22)..(250)

<400> SEQUENCE: 2

Met Thr Leu Ser Lys Ile Thr Ser Ile Ala Gly Leu Leu Ala Ser Ala
    -20                 -15                 -10

Ser Leu Val Ala Gly His Gly Phe Val Ser Gly Ile Val Ala Asp Gly
-5              -1  1               5                   10

Lys Tyr Tyr Gly Gly Tyr Leu Val Asn Gln Tyr Pro Tyr Met Ser Asn
            15                  20                  25

Pro Pro Asp Thr Ile Ala Trp Ser Thr Thr Ala Thr Asp Leu Gly Phe
        30                  35                  40

Val Asp Gly Thr Gly Tyr Gln Ser Pro Asp Ile Ile Cys His Arg Asp
    45                  50                  55

Ala Lys Asn Gly Lys Leu Thr Ala Thr Val Ala Ala Gly Ser Gln Ile
60                  65                  70                  75

Glu Phe Gln Trp Thr Thr Trp Pro Glu Ser His His Gly Pro Leu Ile
                80                  85                  90

Thr Tyr Leu Ala Pro Cys Asn Gly Asp Cys Ala Thr Val Asp Lys Thr
            95                  100                 105

Thr Leu Lys Phe Val Lys Ile Ala Ala Gln Gly Leu Ile Asp Gly Ser
        110                 115                 120

Asn Pro Pro Gly Val Trp Ala Asp Asp Glu Met Ile Ala Asn Asn Asn
    125                 130                 135

Thr Ala Thr Val Thr Ile Pro Ala Ser Tyr Ala Pro Gly Asn Tyr Val
140                 145                 150                 155

Leu Arg His Glu Ile Ile Ala Leu His Ser Ala Gly Asn Leu Asn Gly
                160                 165                 170

Ala Gln Asn Tyr Pro Gln Cys Phe Asn Ile Gln Ile Thr Gly Gly Gly
            175                 180                 185

Ser Ala Gln Gly Ser Gly Thr Ala Gly Thr Ser Leu Tyr Lys Asn Thr
        190                 195                 200

Asp Pro Gly Ile Lys Phe Asp Ile Tyr Ser Asp Leu Ser Gly Gly Tyr
    205                 210                 215

Pro Ile Pro Gly Pro Ala Leu Phe Asn Ala
220                 225


<210> SEQ ID NO 3
<211> LENGTH: 1377
<212> TYPE: DNA
<213> ORGANISM: Trichoderma reesei

<400> SEQUENCE: 3

atggcgccct cagttacact gccgttgacc acggccatcc tggccattgc ccggctcgtc      60

gccgcccagc aaccgggtac cagcaccccc gaggtccatc ccaagttgac aacctacaag     120

tgtacaaagt ccgggggggtg cgtggcccag gacacctcgg tggtccttga ctggaactac    180

cgctggatgc acgacgcaaa ctacaactcg tgcaccgtca acggcggcgt caacaccacg     240
```

```
ctctgccctg acgaggcgac ctgtggcaag aactgcttca tcgagggcgt cgactacgcc     300

gcctcgggcg tcacgacctc gggcagcagc ctcaccatga accagtacat gcccagcagc     360

tctggcggct acagcagcgt ctctcctcgg ctgtatctcc tggactctga cggtgagtac     420

gtgatgctga agctcaacgg ccaggagctg agcttcgacg tcgacctctc tgctctgccg     480

tgtggagaga acggctcgct ctacctgtct cagatggacg agaacggggg cgccaaccag     540

tataacacgg ccggtgccaa ctacgggagc ggctactgcg atgctcagtg ccccgtccag     600

acatggagga acggcaccct caacactagc caccagggct tctgctgcaa cgagatggat     660

atcctggagg gcaactcgag ggcgaatgcc ttgacccctc actcttgcac ggccacggcc     720

tgcgactctg ccggttgcgg cttcaacccc tatggcagcg gctacaaaag ctactacggc     780

cccggagata ccgttgacac ctccaagacc ttcaccatca tcacccagtt caacacggac     840

aacggctcgc cctcgggcaa ccttgtgagc atcacccgca agtaccagca aaacggcgtc     900

gacatcccca gcgcccagcc cggcggcgac accatctcgt cctgcccgtc cgcctcagcc     960

tacggcggcc tcgccaccat gggcaaggcc ctgagcagcg gcatggtgct cgtgttcagc    1020

atttggaacg acaacagcca gtacatgaac tggctcgaca gcggcaacgc cggcccctgc    1080

agcagcaccg agggcaaccc atccaacatc ctggccaaca accccaacac gcacgtcgtc    1140

ttctccaaca tccgctgggg agacattggg tctactacga actcgactgc gcccccgccc    1200

ccgcctgcgt ccagcacgac gttttcgact acacggagga gctcgacgac ttcgagcagc    1260

ccgagctgca cgcagactca ctgggggcag tgcggtggca ttgggtacag cgggtgcaag    1320

acgtgcacgt cgggcactac gtgccagtat agcaacgact actactcgca atgcctt       1377
```

<210> SEQ ID NO 4
<211> LENGTH: 459
<212> TYPE: PRT
<213> ORGANISM: Trichoderma reesei

<400> SEQUENCE: 4

```
Met Ala Pro Ser Val Thr Leu Pro Leu Thr Thr Ala Ile Leu Ala Ile
1               5                   10                  15

Ala Arg Leu Val Ala Ala Gln Gln Pro Gly Thr Ser Thr Pro Glu Val
            20                  25                  30

His Pro Lys Leu Thr Thr Tyr Lys Cys Thr Lys Ser Gly Gly Cys Val
        35                  40                  45

Ala Gln Asp Thr Ser Val Val Leu Asp Trp Asn Tyr Arg Trp Met His
    50                  55                  60

Asp Ala Asn Tyr Asn Ser Cys Thr Val Asn Gly Gly Val Asn Thr Thr
65                  70                  75                  80

Leu Cys Pro Asp Glu Ala Thr Cys Gly Lys Asn Cys Phe Ile Glu Gly
                85                  90                  95

Val Asp Tyr Ala Ala Ser Gly Val Thr Thr Ser Gly Ser Ser Leu Thr
            100                 105                 110

Met Asn Gln Tyr Met Pro Ser Ser Ser Gly Gly Tyr Ser Ser Val Ser
        115                 120                 125

Pro Arg Leu Tyr Leu Leu Asp Ser Asp Gly Glu Tyr Val Met Leu Lys
    130                 135                 140

Leu Asn Gly Gln Glu Leu Ser Phe Asp Val Asp Leu Ser Ala Leu Pro
145                 150                 155                 160

Cys Gly Glu Asn Gly Ser Leu Tyr Leu Ser Gln Met Asp Glu Asn Gly
                165                 170                 175
```

```
Gly Ala Asn Gln Tyr Asn Thr Ala Gly Ala Asn Tyr Gly Ser Gly Tyr
            180                 185                 190

Cys Asp Ala Gln Cys Pro Val Gln Thr Trp Arg Asn Gly Thr Leu Asn
        195                 200                 205

Thr Ser His Gln Gly Phe Cys Cys Asn Glu Met Asp Ile Leu Glu Gly
    210                 215                 220

Asn Ser Arg Ala Asn Ala Leu Thr Pro His Ser Cys Thr Ala Thr Ala
225                 230                 235                 240

Cys Asp Ser Ala Gly Cys Gly Phe Asn Pro Tyr Gly Ser Gly Tyr Lys
                245                 250                 255

Ser Tyr Tyr Gly Pro Gly Asp Thr Val Asp Thr Ser Lys Thr Phe Thr
            260                 265                 270

Ile Ile Thr Gln Phe Asn Thr Asp Asn Gly Ser Pro Ser Gly Asn Leu
        275                 280                 285

Val Ser Ile Thr Arg Lys Tyr Gln Gln Asn Gly Val Asp Ile Pro Ser
    290                 295                 300

Ala Gln Pro Gly Gly Asp Thr Ile Ser Ser Cys Pro Ser Ala Ser Ala
305                 310                 315                 320

Tyr Gly Gly Leu Ala Thr Met Gly Lys Ala Leu Ser Ser Gly Met Val
                325                 330                 335

Leu Val Phe Ser Ile Trp Asn Asp Asn Ser Gln Tyr Met Asn Trp Leu
            340                 345                 350

Asp Ser Gly Asn Ala Gly Pro Cys Ser Ser Thr Glu Gly Asn Pro Ser
        355                 360                 365

Asn Ile Leu Ala Asn Asn Pro Asn Thr His Val Val Phe Ser Asn Ile
    370                 375                 380

Arg Trp Gly Asp Ile Gly Ser Thr Thr Asn Ser Thr Ala Pro Pro Pro
385                 390                 395                 400

Pro Pro Ala Ser Ser Thr Thr Phe Ser Thr Thr Arg Arg Ser Ser Thr
                405                 410                 415

Thr Ser Ser Ser Pro Ser Cys Thr Gln Thr His Trp Gly Gln Cys Gly
            420                 425                 430

Gly Ile Gly Tyr Ser Gly Cys Lys Thr Cys Thr Ser Gly Thr Thr Cys
        435                 440                 445

Gln Tyr Ser Asn Asp Tyr Tyr Ser Gln Cys Leu
    450                 455
```

<210> SEQ ID NO 5
<211> LENGTH: 1254
<212> TYPE: DNA
<213> ORGANISM: Trichoderma reesei

<400> SEQUENCE: 5

```
atgaacaagt ccgtggctcc attgctgctt gcagcgtcca tactatatgg cggcgccgtc      60

gcacagcaga ctgtctgggg ccagtgtgga ggtattggtt ggagcggacc tacgaattgt     120

gctcctggct cagcttgttc gaccctcaat ccttattatg cgcaatgtat tccgggagcc     180

actactatca ccacttcgac ccggccacca tccggtccaa ccaccaccac cagggctacc     240

tcaacaagct catcaactcc acccacgagc tctggggtcc gatttgccgg cgttaacatc     300

gcgggttttg actttggctg taccacagat ggcacttgcg ttacctcgaa ggtttatcct     360

ccgttgaaga acttcaccgg ctcaaacaac taccccgatg gcatcggcca gatgcagcac     420

ttcgtcaacg aggacgggat gactattttc cgcttacctg tcggatggca gtacctcgtc     480
```

```
aacaacaatt tgggcggcaa tcttgattcc acgagcattt ccaagtatga tcagcttgtt    540

caggggtgcc tgtctctggg cgcatactgc atcgtcgaca tccacaatta tgctcgatgg    600

aacggtggga tcattggtca gggcggccct actaatgctc aattcacgag cctttggtcg    660

cagttggcat caaagtacgc atctcagtcg agggtgtggt tcggcatcat gaatgagccc    720

cacgacgtga acatcaacac ctgggctgcc acggtccaag aggttgtaac cgcaatccgc    780

aacgctggtg ctacgtcgca attcatctct ttgcctggaa atgattggca atctgctggg    840

gctttcatat ccgatggcag tgcagccgcc ctgtctcaag tcacgaaccc ggatgggtca    900

acaacgaatc tgatttttga cgtgcacaaa tacttggact cagacaactc cggtactcac    960

gccgaatgta ctacaaataa cattgacggc gccttttctc cgcttgccac ttggctccga   1020

cagaacaatc gccaggctat cctgacagaa accggtggtg gcaacgttca gtcctgcata   1080

caagacatgt gccagcaaat ccaatatctc aaccagaact cagatgtcta tcttggctat   1140

gttggttggg gtgccggatc atttgatagc acgtatgtcc tgacggaaac accgactagc   1200

agtggtaact catggacgga cacatccttg gtcagctcgt gtctcgcaag aaag         1254


<210> SEQ ID NO 6
<211> LENGTH: 418
<212> TYPE: PRT
<213> ORGANISM: Trichoderma reesei

<400> SEQUENCE: 6

Met Asn Lys Ser Val Ala Pro Leu Leu Leu Ala Ala Ser Ile Leu Tyr
1               5                   10                  15

Gly Gly Ala Val Ala Gln Gln Thr Val Trp Gly Gln Cys Gly Gly Ile
            20                  25                  30

Gly Trp Ser Gly Pro Thr Asn Cys Ala Pro Gly Ser Ala Cys Ser Thr
        35                  40                  45

Leu Asn Pro Tyr Tyr Ala Gln Cys Ile Pro Gly Ala Thr Thr Ile Thr
    50                  55                  60

Thr Ser Thr Arg Pro Pro Ser Gly Pro Thr Thr Thr Thr Arg Ala Thr
65                  70                  75                  80

Ser Thr Ser Ser Ser Thr Pro Pro Thr Ser Ser Gly Val Arg Phe Ala
                85                  90                  95

Gly Val Asn Ile Ala Gly Phe Asp Phe Gly Cys Thr Thr Asp Gly Thr
            100                 105                 110

Cys Val Thr Ser Lys Val Tyr Pro Pro Leu Lys Asn Phe Thr Gly Ser
        115                 120                 125

Asn Asn Tyr Pro Asp Gly Ile Gly Gln Met Gln His Phe Val Asn Glu
    130                 135                 140


Asp Gly Met Thr Ile Phe Arg Leu Pro Val Gly Trp Gln Tyr Leu Val
145                 150                 155                 160

Asn Asn Asn Leu Gly Gly Asn Leu Asp Ser Thr Ser Ile Ser Lys Tyr
                165                 170                 175

Asp Gln Leu Val Gln Gly Cys Leu Ser Leu Gly Ala Tyr Cys Ile Val
            180                 185                 190

Asp Ile His Asn Tyr Ala Arg Trp Asn Gly Gly Ile Ile Gly Gln Gly
        195                 200                 205

Gly Pro Thr Asn Ala Gln Phe Thr Ser Leu Trp Ser Gln Leu Ala Ser
    210                 215                 220

Lys Tyr Ala Ser Gln Ser Arg Val Trp Phe Gly Ile Met Asn Glu Pro
225                 230                 235                 240
```

```
His Asp Val Asn Ile Asn Thr Trp Ala Ala Thr Val Gln Glu Val Val
                245                 250                 255

Thr Ala Ile Arg Asn Ala Gly Ala Thr Ser Gln Phe Ile Ser Leu Pro
            260                 265                 270

Gly Asn Asp Trp Gln Ser Ala Gly Ala Phe Ile Ser Asp Gly Ser Ala
        275                 280                 285

Ala Ala Leu Ser Gln Val Thr Asn Pro Asp Gly Ser Thr Thr Asn Leu
    290                 295                 300

Ile Phe Asp Val His Lys Tyr Leu Asp Ser Asp Asn Ser Gly Thr His
305                 310                 315                 320

Ala Glu Cys Thr Thr Asn Asn Ile Asp Gly Ala Phe Ser Pro Leu Ala
                325                 330                 335

Thr Trp Leu Arg Gln Asn Asn Arg Gln Ala Ile Leu Thr Glu Thr Gly
            340                 345                 350

Gly Gly Asn Val Gln Ser Cys Ile Gln Asp Met Cys Gln Gln Ile Gln
        355                 360                 365

Tyr Leu Asn Gln Asn Ser Asp Val Tyr Leu Gly Tyr Val Gly Trp Gly
    370                 375                 380

Ala Gly Ser Phe Asp Ser Thr Tyr Val Leu Thr Glu Thr Pro Thr Ser
385                 390                 395                 400

Ser Gly Asn Ser Trp Thr Asp Thr Ser Leu Val Ser Ser Cys Leu Ala
                405                 410                 415

Arg Lys


<210> SEQ ID NO 7
<211> LENGTH: 702
<212> TYPE: DNA
<213> ORGANISM: Trichoderma reesei

<400> SEQUENCE: 7

atgaagttcc ttcaagtcct ccctgccctc ataccggccg ccctggccca aaccagctgt      60

gaccagtggg caaccttcac tggcaacggc tacacagtca gcaacaacct ttggggagca     120

tcagccggct ctggatttgg ctgcgtgacg gcggtatcgc tcagcggcgg ggcctcctgg     180

cacgcagact ggcagtggtc cggcggccag aacaacgtca agtcgtacca gaactctcag     240

attgccattc cccagaagag gaccgtcaac agcatcagca gcatgcccac cactgccagc     300

tggagctaca gcgggagcaa catccgcgct aatgttgcgt atgacttgtt caccgcagcc     360

aacccgaatc atgtcacgta ctcgggagac tacgaactca tgatctggct tggcaaatac     420

ggcgatattg ggccgattgg gtcctcacag ggaacagtca acgtcggtgg ccagagctgg     480

acgctctact atggctacaa cggagccatg caagtctatt cctttgtggc ccagaccaac     540

actaccaact acagcggaga tgtcaagaac ttcttcaatt atctccgaga caataaagga     600

tacaacgctg caggccaata tgttcttagc taccaatttg gtaccgagcc cttcacgggc     660

agtggaactc tgaacgtcgc atcctggacc gcatctatca ac                        702


<210> SEQ ID NO 8
<211> LENGTH: 234
<212> TYPE: PRT
<213> ORGANISM: Trichoderma reesei

<400> SEQUENCE: 8

Met Lys Phe Leu Gln Val Leu Pro Ala Leu Ile Pro Ala Ala Leu Ala
1               5                   10                  15
```

```
Gln Thr Ser Cys Asp Gln Trp Ala Thr Phe Thr Gly Asn Gly Tyr Thr
            20                  25                  30

Val Ser Asn Asn Leu Trp Gly Ala Ser Ala Gly Ser Gly Phe Gly Cys
        35                  40                  45

Val Thr Ala Val Ser Leu Ser Gly Gly Ala Ser Trp His Ala Asp Trp
    50                  55                  60

Gln Trp Ser Gly Gly Gln Asn Asn Val Lys Ser Tyr Gln Asn Ser Gln
65                  70                  75                  80

Ile Ala Ile Pro Gln Lys Arg Thr Val Asn Ser Ile Ser Ser Met Pro
                85                  90                  95

Thr Thr Ala Ser Trp Ser Tyr Ser Gly Ser Asn Ile Arg Ala Asn Val
            100                 105                 110

Ala Tyr Asp Leu Phe Thr Ala Ala Asn Pro Asn His Val Thr Tyr Ser
        115                 120                 125

Gly Asp Tyr Glu Leu Met Ile Trp Leu Gly Lys Tyr Gly Asp Ile Gly
    130                 135                 140

Pro Ile Gly Ser Ser Gln Gly Thr Val Asn Val Gly Gly Gln Ser Trp
145                 150                 155                 160

Thr Leu Tyr Tyr Gly Tyr Asn Gly Ala Met Gln Val Tyr Ser Phe Val
                165                 170                 175

Ala Gln Thr Asn Thr Thr Asn Tyr Ser Gly Asp Val Lys Asn Phe Phe
            180                 185                 190

Asn Tyr Leu Arg Asp Asn Lys Gly Tyr Asn Ala Ala Gly Gln Tyr Val
        195                 200                 205

Leu Ser Tyr Gln Phe Gly Thr Glu Pro Phe Thr Gly Ser Gly Thr Leu
    210                 215                 220

Asn Val Ala Ser Trp Thr Ala Ser Ile Asn
225                 230
```

<210> SEQ ID NO 9
<211> LENGTH: 726
<212> TYPE: DNA
<213> ORGANISM: Trichoderma reesei

<400> SEQUENCE: 9

```
atgaaggcaa ctctggttct cggctccctc attgtaggcg ccgtttccgc gtacaaggcc      60

accaccacgc gctactacga tgggcaggag ggtgcttgcg gatgcggctc gagctccggc     120

gcattcccgt ggcagctcgg catcggcaac ggagtctaca cggctgccgg ctcccaggct     180

ctcttcgaca cggccggagc ttcatggtgc ggcgccggct gcggtaaatg ctaccagctc     240

acctcgacgg gccaggcgcc ctgctccagc tgcggcacgg gcggtgctgc tggccagagc     300

atcatcgtca tggtgaccaa cctgtgcccg aacaatggga acgcgcagtg gtgcccggtg     360

gtcggcggca ccaaccaata cggctacagc taccatttcg acatcatggc gcagaacgag     420

atctttggag acaatgtcgt cgtcgacttt gagcccattg cttgccccgg gcaggctgcc     480

tctgactggg ggacgtgcct ctgcgtggga cagcaagaga cggatcccac gcccgtcctc     540

ggcaacgaca cgggctcaac tcctcccggg agctcgccgc cagcgacatc gtcgagtccg     600

ccgtctggcg gcggccagca gacgctctat ggccagtgtg gaggtgccgg ctggacggga     660

cctacgacgt gccaggcccc agggacctgc aaggttcaga accagtggta ctcccagtgt     720

cttcct                                                                726
```

<210> SEQ ID NO 10
<211> LENGTH: 242

<212> TYPE: PRT
<213> ORGANISM: Trichoderma reesei

<400> SEQUENCE: 10

```
Met Lys Ala Thr Leu Val Leu Gly Ser Leu Ile Val Gly Ala Val Ser
1               5                   10                  15

Ala Tyr Lys Ala Thr Thr Thr Arg Tyr Tyr Asp Gly Gln Glu Gly Ala
            20                  25                  30

Cys Gly Cys Gly Ser Ser Ser Gly Ala Phe Pro Trp Gln Leu Gly Ile
        35                  40                  45

Gly Asn Gly Val Tyr Thr Ala Ala Gly Ser Gln Ala Leu Phe Asp Thr
    50                  55                  60

Ala Gly Ala Ser Trp Cys Gly Ala Gly Cys Gly Lys Cys Tyr Gln Leu
65                  70                  75                  80

Thr Ser Thr Gly Gln Ala Pro Cys Ser Ser Cys Gly Thr Gly Gly Ala
                85                  90                  95

Ala Gly Gln Ser Ile Ile Val Met Val Thr Asn Leu Cys Pro Asn Asn
            100                 105                 110

Gly Asn Ala Gln Trp Cys Pro Val Val Gly Gly Thr Asn Gln Tyr Gly
        115                 120                 125

Tyr Ser Tyr His Phe Asp Ile Met Ala Gln Asn Glu Ile Phe Gly Asp
    130                 135                 140

Asn Val Val Val Asp Phe Glu Pro Ile Ala Cys Pro Gly Gln Ala Ala
145                 150                 155                 160

Ser Asp Trp Gly Thr Cys Leu Cys Val Gly Gln Gln Glu Thr Asp Pro
                165                 170                 175

Thr Pro Val Leu Gly Asn Asp Thr Gly Ser Thr Pro Pro Gly Ser Ser
            180                 185                 190

Pro Pro Ala Thr Ser Ser Ser Pro Pro Ser Gly Gly Gly Gln Gln Thr
        195                 200                 205

Leu Tyr Gly Gln Cys Gly Gly Ala Gly Trp Thr Gly Pro Thr Thr Cys
    210                 215                 220

Gln Ala Pro Gly Thr Cys Lys Val Gln Asn Gln Trp Tyr Ser Gln Cys
225                 230                 235                 240

Leu Pro
```

<210> SEQ ID NO 11
<211> LENGTH: 923
<212> TYPE: DNA
<213> ORGANISM: Humicola insolens

<400> SEQUENCE: 11

```
atgcgttcct ccccccctcct ccgctccgcc gttgtggccg ccctgccggt gttggccctt      60

gccgctgatg gcaggtccac ccgctactgg gactgctgca agccttcgtg cggctgggcc     120

aagaaggctc ccgtgaacca gcctgtcttt tcctgcaacg ccaacttcca gcgtatcacg     180

gacttcgacg ccaagtccgg ctgcgagccg ggcggtgtcg cctactcgtg cgccgaccag     240

accccatggg ctgtgaacga cgacttcgcg ctcggttttg ctgccacctc tattgccggc     300

agcaatgagg cgggctggtg ctgcgcctgc tacgagctca ccttcacatc cggtcctgtt     360

gctggcaaga agatggtcgt ccagtccacc agcactggcg gtgatcttgg cagcaaccac     420

ttcgatctca acatccccgg cggcggcgtc ggcatcttcg acggatgcac tccccagttc     480

ggcggtctgc ccggccagcg ctacggcggc atctcgtccc gcaacgagtg cgatcggttc     540

cccgacgccc tcaagcccgg ctgctactgg cgcttcgact ggttcaagaa cgccgacaat     600
```

```
ccgagcttca gcttccgtca ggtccagtgc ccagccgagc tcgtcgctcg caccggatgc    660

cgccgcaacg acgacggcaa cttccctgcc gtccagatcc cctccagcag caccagctct    720

ccggtcaacc agcctaccag caccagcacc acgtccacct ccaccacctc gagcccgcca    780

gtccagccta cgactcccag cggctgcact gctgagaggt gggctcagtg cggcggcaat    840

ggctggagcg gctgcaccac ctgcgtcgct ggcagcactt gcacgaagat taatgactgg    900

taccatcagt gcctgtagaa ttc                                            923
```

<210> SEQ ID NO 12
<211> LENGTH: 305
<212> TYPE: PRT
<213> ORGANISM: Humicola insolens

<400> SEQUENCE: 12

```
Met Arg Ser Ser Pro Leu Leu Arg Ser Ala Val Val Ala Ala Leu Pro
1               5                   10                  15

Val Leu Ala Leu Ala Ala Asp Gly Arg Ser Thr Arg Tyr Trp Asp Cys
            20                  25                  30

Cys Lys Pro Ser Cys Gly Trp Ala Lys Lys Ala Pro Val Asn Gln Pro
        35                  40                  45

Val Phe Ser Cys Asn Ala Asn Phe Gln Arg Ile Thr Asp Phe Asp Ala
    50                  55                  60

Lys Ser Gly Cys Glu Pro Gly Gly Val Ala Tyr Ser Cys Ala Asp Gln
65                  70                  75                  80

Thr Pro Trp Ala Val Asn Asp Asp Phe Ala Leu Gly Phe Ala Ala Thr
                85                  90                  95

Ser Ile Ala Gly Ser Asn Glu Ala Gly Trp Cys Cys Ala Cys Tyr Glu
            100                 105                 110

Leu Thr Phe Thr Ser Gly Pro Val Ala Gly Lys Lys Met Val Val Gln
        115                 120                 125

Ser Thr Ser Thr Gly Gly Asp Leu Gly Ser Asn His Phe Asp Leu Asn
    130                 135                 140

Ile Pro Gly Gly Gly Val Gly Ile Phe Asp Gly Cys Thr Pro Gln Phe
145                 150                 155                 160

Gly Gly Leu Pro Gly Gln Arg Tyr Gly Gly Ile Ser Ser Arg Asn Glu
                165                 170                 175

Cys Asp Arg Phe Pro Asp Ala Leu Lys Pro Gly Cys Tyr Trp Arg Phe
            180                 185                 190

Asp Trp Phe Lys Asn Ala Asp Asn Pro Ser Phe Ser Phe Arg Gln Val
        195                 200                 205

Gln Cys Pro Ala Glu Leu Val Ala Arg Thr Gly Cys Arg Arg Asn Asp
    210                 215                 220

Asp Gly Asn Phe Pro Ala Val Gln Ile Pro Ser Ser Ser Thr Ser Ser
225                 230                 235                 240

Pro Val Asn Gln Pro Thr Ser Thr Ser Thr Thr Ser Thr Ser Thr Thr
                245                 250                 255

Ser Ser Pro Pro Val Gln Pro Thr Thr Pro Ser Gly Cys Thr Ala Glu
            260                 265                 270

Arg Trp Ala Gln Cys Gly Gly Asn Gly Trp Ser Gly Cys Thr Thr Cys
        275                 280                 285

Val Ala Gly Ser Thr Cys Thr Lys Ile Asn Asp Trp Tyr His Gln Cys
    290                 295                 300

Leu
```

305

<210> SEQ ID NO 13
<211> LENGTH: 1188
<212> TYPE: DNA
<213> ORGANISM: Myceliophthora thermophila

<400> SEQUENCE: 13
cgacttgaaa cgccccaaat gaagtcctcc atcctcgcca gcgtcttcgc cacgggcgcc 60
gtggctcaaa gtggtccgtg gcagcaatgt ggtggcatcg gatggcaagg atcgaccgac 120
tgtgtgtcgg gctaccactg cgtctaccag aacgattggt acagccagtg cgtgcctggc 180
gcggcgtcga caacgctgca gacatcgacc acgtccaggc ccaccgccac cagcaccgcc 240
cctccgtcgt ccaccacctc gcctagcaag ggcaagctga agtggctcgg cagcaacgag 300
tcgggcgccg agttcgggga gggcaattac cccggcctct ggggcaagca cttcatcttc 360
ccgtcgactt cggcgattca gacgctcatc aatgatggat acaacatctt ccggatcgac 420
ttctcgatgg agcgtctggt gcccaaccag ttgacgtcgt ccttcgacca gggttacctc 480
cgcaacctga ccgaggtggt caacttcgtg acgaacgcgg gcaagtacgc cgtcctggac 540
ccgcacaact acggccggta ctacggcaac atcatcacgg acacgaacgc gttccggacc 600
ttctggacca acctggccaa gcagttcgcc tccaactcgc tcgtcatctt cgacaccaac 660
aacgagtaca acacgatgga ccagaccctg gtgctcaacc tcaaccaggc cgccatcgac 720
ggcatccggg ccgccggcgc gacctcgcag tacatcttcg tcgagggcaa cgcgtggagc 780
ggggcctgga gctggaacac gaccaacacc aacatggccg ccctgacgga cccgcagaac 840
aagatcgtgt acgagatgca ccagtacctc gactcggaca gctcgggcac ccacgccgag 900
tgcgtcagca gcaccatcgg cgcccagcgc gtcgtcggag ccacccagtg gctccgcgcc 960
aacggcaagc tcggcgtcct cggcgagttc gccggcggcg ccaacgccgt ctgccagcag 1020
gccgtcaccg gcctcctcga ccacctccag gacaacagcg acgtctggct gggtgccctc 1080
tggtgggccg ccggtccctg gtggggcgac tacatgtact cgttcgagcc tccttcgggc 1140
accggctatg tcaactacaa ctcgatcttg aagaagtact tgccgtaa 1188

<210> SEQ ID NO 14
<211> LENGTH: 389
<212> TYPE: PRT
<213> ORGANISM: Myceliophthora thermophila

<400> SEQUENCE: 14

Met Lys Ser Ser Ile Leu Ala Ser Val Phe Ala Thr Gly Ala Val Ala
1 5 10 15

Gln Ser Gly Pro Trp Gln Gln Cys Gly Gly Ile Gly Trp Gln Gly Ser
20 25 30

Thr Asp Cys Val Ser Gly Tyr His Cys Val Tyr Gln Asn Asp Trp Tyr
35 40 45

Ser Gln Cys Val Pro Gly Ala Ala Ser Thr Thr Leu Gln Thr Ser Thr
50 55 60

Thr Ser Arg Pro Thr Ala Thr Ser Thr Ala Pro Pro Ser Ser Thr Thr
65 70 75 80

Ser Pro Ser Lys Gly Lys Leu Lys Trp Leu Gly Ser Asn Glu Ser Gly
85 90 95

Ala Glu Phe Gly Glu Gly Asn Tyr Pro Gly Leu Trp Gly Lys His Phe
100 105 110

```
Ile Phe Pro Ser Thr Ser Ala Ile Gln Thr Leu Ile Asn Asp Gly Tyr
        115                 120                 125

Asn Ile Phe Arg Ile Asp Phe Ser Met Glu Arg Leu Val Pro Asn Gln
    130                 135                 140

Leu Thr Ser Ser Phe Asp Gln Gly Tyr Leu Arg Asn Leu Thr Glu Val
145                 150                 155                 160

Val Asn Phe Val Thr Asn Ala Gly Lys Tyr Ala Val Leu Asp Pro His
                165                 170                 175

Asn Tyr Gly Arg Tyr Tyr Gly Asn Ile Ile Thr Asp Thr Asn Ala Phe
            180                 185                 190

Arg Thr Phe Trp Thr Asn Leu Ala Lys Gln Phe Ala Ser Asn Ser Leu
        195                 200                 205

Val Ile Phe Asp Thr Asn Asn Glu Tyr Asn Thr Met Asp Gln Thr Leu
    210                 215                 220

Val Leu Asn Leu Asn Gln Ala Ala Ile Asp Gly Ile Arg Ala Ala Gly
225                 230                 235                 240

Ala Thr Ser Gln Tyr Ile Phe Val Glu Gly Asn Ala Trp Ser Gly Ala
                245                 250                 255

Trp Ser Trp Asn Thr Thr Asn Thr Asn Met Ala Ala Leu Thr Asp Pro
            260                 265                 270

Gln Asn Lys Ile Val Tyr Glu Met His Gln Tyr Leu Asp Ser Asp Ser
        275                 280                 285

Ser Gly Thr His Ala Glu Cys Val Ser Ser Thr Ile Gly Ala Gln Arg
    290                 295                 300

Val Val Gly Ala Thr Gln Trp Leu Arg Ala Asn Gly Lys Leu Gly Val
305                 310                 315                 320

Leu Gly Glu Phe Ala Gly Gly Ala Asn Ala Val Cys Gln Gln Ala Val
                325                 330                 335

Thr Gly Leu Leu Asp His Leu Gln Asp Asn Ser Asp Val Trp Leu Gly
            340                 345                 350

Ala Leu Trp Trp Ala Ala Gly Pro Trp Trp Gly Asp Tyr Met Tyr Ser
        355                 360                 365

Phe Glu Pro Pro Ser Gly Thr Gly Tyr Val Asn Tyr Asn Ser Ile Leu
    370                 375                 380

Lys Lys Tyr Leu Pro
385


<210> SEQ ID NO 15
<211> LENGTH: 1232
<212> TYPE: DNA
<213> ORGANISM: Basidiomycete CBS 495.95

<400> SEQUENCE: 15

ggatccactt agtaacggcc gccagtgtgc tggaaagcat gaagtctctc ttcctgtcac     60

ttgtagcgac cgtcgcgctc agctcgccag tattctctgt cgcagtctgg gggcaatgcg    120

gcggcattgg cttcagcgga agcaccgtct gtgatgcagg cgccggctgt gtgaagctca    180

acgactatta ctctcaatgc caacccggcg ctcccactgc tacatccgcg gcgccaagta    240

gcaacgcacc gtccggcact tcgacggcct cggccccctc ctccagcctt tgctctggca    300

gccgcacgcc gttccagttc ttcggtgtca acgaatccgg cgcggagttc ggcaacctga    360

acatccccgg tgttctgggc accgactaca cctggccgtc gccatccagc attgacttct    420

tcatgggcaa gggaatgaat accttccgta ttccgttcct catggagcgt cttgtccccc    480

ctgccactgg catcacagga cctctcgacc agacgtactt gggcggcctg cagacgattg    540
```

```
tcaactacat caccggcaaa ggcggctttg ctctcattga cccgcacaac tttatgatct    600

acaatggcca gacgatctcc agtaccagcg acttccagaa gttctggcag aacctcgcag    660

gagtgtttaa atcgaacagt cacgtcatct tcgatgttat gaacgagcct cacgatattc    720

ccgcccagac cgtgttccaa ctgaaccaag ccgctgtcaa tggcatccgt gcgagcggtg    780

cgacgtcgca gctcattctg gtcgagggca caagctggac tggagcctgg acctggacga    840

cctctggcaa cagcgatgca ttcggtgcca ttaaggatcc caacaacaac gtcgcgatcc    900

agatgcatca gtacctggat agcgatggct ctggcacttc gcagacctgc gtgtctccca    960

ccatcggtgc cgagcggttg caggctgcga ctcaatggtt gaagcagaac aacctcaagg   1020

gcttcctggg cgagatcggc gccggctcta actccgcttg catcagcgct gtgcagggtg   1080

cgttgtgttc gatgcagcaa tctggtgtgt ggctcggcgc tctctggtgg gctgcgggcc   1140

cgtggtgggg cgactactac cagtccatcg agccgccctc tggcccggcg gtgtccgcga   1200

tcctcccgca ggccctgctg ccgttcgcgt aa                                 1232
```

```
<210> SEQ ID NO 16
<211> LENGTH: 397
<212> TYPE: PRT
<213> ORGANISM: Basidiomycete CBS 495.95

<400> SEQUENCE: 16

Met Lys Ser Leu Phe Leu Ser Leu Val Ala Thr Val Ala Leu Ser Ser
1               5                   10                  15

Pro Val Phe Ser Val Ala Val Trp Gly Gln Cys Gly Gly Ile Gly Phe
            20                  25                  30

Ser Gly Ser Thr Val Cys Asp Ala Gly Ala Gly Cys Val Lys Leu Asn
        35                  40                  45

Asp Tyr Tyr Ser Gln Cys Gln Pro Gly Ala Pro Thr Ala Thr Ser Ala
    50                  55                  60

Ala Pro Ser Ser Asn Ala Pro Ser Gly Thr Ser Thr Ala Ser Ala Pro
65                  70                  75                  80

Ser Ser Ser Leu Cys Ser Gly Ser Arg Thr Pro Phe Gln Phe Phe Gly
                85                  90                  95

Val Asn Glu Ser Gly Ala Glu Phe Gly Asn Leu Asn Ile Pro Gly Val
            100                 105                 110

Leu Gly Thr Asp Tyr Thr Trp Pro Ser Pro Ser Ser Ile Asp Phe Phe
        115                 120                 125

Met Gly Lys Gly Met Asn Thr Phe Arg Ile Pro Phe Leu Met Glu Arg
    130                 135                 140

Leu Val Pro Pro Ala Thr Gly Ile Thr Gly Pro Leu Asp Gln Thr Tyr
145                 150                 155                 160

Leu Gly Gly Leu Gln Thr Ile Val Asn Tyr Ile Thr Gly Lys Gly Gly
                165                 170                 175

Phe Ala Leu Ile Asp Pro His Asn Phe Met Ile Tyr Asn Gly Gln Thr
            180                 185                 190

Ile Ser Ser Thr Ser Asp Phe Gln Lys Phe Trp Gln Asn Leu Ala Gly
        195                 200                 205

Val Phe Lys Ser Asn Ser His Val Ile Phe Asp Val Met Asn Glu Pro
    210                 215                 220

His Asp Ile Pro Ala Gln Thr Val Phe Gln Leu Asn Gln Ala Ala Val
225                 230                 235                 240

Asn Gly Ile Arg Ala Ser Gly Ala Thr Ser Gln Leu Ile Leu Val Glu
```

```
                245                 250                 255

Gly Thr Ser Trp Thr Gly Ala Trp Thr Trp Thr Thr Ser Gly Asn Ser
            260                 265                 270

Asp Ala Phe Gly Ala Ile Lys Asp Pro Asn Asn Asn Val Ala Ile Gln
        275                 280                 285

Met His Gln Tyr Leu Asp Ser Asp Gly Ser Gly Thr Ser Gln Thr Cys
    290                 295                 300

Val Ser Pro Thr Ile Gly Ala Glu Arg Leu Gln Ala Ala Thr Gln Trp
305                 310                 315                 320

Leu Lys Gln Asn Asn Leu Lys Gly Phe Leu Gly Glu Ile Gly Ala Gly
                325                 330                 335

Ser Asn Ser Ala Cys Ile Ser Ala Val Gln Gly Ala Leu Cys Ser Met
            340                 345                 350

Gln Gln Ser Gly Val Trp Leu Gly Ala Leu Trp Trp Ala Ala Gly Pro
        355                 360                 365

Trp Trp Gly Asp Tyr Tyr Gln Ser Ile Glu Pro Pro Ser Gly Pro Ala
    370                 375                 380

Val Ser Ala Ile Leu Pro Gln Ala Leu Leu Pro Phe Ala
385                 390                 395


<210> SEQ ID NO 17
<211> LENGTH: 1303
<212> TYPE: DNA
<213> ORGANISM: Basidiomycete CBS 495.95

<400> SEQUENCE: 17

ggaaagcgtc agtatggtga aatttgcgct tgtggcaact gtcggcgcaa tcttgagcgc      60

ttctgcggcc aatgcggctt ctatctacca gcaatgtgga ggcattggat ggtctgggtc     120

cactgtttgc gacgccggtc tcgcttgcgt tatcctcaat gcgtactact ttcagtgctt     180

gacgcccgcc gcgggccaga caacgacggg ctcgggcgca ccggcgtcaa catcaacctc     240

tcactcaacg gtcactacgg ggagctcaca ctcaacaacc gggacgacgg cgacgaaaac     300

aactaccact ccgtcgacca ccacgaccct acccgccatc tctgtgtctg gtcgcgtctg     360

ctctggctcc aggacgaagt tcaagttctt cggtgtgaat gaaagcggcg ccgaattcgg     420

gaacactgct tggccagggc agctcgggaa agactataca tggccttcgc ctagcagcgt     480

ggactacttc atgggggctg gattcaatac attccgtatc accttcttga tggagcgtat     540

gagccctccg gctaccggac tcactggccc attcaaccag acgtacctgt cgggcctcac     600

caccattgtc gactacatca cgaacaaagg aggatacgct cttattgacc cccacaactt     660

catgcgttac aacaacggca taatcagcag cacatctgac ttcgcgactt ggtggagcaa     720

tttggccact gtattcaaat ccacgaagaa cgccatcttc gacatccaga acgagccgta     780

cggaatcgat gcgcagaccg tatacgaact gaatcaagct gccatcaatt cgatccgcgc     840

cgctggcgct acgtcacagt tgattctggt tgaaggaacg tcatacactg gagcttggac     900

gtgggtctcg tccggaaacg gagctgcttt cgcggccgtt acggatcctt acaacaacac     960

ggcaattgaa atgcaccaat acctcgacag cgacggttct gggacaaacg aagactgtgt    1020

ctcctccacc attgggtcgc aacgtctcca agctgccact gcgtggctgc aacaaacagg    1080

actcaaggga ttcctcggag agacgggtgc tgggtcgaat tcccagtgca tcgacgccgt    1140

gttcgatgaa ctttgctata tgcaacagca aggcggctcc tggatcggtg cactctggtg    1200

ggctgcgggt ccctggtggg gcacgtacat ttactcgatt gaacctccga gcggtgccgc    1260
```

```
tatcccagaa gtccttcctc agggtctcgc tccattcctc tag                  1303


<210> SEQ ID NO 18
<211> LENGTH: 429
<212> TYPE: PRT
<213> ORGANISM: Basidiomycete CBS 495.95

<400> SEQUENCE: 18

Met Val Lys Phe Ala Leu Val Ala Thr Val Gly Ala Ile Leu Ser Ala
1               5                   10                  15

Ser Ala Ala Asn Ala Ala Ser Ile Tyr Gln Gln Cys Gly Gly Ile Gly
            20                  25                  30

Trp Ser Gly Ser Thr Val Cys Asp Ala Gly Leu Ala Cys Val Ile Leu
        35                  40                  45

Asn Ala Tyr Tyr Phe Gln Cys Leu Thr Pro Ala Ala Gly Gln Thr Thr
    50                  55                  60

Thr Gly Ser Gly Ala Pro Ala Ser Thr Ser Thr Ser His Ser Thr Val
65                  70                  75                  80

Thr Thr Gly Ser Ser His Ser Thr Thr Gly Thr Thr Ala Thr Lys Thr
                85                  90                  95

Thr Thr Thr Pro Ser Thr Thr Thr Thr Leu Pro Ala Ile Ser Val Ser
            100                 105                 110

Gly Arg Val Cys Ser Gly Ser Arg Thr Lys Phe Lys Phe Phe Gly Val
        115                 120                 125

Asn Glu Ser Gly Ala Glu Phe Gly Asn Thr Ala Trp Pro Gly Gln Leu
    130                 135                 140

Gly Lys Asp Tyr Thr Trp Pro Ser Pro Ser Ser Val Asp Tyr Phe Met
145                 150                 155                 160

Gly Ala Gly Phe Asn Thr Phe Arg Ile Thr Phe Leu Met Glu Arg Met
                165                 170                 175

Ser Pro Pro Ala Thr Gly Leu Thr Gly Pro Phe Asn Gln Thr Tyr Leu
            180                 185                 190

Ser Gly Leu Thr Thr Ile Val Asp Tyr Ile Thr Asn Lys Gly Gly Tyr
        195                 200                 205

Ala Leu Ile Asp Pro His Asn Phe Met Arg Tyr Asn Asn Gly Ile Ile
    210                 215                 220

Ser Ser Thr Ser Asp Phe Ala Thr Trp Trp Ser Asn Leu Ala Thr Val
225                 230                 235                 240

Phe Lys Ser Thr Lys Asn Ala Ile Phe Asp Ile Gln Asn Glu Pro Tyr
                245                 250                 255

Gly Ile Asp Ala Gln Thr Val Tyr Glu Leu Asn Gln Ala Ala Ile Asn
            260                 265                 270

Ser Ile Arg Ala Ala Gly Ala Thr Ser Gln Leu Ile Leu Val Glu Gly
        275                 280                 285

Thr Ser Tyr Thr Gly Ala Trp Thr Trp Val Ser Ser Gly Asn Gly Ala
    290                 295                 300

Ala Phe Ala Ala Val Thr Asp Pro Tyr Asn Asn Thr Ala Ile Glu Met
305                 310                 315                 320

His Gln Tyr Leu Asp Ser Asp Gly Ser Gly Thr Asn Glu Asp Cys Val
                325                 330                 335

Ser Ser Thr Ile Gly Ser Gln Arg Leu Gln Ala Ala Thr Ala Trp Leu
            340                 345                 350

Gln Gln Thr Gly Leu Lys Gly Phe Leu Gly Glu Thr Gly Ala Gly Ser
        355                 360                 365
```

```
Asn Ser Gln Cys Ile Asp Ala Val Phe Asp Glu Leu Cys Tyr Met Gln
    370                 375                 380

Gln Gln Gly Gly Ser Trp Ile Gly Ala Leu Trp Trp Ala Ala Gly Pro
385                 390                 395                 400

Trp Trp Gly Thr Tyr Ile Tyr Ser Ile Glu Pro Pro Ser Gly Ala Ala
                405                 410                 415

Ile Pro Glu Val Leu Pro Gln Gly Leu Ala Pro Phe Leu
            420                 425


<210> SEQ ID NO 19
<211> LENGTH: 1580
<212> TYPE: DNA
<213> ORGANISM: Thielavia terrestris

<400> SEQUENCE: 19

agccccccgt tcaggcacac ttggcatcag atcagcttag cagcgcctgc acagcatgaa     60

gctctcgcag tcggccgcgc tggcggcact caccgcgacg gcgctcgccg ccccctcgcc    120

cacgacgccg caggcgccga ggcaggcttc agccggctgc tcgtctgcgg tcacgctcga    180

cgccagcacc aacgtttgga agaagtacac gctgcacccc aacagctact accgcaagga    240

ggttgaggcc gcggtggcgc agatctcgga cccggacctc gccgccaagg ccaagaaggt    300

ggccgacgtc ggcaccttcc tgtggctcga ctcgatcgag aacatcggca agctggagcc    360

ggcgatccag gacgtgccct gcgagaacat cctgggcctg gtcatctacg acctgccggg    420

ccgcgactgc gcggccaagg cgtccaacgg cgagctcaag gtcggcgaga tcgaccgcta    480

caagaccgag tacatcgaca gtgagtgctg ccccccgggt tcgagaagag cgtgggggaa    540

agggaaaggg ttgactgact gacacggcgc actgcagaga tcgtgtcgat cctcaaggca    600

caccccaaca cggcgttcgc gctggtcatc gagccggact cgctgcccaa cctggtgacc    660

aacagcaact tggacacgtg ctcgagcagc gcgtcgggct accgcgaagg cgtggcttac    720

gccctcaaga acctcaacct gcccaacgtg atcatgtacc tcgacgccgg ccacggcggc    780

tggctcggct gggacgccaa cctgcagccc ggcgcgcagg agctagccaa ggcgtacaag    840

aacgccggct cgcccaagca gctccgcggc ttctcgacca acgtggccgg ctggaactcc    900

tggtgagctt ttttccattc catttcttct tcctcttctc tcttcgctcc cactctgcag    960

ccccccctcc cccaagcacc cactggcgtt ccggcttgct gactcggcct ccctttcccc   1020

gggcaccagg gatcaatcgc ccggcgaatt ctcccaggcg tccgacgcca agtacaacaa   1080

gtgccagaac gagaagatct acgtcagcac cttcggctcc gcgctccagt cggccggcat   1140

gcccaaccac gccatcgtcg acacgggccg caacggcgtc accggcctgc gcaaggagtg   1200

gggtgactgg tgcaacgtca acggtgcagg ttcgttgtct tctttttctc ctcttttgtt   1260

tgcacgtcgt ggtccttttc aagcagccgt gtttggttgg gggagatgga ctccggctga   1320

tgttctgctt cctctctagg cttcggcgtg cgcccgacga gcaacacggg cctcgagctg   1380

gccgacgcgt tcgtgtgggt caagcccggc ggcgagtcgg acggcaccag cgacagctcg   1440

tcgccgcgct acgacagctt ctgcggcaag gacgacgcct tcaagccctc gcccgaggcc   1500

ggcacctgga acgaggccta cttcgagatg ctgctcaaga acgccgtgcc gtcgttctaa   1560

gacggtccag catcatccgg                                               1580


<210> SEQ ID NO 20
<211> LENGTH: 396
<212> TYPE: PRT
<213> ORGANISM: Thielavia terrestris
```

<400> SEQUENCE: 20

```
Met Lys Leu Ser Gln Ser Ala Ala Leu Ala Ala Leu Thr Ala Thr Ala
1               5                   10                  15

Leu Ala Ala Pro Ser Pro Thr Thr Pro Gln Ala Pro Arg Gln Ala Ser
            20                  25                  30

Ala Gly Cys Ser Ser Ala Val Thr Leu Asp Ala Ser Thr Asn Val Trp
        35                  40                  45

Lys Lys Tyr Thr Leu His Pro Asn Ser Tyr Tyr Arg Lys Glu Val Glu
    50                  55                  60

Ala Ala Val Ala Gln Ile Ser Asp Pro Asp Leu Ala Ala Lys Ala Lys
65                  70                  75                  80

Lys Val Ala Asp Val Gly Thr Phe Leu Trp Leu Asp Ser Ile Glu Asn
                85                  90                  95

Ile Gly Lys Leu Glu Pro Ala Ile Gln Asp Val Pro Cys Glu Asn Ile
            100                 105                 110

Leu Gly Leu Val Ile Tyr Asp Leu Pro Gly Arg Asp Cys Ala Ala Lys
        115                 120                 125

Ala Ser Asn Gly Glu Leu Lys Val Gly Glu Ile Asp Arg Tyr Lys Thr
    130                 135                 140

Glu Tyr Ile Asp Lys Ile Val Ser Ile Leu Lys Ala His Pro Asn Thr
145                 150                 155                 160

Ala Phe Ala Leu Val Ile Glu Pro Asp Ser Leu Pro Asn Leu Val Thr
                165                 170                 175

Asn Ser Asn Leu Asp Thr Cys Ser Ser Ser Ala Ser Gly Tyr Arg Glu
            180                 185                 190

Gly Val Ala Tyr Ala Leu Lys Asn Leu Asn Leu Pro Asn Val Ile Met
        195                 200                 205

Tyr Leu Asp Ala Gly His Gly Gly Trp Leu Gly Trp Asp Ala Asn Leu
    210                 215                 220

Gln Pro Gly Ala Gln Glu Leu Ala Lys Ala Tyr Lys Asn Ala Gly Ser
225                 230                 235                 240

Pro Lys Gln Leu Arg Gly Phe Ser Thr Asn Val Ala Gly Trp Asn Ser
                245                 250                 255

Trp Asp Gln Ser Pro Gly Glu Phe Ser Gln Ala Ser Asp Ala Lys Tyr
            260                 265                 270

Asn Lys Cys Gln Asn Glu Lys Ile Tyr Val Ser Thr Phe Gly Ser Ala
        275                 280                 285

Leu Gln Ser Ala Gly Met Pro Asn His Ala Ile Val Asp Thr Gly Arg
    290                 295                 300

Asn Gly Val Thr Gly Leu Arg Lys Glu Trp Gly Asp Trp Cys Asn Val
305                 310                 315                 320

Asn Gly Ala Gly Phe Gly Val Arg Pro Thr Ser Asn Thr Gly Leu Glu
                325                 330                 335

Leu Ala Asp Ala Phe Val Trp Val Lys Pro Gly Gly Glu Ser Asp Gly
            340                 345                 350

Thr Ser Asp Ser Ser Ser Pro Arg Tyr Asp Ser Phe Cys Gly Lys Asp
        355                 360                 365

Asp Ala Phe Lys Pro Ser Pro Glu Ala Gly Thr Trp Asn Glu Ala Tyr
    370                 375                 380

Phe Glu Met Leu Leu Lys Asn Ala Val Pro Ser Phe
385                 390                 395
```

```
<210> SEQ ID NO 21
<211> LENGTH: 1203
<212> TYPE: DNA
<213> ORGANISM: Thielavia terrestris

<400> SEQUENCE: 21

atgaagtacc tcaacctcct cgcagctctc ctcgccgtcg ctcctctctc cctcgctgca      60

cccagcatcg aggccagaca gtcgaacgtc aacccataca tcggcaagag cccgctcgtt     120

attaggtcgt acgcccaaaa gcttgaggag accgtcagga ccttccagca acgtggcgac     180

cagctcaacg ctgcgaggac acggacggtg cagaacgttg cgactttcgc ctggatctcg     240

gataccaatg gtattggagc cattcgacct ctcatccaag atgctctcgc ccagcaggct     300

cgcactggac agaaggtcat cgtccaaatc gtcgtctaca acctcccaga tcgcgactgc     360

tctgccaacg cctcgactgg agagttcacc gtaggaaacg acggtctcaa ccgatacaag     420

aactttgtca acaccatcgc ccgcgagctc tcgactgctg acgctgacaa gctccacttt     480

gccctcctcc tcgaacccga cgcacttgcc aacctcgtca ccaacgcgaa tgcccccagg     540

tgccgaatcg ccgctcccgc ttacaaggag ggtatcgcct acaccctcgc caccttgtcc     600

aagcccaacg tcgacgtcta catcgacgcc gccaacggtg gctggctcgg ctggaacgac     660

aacctccgcc ccttcgccga actcttcaag gaagtctacg acctcgcccg ccgcatcaac     720

cccaacgcca aggtccgcgg cgtccccgtc aacgtctcca actacaacca gtaccgcgct     780

gaagtccgcg agcccttcac cgagtggaag gacgcctggg acgagagccg ctacgtcaac     840

gtcctcaccc cgcacctcaa cgccgtcggc ttctccgcgc acttcatcgt tgaccaggga     900

cgcggtggca agggcggtat caggacggag tggggccagt ggtgcaacgt taggaacgct     960

gggttcggta tcaggcctac tgcggatcag ggcgtgctcc agaacccgaa tgtggatgcg    1020

attgtgtggg ttaagccggg tggagagtcg gatggcacga gtgatttgaa ctcgaacagg    1080

tatgatccta cgtgcaggag tccggtggcg catgttcccg ctcctgaggc tggccagtgg    1140

ttcaacgagt atgttgttaa cctcgttttg aacgctaacc cccctcttga gcctacctgg    1200

taa                                                                 1203


<210> SEQ ID NO 22
<211> LENGTH: 400
<212> TYPE: PRT
<213> ORGANISM: Thielavia terrestris

<400> SEQUENCE: 22

Met Lys Tyr Leu Asn Leu Leu Ala Ala Leu Leu Ala Val Ala Pro Leu
1               5                   10                  15

Ser Leu Ala Ala Pro Ser Ile Glu Ala Arg Gln Ser Asn Val Asn Pro
            20                  25                  30

Tyr Ile Gly Lys Ser Pro Leu Val Ile Arg Ser Tyr Ala Gln Lys Leu
        35                  40                  45

Glu Glu Thr Val Arg Thr Phe Gln Gln Arg Gly Asp Gln Leu Asn Ala
    50                  55                  60

Ala Arg Thr Arg Thr Val Gln Asn Val Ala Thr Phe Ala Trp Ile Ser
65                  70                  75                  80

Asp Thr Asn Gly Ile Gly Ala Ile Arg Pro Leu Ile Gln Asp Ala Leu
                85                  90                  95

Ala Gln Gln Ala Arg Thr Gly Gln Lys Val Ile Val Gln Ile Val Val
            100                 105                 110

Tyr Asn Leu Pro Asp Arg Asp Cys Ser Ala Asn Ala Ser Thr Gly Glu
```

```
        115                 120                 125

Phe Thr Val Gly Asn Asp Gly Leu Asn Arg Tyr Lys Asn Phe Val Asn
    130                 135                 140

Thr Ile Ala Arg Glu Leu Ser Thr Ala Asp Ala Asp Lys Leu His Phe
145                 150                 155                 160

Ala Leu Leu Leu Glu Pro Asp Ala Leu Ala Asn Leu Val Thr Asn Ala
                165                 170                 175

Asn Ala Pro Arg Cys Arg Ile Ala Ala Pro Ala Tyr Lys Glu Gly Ile
            180                 185                 190

Ala Tyr Thr Leu Ala Thr Leu Ser Lys Pro Asn Val Asp Val Tyr Ile
        195                 200                 205

Asp Ala Ala Asn Gly Gly Trp Leu Gly Trp Asn Asp Asn Leu Arg Pro
    210                 215                 220

Phe Ala Glu Leu Phe Lys Glu Val Tyr Asp Leu Ala Arg Arg Ile Asn
225                 230                 235                 240

Pro Asn Ala Lys Val Arg Gly Val Pro Val Asn Val Ser Asn Tyr Asn
                245                 250                 255

Gln Tyr Arg Ala Glu Val Arg Glu Pro Phe Thr Glu Trp Lys Asp Ala
            260                 265                 270

Trp Asp Glu Ser Arg Tyr Val Asn Val Leu Thr Pro His Leu Asn Ala
        275                 280                 285

Val Gly Phe Ser Ala His Phe Ile Val Asp Gln Gly Arg Gly Gly Lys
    290                 295                 300

Gly Gly Ile Arg Thr Glu Trp Gly Gln Trp Cys Asn Val Arg Asn Ala
305                 310                 315                 320

Gly Phe Gly Ile Arg Pro Thr Ala Asp Gln Gly Val Leu Gln Asn Pro
                325                 330                 335

Asn Val Asp Ala Ile Val Trp Val Lys Pro Gly Gly Glu Ser Asp Gly
            340                 345                 350

Thr Ser Asp Leu Asn Ser Asn Arg Tyr Asp Pro Thr Cys Arg Ser Pro
        355                 360                 365

Val Ala His Val Pro Ala Pro Glu Ala Gly Gln Trp Phe Asn Glu Tyr
    370                 375                 380

Val Val Asn Leu Val Leu Asn Ala Asn Pro Pro Leu Glu Pro Thr Trp
385                 390                 395                 400


<210> SEQ ID NO 23
<211> LENGTH: 1501
<212> TYPE: DNA
<213> ORGANISM: Thielavia terrestris

<400> SEQUENCE: 23

gccgttgtca agatgggcca gaagacgctg cacggattcg ccgccacggc tttggccgtt      60

ctcccctttg tgaaggctca gcagcccggc aacttcacgc cggaggtgca cccgcaactg     120

ccaacgtgga agtgcacgac cgccggcggc tgcgttcagc aggacacttc ggtggtgctc     180

gactggaact accgttggat ccacaatgcc gacggcaccg cctcgtgcac gacgtccagc     240

ggggtcgacc acacgctgtg tccagatgag gcgacctgcg cgaagaactg cttcgtggaa     300

ggcgtcaact acacgagcag cggtgtcacc acatccggca gttcgctgac gatgaggcag     360

tatttcaagg ggagcaacgg gcagaccaac agcgtttcgc ctcgtctcta cctgctcggc     420

tcggatggaa actacgtaat gctcaagctg ctcggccagg agctgagctt cgatgtcgat     480

ctctccacgc tcccctgcgg cgagaacggc gcgctgtacc tgtccgagat ggacgcgacc     540
```

```
ggtggcagga accagtacaa caccggcggt gccaactacg gctcgggcta ctgtgacgcc    600

cagtgtcccg tgcagacgtg gatgaacggc acgctgaaca ccaacgggca gggctactgc    660

tgcaacgaga tggacatcct cgaggccaac tcccgcgcca acgcgatgac acctcacccc    720

tgcgccaacg gcagctgcga caagagcggg tgcggactca acccctacgc cgagggctac    780

aagagctact acggaccggg cctcacggtt gacacgtcga agcccttcac catcattacc    840

cgcttcatca ccgacgacgg cacgaccagc ggcaccctca accagatcca gcggatctat    900

gtgcagaatg gcaagacggt cgcgtcggct gcgtccggag gcgacatcat cacggcatcc    960

ggctgcacct cggcccaggc gttcggcggg ctggccaaca tgggcgcggc gcttggacgg   1020

ggcatggtgc tgaccttcag catctggaac gacgctgggg gctacatgaa ctggctcgac   1080

agcggcaaca acggcccgtg cagcagcacc gagggcaacc cgtccaacat cctggccaac   1140

tacccggaca cccacgtggt cttctccaac atccgctggg gagacatcgg ctcgacggtc   1200

caggtctcgg gaggcggcaa cggcggctcg accaccacca cgtcgaccac cacgctgagg   1260

acctcgacca cgaccaccac caccgccccg acggccactg ccacgcactg ggacaatgc    1320

ggcggaatcg ggtacgtcaa accgcctcct gcattctgtt gaggaagtta actaacgtgg   1380

cctacgcagt ggactggacc gaccgtctgc gaatcgccgt acgcatgcaa ggagctgaac   1440

ccctggtact accagtgcct ctaaagtatt gcagtgaagc catactccgt gctcggcatg   1500

g                                                                   1501
```

```
<210> SEQ ID NO 24
<211> LENGTH: 464
<212> TYPE: PRT
<213> ORGANISM: Thielavia terrestris

<400> SEQUENCE: 24

Met Gly Gln Lys Thr Leu His Gly Phe Ala Ala Thr Ala Leu Ala Val
1               5                   10                  15

Leu Pro Phe Val Lys Ala Gln Gln Pro Gly Asn Phe Thr Pro Glu Val
            20                  25                  30

His Pro Gln Leu Pro Thr Trp Lys Cys Thr Thr Ala Gly Gly Cys Val
        35                  40                  45

Gln Gln Asp Thr Ser Val Val Leu Asp Trp Asn Tyr Arg Trp Ile His
    50                  55                  60

Asn Ala Asp Gly Thr Ala Ser Cys Thr Thr Ser Ser Gly Val Asp His
65                  70                  75                  80

Thr Leu Cys Pro Asp Glu Ala Thr Cys Ala Lys Asn Cys Phe Val Glu
                85                  90                  95

Gly Val Asn Tyr Thr Ser Ser Gly Val Thr Thr Ser Gly Ser Ser Leu
            100                 105                 110

Thr Met Arg Gln Tyr Phe Lys Gly Ser Asn Gly Gln Thr Asn Ser Val
        115                 120                 125

Ser Pro Arg Leu Tyr Leu Leu Gly Ser Asp Gly Asn Tyr Val Met Leu
    130                 135                 140

Lys Leu Leu Gly Gln Glu Leu Ser Phe Asp Val Asp Leu Ser Thr Leu
145                 150                 155                 160

Pro Cys Gly Glu Asn Gly Ala Leu Tyr Leu Ser Glu Met Asp Ala Thr
                165                 170                 175

Gly Gly Arg Asn Gln Tyr Asn Thr Gly Gly Ala Asn Tyr Gly Ser Gly
            180                 185                 190

Tyr Cys Asp Ala Gln Cys Pro Val Gln Thr Trp Met Asn Gly Thr Leu
```

```
        195                 200                 205

Asn Thr Asn Gly Gln Gly Tyr Cys Cys Asn Glu Met Asp Ile Leu Glu
    210                 215                 220

Ala Asn Ser Arg Ala Asn Ala Met Thr Pro His Pro Cys Ala Asn Gly
225                 230                 235                 240

Ser Cys Asp Lys Ser Gly Cys Gly Leu Asn Pro Tyr Ala Glu Gly Tyr
                245                 250                 255

Lys Ser Tyr Tyr Gly Pro Gly Leu Thr Val Asp Thr Ser Lys Pro Phe
            260                 265                 270

Thr Ile Ile Thr Arg Phe Ile Thr Asp Asp Gly Thr Thr Ser Gly Thr
        275                 280                 285

Leu Asn Gln Ile Gln Arg Ile Tyr Val Gln Asn Gly Lys Thr Val Ala
    290                 295                 300

Ser Ala Ala Ser Gly Gly Asp Ile Ile Thr Ala Ser Gly Cys Thr Ser
305                 310                 315                 320

Ala Gln Ala Phe Gly Gly Leu Ala Asn Met Gly Ala Ala Leu Gly Arg
                325                 330                 335

Gly Met Val Leu Thr Phe Ser Ile Trp Asn Asp Ala Gly Gly Tyr Met
            340                 345                 350

Asn Trp Leu Asp Ser Gly Asn Asn Gly Pro Cys Ser Ser Thr Glu Gly
        355                 360                 365

Asn Pro Ser Asn Ile Leu Ala Asn Tyr Pro Asp Thr His Val Val Phe
    370                 375                 380

Ser Asn Ile Arg Trp Gly Asp Ile Gly Ser Thr Val Gln Val Ser Gly
385                 390                 395                 400

Gly Gly Asn Gly Gly Ser Thr Thr Thr Thr Ser Thr Thr Thr Leu Arg
                405                 410                 415

Thr Ser Thr Thr Thr Thr Thr Thr Ala Pro Thr Ala Thr Ala Thr His
            420                 425                 430

Trp Gly Gln Cys Gly Gly Ile Gly Trp Thr Gly Pro Thr Val Cys Glu
        435                 440                 445

Ser Pro Tyr Ala Cys Lys Glu Leu Asn Pro Trp Tyr Tyr Gln Cys Leu
    450                 455                 460
```

<210> SEQ ID NO 25
<211> LENGTH: 1368
<212> TYPE: DNA
<213> ORGANISM: Thielavia terrestris

<400> SEQUENCE: 25

```
accgatccgc tcgaagatgg cgcccaagtc tacagttctg gccgcctggc tgctctcctc     60

gctggccgcg gcccagcaga tcggcaaagc cgtgcccgag gtccacccca aactgacaac    120

gcagaagtgc actctccgcg gcgggtgcaa gcctgtccgc acctcggtcg tgctcgactc    180

gtccgcgcgc tcgctgcaca aggtcgggga ccccaacacc agctgcagcg tcggcggcga    240

cctgtgctcg gacgcgaagt cgtgcggcaa gaactgcgcg ctcgagggcg tcgactacgc    300

ggcccacggc gtggcgacca agggcgacgc cctcacgctg caccagtggc tcaagggggc    360

cgacggcacc tacaggaccg tctcgccgcg cgtatacctc ctgggcgagg acgggaagaa    420

ctacgaggac ttcaagctgc tcaacgccga gctcagcttc gacgtcgacg tgtcccagct    480

cgtctgcggc atgaacggcg ccctgtactt ctccgagatg gagatggacg gcggccgcag    540

cccgctgaac ccggcgggcg ccacgtacgg cacgggctac tgcgacgcgc agtgccccaa    600

gttggacttt atcaacggcg aggtatttct tctctcttct gtttttcttt tccatcgctt    660
```

```
tttctgaccg gaatccgccc tcttagctca acaccaacca cacgtacggg gcgtgctgca    720

acgagatgga catctgggag gccaacgcgc tggcgcaggc gctcacgccg cacccgtgca    780

acgcgacgcg ggtgtacaag tgcgacacgg cggacgagtg cgggcagccg gtgggcgtgt    840

gcgacgaatg gggtgctcg tacaacccgt ccaacttcgg ggtcaaggac tactacgggc     900

gcaacctgac ggtggacacg aaccgcaagt tcacggtgac gacgcagttc gtgacgtcca    960

acgggcgggc ggacggcgag ctgaccgaga tccggcggct gtacgtgcag gacggcgtgg   1020

tgatccagaa ccacgcggtc acggcgggcg gggcgacgta cgacagcatc acggacggct   1080

tctgcaacgc gacggccacc tggacgcagc agcggggcgg gctcgcgcgc atgggcgagg   1140

ccatcggccg cggcatggtg ctcatcttca gcctgtgggt tgacaacggc ggcttcatga   1200

actggctcga cagcggcaac gccgggccct gcaacgccac cgagggcgac ccggccctga   1260

tcctgcagca gcacccggac gccagcgtca ccttctccaa catccgatgg ggcgagatcg   1320

gcagcacgta caagagcgag tgcagccact agagtagagc ttgtaatt                1368
```

<210> SEQ ID NO 26
<211> LENGTH: 423
<212> TYPE: PRT
<213> ORGANISM: Thielavia terrestris

<400> SEQUENCE: 26

```
Met Ala Pro Lys Ser Thr Val Leu Ala Ala Trp Leu Leu Ser Ser Leu
1               5                   10                  15

Ala Ala Ala Gln Gln Ile Gly Lys Ala Val Pro Glu Val His Pro Lys
            20                  25                  30

Leu Thr Thr Gln Lys Cys Thr Leu Arg Gly Gly Cys Lys Pro Val Arg
        35                  40                  45

Thr Ser Val Val Leu Asp Ser Ser Ala Arg Ser Leu His Lys Val Gly
    50                  55                  60

Asp Pro Asn Thr Ser Cys Ser Val Gly Gly Asp Leu Cys Ser Asp Ala
65                  70                  75                  80

Lys Ser Cys Gly Lys Asn Cys Ala Leu Glu Gly Val Asp Tyr Ala Ala
                85                  90                  95

His Gly Val Ala Thr Lys Gly Asp Ala Leu Thr Leu His Gln Trp Leu
            100                 105                 110

Lys Gly Ala Asp Gly Thr Tyr Arg Thr Val Ser Pro Arg Val Tyr Leu
        115                 120                 125

Leu Gly Glu Asp Gly Lys Asn Tyr Glu Asp Phe Lys Leu Leu Asn Ala
    130                 135                 140

Glu Leu Ser Phe Asp Val Asp Val Ser Gln Leu Val Cys Gly Met Asn
145                 150                 155                 160

Gly Ala Leu Tyr Phe Ser Glu Met Glu Met Asp Gly Gly Arg Ser Pro
                165                 170                 175

Leu Asn Pro Ala Gly Ala Thr Tyr Gly Thr Gly Tyr Cys Asp Ala Gln
            180                 185                 190

Cys Pro Lys Leu Asp Phe Ile Asn Gly Glu Leu Asn Thr Asn His Thr
        195                 200                 205

Tyr Gly Ala Cys Cys Asn Glu Met Asp Ile Trp Glu Ala Asn Ala Leu
    210                 215                 220

Ala Gln Ala Leu Thr Pro His Pro Cys Asn Ala Thr Arg Val Tyr Lys
225                 230                 235                 240

Cys Asp Thr Ala Asp Glu Cys Gly Gln Pro Val Gly Val Cys Asp Glu
```

```
                245                 250                 255

Trp Gly Cys Ser Tyr Asn Pro Ser Asn Phe Gly Val Lys Asp Tyr Tyr
            260                 265                 270

Gly Arg Asn Leu Thr Val Asp Thr Asn Arg Lys Phe Thr Val Thr Thr
        275                 280                 285

Gln Phe Val Thr Ser Asn Gly Arg Ala Asp Gly Glu Leu Thr Glu Ile
    290                 295                 300

Arg Arg Leu Tyr Val Gln Asp Gly Val Val Ile Gln Asn His Ala Val
305                 310                 315                 320

Thr Ala Gly Gly Ala Thr Tyr Asp Ser Ile Thr Asp Gly Phe Cys Asn
                325                 330                 335

Ala Thr Ala Thr Trp Thr Gln Gln Arg Gly Gly Leu Ala Arg Met Gly
            340                 345                 350

Glu Ala Ile Gly Arg Gly Met Val Leu Ile Phe Ser Leu Trp Val Asp
        355                 360                 365

Asn Gly Gly Phe Met Asn Trp Leu Asp Ser Gly Asn Ala Gly Pro Cys
    370                 375                 380

Asn Ala Thr Glu Gly Asp Pro Ala Leu Ile Leu Gln Gln His Pro Asp
385                 390                 395                 400

Ala Ser Val Thr Phe Ser Asn Ile Arg Trp Gly Glu Ile Gly Ser Thr
                405                 410                 415

Tyr Lys Ser Glu Cys Ser His
            420


<210> SEQ ID NO 27
<211> LENGTH: 1011
<212> TYPE: DNA
<213> ORGANISM: Thielavia terrestris

<400> SEQUENCE: 27

atgaccctac ggctccctgt catcagcctg ctggcctcgc tggcagcagg cgccgtcgtc      60

gtcccacggg cggagtttca ccccccctctc ccgacttgga aatgcacgac ctccgggggc     120

tgcgtgcagc agaacaccag cgtcgtcctg gaccgtgact cgaagtacgc cgcacacagc     180

gccggctcgc ggacggaatc ggattacgcg gcaatgggag tgtccacttc gggcaatgcc     240

gtgacgctgt accactacgt caagaccaac ggcaccctcg tccccgcttc gccgcgcatc     300

tacctcctgg gcgcggacgg caagtacgtg cttatggacc tcctcaacca ggagctgtcg     360

gtggacgtcg acttctcggc gctgccgtgc ggcgagaacg gggccttcta cctgtccgag     420

atggcggcgg acgggcgggg cgacgcgggg gcgggcgacg ggtactgcga cgcgcagtgc     480

cagggctact gctgcaacga gatggacatc ctcgaggcca actcgatggc gacggccatg     540

acgccgcacc cgtgcaaggg caacaactgc gaccgcagcg gctgcggcta caacccgtac     600

gccagcggcc agcgcggctt ctacgggccc ggcaagacgg tcgacacgag caagcccttc     660

accgtcgtca cgcagttcgc cgccagcggc ggcaagctga cccagatcac ccgcaagtac     720

atccagaacg gccgggagat cggcggcggc ggcaccatct ccagctgcgg ctccgagtct     780

tcgacgggcg gcctgaccgg catgggcgag gcgctggggc gcggaatggt gctggccatg     840

agcatctgga acgacgcggc ccaggagatg gcatggctcg atgccggcaa caacggccct     900

tgcgccagtg gccagggcag cccgtccgtc attcagtcgc agcatcccga cacccacgtc     960

gtcttctcca acatcaggtg gggcgacatc gggtctacca cgaagaacta g              1011


<210> SEQ ID NO 28
```

<211> LENGTH: 336
<212> TYPE: PRT
<213> ORGANISM: Thielavia terrestris

<400> SEQUENCE: 28

Met Thr Leu Arg Leu Pro Val Ile Ser Leu Leu Ala Ser Leu Ala Ala
1 5 10 15

Gly Ala Val Val Val Pro Arg Ala Glu Phe His Pro Pro Leu Pro Thr
20 25 30

Trp Lys Cys Thr Thr Ser Gly Gly Cys Val Gln Gln Asn Thr Ser Val
35 40 45

Val Leu Asp Arg Asp Ser Lys Tyr Ala Ala His Ser Ala Gly Ser Arg
50 55 60

Thr Glu Ser Asp Tyr Ala Ala Met Gly Val Ser Thr Ser Gly Asn Ala
65 70 75 80

Val Thr Leu Tyr His Tyr Val Lys Thr Asn Gly Thr Leu Val Pro Ala
85 90 95

Ser Pro Arg Ile Tyr Leu Leu Gly Ala Asp Gly Lys Tyr Val Leu Met
100 105 110

Asp Leu Leu Asn Gln Glu Leu Ser Val Asp Val Asp Phe Ser Ala Leu
115 120 125

Pro Cys Gly Glu Asn Gly Ala Phe Tyr Leu Ser Glu Met Ala Ala Asp
130 135 140

Gly Arg Gly Asp Ala Gly Ala Gly Asp Gly Tyr Cys Asp Ala Gln Cys
145 150 155 160

Gln Gly Tyr Cys Cys Asn Glu Met Asp Ile Leu Glu Ala Asn Ser Met
165 170 175

Ala Thr Ala Met Thr Pro His Pro Cys Lys Gly Asn Asn Cys Asp Arg
180 185 190

Ser Gly Cys Gly Tyr Asn Pro Tyr Ala Ser Gly Gln Arg Gly Phe Tyr
195 200 205

Gly Pro Gly Lys Thr Val Asp Thr Ser Lys Pro Phe Thr Val Val Thr
210 215 220

Gln Phe Ala Ala Ser Gly Gly Lys Leu Thr Gln Ile Thr Arg Lys Tyr
225 230 235 240

Ile Gln Asn Gly Arg Glu Ile Gly Gly Gly Gly Thr Ile Ser Ser Cys
245 250 255

Gly Ser Glu Ser Ser Thr Gly Gly Leu Thr Gly Met Gly Glu Ala Leu
260 265 270

Gly Arg Gly Met Val Leu Ala Met Ser Ile Trp Asn Asp Ala Ala Gln
275 280 285

Glu Met Ala Trp Leu Asp Ala Gly Asn Asn Gly Pro Cys Ala Ser Gly
290 295 300

Gln Gly Ser Pro Ser Val Ile Gln Ser Gln His Pro Asp Thr His Val
305 310 315 320

Val Phe Ser Asn Ile Arg Trp Gly Asp Ile Gly Ser Thr Thr Lys Asn
325 330 335

<210> SEQ ID NO 29
<211> LENGTH: 1480
<212> TYPE: DNA
<213> ORGANISM: Cladorrhinum foecundissimum

<400> SEQUENCE: 29
gatccgaatt cctcctctcg ttctttagtc acagaccaga catctgccca cgatggttca 60

```
caagttcgcc ctcctcaccg gcctcgccgc ctccctcgca tctgcccagc agatcggcac    120

cgtcgtcccc gagtctcacc ccaagcttcc caccaagcgc tgcactctcg ccggtggctg    180

ccagaccgtc gacacctcca tcgtcatcga cgccttccag cgtcccctcc acaagatcgg    240

cgacccttcc actccttgcg tcgtcggcgg ccctctctgc cccgacgcca agtcctgcgc    300

tgagaactgc gcgctcgagg gtgtcgacta tgcctcctgg ggcatcaaga ccgagggcga    360

cgccctaact ctcaaccagt ggatgcccga cccggcgaac cctggccagt acaagacgac    420

tactccccgt acttaccttg ttgctgagga cggcaagaac tacgaggatg tgaagctcct    480

ggctaaggag atctcgtttg atgccgatgt cagcaacctt ccctgcggca tgaacggtgc    540

tttctacttg tctgagatgt tgatggatgg tggacgtggc gacctcaacc ctgctggtgc    600

cgagtatggt accggttact gtgatgcgca gtgcttcaag ttggatttca tcaacggcga    660

ggccaacatc gaccaaaagc acggcgcctg ctgcaacgaa atggacattt tcgaatccaa    720

ctcgcgcgcc aagaccttcg tcccccaccc ctgcaacatc acgcaggtct acaagtgcga    780

aggcgaagac gagtgcggcc agcccgtcgg cgtgtgcgac aagtgggggt gcggcttcaa    840

cgagtacaaa tggggcgtcg agtccttcta cggccggggc tcgcagttcg ccatcgactc    900

ctccaagaag ttcaccgtca ccacgcagtt cctgaccgac aacggcaagg aggacggcgt    960

cctcgtcgag atccgccgct tgtggcacca ggatggcaag ctgatcaaga acaccgctat   1020

ccaggttgag gagaactaca gcacggactc ggtgagcacc gagttctgcg agaagactgc   1080

ttctttcacc atgcagcgcg gtggtctcaa ggcgatgggc gaggctatcg gtcgtggtat   1140

ggtgctggtt ttcagcatct gggcggatga ttcgggtttt atgaactggt tggatgcgga   1200

gggtaatggc ccttgcagcg cgactgaggg cgatccgaag gagattgtca agaataagcc   1260

ggatgctagg gttacgttct caaacattag gattggtgag gttggtagca cgtatgctcc   1320

gggtgggaag tgcggtgtta agagcagggt tgctaggggg cttactgctt cttaaggggg   1380

gtgtgaagag aggaggaggt gttgttgggg gttggagatg ataattgggc gagatggtgt   1440

agagcgggtt ggttggatat gaatacgttg aattggatgt                          1480
```

<210> SEQ ID NO 30
<211> LENGTH: 440
<212> TYPE: PRT
<213> ORGANISM: Cladorrhinum foecundissimum

<400> SEQUENCE: 30

```
Met Val His Lys Phe Ala Leu Leu Thr Gly Leu Ala Ala Ser Leu Ala
1               5                   10                  15

Ser Ala Gln Gln Ile Gly Thr Val Val Pro Glu Ser His Pro Lys Leu
            20                  25                  30

Pro Thr Lys Arg Cys Thr Leu Ala Gly Gly Cys Gln Thr Val Asp Thr
        35                  40                  45

Ser Ile Val Ile Asp Ala Phe Gln Arg Pro Leu His Lys Ile Gly Asp
    50                  55                  60

Pro Ser Thr Pro Cys Val Val Gly Gly Pro Leu Cys Pro Asp Ala Lys
65                  70                  75                  80

Ser Cys Ala Glu Asn Cys Ala Leu Glu Gly Val Asp Tyr Ala Ser Trp
                85                  90                  95

Gly Ile Lys Thr Glu Gly Asp Ala Leu Thr Leu Asn Gln Trp Met Pro
            100                 105                 110

Asp Pro Ala Asn Pro Gly Gln Tyr Lys Thr Thr Thr Pro Arg Thr Tyr
        115                 120                 125
```

```
Leu Val Ala Glu Asp Gly Lys Asn Tyr Glu Asp Val Lys Leu Leu Ala
    130                 135                 140

Lys Glu Ile Ser Phe Asp Ala Asp Val Ser Asn Leu Pro Cys Gly Met
145                 150                 155                 160

Asn Gly Ala Phe Tyr Leu Ser Glu Met Leu Met Asp Gly Gly Arg Gly
                165                 170                 175

Asp Leu Asn Pro Ala Gly Ala Glu Tyr Gly Thr Gly Tyr Cys Asp Ala
            180                 185                 190

Gln Cys Phe Lys Leu Asp Phe Ile Asn Gly Glu Ala Asn Ile Asp Gln
        195                 200                 205

Lys His Gly Ala Cys Cys Asn Glu Met Asp Ile Phe Glu Ser Asn Ser
    210                 215                 220

Arg Ala Lys Thr Phe Val Pro His Pro Cys Asn Ile Thr Gln Val Tyr
225                 230                 235                 240

Lys Cys Glu Gly Glu Asp Glu Cys Gly Gln Pro Val Gly Val Cys Asp
                245                 250                 255

Lys Trp Gly Cys Gly Phe Asn Glu Tyr Lys Trp Gly Val Glu Ser Phe
            260                 265                 270

Tyr Gly Arg Gly Ser Gln Phe Ala Ile Asp Ser Ser Lys Lys Phe Thr
        275                 280                 285

Val Thr Thr Gln Phe Leu Thr Asp Asn Gly Lys Glu Asp Gly Val Leu
    290                 295                 300

Val Glu Ile Arg Arg Leu Trp His Gln Asp Gly Lys Leu Ile Lys Asn
305                 310                 315                 320

Thr Ala Ile Gln Val Glu Glu Asn Tyr Ser Thr Asp Ser Val Ser Thr
                325                 330                 335

Glu Phe Cys Glu Lys Thr Ala Ser Phe Thr Met Gln Arg Gly Gly Leu
            340                 345                 350

Lys Ala Met Gly Glu Ala Ile Gly Arg Gly Met Val Leu Val Phe Ser
        355                 360                 365

Ile Trp Ala Asp Asp Ser Gly Phe Met Asn Trp Leu Asp Ala Glu Gly
    370                 375                 380

Asn Gly Pro Cys Ser Ala Thr Glu Gly Asp Pro Lys Glu Ile Val Lys
385                 390                 395                 400

Asn Lys Pro Asp Ala Arg Val Thr Phe Ser Asn Ile Arg Ile Gly Glu
                405                 410                 415

Val Gly Ser Thr Tyr Ala Pro Gly Gly Lys Cys Gly Val Lys Ser Arg
            420                 425                 430

Val Ala Arg Gly Leu Thr Ala Ser
        435                 440
```

<210> SEQ ID NO 31
<211> LENGTH: 1380
<212> TYPE: DNA
<213> ORGANISM: Trichoderma reesei

<400> SEQUENCE: 31

```
atggcgccct cagttacact gccgttgacc acggccatcc tggccattgc ccggctcgtc      60

gccgcccagc aaccgggtac cagcaccccc gaggtccatc ccaagttgac aacctacaag     120

tgtacaaagt ccgggggggtg cgtggcccag gacacctcgg tggtccttga ctggaactac     180

cgctggatgc acgacgcaaa ctacaactcg tgcaccgtca acggcggcgt caacaccacg     240

ctctgccctg acgaggcgac ctgtggcaag aactgcttca tcgagggcgt cgactacgcc     300
```

```
gcctcgggcg tcacgacctc gggcagcagc ctcaccatga accagtacat gcccagcagc    360

tctggcggct acagcagcgt ctctcctcgg ctgtatctcc tggactctga cggtgagtac    420

gtgatgctga agctcaacgg ccaggagctg agcttcgacg tcgacctctc tgctctgccg    480

tgtggagaga acggctcgct ctacctgtct cagatggacg agaacggggg cgccaaccag    540

tataacacgg ccggtgccaa ctacgggagc ggctactgcg atgctcagtg ccccgtccag    600

acatggagga acggcaccct caacactagc caccagggct tctgctgcaa cgagatggat    660

atcctggagg gcaactcgag ggcgaatgcc ttgacccctc actcttgcac ggccacggcc    720

tgcgactctg ccggttgcgg cttcaacccc tatggcagcg gctacaaaag ctactacggc    780

cccggagata ccgttgacac ctccaagacc ttcaccatca tcacccagtt caacacggac    840

aacggctcgc cctcgggcaa ccttgtgagc atcacccgca agtaccagca aaacggcgtc    900

gacatcccca gcgcccagcc cggcggcgac accatctcgt cctgcccgtc cgcctcagcc    960

tacggcggcc tcgccaccat gggcaaggcc ctgagcagcg gcatggtgct cgtgttcagc   1020

atttggaacg acaacagcca gtacatgaac tggctcgaca gcggcaacgc cggcccctgc   1080

agcagcaccg agggcaaccc atccaacatc ctggccaaca accccaacac gcacgtcgtc   1140

ttctccaaca tccgctgggg agacattggg tctactacga actcgactgc gcccccgccc   1200

ccgcctgcgt ccagcacgac gttttcgact acacggagga gctcgacgac ttcgagcagc   1260

ccgagctgca cgcagactca ctgggggcag tgcggtggca ttgggtacag cgggtgcaag   1320

acgtgcacgt cgggcactac gtgccagtat agcaacgact actactcgca atgcctttag   1380
```

```
<210> SEQ ID NO 32
<211> LENGTH: 459
<212> TYPE: PRT
<213> ORGANISM: Trichoderma reesei

<400> SEQUENCE: 32

Met Ala Pro Ser Val Thr Leu Pro Leu Thr Thr Ala Ile Leu Ala Ile
1               5                   10                  15

Ala Arg Leu Val Ala Ala Gln Gln Pro Gly Thr Ser Thr Pro Glu Val
            20                  25                  30

His Pro Lys Leu Thr Thr Tyr Lys Cys Thr Lys Ser Gly Gly Cys Val
        35                  40                  45

Ala Gln Asp Thr Ser Val Val Leu Asp Trp Asn Tyr Arg Trp Met His
    50                  55                  60

Asp Ala Asn Tyr Asn Ser Cys Thr Val Asn Gly Gly Val Asn Thr Thr
65                  70                  75                  80

Leu Cys Pro Asp Glu Ala Thr Cys Gly Lys Asn Cys Phe Ile Glu Gly
                85                  90                  95

Val Asp Tyr Ala Ala Ser Gly Val Thr Thr Ser Gly Ser Ser Leu Thr
            100                 105                 110

Met Asn Gln Tyr Met Pro Ser Ser Ser Gly Gly Tyr Ser Ser Val Ser
        115                 120                 125

Pro Arg Leu Tyr Leu Leu Asp Ser Asp Gly Glu Tyr Val Met Leu Lys
    130                 135                 140

Leu Asn Gly Gln Glu Leu Ser Phe Asp Val Asp Leu Ser Ala Leu Pro
145                 150                 155                 160

Cys Gly Glu Asn Gly Ser Leu Tyr Leu Ser Gln Met Asp Glu Asn Gly
                165                 170                 175

Gly Ala Asn Gln Tyr Asn Thr Ala Gly Ala Asn Tyr Gly Ser Gly Tyr
            180                 185                 190
```

```
Cys Asp Ala Gln Cys Pro Val Gln Thr Trp Arg Asn Gly Thr Leu Asn
        195                 200                 205

Thr Ser His Gln Gly Phe Cys Cys Asn Glu Met Asp Ile Leu Glu Gly
    210                 215                 220

Asn Ser Arg Ala Asn Ala Leu Thr Pro His Ser Cys Thr Ala Thr Ala
225                 230                 235                 240

Cys Asp Ser Ala Gly Cys Gly Phe Asn Pro Tyr Gly Ser Gly Tyr Lys
                245                 250                 255

Ser Tyr Tyr Gly Pro Gly Asp Thr Val Asp Thr Ser Lys Thr Phe Thr
            260                 265                 270

Ile Ile Thr Gln Phe Asn Thr Asp Asn Gly Ser Pro Ser Gly Asn Leu
        275                 280                 285

Val Ser Ile Thr Arg Lys Tyr Gln Gln Asn Gly Val Asp Ile Pro Ser
    290                 295                 300

Ala Gln Pro Gly Gly Asp Thr Ile Ser Ser Cys Pro Ser Ala Ser Ala
305                 310                 315                 320

Tyr Gly Gly Leu Ala Thr Met Gly Lys Ala Leu Ser Ser Gly Met Val
                325                 330                 335

Leu Val Phe Ser Ile Trp Asn Asp Asn Ser Gln Tyr Met Asn Trp Leu
            340                 345                 350

Asp Ser Gly Asn Ala Gly Pro Cys Ser Ser Thr Glu Gly Asn Pro Ser
        355                 360                 365

Asn Ile Leu Ala Asn Asn Pro Asn Thr His Val Val Phe Ser Asn Ile
    370                 375                 380

Arg Trp Gly Asp Ile Gly Ser Thr Thr Asn Ser Thr Ala Pro Pro Pro
385                 390                 395                 400

Pro Pro Ala Ser Ser Thr Thr Phe Ser Thr Thr Arg Arg Ser Ser Thr
                405                 410                 415

Thr Ser Ser Ser Pro Ser Cys Thr Gln Thr His Trp Gly Gln Cys Gly
            420                 425                 430

Gly Ile Gly Tyr Ser Gly Cys Lys Thr Cys Thr Ser Gly Thr Thr Cys
        435                 440                 445

Gln Tyr Ser Asn Asp Tyr Tyr Ser Gln Cys Leu
    450                 455
```

<210> SEQ ID NO 33
<211> LENGTH: 1545
<212> TYPE: DNA
<213> ORGANISM: Trichoderma reesei

<400> SEQUENCE: 33

```
atgtatcgga agttggccgt catctcggcc ttcttggcca cagctcgtgc tcagtcggcc     60

tgcactctcc aatcggagac tcacccgcct ctgacatggc agaaatgctc gtctggtggc    120

acgtgcactc aacagacagg ctccgtggtc atcgacgcca actggcgctg gactcacgct    180

acgaacagca gcacgaactg ctacgatggc aacacttgga gctcgaccct atgtcctgac    240

aacgagacct gcgcgaagaa ctgctgtctg gacggtgccg cctacgcgtc cacgtacgga    300

gttaccacga gcggtaacag cctctccatt ggctttgtca cccagtctgc gcagaagaac    360

gttggcgctc gcctttacct tatggcgagc gacacgacct accaggaatt caccctgctt    420

ggcaacgagt tctctttcga tgttgatgtt tcgcagctgc cgtgcggctt gaacggagct    480

ctctacttcg tgtccatgga cgcggatggt ggcgtgagca agtatcccac caacaccgct    540

ggcgccaagt acggcacggg gtactgtgac agccagtgtc cccgcgatct gaagttcatc    600
```

```
aatggccagg ccaacgttga gggctgggag ccgtcatcca acaacgcgaa cacgggcatt    660

ggaggacacg gaagctgctg ctctgagatg gatatctggg aggccaactc catctccgag    720

gctcttaccc cccacccttg cacgactgtc ggccaggaga tctgcgaggg tgatgggtgc    780

ggcggaactt actccgataa cagatatggc ggcacttgcg atcccgatgg ctgcgactgg    840

aacccatacc gcctgggcaa caccagcttc tacggccctg gctcaagctt taccctcgat    900

accaccaaga aattgaccgt tgtcacccag ttcgagacgt cgggtgccat caaccgatac    960

tatgtccaga atggcgtcac tttccagcag cccaacgccg agcttggtag ttactctggc   1020

aacgagctca acgatgatta ctgcacagct gaggaggcag aattcggcgg atcctctttc   1080

tcagacaagg gcggcctgac tcagttcaag aaggctacct ctggcggcat ggttctggtc   1140

atgagtctgt gggatgatta ctacgccaac atgctgtggc tggactccac ctacccgaca   1200

aacgagacct cctccacacc cggtgccgtg cgcggaagct gctccaccag ctccggtgtc   1260

cctgctcagg tcgaatctca gtctcccaac gccaaggtca ccttctccaa catcaagttc   1320

ggacccattg gcagcaccgg caaccctagc ggcggcaacc ctcccggcgg aaacccgcct   1380

ggcaccacca ccacccgccg cccagccact accactggaa gctctcccgg acctacccag   1440

tctcactacg gccagtgcgg cggtattggc tacagcggcc ccacggtctg cgccagcggc   1500

acaacttgcc aggtcctgaa cccttactac tctcagtgcc tgtaa                   1545
```

```
<210> SEQ ID NO 34
<211> LENGTH: 514
<212> TYPE: PRT
<213> ORGANISM: Trichoderma reesei

<400> SEQUENCE: 34

Met Tyr Arg Lys Leu Ala Val Ile Ser Ala Phe Leu Ala Thr Ala Arg
1               5                   10                  15

Ala Gln Ser Ala Cys Thr Leu Gln Ser Glu Thr His Pro Pro Leu Thr
            20                  25                  30

Trp Gln Lys Cys Ser Ser Gly Gly Thr Cys Thr Gln Gln Thr Gly Ser
        35                  40                  45

Val Val Ile Asp Ala Asn Trp Arg Trp Thr His Ala Thr Asn Ser Ser
    50                  55                  60

Thr Asn Cys Tyr Asp Gly Asn Thr Trp Ser Ser Thr Leu Cys Pro Asp
65                  70                  75                  80

Asn Glu Thr Cys Ala Lys Asn Cys Cys Leu Asp Gly Ala Ala Tyr Ala
                85                  90                  95

Ser Thr Tyr Gly Val Thr Thr Ser Gly Asn Ser Leu Ser Ile Gly Phe
            100                 105                 110

Val Thr Gln Ser Ala Gln Lys Asn Val Gly Ala Arg Leu Tyr Leu Met
        115                 120                 125

Ala Ser Asp Thr Thr Tyr Gln Glu Phe Thr Leu Leu Gly Asn Glu Phe
    130                 135                 140

Ser Phe Asp Val Asp Val Ser Gln Leu Pro Cys Gly Leu Asn Gly Ala
145                 150                 155                 160

Leu Tyr Phe Val Ser Met Asp Ala Asp Gly Gly Val Ser Lys Tyr Pro
                165                 170                 175

Thr Asn Thr Ala Gly Ala Lys Tyr Gly Thr Gly Tyr Cys Asp Ser Gln
            180                 185                 190

Cys Pro Arg Asp Leu Lys Phe Ile Asn Gly Gln Ala Asn Val Glu Gly
        195                 200                 205
```

```
Trp Glu Pro Ser Ser Asn Asn Ala Asn Thr Gly Ile Gly Gly His Gly
    210                 215                 220

Ser Cys Cys Ser Glu Met Asp Ile Trp Glu Ala Asn Ser Ile Ser Glu
225                 230                 235                 240

Ala Leu Thr Pro His Pro Cys Thr Thr Val Gly Gln Glu Ile Cys Glu
                245                 250                 255

Gly Asp Gly Cys Gly Gly Thr Tyr Ser Asp Asn Arg Tyr Gly Gly Thr
            260                 265                 270

Cys Asp Pro Asp Gly Cys Asp Trp Asn Pro Tyr Arg Leu Gly Asn Thr
        275                 280                 285

Ser Phe Tyr Gly Pro Gly Ser Ser Phe Thr Leu Asp Thr Thr Lys Lys
    290                 295                 300

Leu Thr Val Val Thr Gln Phe Glu Thr Ser Gly Ala Ile Asn Arg Tyr
305                 310                 315                 320

Tyr Val Gln Asn Gly Val Thr Phe Gln Gln Pro Asn Ala Glu Leu Gly
                325                 330                 335

Ser Tyr Ser Gly Asn Glu Leu Asn Asp Asp Tyr Cys Thr Ala Glu Glu
            340                 345                 350

Ala Glu Phe Gly Gly Ser Ser Phe Ser Asp Lys Gly Gly Leu Thr Gln
        355                 360                 365

Phe Lys Lys Ala Thr Ser Gly Gly Met Val Leu Val Met Ser Leu Trp
    370                 375                 380

Asp Asp Tyr Tyr Ala Asn Met Leu Trp Leu Asp Ser Thr Tyr Pro Thr
385                 390                 395                 400

Asn Glu Thr Ser Ser Thr Pro Gly Ala Val Arg Gly Ser Cys Ser Thr
                405                 410                 415

Ser Ser Gly Val Pro Ala Gln Val Glu Ser Gln Ser Pro Asn Ala Lys
            420                 425                 430

Val Thr Phe Ser Asn Ile Lys Phe Gly Pro Ile Gly Ser Thr Gly Asn
        435                 440                 445

Pro Ser Gly Gly Asn Pro Pro Gly Gly Asn Pro Pro Gly Thr Thr Thr
    450                 455                 460

Thr Arg Arg Pro Ala Thr Thr Thr Gly Ser Ser Pro Gly Pro Thr Gln
465                 470                 475                 480

Ser His Tyr Gly Gln Cys Gly Gly Ile Gly Tyr Ser Gly Pro Thr Val
                485                 490                 495

Cys Ala Ser Gly Thr Thr Cys Gln Val Leu Asn Pro Tyr Tyr Ser Gln
            500                 505                 510

Cys Leu
```

<210> SEQ ID NO 35
<211> LENGTH: 1611
<212> TYPE: DNA
<213> ORGANISM: Trichoderma reesei

<400> SEQUENCE: 35

```
atgattgtcg gcattctcac cacgctggct acgctggcca cactcgcagc tagtgtgcct      60

ctagaggagc ggcaagcttg ctcaagcgtc tggtaattat gtgaaccctc tcaagagacc     120

caaatactga gatatgtcaa ggggccaatg tggtggccag aattggtcgg gtccgacttg     180

ctgtgcttcc ggaagcacat gcgtctactc caacgactat tactcccagt gtcttcccgg     240

cgctgcaagc tcaagctcgt ccacgcgcgc cgcgtcgacg acttctcgag tatcccccac     300

aacatcccgg tcgagctccg cgacgcctcc acctggttct actactacca gagtacctcc     360
```

```
agtcggatcg ggaaccgcta cgtattcagg caacccttt gttggggtca ctccttgggc    420
caatgcatat tacgcctctg aagttagcag cctcgctatt cctagcttga ctggagccat    480
ggccactgct gcagcagctg tcgcaaaggt tccctctttt atgtggctgt aggtcctccc    540
ggaaccaagg caatctgtta ctgaaggctc atcattcact gcagagatac tcttgacaag    600
acccctctca tggagcaaac cttggccgac atccgcaccg ccaacaagaa tggcggtaac    660
tatgccggac agtttgtggt gtatgacttg ccggatcgcg attgcgctgc ccttgcctcg    720
aatggcgaat actctattgc cgatggtggc gtcgccaaat ataagaacta tatcgacacc    780
attcgtcaaa ttgtcgtgga atattccgat atccggaccc tcctggttat tggtatgagt    840
ttaaacacct gcctcccccc cccttccct tcctttcccg ccggcatctt gtcgttgtgc    900
taactattgt tccctcttcc agagcctgac tctcttgcca acctggtgac caacctcggt    960
actccaaagt gtgccaatgc tcagtcagcc taccttgagt gcatcaacta cgccgtcaca   1020
cagctgaacc ttccaaatgt tgcgatgtat ttggacgctg gccatgcagg atggcttggc   1080
tggccggcaa accaagaccc ggccgctcag ctatttgcaa atgtttacaa gaatgcatcg   1140
tctccgagag ctcttcgcgg attggcaacc aatgtcgcca actacaacgg gtggaacatt   1200
accagccccc catcgtacac gcaaggcaac gctgtctaca acgagaagct gtacatccac   1260
gctattggac gtcttcttgc caatcacggc tggtccaacg ccttcttcat cactgatcaa   1320
ggtcgatcgg gaaagcagcc taccggacag caacagtggg gagactggtg caatgtgatc   1380
ggcaccggat ttggtattcg cccatccgca aacactgggg actcgttgct ggattcgttt   1440
gtctgggtca agccaggcgg cgagtgtgac ggcaccagcg acagcagtgc gccacgattt   1500
gactcccact gtgcgctccc agatgccttg caaccggcgc ctcaagctgg tgcttggttc   1560
caagcctact ttgtgcagct tctcacaaac gcaaacccat cgttcctgta a            1611
```

<210> SEQ ID NO 36
<211> LENGTH: 471
<212> TYPE: PRT
<213> ORGANISM: Trichoderma reesei

<400> SEQUENCE: 36

```
Met Ile Val Gly Ile Leu Thr Thr Leu Ala Thr Leu Ala Thr Leu Ala
1               5                   10                  15

Ala Ser Val Pro Leu Glu Glu Arg Gln Ala Cys Ser Ser Val Trp Gly
            20                  25                  30

Gln Cys Gly Gly Gln Asn Trp Ser Gly Pro Thr Cys Cys Ala Ser Gly
        35                  40                  45

Ser Thr Cys Val Tyr Ser Asn Asp Tyr Tyr Ser Gln Cys Leu Pro Gly
    50                  55                  60

Ala Ala Ser Ser Ser Ser Ser Thr Arg Ala Ala Ser Thr Thr Ser Arg
65                  70                  75                  80

Val Ser Pro Thr Thr Ser Arg Ser Ser Ser Ala Thr Pro Pro Pro Gly
                85                  90                  95

Ser Thr Thr Thr Arg Val Pro Pro Val Gly Ser Gly Thr Ala Thr Tyr
            100                 105                 110

Ser Gly Asn Pro Phe Val Gly Val Thr Pro Trp Ala Asn Ala Tyr Tyr
        115                 120                 125

Ala Ser Glu Val Ser Ser Leu Ala Ile Pro Ser Leu Thr Gly Ala Met
    130                 135                 140

Ala Thr Ala Ala Ala Ala Val Ala Lys Val Pro Ser Phe Met Trp Leu
```

```
145                 150                 155                 160

Asp Thr Leu Asp Lys Thr Pro Leu Met Glu Gln Thr Leu Ala Asp Ile
                165                 170                 175

Arg Thr Ala Asn Lys Asn Gly Gly Asn Tyr Ala Gly Gln Phe Val Val
            180                 185                 190

Tyr Asp Leu Pro Asp Arg Asp Cys Ala Ala Leu Ala Ser Asn Gly Glu
        195                 200                 205

Tyr Ser Ile Ala Asp Gly Gly Val Ala Lys Tyr Lys Asn Tyr Ile Asp
    210                 215                 220

Thr Ile Arg Gln Ile Val Val Glu Tyr Ser Asp Ile Arg Thr Leu Leu
225                 230                 235                 240

Val Ile Glu Pro Asp Ser Leu Ala Asn Leu Val Thr Asn Leu Gly Thr
                245                 250                 255

Pro Lys Cys Ala Asn Ala Gln Ser Ala Tyr Leu Glu Cys Ile Asn Tyr
            260                 265                 270

Ala Val Thr Gln Leu Asn Leu Pro Asn Val Ala Met Tyr Leu Asp Ala
        275                 280                 285

Gly His Ala Gly Trp Leu Gly Trp Pro Ala Asn Gln Asp Pro Ala Ala
    290                 295                 300

Gln Leu Phe Ala Asn Val Tyr Lys Asn Ala Ser Ser Pro Arg Ala Leu
305                 310                 315                 320

Arg Gly Leu Ala Thr Asn Val Ala Asn Tyr Asn Gly Trp Asn Ile Thr
                325                 330                 335

Ser Pro Pro Ser Tyr Thr Gln Gly Asn Ala Val Tyr Asn Glu Lys Leu
            340                 345                 350

Tyr Ile His Ala Ile Gly Arg Leu Leu Ala Asn His Gly Trp Ser Asn
        355                 360                 365

Ala Phe Phe Ile Thr Asp Gln Gly Arg Ser Gly Lys Gln Pro Thr Gly
    370                 375                 380

Gln Gln Gln Trp Gly Asp Trp Cys Asn Val Ile Gly Thr Gly Phe Gly
385                 390                 395                 400

Ile Arg Pro Ser Ala Asn Thr Gly Asp Ser Leu Leu Asp Ser Phe Val
                405                 410                 415

Trp Val Lys Pro Gly Gly Glu Cys Asp Gly Thr Ser Asp Ser Ser Ala
            420                 425                 430

Pro Arg Phe Asp Ser His Cys Ala Leu Pro Asp Ala Leu Gln Pro Ala
        435                 440                 445

Pro Gln Ala Gly Ala Trp Phe Gln Ala Tyr Phe Val Gln Leu Leu Thr
    450                 455                 460

Asn Ala Asn Pro Ser Phe Leu
465                 470
```

<210> SEQ ID NO 37
<211> LENGTH: 2046
<212> TYPE: DNA
<213> ORGANISM: Humicola insolens

<400> SEQUENCE: 37

```
gccgtgacct tgcgcgcttt gggtggcggt ggcgagtcgt ggacggtgct tgctggtcgc      60

cggccttccc ggcgatccgc gtgatgagag ggccaccaac ggcgggatga tgctccatgg     120

ggaacttccc catggagaag agagagaaac ttgcggagcc gtgatctggg gaaagatgct     180

ccgtgtctcg tctatataac tcgagtctcc ccgagccctc aacaccacca gctctgatct     240

caccatcccc atcgacaatc acgcaaacac agcagttgtc gggccattcc ttcagacaca     300
```

```
tcagtcaccc tccttcaaaa tgcgtaccgc caagttcgcc accctcgccg cccttgtggc    360

ctcggccgcc gcccagcagg cgtgcagtct caccaccgag aggcaccctt ccctctcttg    420

gaacaagtgc accgccggcg gccagtgcca gaccgtccag gcttccatca ctctcgactc    480

caactggcgc tggactcacc aggtgtctgg ctccaccaac tgctacacgg gcaacaagtg    540

ggatactagc atctgcactg atgccaagtc gtgcgctcag aactgctgcg tcgatggtgc    600

cgactacacc agcacctatg gcatcaccac caacggtgat tccctgagcc tcaagttcgt    660

caccaagggc cagcactcga ccaacgtcgg ctcgcgtacc tacctgatgg acggcgagga    720

caagtatcag agtacgttct atcttcagcc ttctcgcgcc ttgaatcctg gctaacgttt    780

acacttcaca gccttcgagc tcctcggcaa cgagttcacc ttcgatgtcg atgtctccaa    840

catcggctgc ggtctcaacg gcgccctgta cttcgtctcc atggacgccg atggtggtct    900

cagccgctat cctggcaaca aggctggtgc caagtacggt accggctact gcgatgctca    960

gtgcccccgt gacatcaagt tcatcaacgg cgaggccaac attgagggct ggaccggctc   1020

caccaacgac cccaacgccg gcgcgggccg ctatggtacc tgctgctctg agatggatat   1080

ctgggaagcc aacaacatgg ctactgcctt cactcctcac ccttgcacca tcattggcca   1140

gagccgctgc gagggcgact cgtgcggtgg cacctacagc aacgagcgct acgccggcgt   1200

ctgcgacccc gatggctgcg acttcaactc gtaccgccag ggcaacaaga ccttctacgg   1260

caagggcatg accgtcgaca ccaccaagaa gatcactgtc gtcacccagt tcctcaagga   1320

tgccaacggc gatctcggcg agatcaagcg cttctacgtc caggatggca agatcatccc   1380

caactccgag tccaccatcc ccggcgtcga gggcaattcc atcacccagg actggtgcga   1440

ccgccagaag gttgcctttg gcgacattga cgacttcaac cgcaagggcg gcatgaagca   1500

gatgggcaag gccctcgccg gccccatggt cctggtcatg tccatctggg atgaccacgc   1560

ctccaacatg ctctggctcg actcgacctt ccctgtcgat gccgctggca agcccggcgc   1620

cgagcgcggt gcctgcccga ccacctcggg tgtccctgct gaggttgagg ccgaggcccc   1680

caacagcaac gtcgtcttct ccaacatccg cttcggcccc atcggctcga ccgttgctgg   1740

tctccccggc gcgggcaacg gcggcaacaa cggcggcaac cccccgcccc ccaccaccac   1800

cacctcctcg gctccggcca ccaccaccac cgccagcgct ggccccaagg ctggccgctg   1860

gcagcagtgc ggcggcatcg gcttcactgg cccgacccag tgcgaggagc cctacatttg   1920

caccaagctc aacgactggt actctcagtg cctgtaaatt ctgagtcgct gactcgacga   1980

tcacggccgg tttttgcatg aaaggaaaca aacgaccgcg ataaaaatgg agggtaatga   2040

gatgtc                                                              2046
```

```
<210> SEQ ID NO 38
<211> LENGTH: 525
<212> TYPE: PRT
<213> ORGANISM: Humicola insolens

<400> SEQUENCE: 38

Met Arg Thr Ala Lys Phe Ala Thr Leu Ala Ala Leu Val Ala Ser Ala
1               5                   10                  15

Ala Ala Gln Gln Ala Cys Ser Leu Thr Thr Glu Arg His Pro Ser Leu
            20                  25                  30

Ser Trp Asn Lys Cys Thr Ala Gly Gly Gln Cys Gln Thr Val Gln Ala
        35                  40                  45

Ser Ile Thr Leu Asp Ser Asn Trp Arg Trp Thr His Gln Val Ser Gly
```

```
    50                  55                  60

Ser Thr Asn Cys Tyr Thr Gly Asn Lys Trp Asp Thr Ser Ile Cys Thr
65                  70                  75                  80

Asp Ala Lys Ser Cys Ala Gln Asn Cys Cys Val Asp Gly Ala Asp Tyr
                85                  90                  95

Thr Ser Thr Tyr Gly Ile Thr Thr Asn Gly Asp Ser Leu Ser Leu Lys
            100                 105                 110

Phe Val Thr Lys Gly Gln His Ser Thr Asn Val Gly Ser Arg Thr Tyr
        115                 120                 125

Leu Met Asp Gly Glu Asp Lys Tyr Gln Thr Phe Glu Leu Leu Gly Asn
    130                 135                 140

Glu Phe Thr Phe Asp Val Asp Val Ser Asn Ile Gly Cys Gly Leu Asn
145                 150                 155                 160

Gly Ala Leu Tyr Phe Val Ser Met Asp Ala Asp Gly Gly Leu Ser Arg
                165                 170                 175

Tyr Pro Gly Asn Lys Ala Gly Ala Lys Tyr Gly Thr Gly Tyr Cys Asp
            180                 185                 190

Ala Gln Cys Pro Arg Asp Ile Lys Phe Ile Asn Gly Glu Ala Asn Ile
        195                 200                 205

Glu Gly Trp Thr Gly Ser Thr Asn Asp Pro Asn Ala Gly Ala Gly Arg
    210                 215                 220

Tyr Gly Thr Cys Cys Ser Glu Met Asp Ile Trp Glu Ala Asn Asn Met
225                 230                 235                 240

Ala Thr Ala Phe Thr Pro His Pro Cys Thr Ile Ile Gly Gln Ser Arg
                245                 250                 255

Cys Glu Gly Asp Ser Cys Gly Gly Thr Tyr Ser Asn Glu Arg Tyr Ala
            260                 265                 270

Gly Val Cys Asp Pro Asp Gly Cys Asp Phe Asn Ser Tyr Arg Gln Gly
        275                 280                 285

Asn Lys Thr Phe Tyr Gly Lys Gly Met Thr Val Asp Thr Thr Lys Lys
    290                 295                 300

Ile Thr Val Val Thr Gln Phe Leu Lys Asp Ala Asn Gly Asp Leu Gly
305                 310                 315                 320

Glu Ile Lys Arg Phe Tyr Val Gln Asp Gly Lys Ile Ile Pro Asn Ser
                325                 330                 335

Glu Ser Thr Ile Pro Gly Val Glu Gly Asn Ser Ile Thr Gln Asp Trp
            340                 345                 350

Cys Asp Arg Gln Lys Val Ala Phe Gly Asp Ile Asp Asp Phe Asn Arg
        355                 360                 365

Lys Gly Gly Met Lys Gln Met Gly Lys Ala Leu Ala Gly Pro Met Val
    370                 375                 380

Leu Val Met Ser Ile Trp Asp Asp His Ala Ser Asn Met Leu Trp Leu
385                 390                 395                 400

Asp Ser Thr Phe Pro Val Asp Ala Ala Gly Lys Pro Gly Ala Glu Arg
                405                 410                 415

Gly Ala Cys Pro Thr Thr Ser Gly Val Pro Ala Glu Val Glu Ala Glu
            420                 425                 430

Ala Pro Asn Ser Asn Val Val Phe Ser Asn Ile Arg Phe Gly Pro Ile
        435                 440                 445

Gly Ser Thr Val Ala Gly Leu Pro Gly Ala Gly Asn Gly Gly Asn Asn
    450                 455                 460

Gly Gly Asn Pro Pro Pro Pro Thr Thr Thr Thr Ser Ser Ala Pro Ala
465                 470                 475                 480
```

```
Thr Thr Thr Thr Ala Ser Ala Gly Pro Lys Ala Gly Arg Trp Gln Gln
                485                 490                 495

Cys Gly Gly Ile Gly Phe Thr Gly Pro Thr Gln Cys Glu Glu Pro Tyr
            500                 505                 510

Ile Cys Thr Lys Leu Asn Asp Trp Tyr Ser Gln Cys Leu
        515                 520                 525


<210> SEQ ID NO 39
<211> LENGTH: 1812
<212> TYPE: DNA
<213> ORGANISM: Myceliophthora thermophila

<400> SEQUENCE: 39

atggccaaga agcttttcat caccgccgcc cttgcggctg ccgtgttggc ggcccccgtc      60

attgaggagc gccagaactg cggcgctgtg tggtaagaaa gcccggtctg agtttcccat     120

gactttctca tcgagtaatg gcataaggcc cacccccttcg actgactgtg agaatcgatc    180

aaatccagga ctcaatgcgg cggcaacggg tggcagggtc ccacatgctg cgcctcgggc     240

tcgacctgcg ttgcgcagaa cgagtggtac tctcagtgcc tgcccaacaa tcaggtgacg     300

agttccaaca ctccgtcgtc gacttccacc tcgcagcgca gcagcagcac ctccagcagc     360

agcaccagga gcggcagctc ctcctcctcc accaccacgc cccctcccgt ctccagcccc     420

gtgactagca ttcccggcgg tgcgaccacc acggcgagct actctggcaa ccccttctcg     480

ggcgtccggc tcttcgccaa cgactactac aggtccgagg tccacaatct cgccattcct     540

agcatgaccg gtactctggc ggccaaggct tccgccgtcg ccgaagtccc tagcttccag     600

tggctcgacc ggaacgtcac catcgacacc ctgatggtcc agactctgtc ccagatccgg     660

gctgccaata atgccggtgc caatcctccc tatgctggtg agttacatgg cggcgacttg     720

ccttctcgtc ccccaccttt cttgacggga tcggttacct gacctggagg caaaacaaaa     780

ccagcccaac ttgtcgtcta cgacctcccc gaccgtgact gcgccgccgc tgcgtccaac     840

ggcgagtttt cgattgcaaa cggcggcgcc gccaactaca ggagctacat cgacgctatc     900

cgcaagcaca tcattgagta ctcggacatc cggatcatcc tggttatcga gcccgactcg     960

atggccaaca tggtgaccaa catgaacgtg gccaagtgca gcaacgccgc gtcgacgtac    1020

cacgagttga ccgtgtacgc gctcaagcag ctgaacctgc ccaacgtcgc catgtatctc    1080

gacgccggcc acgccggctg gctcggctgg cccgccaaca tccagcccgc cgccgacctg    1140

tttgccggca tctacaatga cgccggcaag ccggctgccg tccgcggcct ggccactaac    1200

gtcgccaact acaacgcctg gagtatcgct tcggccccgt cgtacacgtc ccctaaccct    1260

aactacgacg agaagcacta catcgaggcc ttcagcccgc tcctgaacgc ggccggcttc    1320

cccgcacgct tcattgtcga cactggccgc aacggcaaac aacctaccgg tatggttttt    1380

ttcttttttt ttctctgttc cctccccct tccccttcag ttggcgtcca caaggtctct     1440

tagtcttgct tcttctcgga ccaaccttcc cccaccccca aaacgcaccg cccacaaccg    1500

ttcgactcta tactcttggg aatgggcgcc gaaactgacc gttcgacagg ccaacaacag    1560

tggggtgact ggtgcaatgt caagggcact ggctttggcg tgcgcccgac ggccaacacg    1620

ggccacgacc tggtcgatgc ctttgtctgg gtcaagcccg gcggcgagtc cgacggcaca    1680

agcgacacca gcgccgcccg ctacgactac cactgcggcc tgtccgatgc cctgcagcct    1740

gctccggagg ctggacagtg gttccaggcc tacttcgagc agctgctcac caacgccaac    1800

ccgcccttct aa                                                        1812
```

<210> SEQ ID NO 40
<211> LENGTH: 482
<212> TYPE: PRT
<213> ORGANISM: Myceliophthora thermophila

<400> SEQUENCE: 40

```
Met Ala Lys Lys Leu Phe Ile Thr Ala Ala Leu Ala Ala Ala Val Leu
1               5                   10                  15

Ala Ala Pro Val Ile Glu Glu Arg Gln Asn Cys Gly Ala Val Trp Thr
            20                  25                  30

Gln Cys Gly Gly Asn Gly Trp Gln Gly Pro Thr Cys Cys Ala Ser Gly
        35                  40                  45

Ser Thr Cys Val Ala Gln Asn Glu Trp Tyr Ser Gln Cys Leu Pro Asn
    50                  55                  60

Asn Gln Val Thr Ser Ser Asn Thr Pro Ser Ser Thr Ser Thr Ser Gln
65                  70                  75                  80

Arg Ser Ser Ser Thr Ser Ser Ser Ser Thr Arg Ser Gly Ser Ser Ser
                85                  90                  95

Ser Ser Thr Thr Thr Pro Pro Pro Val Ser Ser Pro Val Thr Ser Ile
            100                 105                 110

Pro Gly Gly Ala Thr Thr Thr Ala Ser Tyr Ser Gly Asn Pro Phe Ser
        115                 120                 125

Gly Val Arg Leu Phe Ala Asn Asp Tyr Tyr Arg Ser Glu Val His Asn
    130                 135                 140

Leu Ala Ile Pro Ser Met Thr Gly Thr Leu Ala Ala Lys Ala Ser Ala
145                 150                 155                 160

Val Ala Glu Val Pro Ser Phe Gln Trp Leu Asp Arg Asn Val Thr Ile
                165                 170                 175

Asp Thr Leu Met Val Gln Thr Leu Ser Gln Ile Arg Ala Ala Asn Asn
            180                 185                 190

Ala Gly Ala Asn Pro Pro Tyr Ala Ala Gln Leu Val Val Tyr Asp Leu
        195                 200                 205

Pro Asp Arg Asp Cys Ala Ala Ala Ala Ser Asn Gly Glu Phe Ser Ile
    210                 215                 220

Ala Asn Gly Gly Ala Ala Asn Tyr Arg Ser Tyr Ile Asp Ala Ile Arg
225                 230                 235                 240

Lys His Ile Ile Glu Tyr Ser Asp Ile Arg Ile Ile Leu Val Ile Glu
                245                 250                 255

Pro Asp Ser Met Ala Asn Met Val Thr Asn Met Asn Val Ala Lys Cys
            260                 265                 270

Ser Asn Ala Ala Ser Thr Tyr His Glu Leu Thr Val Tyr Ala Leu Lys
        275                 280                 285

Gln Leu Asn Leu Pro Asn Val Ala Met Tyr Leu Asp Ala Gly His Ala
    290                 295                 300

Gly Trp Leu Gly Trp Pro Ala Asn Ile Gln Pro Ala Ala Asp Leu Phe
305                 310                 315                 320

Ala Gly Ile Tyr Asn Asp Ala Gly Lys Pro Ala Ala Val Arg Gly Leu
                325                 330                 335

Ala Thr Asn Val Ala Asn Tyr Asn Ala Trp Ser Ile Ala Ser Ala Pro
            340                 345                 350

Ser Tyr Thr Ser Pro Asn Pro Asn Tyr Asp Glu Lys His Tyr Ile Glu
        355                 360                 365

Ala Phe Ser Pro Leu Leu Asn Ala Ala Gly Phe Pro Ala Arg Phe Ile
```

```
    370                 375                 380

Val Asp Thr Gly Arg Asn Gly Lys Gln Pro Thr Gly Gln Gln Gln Trp
385                 390                 395                 400

Gly Asp Trp Cys Asn Val Lys Gly Thr Gly Phe Gly Val Arg Pro Thr
                405                 410                 415

Ala Asn Thr Gly His Asp Leu Val Asp Ala Phe Val Trp Val Lys Pro
            420                 425                 430

Gly Gly Glu Ser Asp Gly Thr Ser Asp Thr Ser Ala Ala Arg Tyr Asp
        435                 440                 445

Tyr His Cys Gly Leu Ser Asp Ala Leu Gln Pro Ala Pro Glu Ala Gly
    450                 455                 460

Gln Trp Phe Gln Ala Tyr Phe Glu Gln Leu Leu Thr Asn Ala Asn Pro
465                 470                 475                 480

Pro Phe


<210> SEQ ID NO 41
<211> LENGTH: 1802
<212> TYPE: DNA
<213> ORGANISM: Myceliophthora thermophila

<400> SEQUENCE: 41

atggccaaga agcttttcat caccgccgcg cttgcggctg ccgtgttggc ggcccccgtc     60

attgaggagc gccagaactg cggcgctgtg tggtaagaaa gcccggtccg agtctcccat    120

gattttctcg tcgagtaatg gcataagggc caccccttcg actgaccgtg agaatcgatc    180

aaatccagga ctcaatgcgg cggtaacggg tggcaaggtc ccacatgctg cgcctcgggc    240

tcgacctgcg ttgcgcagaa cgagtggtac tctcagtgcc tgcccaacag ccaggtgacg    300

agttccacca ctccgtcgtc gacttccacc tcgcagcgca gcaccagcac ctccagcagc    360

accaccagga gcggcagctc ctcctcctcc tccaccacgc ccccgcccgt ctccagcccc    420

gtgaccagca ttcccggcgg tgcgacctcc acggcgagct actctggcaa ccccttctcg    480

ggcgtccggc tcttcgccaa cgactactac aggtccgagg tccacaatct cgccattcct    540

agcatgactg gtactctggc ggccaaggct tccgccgtcg ccgaagtccc tagcttccag    600

tggctcgacc ggaacgtcac catcgacacc ctgatggtcc agactctgtc ccaggtccgg    660

gctctcaata aggccggtgc caatcctccc tatgctggtg agttacatgg cgacttgcct    720

tctcgtcccc tacctttctt gacgggatcg gttacctgac ctggaggcaa aacaacaaca    780

gcccaactcg tcgtctacga cctccccgac cgtgactgtg ccgccgctgc gtccaacggc    840

gagttttcga ttgcaaacgg cggcgccgcc aactacagga gctacatcga cgctatccgc    900

aagcacatca ttgagtactc ggacatccgg atcatcctgg ttatcgagcc cgactcgatg    960

gccaacatgg tgaccaacat gaacgtggcc aagtgcagca acgccgcgtc gacgtaccac   1020

gagttgaccg tgtacgcgct caagcagctg aacctgccca acgtcgccat gtatctcgac   1080

gccggccacg ccggctggct cggctggccc gccaacatcc agcccgccgc cgagctgttt   1140

gccggcatct acaatgatgc cggcaagccg gctgccgtcc gcggcctggc cactaacgtc   1200

gccaactaca acgcctggag catcgcttcg gccccgtcgt acacgtcgcc taaccctaac   1260

tacgacgaga agcactacat cgaggccttc agcccgctct tgaactcggc cggcttcccc   1320

gcacgcttca ttgtcgacac tggccgcaac ggcaaacaac ctaccggtat gttttttttt   1380

cttttgtctc tgtccccccc ttttctcccc cttcagttgg cgtccacaag gtctcttagt   1440

cctgcttcat ctgtgaccaa cctccccccc cccggcaccg cccacaaccg tttgactcta   1500
```

```
tactcttggg aatgggcgcc gaaactgacc gttccacagg ccaacaacag tggggtgact   1560

ggtgcaatgt caagggcacc ggctttggcg tgcgcccgac ggccaacacg ggccacgagc   1620

tggtcgatgc ctttgtctgg gtcaagcccg gcggcgagtc cgacggcaca agcgacacca   1680

gcgccgcccg ctacgactac cactgcggcc tgtccgatgc cctgcagcct gcccccgagg   1740

ctggacagtg gttccaggcc tacttcgagc agctgctcac caacgccaac ccgcccttct   1800

aa                                                                  1802
```

```
<210> SEQ ID NO 42
<211> LENGTH: 481
<212> TYPE: PRT
<213> ORGANISM: Myceliophthora thermophila

<400> SEQUENCE: 42

Met Ala Lys Lys Leu Phe Ile Thr Ala Ala Leu Ala Ala Ala Val Leu
1               5                   10                  15

Ala Ala Pro Val Ile Glu Glu Arg Gln Asn Cys Gly Ala Val Trp Thr
            20                  25                  30

Gln Cys Gly Gly Asn Gly Trp Gln Gly Pro Thr Cys Cys Ala Ser Gly
        35                  40                  45

Ser Thr Cys Val Ala Gln Asn Glu Trp Tyr Ser Gln Cys Leu Pro Asn
    50                  55                  60

Ser Gln Val Thr Ser Ser Thr Thr Pro Ser Ser Thr Ser Thr Ser Gln
65                  70                  75                  80

Arg Ser Thr Ser Thr Ser Ser Ser Thr Thr Arg Ser Gly Ser Ser Ser
                85                  90                  95

Ser Ser Ser Thr Thr Pro Pro Pro Val Ser Ser Pro Val Thr Ser Ile
            100                 105                 110

Pro Gly Gly Ala Thr Ser Thr Ala Ser Tyr Ser Gly Asn Pro Phe Ser
        115                 120                 125

Gly Val Arg Leu Phe Ala Asn Asp Tyr Tyr Arg Ser Glu Val His Asn
    130                 135                 140

Leu Ala Ile Pro Ser Met Thr Gly Thr Leu Ala Ala Lys Ala Ser Ala
145                 150                 155                 160

Val Ala Glu Val Pro Ser Phe Gln Trp Leu Asp Arg Asn Val Thr Ile
                165                 170                 175

Asp Thr Leu Met Val Gln Thr Leu Ser Gln Val Arg Ala Leu Asn Lys
            180                 185                 190

Ala Gly Ala Asn Pro Pro Tyr Ala Ala Gln Leu Val Val Tyr Asp Leu
        195                 200                 205

Pro Asp Arg Asp Cys Ala Ala Ala Ala Ser Asn Gly Glu Phe Ser Ile
    210                 215                 220

Ala Asn Gly Gly Ala Ala Asn Tyr Arg Ser Tyr Ile Asp Ala Ile Arg
225                 230                 235                 240

Lys His Ile Ile Glu Tyr Ser Asp Ile Arg Ile Ile Leu Val Ile Glu
                245                 250                 255

Pro Asp Ser Met Ala Asn Met Val Thr Asn Met Asn Val Ala Lys Cys
            260                 265                 270

Ser Asn Ala Ala Ser Thr Tyr His Glu Leu Thr Val Tyr Ala Leu Lys
        275                 280                 285

Gln Leu Asn Leu Pro Asn Val Ala Met Tyr Leu Asp Ala Gly His Ala
    290                 295                 300

Gly Trp Leu Gly Trp Pro Ala Asn Ile Gln Pro Ala Ala Glu Leu Phe
```

```
305                 310                 315                 320

Ala Gly Ile Tyr Asn Asp Ala Gly Lys Pro Ala Ala Val Arg Gly Leu
                325                 330                 335

Ala Thr Asn Val Ala Asn Tyr Asn Ala Trp Ser Ile Ala Ser Ala Pro
            340                 345                 350

Ser Tyr Thr Ser Pro Asn Pro Asn Tyr Asp Glu Lys His Tyr Ile Glu
        355                 360                 365

Ala Phe Ser Pro Leu Leu Asn Ser Ala Gly Phe Pro Ala Arg Phe Ile
    370                 375                 380

Val Asp Thr Gly Arg Asn Gly Lys Gln Pro Thr Gly Gln Gln Gln Trp
385                 390                 395                 400

Gly Asp Trp Cys Asn Val Lys Gly Thr Gly Phe Gly Val Arg Pro Thr
                405                 410                 415

Ala Asn Thr Gly His Glu Leu Val Asp Ala Phe Val Trp Val Lys Pro
            420                 425                 430

Gly Gly Glu Ser Asp Gly Thr Ser Asp Thr Ser Ala Ala Arg Tyr Asp
        435                 440                 445

Tyr His Cys Gly Leu Ser Asp Ala Leu Gln Pro Ala Pro Glu Ala Gly
    450                 455                 460

Gln Trp Phe Gln Ala Tyr Phe Glu Gln Leu Leu Thr Asn Ala Asn Pro
465                 470                 475                 480

Pro
```

<210> SEQ ID NO 43
<211> LENGTH: 1446
<212> TYPE: DNA
<213> ORGANISM: Thielavia terrestris

<400> SEQUENCE: 43

```
atggctcaga agctccttct cgccgccgcc cttgcggcca gcgccctcgc tgctcccgtc      60

gtcgaggagc gccagaactg cggttccgtc tggagccaat gcggcggcat tggctggtcc     120

ggcgcgacct gctgcgcttc gggcaatacc tgcgttgagc tgaacccgta ctactcgcag     180

tgcctgccca acagccaggt gactacctcg accagcaaga ccacctccac caccaccagg     240

agcagcacca ccagccacag cagcggtccc accagcacga gcaccaccac caccagcagt     300

cccgtggtca ctaccccgcc gagtacctcc atccccggcg gtgcctcgtc aacggccagc     360

tggtccggca acccgttctc gggcgtgcag atgtgggcca acgactacta cgcctccgag     420

gtctcgtcgc tggccatccc cagcatgacg ggcgccatgg ccaccaaggc ggccgaggtg     480

gccaaggtgc ccagcttcca gtggcttgac cgcaacgtca ccatcgacac gctgttcgcc     540

cacacgctgt cgcagatccg cgcggccaac cagaaaggcg ccaacccgcc ctacgcgggc     600

atcttcgtgg tctacgacct tccggaccgc gactgcgccg ccgccgcgtc caacggcgag     660

ttctccatcg cgaacaacgg ggcggccaac tacaagacgt acatcgacgc gatccggagc     720

ctcgtcatcc agtactcaga catccgcatc atcttcgtca tcgagcccga ctcgctggcc     780

aacatggtga ccaacctgaa cgtggccaag tgcgccaacg ccgagtcgac ctacaaggag     840

ttgaccgtct acgcgctgca gcagctgaac ctgcccaacg tggccatgta cctggacgcc     900

ggccacgccg gctggctcgg ctggcccgcc aacatccagc cggccgccaa cctcttcgcc     960

gagatctaca cgagcgccgg caagccggcc gccgtgcgcg gcctcgccac caacgtggcc    1020

aactacaacg gctggagcct ggccacgccg ccctcgtaca cccagggcga ccccaactac    1080

gacgagagcc actacgtcca ggccctcgcc ccgctgctca ccgccaacgg cttccccgcc    1140
```

```
cacttcatca ccgacaccgg ccgcaacggc aagcagccga ccggacaacg gcaatgggga   1200

gactggtgca acgttatcgg aactggcttc ggcgtgcgcc cgacgacaaa caccggcctc   1260

gacatcgagg acgccttcgt ctgggtcaag cccggcggcg agtgcgacgg cacgagcaac   1320

acgacctctc cccgctacga ctaccactgc ggcctgtcgg acgcgctgca gcctgctccg   1380

gaggccggca cttggttcca ggcctacttc gagcagctcc tgaccaacgc caacccgccc   1440

ttttaa                                                              1446
```

```
<210> SEQ ID NO 44
<211> LENGTH: 481
<212> TYPE: PRT
<213> ORGANISM: Thielavia terrestris

<400> SEQUENCE: 44

Met Ala Gln Lys Leu Leu Leu Ala Ala Ala Leu Ala Ala Ser Ala Leu
1               5                   10                  15

Ala Ala Pro Val Val Glu Glu Arg Gln Asn Cys Gly Ser Val Trp Ser
            20                  25                  30

Gln Cys Gly Gly Ile Gly Trp Ser Gly Ala Thr Cys Cys Ala Ser Gly
        35                  40                  45

Asn Thr Cys Val Glu Leu Asn Pro Tyr Tyr Ser Gln Cys Leu Pro Asn
    50                  55                  60

Ser Gln Val Thr Thr Ser Thr Ser Lys Thr Thr Ser Thr Thr Thr Arg
65                  70                  75                  80

Ser Ser Thr Thr Ser His Ser Ser Gly Pro Thr Ser Thr Ser Thr Thr
                85                  90                  95

Thr Thr Ser Ser Pro Val Val Thr Thr Pro Pro Ser Thr Ser Ile Pro
            100                 105                 110

Gly Gly Ala Ser Ser Thr Ala Ser Trp Ser Gly Asn Pro Phe Ser Gly
        115                 120                 125

Val Gln Met Trp Ala Asn Asp Tyr Tyr Ala Ser Glu Val Ser Ser Leu
    130                 135                 140

Ala Ile Pro Ser Met Thr Gly Ala Met Ala Thr Lys Ala Ala Glu Val
145                 150                 155                 160

Ala Lys Val Pro Ser Phe Gln Trp Leu Asp Arg Asn Val Thr Ile Asp
                165                 170                 175

Thr Leu Phe Ala His Thr Leu Ser Gln Ile Arg Ala Ala Asn Gln Lys
            180                 185                 190

Gly Ala Asn Pro Pro Tyr Ala Gly Ile Phe Val Val Tyr Asp Leu Pro
        195                 200                 205

Asp Arg Asp Cys Ala Ala Ala Ala Ser Asn Gly Glu Phe Ser Ile Ala
    210                 215                 220

Asn Asn Gly Ala Ala Asn Tyr Lys Thr Tyr Ile Asp Ala Ile Arg Ser
225                 230                 235                 240

Leu Val Ile Gln Tyr Ser Asp Ile Arg Ile Ile Phe Val Ile Glu Pro
                245                 250                 255

Asp Ser Leu Ala Asn Met Val Thr Asn Leu Asn Val Ala Lys Cys Ala
            260                 265                 270

Asn Ala Glu Ser Thr Tyr Lys Glu Leu Thr Val Tyr Ala Leu Gln Gln
        275                 280                 285

Leu Asn Leu Pro Asn Val Ala Met Tyr Leu Asp Ala Gly His Ala Gly
    290                 295                 300

Trp Leu Gly Trp Pro Ala Asn Ile Gln Pro Ala Ala Asn Leu Phe Ala
```

```
305                 310                 315                 320

Glu Ile Tyr Thr Ser Ala Gly Lys Pro Ala Ala Val Arg Gly Leu Ala
                325                 330                 335

Thr Asn Val Ala Asn Tyr Asn Gly Trp Ser Leu Ala Thr Pro Pro Ser
            340                 345                 350

Tyr Thr Gln Gly Asp Pro Asn Tyr Asp Glu Ser His Tyr Val Gln Ala
        355                 360                 365

Leu Ala Pro Leu Leu Thr Ala Asn Gly Phe Pro Ala His Phe Ile Thr
    370                 375                 380

Asp Thr Gly Arg Asn Gly Lys Gln Pro Thr Gly Gln Arg Gln Trp Gly
385                 390                 395                 400

Asp Trp Cys Asn Val Ile Gly Thr Gly Phe Gly Val Arg Pro Thr Thr
                405                 410                 415

Asn Thr Gly Leu Asp Ile Glu Asp Ala Phe Val Trp Val Lys Pro Gly
            420                 425                 430

Gly Glu Cys Asp Gly Thr Ser Asn Thr Thr Ser Pro Arg Tyr Asp Tyr
        435                 440                 445

His Cys Gly Leu Ser Asp Ala Leu Gln Pro Ala Pro Glu Ala Gly Thr
    450                 455                 460

Trp Phe Gln Ala Tyr Phe Glu Gln Leu Leu Thr Asn Ala Asn Pro Pro
465                 470                 475                 480

Phe
```

```
<210> SEQ ID NO 45
<211> LENGTH: 1593
<212> TYPE: DNA
<213> ORGANISM: Chaetomium thermophilum

<400> SEQUENCE: 45

atgatgtaca agaagttcgc cgctctcgcc gccctcgtgg ctggcgccgc cgcccagcag      60

gcttgctccc tcaccactga gacccacccc agactcactt ggaagcgctg cacctctggc     120

ggcaactgct cgaccgtgaa cggcgccgtc accatcgatg ccaactggcg ctggactcac     180

actgtttccg gctcgaccaa ctgctacacc ggcaacgagt gggatacctc catctgctct     240

gatggcaaga gctgcgccca gacctgctgc gtcgacggcg ctgactactc ttcgacctat     300

ggtatcacca ccagcggtga ctccctgaac ctcaagttcg tcaccaagca ccagcacggc     360

accaatgtcg gctctcgtgt ctacctgatg gagaacgaca ccaagtacca gatgttcgag     420

ctcctcggca acgagttcac cttcgatgtc gatgtctcta acctgggctg cggtctcaac     480

ggcgccctct acttcgtctc catggacgct gatggtggta tgagcaagta ctctggcaac     540

aaggctggcg ccaagtacgg taccggctac tgcgatgctc agtgcccgcg cgaccttaag     600

ttcatcaacg gcgaggccaa cattgagaac tggacccctt cgaccaatga tgccaacgcc     660

ggtttcggcc gctatggcag ctgctgctct gagatggata tctgggatgc caacaacatg     720

gctactgcct tcactcctca cccttgcacc attatcggcc agagccgctg cgagggcaac     780

agctgcggtg gcacctacag ctctgagcgc tatgctggtg tttgcgatcc tgatggctgc     840

gacttcaacg cctaccgcca gggcgacaag accttctacg gcaagggcat gaccgtcgac     900

accaccaaga agatgaccgt cgtcacccag ttccacaaga actcggctgg cgtcctcagc     960

gagatcaagc gcttctacgt tcaggacggc aagatcattg ccaacgccga gtccaagatc    1020

cccggcaacc ccggcaactc catcacccag gagtggtgcg atgcccagaa ggtcgccttc    1080

ggtgacatcg atgacttcaa ccgcaagggc ggtatggctc agatgagcaa ggccctcgag    1140
```

```
ggccctatgg tcctggtcat gtccgtctgg gatgaccact acgccaacat gctctggctc   1200

gactcgacct accccattga caaggccggc acccccggcg ccgagcgcgg tgcttgcccg   1260

accacctccg gtgtccctgc cgagattgag gcccaggtcc ccaacagcaa cgttatcttc   1320

tccaacatcc gcttcggccc catcggctcg accgtccctg gcctcgacgg cagcaccccc   1380

agcaacccga ccgccaccgt tgctcctccc acttctacca ccaccagcgt gagaagcagc   1440

actactcaga tttccacccc gactagccag cccggcggct gcaccaccca gaagtggggc   1500

cagtgcggtg gtatcggcta caccggctgc actaactgcg ttgctggcac tacctgcact   1560

gagctcaacc cctggtacag ccagtgcctg taa                                1593


<210> SEQ ID NO 46
<211> LENGTH: 530
<212> TYPE: PRT
<213> ORGANISM: Chaetomium thermophilum

<400> SEQUENCE: 46

Met Met Tyr Lys Lys Phe Ala Ala Leu Ala Ala Leu Val Ala Gly Ala
1               5                   10                  15

Ala Ala Gln Gln Ala Cys Ser Leu Thr Thr Glu Thr His Pro Arg Leu
            20                  25                  30

Thr Trp Lys Arg Cys Thr Ser Gly Gly Asn Cys Ser Thr Val Asn Gly
        35                  40                  45

Ala Val Thr Ile Asp Ala Asn Trp Arg Trp Thr His Thr Val Ser Gly
    50                  55                  60

Ser Thr Asn Cys Tyr Thr Gly Asn Glu Trp Asp Thr Ser Ile Cys Ser
65                  70                  75                  80

Asp Gly Lys Ser Cys Ala Gln Thr Cys Cys Val Asp Gly Ala Asp Tyr
                85                  90                  95

Ser Ser Thr Tyr Gly Ile Thr Thr Ser Gly Asp Ser Leu Asn Leu Lys
            100                 105                 110

Phe Val Thr Lys His Gln His Gly Thr Asn Val Gly Ser Arg Val Tyr
        115                 120                 125

Leu Met Glu Asn Asp Thr Lys Tyr Gln Met Phe Glu Leu Leu Gly Asn
    130                 135                 140

Glu Phe Thr Phe Asp Val Asp Val Ser Asn Leu Gly Cys Gly Leu Asn
145                 150                 155                 160

Gly Ala Leu Tyr Phe Val Ser Met Asp Ala Asp Gly Gly Met Ser Lys
                165                 170                 175

Tyr Ser Gly Asn Lys Ala Gly Ala Lys Tyr Gly Thr Gly Tyr Cys Asp
            180                 185                 190

Ala Gln Cys Pro Arg Asp Leu Lys Phe Ile Asn Gly Glu Ala Asn Ile
        195                 200                 205

Glu Asn Trp Thr Pro Ser Thr Asn Asp Ala Asn Ala Gly Phe Gly Arg
    210                 215                 220

Tyr Gly Ser Cys Cys Ser Glu Met Asp Ile Trp Asp Ala Asn Asn Met
225                 230                 235                 240

Ala Thr Ala Phe Thr Pro His Pro Cys Thr Ile Ile Gly Gln Ser Arg
                245                 250                 255

Cys Glu Gly Asn Ser Cys Gly Gly Thr Tyr Ser Ser Glu Arg Tyr Ala
            260                 265                 270

Gly Val Cys Asp Pro Asp Gly Cys Asp Phe Asn Ala Tyr Arg Gln Gly
        275                 280                 285
```

```
Asp Lys Thr Phe Tyr Gly Lys Gly Met Thr Val Asp Thr Thr Lys Lys
    290                 295                 300

Met Thr Val Val Thr Gln Phe His Lys Asn Ser Ala Gly Val Leu Ser
305                 310                 315                 320

Glu Ile Lys Arg Phe Tyr Val Gln Asp Gly Lys Ile Ile Ala Asn Ala
                325                 330                 335

Glu Ser Lys Ile Pro Gly Asn Pro Gly Asn Ser Ile Thr Gln Glu Trp
            340                 345                 350

Cys Asp Ala Gln Lys Val Ala Phe Gly Asp Ile Asp Asp Phe Asn Arg
        355                 360                 365

Lys Gly Gly Met Ala Gln Met Ser Lys Ala Leu Glu Gly Pro Met Val
    370                 375                 380

Leu Val Met Ser Val Trp Asp Asp His Tyr Ala Asn Met Leu Trp Leu
385                 390                 395                 400

Asp Ser Thr Tyr Pro Ile Asp Lys Ala Gly Thr Pro Gly Ala Glu Arg
                405                 410                 415

Gly Ala Cys Pro Thr Thr Ser Gly Val Pro Ala Glu Ile Glu Ala Gln
            420                 425                 430

Val Pro Asn Ser Asn Val Ile Phe Ser Asn Ile Arg Phe Gly Pro Ile
        435                 440                 445

Gly Ser Thr Val Pro Gly Leu Asp Gly Ser Thr Pro Ser Asn Pro Thr
    450                 455                 460

Ala Thr Val Ala Pro Pro Thr Ser Thr Thr Thr Ser Val Arg Ser Ser
465                 470                 475                 480

Thr Thr Gln Ile Ser Thr Pro Thr Ser Gln Pro Gly Gly Cys Thr Thr
                485                 490                 495

Gln Lys Trp Gly Gln Cys Gly Gly Ile Gly Tyr Thr Gly Cys Thr Asn
            500                 505                 510

Cys Val Ala Gly Thr Thr Cys Thr Glu Leu Asn Pro Trp Tyr Ser Gln
        515                 520                 525

Cys Leu
    530
```

<210> SEQ ID NO 47
<211> LENGTH: 1434
<212> TYPE: DNA
<213> ORGANISM: Chaetomium thermophilum

<400> SEQUENCE: 47

```
atggctaagc agctgctgct cactgccgct cttgcggcca cttcgctggc tgcccctctc      60

cttgaggagc gccagagctg ctcctccgtc tggggtcaat gcggtggcat caattacaac     120

ggcccgacct gctgccagtc cggcagtgtt tgcacttacc tgaatgactg gtacagccag     180

tgcattcccg gtcaggctca gcccggcacg actagcacca cggctcggac caccagcacc     240

agcaccacca gcacttcgtc ggtccgcccg accacctcga ataccccctgt gacgactgct    300

cccccgacga ccaccatccc gggcggcgcc tcgagcacgg ccagctacaa cggcaacccg     360

ttttcgggtg ttcaactttg ggccaacacc tactactcgt ccgaggtgca cactttggcc     420

atccccagct tgtctcctga gctggctgcc aaggccgcca aggtcgctga ggttcccagc     480

ttccagtggc tcgaccgcaa tgtgactgtt gacactctct tctccggcac tcttgccgaa     540

atccgcgccg ccaaccagcg cggtgccaac ccgccttatg ccggcatttt cgtggtttat     600

gacttaccag accgtgattg cgcggctgct gcttcgaacg gcgagtggtc tatcgccaac     660

aatggtgcca acaactacaa gcgctacatc gaccggatcc gtgagctcct tatccagtac     720
```

```
tccgatatcc gcactattct ggtcattgaa cctgattccc tggccaacat ggtcaccaac    780

atgaacgtcc agaagtgctc gaacgctgcc tccacttaca aggagcttac tgtctatgcc    840

ctcaaacagc tcaatcttcc tcacgttgcc atgtacatgg atgctggcca cgctggctgg    900

cttggctggc ccgccaacat ccagcctgct gctgagctct ttgctcaaat ctaccgcgac    960

gctggcaggc ccgctgctgt ccgcggtctt gcgaccaacg ttgccaacta caatgcttgg   1020

tcgatcgcca gccctccgtc ctacacctct cctaacccga actacgacga gaagcactat   1080

attgaggcct ttgctcctct tctccgcaac cagggcttcg acgcaaagtt catcgtcgac   1140

accggccgta acggcaagca gcccactggc cagcttgaat ggggtcactg gtgcaatgtc   1200

aagggaactg gcttcggtgt gcgccctact gctaacactg ggcatgaact tgttgatgct   1260

ttcgtgtggg tcaagcccgg tggcgagtcc gacggcacca gtgcggacac cagcgctgct   1320

cgttatgact atcactgcgg cctttccgac gcactgactc cggcgcctga ggctggccaa   1380

tggttccagg cttatttcga acagctgctc atcaatgcca accctccgct ctga         1434


<210> SEQ ID NO 48
<211> LENGTH: 477
<212> TYPE: PRT
<213> ORGANISM: Chaetomium thermophilum

<400> SEQUENCE: 48

Met Ala Lys Gln Leu Leu Leu Thr Ala Ala Leu Ala Ala Thr Ser Leu
1               5                   10                  15

Ala Ala Pro Leu Leu Glu Glu Arg Gln Ser Cys Ser Ser Val Trp Gly
            20                  25                  30

Gln Cys Gly Gly Ile Asn Tyr Asn Gly Pro Thr Cys Cys Gln Ser Gly
        35                  40                  45

Ser Val Cys Thr Tyr Leu Asn Asp Trp Tyr Ser Gln Cys Ile Pro Gly
    50                  55                  60

Gln Ala Gln Pro Gly Thr Thr Ser Thr Thr Ala Arg Thr Thr Ser Thr
65                  70                  75                  80

Ser Thr Thr Ser Thr Ser Ser Val Arg Pro Thr Thr Ser Asn Thr Pro
                85                  90                  95

Val Thr Thr Ala Pro Pro Thr Thr Thr Ile Pro Gly Gly Ala Ser Ser
            100                 105                 110

Thr Ala Ser Tyr Asn Gly Asn Pro Phe Ser Gly Val Gln Leu Trp Ala
        115                 120                 125

Asn Thr Tyr Tyr Ser Ser Glu Val His Thr Leu Ala Ile Pro Ser Leu
    130                 135                 140

Ser Pro Glu Leu Ala Ala Lys Ala Ala Lys Val Ala Glu Val Pro Ser
145                 150                 155                 160

Phe Gln Trp Leu Asp Arg Asn Val Thr Val Asp Thr Leu Phe Ser Gly
                165                 170                 175

Thr Leu Ala Glu Ile Arg Ala Ala Asn Gln Arg Gly Ala Asn Pro Pro
            180                 185                 190

Tyr Ala Gly Ile Phe Val Val Tyr Asp Leu Pro Asp Arg Asp Cys Ala
        195                 200                 205

Ala Ala Ala Ser Asn Gly Glu Trp Ser Ile Ala Asn Asn Gly Ala Asn
    210                 215                 220

Asn Tyr Lys Arg Tyr Ile Asp Arg Ile Arg Glu Leu Leu Ile Gln Tyr
225                 230                 235                 240

Ser Asp Ile Arg Thr Ile Leu Val Ile Glu Pro Asp Ser Leu Ala Asn
```

```
                245                 250                 255

Met Val Thr Asn Met Asn Val Gln Lys Cys Ser Asn Ala Ala Ser Thr
            260                 265                 270

Tyr Lys Glu Leu Thr Val Tyr Ala Leu Lys Gln Leu Asn Leu Pro His
        275                 280                 285

Val Ala Met Tyr Met Asp Ala Gly His Ala Gly Trp Leu Gly Trp Pro
    290                 295                 300

Ala Asn Ile Gln Pro Ala Ala Glu Leu Phe Ala Gln Ile Tyr Arg Asp
305                 310                 315                 320

Ala Gly Arg Pro Ala Ala Val Arg Gly Leu Ala Thr Asn Val Ala Asn
                325                 330                 335

Tyr Asn Ala Trp Ser Ile Ala Ser Pro Pro Ser Tyr Thr Ser Pro Asn
            340                 345                 350

Pro Asn Tyr Asp Glu Lys His Tyr Ile Glu Ala Phe Ala Pro Leu Leu
        355                 360                 365

Arg Asn Gln Gly Phe Asp Ala Lys Phe Ile Val Asp Thr Gly Arg Asn
    370                 375                 380

Gly Lys Gln Pro Thr Gly Gln Leu Glu Trp Gly His Trp Cys Asn Val
385                 390                 395                 400

Lys Gly Thr Gly Phe Gly Val Arg Pro Thr Ala Asn Thr Gly His Glu
                405                 410                 415

Leu Val Asp Ala Phe Val Trp Val Lys Pro Gly Gly Glu Ser Asp Gly
            420                 425                 430

Thr Ser Ala Asp Thr Ser Ala Ala Arg Tyr Asp Tyr His Cys Gly Leu
        435                 440                 445

Ser Asp Ala Leu Thr Pro Ala Pro Glu Ala Gly Gln Trp Phe Gln Ala
    450                 455                 460

Tyr Phe Glu Gln Leu Leu Ile Asn Ala Asn Pro Pro Leu
465                 470                 475
```

<210> SEQ ID NO 49
<211> LENGTH: 1599
<212> TYPE: DNA
<213> ORGANISM: Aspergillus fumigatus

<400> SEQUENCE: 49

```
atgctggcct ccaccttctc ctaccgcatg tacaagaccg cgctcatcct ggccgccctt      60

ctgggctctg gccaggctca gcaggtcggt acttcccagg cggaagtgca tccgtccatg     120

acctggcaga gctgcacggc tggcggcagc tgcaccacca acaacggcaa ggtggtcatc     180

gacgcgaact ggcgttgggt gcacaaagtc ggcgactaca ccaactgcta caccggcaac     240

acctgggaca cgactatctg ccctgacgat gcgacctgcg catccaactg cgcccttgag     300

ggtgccaact acgaatccac ctatggtgtg accgccagcg gcaattccct ccgcctcaac     360

ttcgtcacca ccagccagca gaagaacatt ggctcgcgtc tgtacatgat gaaggacgac     420

tcgacctacg agatgtttaa gctgctgaac caggagttca ccttcgatgt cgatgtctcc     480

aacctcccct gcggtctcaa cggtgctctg tactttgtcg ccatggacgc cgacggtggc     540

atgtccaagt acccaaccaa caaggccggt gccaagtacg gtactggata ctgtgactcg     600

cagtgccctc gcgacctcaa gttcatcaac ggtcaggcca acgtcgaagg gtggcagccc     660

tcctccaacg atgccaatgc gggtaccggc aaccacgggt cctgctgcgc ggagatggat     720

atctgggagg ccaacagcat ctccacggcc ttcaccccc atccgtgcga cacgcccggc     780

caggtgatgt gcaccggtga tgcctgcggt ggcacctaca gctccgaccg ctacggcggc     840
```

```
acctgcgacc ccgacggatg tgatttcaac tccttccgcc agggcaacaa gaccttctac    900

ggccctggca tgaccgtcga caccaagagc aagtttaccg tcgtcaccca gttcatcacc    960

gacgacggca cctccagcgg caccctcaag gagatcaagc gcttctacgt gcagaacggc   1020

aaggtgatcc ccaactcgga gtcgacctgg accggcgtca gcggcaactc catcaccacc   1080

gagtactgca ccgcccagaa gagcctgttc caggaccaga acgtcttcga aaagcacggc   1140

ggcctcgagg gcatgggtgc tgccctcgcc cagggtatgg ttctcgtcat gtccctgtgg   1200

gatgatcact cggccaacat gctctggctc gacagcaact acccgaccac tgcctcttcc   1260

accactcccg gcgtcgcccg tggtacctgc gacatctcct ccggcgtccc tgcggatgtc   1320

gaggcgaacc accccgacgc ctacgtcgtc tactccaaca tcaaggtcgg ccccatcggc   1380

tcgaccttca acagcggtgg ctcgaacccc ggtggcggaa ccaccacgac aactaccacc   1440

cagcctacta ccaccacgac cacggctgga aaccctggcg gcaccggagt cgcacagcac   1500

tatggccagt gtggtggaat cggatggacc ggacccacaa cctgtgccag cccttatacc   1560

tgccagaagc tgaatgatta ttactctcag tgcctgtag                          1599
```

```
<210> SEQ ID NO 50
<211> LENGTH: 532
<212> TYPE: PRT
<213> ORGANISM: Aspergillus fumigatus

<400> SEQUENCE: 50

Met Leu Ala Ser Thr Phe Ser Tyr Arg Met Tyr Lys Thr Ala Leu Ile
1               5                   10                  15

Leu Ala Ala Leu Leu Gly Ser Gly Gln Ala Gln Gln Val Gly Thr Ser
            20                  25                  30

Gln Ala Glu Val His Pro Ser Met Thr Trp Gln Ser Cys Thr Ala Gly
        35                  40                  45

Gly Ser Cys Thr Thr Asn Asn Gly Lys Val Val Ile Asp Ala Asn Trp
    50                  55                  60

Arg Trp Val His Lys Val Gly Asp Tyr Thr Asn Cys Tyr Thr Gly Asn
65                  70                  75                  80

Thr Trp Asp Thr Thr Ile Cys Pro Asp Asp Ala Thr Cys Ala Ser Asn
                85                  90                  95

Cys Ala Leu Glu Gly Ala Asn Tyr Glu Ser Thr Tyr Gly Val Thr Ala
            100                 105                 110

Ser Gly Asn Ser Leu Arg Leu Asn Phe Val Thr Thr Ser Gln Gln Lys
        115                 120                 125

Asn Ile Gly Ser Arg Leu Tyr Met Met Lys Asp Asp Ser Thr Tyr Glu
    130                 135                 140

Met Phe Lys Leu Leu Asn Gln Glu Phe Thr Phe Asp Val Asp Val Ser
145                 150                 155                 160

Asn Leu Pro Cys Gly Leu Asn Gly Ala Leu Tyr Phe Val Ala Met Asp
                165                 170                 175

Ala Asp Gly Gly Met Ser Lys Tyr Pro Thr Asn Lys Ala Gly Ala Lys
            180                 185                 190

Tyr Gly Thr Gly Tyr Cys Asp Ser Gln Cys Pro Arg Asp Leu Lys Phe
        195                 200                 205

Ile Asn Gly Gln Ala Asn Val Glu Gly Trp Gln Pro Ser Ser Asn Asp
    210                 215                 220

Ala Asn Ala Gly Thr Gly Asn His Gly Ser Cys Cys Ala Glu Met Asp
225                 230                 235                 240
```

```
Ile Trp Glu Ala Asn Ser Ile Ser Thr Ala Phe Thr Pro His Pro Cys
                245                 250                 255

Asp Thr Pro Gly Gln Val Met Cys Thr Gly Asp Ala Cys Gly Gly Thr
            260                 265                 270

Tyr Ser Ser Asp Arg Tyr Gly Gly Thr Cys Asp Pro Asp Gly Cys Asp
        275                 280                 285

Phe Asn Ser Phe Arg Gln Gly Asn Lys Thr Phe Tyr Gly Pro Gly Met
    290                 295                 300

Thr Val Asp Thr Lys Ser Lys Phe Thr Val Val Thr Gln Phe Ile Thr
305                 310                 315                 320

Asp Asp Gly Thr Ser Ser Gly Thr Leu Lys Glu Ile Lys Arg Phe Tyr
                325                 330                 335

Val Gln Asn Gly Lys Val Ile Pro Asn Ser Glu Ser Thr Trp Thr Gly
            340                 345                 350

Val Ser Gly Asn Ser Ile Thr Thr Glu Tyr Cys Thr Ala Gln Lys Ser
        355                 360                 365

Leu Phe Gln Asp Gln Asn Val Phe Glu Lys His Gly Gly Leu Glu Gly
    370                 375                 380

Met Gly Ala Ala Leu Ala Gln Gly Met Val Leu Val Met Ser Leu Trp
385                 390                 395                 400

Asp Asp His Ser Ala Asn Met Leu Trp Leu Asp Ser Asn Tyr Pro Thr
                405                 410                 415

Thr Ala Ser Ser Thr Thr Pro Gly Val Ala Arg Gly Thr Cys Asp Ile
            420                 425                 430

Ser Ser Gly Val Pro Ala Asp Val Glu Ala Asn His Pro Asp Ala Tyr
        435                 440                 445

Val Val Tyr Ser Asn Ile Lys Val Gly Pro Ile Gly Ser Thr Phe Asn
    450                 455                 460

Ser Gly Gly Ser Asn Pro Gly Gly Gly Thr Thr Thr Thr Thr Thr Thr
465                 470                 475                 480

Gln Pro Thr Thr Thr Thr Thr Thr Ala Gly Asn Pro Gly Gly Thr Gly
                485                 490                 495

Val Ala Gln His Tyr Gly Gln Cys Gly Gly Ile Gly Trp Thr Gly Pro
            500                 505                 510

Thr Thr Cys Ala Ser Pro Tyr Thr Cys Gln Lys Leu Asn Asp Tyr Tyr
        515                 520                 525

Ser Gln Cys Leu
    530
```

<210> SEQ ID NO 51
<211> LENGTH: 1713
<212> TYPE: DNA
<213> ORGANISM: Aspergillus fumigatus

<400> SEQUENCE: 51

```
atgaagcacc ttgcatcttc catcgcattg actctactgt tgcctgccgt gcaggcccag      60

cagaccgtat ggggccaatg tatgttctgg ctgtcactgg aataagactg tatcaactgc     120

tgatatgctt ctaggtggcg gccaaggctg gtctggcccg acgagctgtg ttgccggcgc     180

agcctgtagc acactgaatc cctgtatgtt agatatcgtc ctgagtggag acttatactg     240

acttccttag actacgctca gtgtatcccg ggagccaccg cgacgtccac caccctcacg     300

acgacgacgg cggcgacgac gacatcccag accaccacca aacctaccac gactggtcca     360

actacatccg cacccaccgt gaccgcatcc ggtaaccctt tcagcggcta ccagctgtat     420
```

```
gccaacccct actactcctc cgaggtccat actctggcca tgccttctct gcccagctcg    480
ctgcagccca aggctagtgc tgttgctgaa gtgccctcat ttgtttggct gtaagtggcc    540
ttatcccaat actgagacca actctctgac agtcgtagcg acgttgccgc caaggtgccc    600
actatgggaa cctacctggc cgacattcag gccaagaaca aggccggcgc caaccctcct    660
atcgctggta tcttcgtggt ctacgacttg ccggaccgtg actgcgccgc tctggccagt    720
aatggcgagt actcaattgc caacaacggt gtggccaact acaaggcgta cattgacgcc    780
atccgtgctc agctggtgaa gtactctgac gttcacacca tcctcgtcat cggtaggccg    840
tacacctccg ttgcgcgccg cctttctctg acatcttgca gaacccgaca gcttggccaa    900
cctggtgacc aacctcaacg tcgccaaatg cgccaatgcg cagagcgcct acctggagtg    960
tgtcgactat gctctgaagc agctcaacct gcccaacgtc gccatgtacc tcgacgcagg   1020
tatgcctcac ttcccgcatt ctgtatccct tccagacact aactcatcag gccatgcggg   1080
ctggctcgga tggcccgcca acttgggccc cgccgcaaca ctcttcgcca aagtctacac   1140
cgacgcgggt tcccccgcgg ctgttcgtgg cctggccacc aacgtcgcca actacaacgc   1200
ctggtcgctc agtacctgcc cctcctacac ccagggagac cccaactgcg acgagaagaa   1260
gtacatcaac gccatggcgc ctcttctcaa ggaagccggc ttcgatgccc acttcatcat   1320
ggatacctgt aagtgcttat tccaatcgcc gatgtgtgcc gactaatcaa tgtttcagcc   1380
cggaatggcg tccagcccac gaagcaaaac gcctggggtg actggtgcaa cgtcatcggc   1440
accggcttcg gtgttcgccc ctcgactaac accggcgatc cgctccagga tgcctttgtg   1500
tggatcaagc ccggtggaga gagtgatggc acgtccaact cgacttcccc ccggtatgac   1560
gcgcactgcg gatatagtga tgctctgcag cctgctcctg aggctggtac ttggttccag   1620
gtatgtcatc cattagccag atgagggata agtgactgac ggacctaggc ctactttgag   1680
cagcttctga ccaacgctaa cccgtccttt taa                                1713
```

<210> SEQ ID NO 52
<211> LENGTH: 454
<212> TYPE: PRT
<213> ORGANISM: Aspergillus fumigatus

<400> SEQUENCE: 52

```
Met Lys His Leu Ala Ser Ser Ile Ala Leu Thr Leu Leu Leu Pro Ala
1               5                   10                  15

Val Gln Ala Gln Gln Thr Val Trp Gly Gln Cys Gly Gly Gln Gly Trp
            20                  25                  30

Ser Gly Pro Thr Ser Cys Val Ala Gly Ala Ala Cys Ser Thr Leu Asn
        35                  40                  45

Pro Tyr Tyr Ala Gln Cys Ile Pro Gly Ala Thr Ala Thr Ser Thr Thr
    50                  55                  60

Leu Thr Thr Thr Thr Ala Ala Thr Thr Thr Ser Gln Thr Thr Thr Lys
65                  70                  75                  80

Pro Thr Thr Thr Gly Pro Thr Thr Ser Ala Pro Thr Val Thr Ala Ser
                85                  90                  95

Gly Asn Pro Phe Ser Gly Tyr Gln Leu Tyr Ala Asn Pro Tyr Tyr Ser
            100                 105                 110

Ser Glu Val His Thr Leu Ala Met Pro Ser Leu Pro Ser Ser Leu Gln
        115                 120                 125

Pro Lys Ala Ser Ala Val Ala Glu Val Pro Ser Phe Val Trp Leu Asp
    130                 135                 140
```

```
Val Ala Ala Lys Val Pro Thr Met Gly Thr Tyr Leu Ala Asp Ile Gln
145                 150                 155                 160

Ala Lys Asn Lys Ala Gly Ala Asn Pro Pro Ile Ala Gly Ile Phe Val
                165                 170                 175

Val Tyr Asp Leu Pro Asp Arg Asp Cys Ala Ala Leu Ala Ser Asn Gly
            180                 185                 190

Glu Tyr Ser Ile Ala Asn Asn Gly Val Ala Asn Tyr Lys Ala Tyr Ile
        195                 200                 205

Asp Ala Ile Arg Ala Gln Leu Val Lys Tyr Ser Asp Val His Thr Ile
    210                 215                 220

Leu Val Ile Glu Pro Asp Ser Leu Ala Asn Leu Val Thr Asn Leu Asn
225                 230                 235                 240

Val Ala Lys Cys Ala Asn Ala Gln Ser Ala Tyr Leu Glu Cys Val Asp
                245                 250                 255

Tyr Ala Leu Lys Gln Leu Asn Leu Pro Asn Val Ala Met Tyr Leu Asp
            260                 265                 270

Ala Gly His Ala Gly Trp Leu Gly Trp Pro Ala Asn Leu Gly Pro Ala
        275                 280                 285

Ala Thr Leu Phe Ala Lys Val Tyr Thr Asp Ala Gly Ser Pro Ala Ala
    290                 295                 300

Val Arg Gly Leu Ala Thr Asn Val Ala Asn Tyr Asn Ala Trp Ser Leu
305                 310                 315                 320

Ser Thr Cys Pro Ser Tyr Thr Gln Gly Asp Pro Asn Cys Asp Glu Lys
                325                 330                 335

Lys Tyr Ile Asn Ala Met Ala Pro Leu Leu Lys Glu Ala Gly Phe Asp
            340                 345                 350

Ala His Phe Ile Met Asp Thr Ser Arg Asn Gly Val Gln Pro Thr Lys
        355                 360                 365

Gln Asn Ala Trp Gly Asp Trp Cys Asn Val Ile Gly Thr Gly Phe Gly
    370                 375                 380

Val Arg Pro Ser Thr Asn Thr Gly Asp Pro Leu Gln Asp Ala Phe Val
385                 390                 395                 400

Trp Ile Lys Pro Gly Gly Glu Ser Asp Gly Thr Ser Asn Ser Thr Ser
                405                 410                 415

Pro Arg Tyr Asp Ala His Cys Gly Tyr Ser Asp Ala Leu Gln Pro Ala
            420                 425                 430

Pro Glu Ala Gly Thr Trp Phe Gln Ala Tyr Phe Glu Gln Leu Leu Thr
        435                 440                 445

Asn Ala Asn Pro Ser Phe
    450
```

<210> SEQ ID NO 53
<211> LENGTH: 2586
<212> TYPE: DNA
<213> ORGANISM: Aspergillus oryzae

<400> SEQUENCE: 53

```
atgaagcttg gttggatcga ggtggccgca ttggcggctg cctcagtagt cagtgccaag     60

gatgatctcg cgtactcccc tcctttctac ccttccccat gggcagatgg tcagggtgaa    120

tgggcggaag tatacaaacg cgctgtagac atagtttccc agatgacgtt gacagagaaa    180

gtcaacttaa cgactggaac aggatggcaa ctagagaggt gtgttggaca aactggcagt    240

gttcccagac tcaacatccc cagcttgtgt ttgcaggata gtcctcttgg tattcgtttc    300
```

```
tcggactaca attcagcttt ccctgcgggt gttaatgtcg ctgccacctg ggacaagacg    360
ctcgcctacc ttcgtggtca ggcaatgggt gaggagttca gtgataaggg tattgacgtt    420
cagctgggtc ctgctgctgg ccctctcggt gctcatccgg atggcggtag aaactgggaa    480
ggtttctcac cagatccagc cctcaccggt gtactttttg cggagacgat taagggtatt    540
caagatgctg gtgtcattgc gacagctaag cattatatca tgaacgaaca agagcatttc    600
cgccaacaac ccgaggctgc gggttacgga ttcaacgtaa gcgacagttt gagttccaac    660
gttgatgaca agactatgca tgaattgtac ctctggccct tcgcggatgc agtacgcgct    720
ggagtcggtg ctgtcatgtg ctcttacaac caaatcaaca acagctacgg ttgcgagaat    780
agcgaaactc tgaacaagct tttgaaggcg gagcttggtt tccaaggctt cgtcatgagt    840
gattggaccg ctcatcacag cggcgtaggc gctgctttag caggtctgga tatgtcgatg    900
cccggtgatg ttaccttcga tagtggtacg tctttctggg gtgcaaactt gacggtcggt    960
gtccttaacg gtacaatccc ccaatggcgt gttgatgaca tggctgtccg tatcatggcc   1020
gcttattaca aggttggccg cgacaccaaa tacacccctc ccaacttcag ctcgtggacc   1080
agggacgaat atggtttcgc gcataaccat gtttcggaag gtgcttacga gagggtcaac   1140
gaattcgtgg acgtgcaacg cgatcatgcc gacctaatcc gtcgcatcgg cgcgcagagc   1200
actgttctgc tgaagaacaa gggtgccttg cccttgagcc gcaaggaaaa gctggtcgcc   1260
cttctgggag aggatgcggg ttccaactcg tggggcgcta acggctgtga tgaccgtggt   1320
tgcgataacg gtacccttgc catggcctgg ggtagcggta ctgcgaattt cccatacctc   1380
gtgacaccag agcaggcgat tcagaacgaa gttcttcagg gccgtggtaa tgtcttcgcc   1440
gtgaccgaca gttgggcgct cgacaagatc gctgcggctg cccgccaggc cagcgtatct   1500
ctcgtgttcg tcaactccga ctcaggagaa ggctatctta gtgtggatgg aaatgagggc   1560
gatcgtaaca acatcactct gtggaagaac ggcgacaatg tggtcaagac cgcagcgaat   1620
aactgtaaca acaccgttgt catcatccac tccgtcggac cagttttgat cgatgaatgg   1680
tatgaccacc ccaatgtcac tggtattctc tgggctggtc tgccaggcca ggagtctggt   1740
aactccattg ccgatgtgct gtacggtcgt gtcaaccctg gcgccaagtc tcctttcact   1800
tggggcaaga cccgggagtc gtatggttct cccttggtca aggatgccaa caatggcaac   1860
ggagcgcccc agtctgattt cacccagggt gttttcatcg attaccgcca tttcgataag   1920
ttcaatgaga cccctatcta cgagtttggc tacggcttga gctacaccac cttcgagctc   1980
tccgacctcc atgttcagcc cctgaacgcg tcccgataca ctcccaccag tggcatgact   2040
gaagctgcaa agaactttgg tgaaattggc gatgcgtcgg agtacgtgta tccggagggg   2100
ctggaaagga tccatgagtt tatctatccc tggatcaact ctaccgacct gaaggcatcg   2160
tctgacgatt ctaactacgg ctgggaagac tccaagtata ttcccgaagg cgccacggat   2220
gggtctgccc agccccgttt gcccgctagt ggtggtgccg gaggaaaccc cggtctgtac   2280
gaggatcttt tccgcgtctc tgtgaaggtc aagaacacgg gcaatgtcgc cggtgatgaa   2340
gttcctcagc tgtacgtttc cctaggcggc ccgaatgagc ccaaggtggt actgcgcaag   2400
tttgagcgta ttcacttggc cccttcgcag gaggccgtgt ggacaacgac ccttacccgt   2460
cgtgaccttg caaactggga cgtttcggct caggactgga ccgtcactcc ttaccccaag   2520
acgatctacg ttggaaactc ctcacggaaa ctgccgctcc aggcctcgct gcctaaggcc   2580
cagtaa                                                              2586
```

<210> SEQ ID NO 54
<211> LENGTH: 861
<212> TYPE: PRT
<213> ORGANISM: Aspergillus oryzae

<400> SEQUENCE: 54

```
Met Lys Leu Gly Trp Ile Glu Val Ala Ala Leu Ala Ala Ala Ser Val
1               5                   10                  15

Val Ser Ala Lys Asp Asp Leu Ala Tyr Ser Pro Pro Phe Tyr Pro Ser
            20                  25                  30

Pro Trp Ala Asp Gly Gln Gly Glu Trp Ala Glu Val Tyr Lys Arg Ala
        35                  40                  45

Val Asp Ile Val Ser Gln Met Thr Leu Thr Glu Lys Val Asn Leu Thr
    50                  55                  60

Thr Gly Thr Gly Trp Gln Leu Glu Arg Cys Val Gly Gln Thr Gly Ser
65                  70                  75                  80

Val Pro Arg Leu Asn Ile Pro Ser Leu Cys Leu Gln Asp Ser Pro Leu
                85                  90                  95

Gly Ile Arg Phe Ser Asp Tyr Asn Ser Ala Phe Pro Ala Gly Val Asn
            100                 105                 110

Val Ala Ala Thr Trp Asp Lys Thr Leu Ala Tyr Leu Arg Gly Gln Ala
        115                 120                 125

Met Gly Glu Glu Phe Ser Asp Lys Gly Ile Asp Val Gln Leu Gly Pro
    130                 135                 140

Ala Ala Gly Pro Leu Gly Ala His Pro Asp Gly Gly Arg Asn Trp Glu
145                 150                 155                 160

Gly Phe Ser Pro Asp Pro Ala Leu Thr Gly Val Leu Phe Ala Glu Thr
                165                 170                 175

Ile Lys Gly Ile Gln Asp Ala Gly Val Ile Ala Thr Ala Lys His Tyr
            180                 185                 190

Ile Met Asn Glu Gln Glu His Phe Arg Gln Gln Pro Glu Ala Ala Gly
        195                 200                 205

Tyr Gly Phe Asn Val Ser Asp Ser Leu Ser Ser Asn Val Asp Asp Lys
    210                 215                 220

Thr Met His Glu Leu Tyr Leu Trp Pro Phe Ala Asp Ala Val Arg Ala
225                 230                 235                 240

Gly Val Gly Ala Val Met Cys Ser Tyr Asn Gln Ile Asn Asn Ser Tyr
                245                 250                 255

Gly Cys Glu Asn Ser Glu Thr Leu Asn Lys Leu Leu Lys Ala Glu Leu
            260                 265                 270

Gly Phe Gln Gly Phe Val Met Ser Asp Trp Thr Ala His His Ser Gly
        275                 280                 285

Val Gly Ala Ala Leu Ala Gly Leu Asp Met Ser Met Pro Gly Asp Val
    290                 295                 300

Thr Phe Asp Ser Gly Thr Ser Phe Trp Gly Ala Asn Leu Thr Val Gly
305                 310                 315                 320

Val Leu Asn Gly Thr Ile Pro Gln Trp Arg Val Asp Asp Met Ala Val
                325                 330                 335

Arg Ile Met Ala Ala Tyr Tyr Lys Val Gly Arg Asp Thr Lys Tyr Thr
            340                 345                 350

Pro Pro Asn Phe Ser Ser Trp Thr Arg Asp Glu Tyr Gly Phe Ala His
        355                 360                 365

Asn His Val Ser Glu Gly Ala Tyr Glu Arg Val Asn Glu Phe Val Asp
    370                 375                 380
```

```
Val Gln Arg Asp His Ala Asp Leu Ile Arg Arg Ile Gly Ala Gln Ser
385                 390                 395                 400

Thr Val Leu Leu Lys Asn Lys Gly Ala Leu Pro Leu Ser Arg Lys Glu
                405                 410                 415

Lys Leu Val Ala Leu Leu Gly Glu Asp Ala Gly Ser Asn Ser Trp Gly
            420                 425                 430

Ala Asn Gly Cys Asp Asp Arg Gly Cys Asp Asn Gly Thr Leu Ala Met
        435                 440                 445

Ala Trp Gly Ser Gly Thr Ala Asn Phe Pro Tyr Leu Val Thr Pro Glu
    450                 455                 460

Gln Ala Ile Gln Asn Glu Val Leu Gln Gly Arg Gly Asn Val Phe Ala
465                 470                 475                 480

Val Thr Asp Ser Trp Ala Leu Asp Lys Ile Ala Ala Ala Ala Arg Gln
                485                 490                 495

Ala Ser Val Ser Leu Val Phe Val Asn Ser Asp Ser Gly Glu Gly Tyr
            500                 505                 510

Leu Ser Val Asp Gly Asn Glu Gly Asp Arg Asn Asn Ile Thr Leu Trp
        515                 520                 525

Lys Asn Gly Asp Asn Val Val Lys Thr Ala Ala Asn Asn Cys Asn Asn
    530                 535                 540

Thr Val Val Ile Ile His Ser Val Gly Pro Val Leu Ile Asp Glu Trp
545                 550                 555                 560

Tyr Asp His Pro Asn Val Thr Gly Ile Leu Trp Ala Gly Leu Pro Gly
                565                 570                 575

Gln Glu Ser Gly Asn Ser Ile Ala Asp Val Leu Tyr Gly Arg Val Asn
            580                 585                 590

Pro Gly Ala Lys Ser Pro Phe Thr Trp Gly Lys Thr Arg Glu Ser Tyr
        595                 600                 605

Gly Ser Pro Leu Val Lys Asp Ala Asn Asn Gly Asn Gly Ala Pro Gln
    610                 615                 620

Ser Asp Phe Thr Gln Gly Val Phe Ile Asp Tyr Arg His Phe Asp Lys
625                 630                 635                 640

Phe Asn Glu Thr Pro Ile Tyr Glu Phe Gly Tyr Gly Leu Ser Tyr Thr
                645                 650                 655

Thr Phe Glu Leu Ser Asp Leu His Val Gln Pro Leu Asn Ala Ser Arg
            660                 665                 670

Tyr Thr Pro Thr Ser Gly Met Thr Glu Ala Ala Lys Asn Phe Gly Glu
        675                 680                 685

Ile Gly Asp Ala Ser Glu Tyr Val Tyr Pro Glu Gly Leu Glu Arg Ile
    690                 695                 700

His Glu Phe Ile Tyr Pro Trp Ile Asn Ser Thr Asp Leu Lys Ala Ser
705                 710                 715                 720

Ser Asp Asp Ser Asn Tyr Gly Trp Glu Asp Ser Lys Tyr Ile Pro Glu
                725                 730                 735

Gly Ala Thr Asp Gly Ser Ala Gln Pro Arg Leu Pro Ala Ser Gly Gly
            740                 745                 750

Ala Gly Gly Asn Pro Gly Leu Tyr Glu Asp Leu Phe Arg Val Ser Val
        755                 760                 765

Lys Val Lys Asn Thr Gly Asn Val Ala Gly Asp Glu Val Pro Gln Leu
    770                 775                 780

Tyr Val Ser Leu Gly Gly Pro Asn Glu Pro Lys Val Val Leu Arg Lys
785                 790                 795                 800

Phe Glu Arg Ile His Leu Ala Pro Ser Gln Glu Ala Val Trp Thr Thr
```

805 810 815

Thr Leu Thr Arg Arg Asp Leu Ala Asn Trp Asp Val Ser Ala Gln Asp
820 825 830

Trp Thr Val Thr Pro Tyr Pro Lys Thr Ile Tyr Val Gly Asn Ser Ser
835 840 845

Arg Lys Leu Pro Leu Gln Ala Ser Leu Pro Lys Ala Gln
850 855 860

<210> SEQ ID NO 55
<211> LENGTH: 3060
<212> TYPE: DNA
<213> ORGANISM: Aspergillus fumigatus

<400> SEQUENCE: 55

```
atgagattcg gttggctcga ggtggccgct ctgacggccg cttctgtagc caatgcccag     60
gtttgtgatg ctttcccgtc attgtttcgg atatagttga caatagtcat ggaaataatc    120
aggaattggc tttctctcca ccattctacc cttcgccttg ggctgatggc cagggagagt    180
gggcagatgc ccatcgacgc gccgtcgaga tcgtttctca gatgacactg gcggagaagg    240
ttaaccttac aacgggtact gggtgggttg cgactttttt gttgacagtg agctttcttc    300
actgaccatc tacacagatg ggaaatggac cgatgcgtcg gtcaaaccgg cagcgttccc    360
aggtaagctt gcaattctgc aacaacgtgc aagtgtagtt gctaaaacgc ggtggtgcag    420
acttggtatc aactggggtc tttgtggcca ggattcccct ttgggtatcc gtttctgtga    480
gctatacccg cggagtcttt cagtccttgt attatgtgct gatgattgtc tctgtatagc    540
tgacctcaac tccgccttcc ctgctggtac taatgtcgcc gcgacatggg acaagacact    600
cgcctacctt cgtggcaagg ccatgggtga ggaattcaac gacaagggcg tggacatttt    660
gctggggcct gctgctggtc ctctcggcaa atacccggac ggcggcagaa tctgggaagg    720
cttctctcct gatccggttc tcactggtgt acttttcgcc gaaactatca agggtatcca    780
agacgcgggt gtgattgcta ctgccaagca ttacattctg aatgaacagg agcatttccg    840
acaggttggc gaggcccagg gatatggtta caacatcacg gagacgatca gctccaacgt    900
ggatgacaag accatgcacg agttgtacct ttggtgagta gttgacactg caaatgagga    960
ccttgattga tttgactgac ctggaatgca ggccctttgc agatgctgtg cgcggtaaga   1020
ttttccgtag acttgacctc gcgacgaaga aatcgctgac gaaccatcgt agctggcgtt   1080
ggcgctgtca tgtgttccta caatcaaatc aacaacagct acggttgtca aaacagtcaa   1140
actctcaaca agctcctcaa ggctgagctg ggcttccaag gcttcgtcat gagtgactgg   1200
agcgctcacc acagcggtgt cggcgctgcc ctcgctgggt tggatatgtc gatgcctgga   1260
gacatttcct tcgacgacgg actctccttc tggggcacga acctaactgt cagtgttctt   1320
aacggcaccg ttccagcctg gcgtgtcgat gacatggctg ttcgtatcat gaccgcgtac   1380
tacaaggttg gtcgtgaccg tcttcgtatt ccccctaact tcagctcctg gacccgggat   1440
gagtacggct gggagcattc tgctgtctcc gagggagcct ggaccaaggt gaacgacttc   1500
gtcaatgtgc agcgcagtca ctctcagatc atccgtgaga ttggtgccgc tagtacagtg   1560
ctcttgaaga acacgggtgc tcttcctttg accggcaagg aggttaaagt gggtgttctc   1620
ggtgaagacg ctggttccaa cccgtggggt gctaacggct gccccgaccg cggctgtgat   1680
aacggcactc ttgctatggc ctggggtagt ggtactgcca acttccctta ccttgtcacc   1740
cccgagcagg ctatccagcg agaggtcatc agcaacggcg gcaatgtctt tgctgtgact   1800
```

```
gataacgggg ctctcagcca gatggcagat gttgcatctc aatccaggtg agtgcgggct   1860
cttagaaaaa gaacgttctc tgaatgaagt tttttaacca ttgcgaacag cgtgtctttg   1920
gtgtttgtca acgccgactc tggagagggt ttcatcagtg tcgacggcaa cgagggtgac   1980
cgcaaaaatc tcactctgtg gaagaacggc gaggccgtca ttgacactgt tgtcagccac   2040
tgcaacaaca cgattgtggt tattcacagt gttgggcccg tcttgatcga ccggtggtat   2100
gataacccca acgtcactgc catcatctgg gccggcttgc ccggtcagga gagtggcaac   2160
tccctggtcg acgtgctcta tggccgcgtc aaccccagcg ccaagacccc gttcacctgg   2220
ggcaagactc gggagtctta cggggctccc ttgctcaccg agcctaacaa tggcaatggt   2280
gctccccagg atgatttcaa cgagggcgtc ttcattgact accgtcactt tgacaagcgc   2340
aatgagaccc ccatttatga gtttggccat ggcttgagct acaccacctt tggttactct   2400
caccttcggg ttcaggccct caatagttcg agttcggcat atgtcccgac tagcggagag   2460
accaagcctg cgccaaccta tggtgagatc ggtagtgccg ccgactacct gtatcccgag   2520
ggtctcaaaa gaattaccaa gtttatttac ccttggctca actcgaccga cctcgaggat   2580
tcttctgacg acccgaacta cggctgggag gactcggagt acattcccga aggcgctagg   2640
gatgggtctc ctcaacccct cctgaaggct ggcggcgctc ctggtggtaa ccctaccctt   2700
tatcaggatc ttgttagggt gtcggccacc ataaccaaca ctggtaacgt cgccggttat   2760
gaagtccctc aattggtgag tgacccgcat gttccttgcg ttgcaatttg gctaactcgc   2820
ttctagtatg tttcactggg cggaccgaac gagcctcggg tcgttctgcg caagttcgac   2880
cgaatcttcc tggctcctgg ggagcaaaag gtttggacca cgactcttaa ccgtcgtgat   2940
ctcgccaatt gggatgtgga ggctcaggac tgggtcatca caaagtaccc caagaaagtg   3000
cacgtcggca gctcctcgcg taagctgcct ctgagagcgc ctctgccccg tgtctactag   3060
```

<210> SEQ ID NO 56
<211> LENGTH: 863
<212> TYPE: PRT
<213> ORGANISM: Aspergillus fumigatus

<400> SEQUENCE: 56

```
Met Arg Phe Gly Trp Leu Glu Val Ala Ala Leu Thr Ala Ala Ser Val
1               5                   10                  15

Ala Asn Ala Gln Glu Leu Ala Phe Ser Pro Pro Phe Tyr Pro Ser Pro
            20                  25                  30

Trp Ala Asp Gly Gln Gly Glu Trp Ala Asp Ala His Arg Arg Ala Val
        35                  40                  45

Glu Ile Val Ser Gln Met Thr Leu Ala Glu Lys Val Asn Leu Thr Thr
    50                  55                  60

Gly Thr Gly Trp Glu Met Asp Arg Cys Val Gly Gln Thr Gly Ser Val
65                  70                  75                  80

Pro Arg Leu Gly Ile Asn Trp Gly Leu Cys Gly Gln Asp Ser Pro Leu
                85                  90                  95

Gly Ile Arg Phe Ser Asp Leu Asn Ser Ala Phe Pro Ala Gly Thr Asn
            100                 105                 110

Val Ala Ala Thr Trp Asp Lys Thr Leu Ala Tyr Leu Arg Gly Lys Ala
        115                 120                 125

Met Gly Glu Glu Phe Asn Asp Lys Gly Val Asp Ile Leu Leu Gly Pro
    130                 135                 140

Ala Ala Gly Pro Leu Gly Lys Tyr Pro Asp Gly Gly Arg Ile Trp Glu
145                 150                 155                 160
```

-continued

```
Gly Phe Ser Pro Asp Pro Val Leu Thr Gly Val Leu Phe Ala Glu Thr
                165                 170                 175

Ile Lys Gly Ile Gln Asp Ala Gly Val Ile Ala Thr Ala Lys His Tyr
            180                 185                 190

Ile Leu Asn Glu Gln Glu His Phe Arg Gln Val Gly Glu Ala Gln Gly
        195                 200                 205

Tyr Gly Tyr Asn Ile Thr Glu Thr Ile Ser Ser Asn Val Asp Asp Lys
    210                 215                 220

Thr Met His Glu Leu Tyr Leu Trp Pro Phe Ala Asp Ala Val Arg Ala
225                 230                 235                 240

Gly Val Gly Ala Val Met Cys Ser Tyr Asn Gln Ile Asn Asn Ser Tyr
                245                 250                 255

Gly Cys Gln Asn Ser Gln Thr Leu Asn Lys Leu Leu Lys Ala Glu Leu
            260                 265                 270

Gly Phe Gln Gly Phe Val Met Ser Asp Trp Ser Ala His His Ser Gly
        275                 280                 285

Val Gly Ala Ala Leu Ala Gly Leu Asp Met Ser Met Pro Gly Asp Ile
    290                 295                 300

Ser Phe Asp Asp Gly Leu Ser Phe Trp Gly Thr Asn Leu Thr Val Ser
305                 310                 315                 320

Val Leu Asn Gly Thr Val Pro Ala Trp Arg Val Asp Asp Met Ala Val
                325                 330                 335

Arg Ile Met Thr Ala Tyr Tyr Lys Val Gly Arg Asp Arg Leu Arg Ile
            340                 345                 350

Pro Pro Asn Phe Ser Ser Trp Thr Arg Asp Glu Tyr Gly Trp Glu His
        355                 360                 365

Ser Ala Val Ser Glu Gly Ala Trp Thr Lys Val Asn Asp Phe Val Asn
    370                 375                 380

Val Gln Arg Ser His Ser Gln Ile Ile Arg Glu Ile Gly Ala Ala Ser
385                 390                 395                 400

Thr Val Leu Leu Lys Asn Thr Gly Ala Leu Pro Leu Thr Gly Lys Glu
                405                 410                 415

Val Lys Val Gly Val Leu Gly Glu Asp Ala Gly Ser Asn Pro Trp Gly
            420                 425                 430

Ala Asn Gly Cys Pro Asp Arg Gly Cys Asp Asn Gly Thr Leu Ala Met
        435                 440                 445

Ala Trp Gly Ser Gly Thr Ala Asn Phe Pro Tyr Leu Val Thr Pro Glu
    450                 455                 460

Gln Ala Ile Gln Arg Glu Val Ile Ser Asn Gly Gly Asn Val Phe Ala
465                 470                 475                 480

Val Thr Asp Asn Gly Ala Leu Ser Gln Met Ala Asp Val Ala Ser Gln
                485                 490                 495

Ser Ser Val Ser Leu Val Phe Val Asn Ala Asp Ser Gly Glu Gly Phe
            500                 505                 510

Ile Ser Val Asp Gly Asn Glu Gly Asp Arg Lys Asn Leu Thr Leu Trp
        515                 520                 525

Lys Asn Gly Glu Ala Val Ile Asp Thr Val Val Ser His Cys Asn Asn
    530                 535                 540

Thr Ile Val Val Ile His Ser Val Gly Pro Val Leu Ile Asp Arg Trp
545                 550                 555                 560

Tyr Asp Asn Pro Asn Val Thr Ala Ile Ile Trp Ala Gly Leu Pro Gly
                565                 570                 575
```

```
Gln Glu Ser Gly Asn Ser Leu Val Asp Val Leu Tyr Gly Arg Val Asn
            580                 585                 590

Pro Ser Ala Lys Thr Pro Phe Thr Trp Gly Lys Thr Arg Glu Ser Tyr
        595                 600                 605

Gly Ala Pro Leu Leu Thr Glu Pro Asn Asn Gly Asn Gly Ala Pro Gln
    610                 615                 620

Asp Asp Phe Asn Glu Gly Val Phe Ile Asp Tyr Arg His Phe Asp Lys
625                 630                 635                 640

Arg Asn Glu Thr Pro Ile Tyr Glu Phe Gly His Gly Leu Ser Tyr Thr
                645                 650                 655

Thr Phe Gly Tyr Ser His Leu Arg Val Gln Ala Leu Asn Ser Ser Ser
            660                 665                 670

Ser Ala Tyr Val Pro Thr Ser Gly Glu Thr Lys Pro Ala Pro Thr Tyr
        675                 680                 685

Gly Glu Ile Gly Ser Ala Ala Asp Tyr Leu Tyr Pro Glu Gly Leu Lys
    690                 695                 700

Arg Ile Thr Lys Phe Ile Tyr Pro Trp Leu Asn Ser Thr Asp Leu Glu
705                 710                 715                 720

Asp Ser Ser Asp Asp Pro Asn Tyr Gly Trp Glu Asp Ser Glu Tyr Ile
                725                 730                 735

Pro Glu Gly Ala Arg Asp Gly Ser Pro Gln Pro Leu Leu Lys Ala Gly
            740                 745                 750

Gly Ala Pro Gly Gly Asn Pro Thr Leu Tyr Gln Asp Leu Val Arg Val
        755                 760                 765

Ser Ala Thr Ile Thr Asn Thr Gly Asn Val Ala Gly Tyr Glu Val Pro
    770                 775                 780

Gln Leu Tyr Val Ser Leu Gly Gly Pro Asn Glu Pro Arg Val Val Leu
785                 790                 795                 800

Arg Lys Phe Asp Arg Ile Phe Leu Ala Pro Gly Glu Gln Lys Val Trp
                805                 810                 815

Thr Thr Thr Leu Asn Arg Arg Asp Leu Ala Asn Trp Asp Val Glu Ala
            820                 825                 830

Gln Asp Trp Val Ile Thr Lys Tyr Pro Lys Lys Val His Val Gly Ser
        835                 840                 845

Ser Ser Arg Lys Leu Pro Leu Arg Ala Pro Leu Pro Arg Val Tyr
    850                 855                 860
```

<210> SEQ ID NO 57
<211> LENGTH: 2800
<212> TYPE: DNA
<213> ORGANISM: Penicillium brasilianum

<400> SEQUENCE: 57

```
tgaaaatgca gggttctaca atctttctgg ctttcgcctc atgggcgagc caggttgctg      60

ccattgcgca gcccatacag aagcacgagg tttgttttat cttgctcatg gacgtgcttt     120

gacttgacta attgttttac atacagcccg gatttctgca cgggccccaa gccatagaat     180

cgttctcaga accgttctac ccgtcgccct ggatgaatcc tcacgccgag ggctgggagg     240

ccgcatatca gaaagctcaa gattttgtct cgcaactcac tatcttggag aaaataaatc     300

tgaccaccgg tgttgggtaa gtctctccga ctgcttctgg gtcacggtgc gacgagccac     360

tgactttttg aagctgggaa aatgggccgt gtgtaggaaa cactggatca attcctcgtc     420

tcggattcaa aggattttgt acccaggatt caccacaggg tgttcggttc gcagattatt     480

cctccgcttt cacatctagc caaatggccg ccgcaacatt tgaccgctca attctttatc     540
```

```
aacgaggcca agccatggca caggaacaca aggctaaggg tatcacaatt caattgggcc    600
ctgttgccgg ccctctcggt cgcatccccg agggcggccg caactgggaa ggattctccc    660
ctgatcctgt cttgactggt atagccatgg ctgagacaat taagggcatg caggatactg    720
gagtgattgc ttgcgctaaa cattatattg gaaacgagca ggagcacttc cgtcaagtgg    780
gtgaagctgc gggtcacgga tacactattt ccgatactat ttcatctaat attgacgacc    840
gtgctatgca tgagctatac ttgtggccat ttgctgatgc cgttcgcgct ggtgtgggtt    900
ctttcatgtg ctcatactct cagatcaaca actcctacgg atgccaaaac agtcagaccc    960
tcaacaagct cctcaagagc gaattgggct tccaaggctt tgtcatgagc gattggggtg   1020
cccatcactc tggagtgtca tcggcgctag ctggacttga tatgagcatg ccgggtgata   1080
ccgaatttga ttctggcttg agcttctggg gctctaacct caccattgca attctgaacg   1140
gcacggttcc cgaatggcgc ctggatgaca tggcgatgcg aattatggct gcatacttca   1200
aagttggcct tactattgag gatcaaccag atgtcaactt caatgcctgg acccatgaca   1260
cctacggata taaatacgct tatagcaagg aagattacga gcaggtcaac tggcatgtcg   1320
atgttcgcag cgaccacaat aagctcattc gcgagactgc cgcgaagggt acagttctgc   1380
tgaagaacaa ctttcatgct ctccctctga agcagcccag gttcgtggcc gtcgttggtc   1440
aggatgccgg gccaaacccc aagggcccta acggctgcgc agaccgagga tgcgaccaag   1500
gcactctcgc aatgggatgg ggctcagggt ctaccgaatt cccttacctg gtcactcctg   1560
acactgctat tcagtcaaag gtcctcgaat acgggggtcg atacgagagt atttttgata   1620
actatgacga caatgctatc ttgtcgcttg tctcacagcc tgatgcaacc tgtatcgttt   1680
ttgcaaatgc cgattccggt gaaggctaca tcactgtcga caacaactgg ggtgaccgca   1740
acaatctgac cctctggcaa aatgccgatc aagtgattag cactgtcagc tcgcgatgca   1800
acaacacaat cgttgttctc cactctgtcg gaccagtgtt gctaaatggt atatatgagc   1860
acccgaacat cacagctatt gtctgggcag ggatgccagg cgaagaatct ggcaatgctc   1920
tcgtggatat tctttggggc aatgttaacc ctgccggtcg cactccgttc acctgggcca   1980
aaagtcgaga ggactatggc actgatataa tgtacgagcc caacaacggc cagcgtgcgc   2040
ctcagcagga tttcaccgag agcatctacc tcgactaccg ccatttcgac aaagctggta   2100
tcgagccaat ttacgagttt ggattcggcc tctcctatac caccttcgaa tactctgacc   2160
tccgtgttgt gaagaagtat gttcaaccat acagtcccac gaccggcacc ggtgctcaag   2220
caccttccat cggacagcca cctagccaga acctggatac ctacaagttc cctgctacat   2280
acaagtacat caaaaccttc atttatccct acctgaacag cactgtctcc ctccgcgctg   2340
cttccaagga tcccgaatac ggtcgtacag actttatccc accccacgcg cgtgatggct   2400
cccctcaacc tctcaacccc gctggagacc cagtggccag tggtggaaac aacatgctct   2460
acgacgaact ttacgaggtc actgcacaga tcaaaaacac tggcgacgtg gccggcgacg   2520
aagtcgtcca gctttacgta gatctcgggg gtgacaaccc gcctcgtcag ttgagaaact   2580
ttgacaggtt ttatctgctg cccggtcaga gctcaacatt ccgggctaca ttgacgcgcc   2640
gtgatttgag caactgggat attgaggcgc agaactggcg agttacggaa tcgcctaaga   2700
gagtgtatgt tggacggtcg agtcgggatt tgccgctgag ctcacaattg gagtaatgat   2760
catgtctacc aatagatgtt gaatgtctgg tgtggatatt                         2800
```

<210> SEQ ID NO 58

```
<211> LENGTH: 878
<212> TYPE: PRT
<213> ORGANISM: Penicillium brasilianum

<400> SEQUENCE: 58

Met Gln Gly Ser Thr Ile Phe Leu Ala Phe Ala Ser Trp Ala Ser Gln
1               5                   10                  15

Val Ala Ala Ile Ala Gln Pro Ile Gln Lys His Glu Pro Gly Phe Leu
            20                  25                  30

His Gly Pro Gln Ala Ile Glu Ser Phe Ser Glu Pro Phe Tyr Pro Ser
        35                  40                  45

Pro Trp Met Asn Pro His Ala Glu Gly Trp Glu Ala Ala Tyr Gln Lys
    50                  55                  60

Ala Gln Asp Phe Val Ser Gln Leu Thr Ile Leu Glu Lys Ile Asn Leu
65                  70                  75                  80

Thr Thr Gly Val Gly Trp Glu Asn Gly Pro Cys Val Gly Asn Thr Gly
                85                  90                  95

Ser Ile Pro Arg Leu Gly Phe Lys Gly Phe Cys Thr Gln Asp Ser Pro
            100                 105                 110

Gln Gly Val Arg Phe Ala Asp Tyr Ser Ser Ala Phe Thr Ser Ser Gln
        115                 120                 125

Met Ala Ala Ala Thr Phe Asp Arg Ser Ile Leu Tyr Gln Arg Gly Gln
    130                 135                 140

Ala Met Ala Gln Glu His Lys Ala Lys Gly Ile Thr Ile Gln Leu Gly
145                 150                 155                 160

Pro Val Ala Gly Pro Leu Gly Arg Ile Pro Glu Gly Gly Arg Asn Trp
                165                 170                 175

Glu Gly Phe Ser Pro Asp Pro Val Leu Thr Gly Ile Ala Met Ala Glu
            180                 185                 190

Thr Ile Lys Gly Met Gln Asp Thr Gly Val Ile Ala Cys Ala Lys His
        195                 200                 205

Tyr Ile Gly Asn Glu Gln Glu His Phe Arg Gln Val Gly Glu Ala Ala
    210                 215                 220

Gly His Gly Tyr Thr Ile Ser Asp Thr Ile Ser Ser Asn Ile Asp Asp
225                 230                 235                 240

Arg Ala Met His Glu Leu Tyr Leu Trp Pro Phe Ala Asp Ala Val Arg
                245                 250                 255

Ala Gly Val Gly Ser Phe Met Cys Ser Tyr Ser Gln Ile Asn Asn Ser
            260                 265                 270

Tyr Gly Cys Gln Asn Ser Gln Thr Leu Asn Lys Leu Leu Lys Ser Glu
        275                 280                 285

Leu Gly Phe Gln Gly Phe Val Met Ser Asp Trp Gly Ala His His Ser
    290                 295                 300

Gly Val Ser Ser Ala Leu Ala Gly Leu Asp Met Ser Met Pro Gly Asp
305                 310                 315                 320

Thr Glu Phe Asp Ser Gly Leu Ser Phe Trp Gly Ser Asn Leu Thr Ile
                325                 330                 335

Ala Ile Leu Asn Gly Thr Val Pro Glu Trp Arg Leu Asp Asp Met Ala
            340                 345                 350

Met Arg Ile Met Ala Ala Tyr Phe Lys Val Gly Leu Thr Ile Glu Asp
        355                 360                 365

Gln Pro Asp Val Asn Phe Asn Ala Trp Thr His Asp Thr Tyr Gly Tyr
    370                 375                 380

Lys Tyr Ala Tyr Ser Lys Glu Asp Tyr Glu Gln Val Asn Trp His Val
```

```
385                 390                 395                 400

Asp Val Arg Ser Asp His Asn Lys Leu Ile Arg Glu Thr Ala Ala Lys
                405                 410                 415

Gly Thr Val Leu Leu Lys Asn Asn Phe His Ala Leu Pro Leu Lys Gln
            420                 425                 430

Pro Arg Phe Val Ala Val Val Gly Gln Asp Ala Gly Pro Asn Pro Lys
        435                 440                 445

Gly Pro Asn Gly Cys Ala Asp Arg Gly Cys Asp Gln Gly Thr Leu Ala
    450                 455                 460

Met Gly Trp Gly Ser Gly Ser Thr Glu Phe Pro Tyr Leu Val Thr Pro
465                 470                 475                 480

Asp Thr Ala Ile Gln Ser Lys Val Leu Glu Tyr Gly Gly Arg Tyr Glu
                485                 490                 495

Ser Ile Phe Asp Asn Tyr Asp Asp Asn Ala Ile Leu Ser Leu Val Ser
            500                 505                 510

Gln Pro Asp Ala Thr Cys Ile Val Phe Ala Asn Ala Asp Ser Gly Glu
        515                 520                 525

Gly Tyr Ile Thr Val Asp Asn Asn Trp Gly Asp Arg Asn Asn Leu Thr
    530                 535                 540

Leu Trp Gln Asn Ala Asp Gln Val Ile Ser Thr Val Ser Ser Arg Cys
545                 550                 555                 560

Asn Asn Thr Ile Val Val Leu His Ser Val Gly Pro Val Leu Leu Asn
                565                 570                 575

Gly Ile Tyr Glu His Pro Asn Ile Thr Ala Ile Val Trp Ala Gly Met
            580                 585                 590

Pro Gly Glu Glu Ser Gly Asn Ala Leu Val Asp Ile Leu Trp Gly Asn
        595                 600                 605

Val Asn Pro Ala Gly Arg Thr Pro Phe Thr Trp Ala Lys Ser Arg Glu
    610                 615                 620

Asp Tyr Gly Thr Asp Ile Met Tyr Glu Pro Asn Asn Gly Gln Arg Ala
625                 630                 635                 640

Pro Gln Gln Asp Phe Thr Glu Ser Ile Tyr Leu Asp Tyr Arg His Phe
                645                 650                 655

Asp Lys Ala Gly Ile Glu Pro Ile Tyr Glu Phe Gly Phe Gly Leu Ser
            660                 665                 670

Tyr Thr Thr Phe Glu Tyr Ser Asp Leu Arg Val Val Lys Lys Tyr Val
        675                 680                 685

Gln Pro Tyr Ser Pro Thr Thr Gly Thr Gly Ala Gln Ala Pro Ser Ile
    690                 695                 700

Gly Gln Pro Pro Ser Gln Asn Leu Asp Thr Tyr Lys Phe Pro Ala Thr
705                 710                 715                 720

Tyr Lys Tyr Ile Lys Thr Phe Ile Tyr Pro Tyr Leu Asn Ser Thr Val
                725                 730                 735

Ser Leu Arg Ala Ala Ser Lys Asp Pro Glu Tyr Gly Arg Thr Asp Phe
            740                 745                 750

Ile Pro Pro His Ala Arg Asp Gly Ser Pro Gln Pro Leu Asn Pro Ala
        755                 760                 765

Gly Asp Pro Val Ala Ser Gly Gly Asn Asn Met Leu Tyr Asp Glu Leu
    770                 775                 780

Tyr Glu Val Thr Ala Gln Ile Lys Asn Thr Gly Asp Val Ala Gly Asp
785                 790                 795                 800

Glu Val Val Gln Leu Tyr Val Asp Leu Gly Gly Asp Asn Pro Pro Arg
                805                 810                 815
```

```
Gln Leu Arg Asn Phe Asp Arg Phe Tyr Leu Leu Pro Gly Gln Ser Ser
            820                 825                 830

Thr Phe Arg Ala Thr Leu Thr Arg Arg Asp Leu Ser Asn Trp Asp Ile
        835                 840                 845

Glu Ala Gln Asn Trp Arg Val Thr Glu Ser Pro Lys Arg Val Tyr Val
    850                 855                 860

Gly Arg Ser Ser Arg Asp Leu Pro Leu Ser Ser Gln Leu Glu
865                 870                 875


<210> SEQ ID NO 59
<211> LENGTH: 2583
<212> TYPE: DNA
<213> ORGANISM: Aspergillus niger

<400> SEQUENCE: 59

atgaggttca ctttgatcga ggcggtggct ctgactgccg tctcgctggc cagcgctgat      60

gaattggcct actccccacc gtattaccca tccccttggg ccaatggcca gggcgactgg     120

gcgcaggcat accagcgcgc tgttgatatt gtctcgcaaa tgacattgga tgagaaggtc     180

aatctgacca caggaactgg atgggaattg gaactatgtg ttggtcagac tggcggtgtt     240

ccccgattgg gagttccggg aatgtgttta caggatagcc ctctgggcgt tcgcgactcc     300

gactacaact ctgctttccc tgccggcatg aacgtggctg caacctggga caagaatctg     360

gcataccttc gcggcaaggc tatgggtcag gaatttagtg acaagggtgc cgatatccaa     420

ttgggtccag ctgccggccc tctcggtaga agtcccgacg gtggtcgtaa ctgggagggc     480

ttctccccag accctgccct aagtggtgtg ctctttgccg agaccatcaa gggtatccaa     540

gatgctggtg tggttgcgac ggctaagcac tacattgctt acgagcaaga gcatttccgt     600

caggcgcctg aagcccaagg ttttggattt aatatttccg agagtggaag tgcgaacctc     660

gatgataaga ctatgcacga gctgtacctc tggcccttcg cggatgccat ccgtgcaggt     720

gctggcgctg tgatgtgctc ctacaaccag atcaacaaca gttatggctg ccagaacagc     780

tacactctga acaagctgct caaggccgag ctgggcttcc agggctttgt catgagtgat     840

tgggctgctc accatgctgg tgtgagtggt gctttggcag gattggatat gtctatgcca     900

ggagacgtcg actacgacag tggtacgtct tactggggta caaacttgac cattagcgtg     960

ctcaacggaa cggtgcccca atggcgtgtt gatgacatgg ctgtccgcat catggccgcc    1020

tactacaagg tcggccgtga ccgtctgtgg actcctccca acttcagctc atggaccaga    1080

gatgaatacg gctacaagta ctactacgtg tcggagggac cgtacgagaa ggtcaaccag    1140

tacgtgaatg tgcaacgcaa ccacagcgaa ctgattcgcc gcattggagc ggacagcacg    1200

gtgctcctca agaacgacgg cgctctgcct ttgactggta aggagcgcct ggtcgcgctt    1260

atcggagaag atgcgggctc caacccttat ggtgccaacg gctgcagtga ccgtggatgc    1320

gacaatggaa cattggcgat gggctgggga agtggtactg ccaacttccc atacctggtg    1380

acccccgagc aggccatctc aaacgaggtg cttaagcaca agaatggtgt attcaccgcc    1440

accgataact gggctatcga tcagattgag gcgcttgcta agaccgccag tgtctctctt    1500

gtctttgtca acgccgactc tggtgagggt tacatcaatg tggacggaaa cctgggtgac    1560

cgcaggaacc tgaccctgtg gaggaacggc gataatgtga tcaaggctgc tgctagcaac    1620

tgcaacaaca caatcgttgt cattcactct gtcggaccag tcttggttaa cgagtggtac    1680

gacaacccca atgttaccgc tatcctctgg ggtggtttgc ccggtcagga gtctggcaac    1740
```

```
tctcttgccg acgtcctcta tggccgtgtc aaccccggtg ccaagtcgcc ctttacctgg   1800

ggcaagactc gtgaggccta ccaagactac ttggtcaccg agcccaacaa cggcaacgga   1860

gcccctcagg aagactttgt cgagggcgtc ttcattgact accgtggatt tgacaagcgc   1920

aacgagaccc cgatctacga gttcggctat ggtctgagct acaccacttt caactactcg   1980

aaccttgagg tgcaggtgct gagcgcccct gcatacgagc ctgcttcggg tgagaccgag   2040

gcagcgccaa ccttcggaga ggttggaaat gcgtcggatt acctctaccc cagcggattg   2100

cagagaatta ccaagttcat ctacccctgg ctcaacggta ccgatctcga ggcatcttcc   2160

ggggatgcta gctacgggca ggactcctcc gactatcttc ccgagggagc caccgatggc   2220

tctgcgcaac cgatcctgcc tgccggtggc ggtcctggcg gcaaccctcg cctgtacgac   2280

gagctcatcc gcgtgtcagt gaccatcaag aacaccggca aggttgctgg tgatgaagtt   2340

ccccaactgt atgtttccct tggcggtccc aatgagccca agatcgtgct gcgtcaattc   2400

gagcgcatca cgctgcagcc gtcggaggag acgaagtgga gcacgactct gacgcgccgt   2460

gaccttgcaa actggaatgt tgagaagcag gactgggaga ttacgtcgta tcccaagatg   2520

gtgtttgtcg gaagctcctc gcggaagctg ccgctccggg cgtctctgcc tactgttcac   2580

taa                                                                 2583
```

<210> SEQ ID NO 60
<211> LENGTH: 860
<212> TYPE: PRT
<213> ORGANISM: Aspergillus niger

<400> SEQUENCE: 60

```
Met Arg Phe Thr Leu Ile Glu Ala Val Ala Leu Thr Ala Val Ser Leu
1               5                   10                  15

Ala Ser Ala Asp Glu Leu Ala Tyr Ser Pro Pro Tyr Tyr Pro Ser Pro
            20                  25                  30

Trp Ala Asn Gly Gln Gly Asp Trp Ala Gln Ala Tyr Gln Arg Ala Val
        35                  40                  45

Asp Ile Val Ser Gln Met Thr Leu Asp Glu Lys Val Asn Leu Thr Thr
    50                  55                  60

Gly Thr Gly Trp Glu Leu Glu Leu Cys Val Gly Gln Thr Gly Gly Val
65                  70                  75                  80

Pro Arg Leu Gly Val Pro Gly Met Cys Leu Gln Asp Ser Pro Leu Gly
                85                  90                  95

Val Arg Asp Ser Asp Tyr Asn Ser Ala Phe Pro Ala Gly Met Asn Val
            100                 105                 110

Ala Ala Thr Trp Asp Lys Asn Leu Ala Tyr Leu Arg Gly Lys Ala Met
        115                 120                 125

Gly Gln Glu Phe Ser Asp Lys Gly Ala Asp Ile Gln Leu Gly Pro Ala
    130                 135                 140

Ala Gly Pro Leu Gly Arg Ser Pro Asp Gly Gly Arg Asn Trp Glu Gly
145                 150                 155                 160

Phe Ser Pro Asp Pro Ala Leu Ser Gly Val Leu Phe Ala Glu Thr Ile
                165                 170                 175

Lys Gly Ile Gln Asp Ala Gly Val Val Ala Thr Ala Lys His Tyr Ile
            180                 185                 190

Ala Tyr Glu Gln Glu His Phe Arg Gln Ala Pro Glu Ala Gln Gly Phe
        195                 200                 205

Gly Phe Asn Ile Ser Glu Ser Gly Ser Ala Asn Leu Asp Asp Lys Thr
    210                 215                 220
```

```
Met His Glu Leu Tyr Leu Trp Pro Phe Ala Asp Ala Ile Arg Ala Gly
225                 230                 235                 240

Ala Gly Ala Val Met Cys Ser Tyr Asn Gln Ile Asn Asn Ser Tyr Gly
                245                 250                 255

Cys Gln Asn Ser Tyr Thr Leu Asn Lys Leu Leu Lys Ala Glu Leu Gly
            260                 265                 270

Phe Gln Gly Phe Val Met Ser Asp Trp Ala Ala His His Ala Gly Val
        275                 280                 285

Ser Gly Ala Leu Ala Gly Leu Asp Met Ser Met Pro Gly Asp Val Asp
    290                 295                 300

Tyr Asp Ser Gly Thr Ser Tyr Trp Gly Thr Asn Leu Thr Ile Ser Val
305                 310                 315                 320

Leu Asn Gly Thr Val Pro Gln Trp Arg Val Asp Asp Met Ala Val Arg
                325                 330                 335

Ile Met Ala Ala Tyr Tyr Lys Val Gly Arg Asp Arg Leu Trp Thr Pro
            340                 345                 350

Pro Asn Phe Ser Ser Trp Thr Arg Asp Glu Tyr Gly Tyr Lys Tyr Tyr
        355                 360                 365

Tyr Val Ser Glu Gly Pro Tyr Glu Lys Val Asn Gln Tyr Val Asn Val
    370                 375                 380

Gln Arg Asn His Ser Glu Leu Ile Arg Arg Ile Gly Ala Asp Ser Thr
385                 390                 395                 400

Val Leu Leu Lys Asn Asp Gly Ala Leu Pro Leu Thr Gly Lys Glu Arg
                405                 410                 415

Leu Val Ala Leu Ile Gly Glu Asp Ala Gly Ser Asn Pro Tyr Gly Ala
            420                 425                 430

Asn Gly Cys Ser Asp Arg Gly Cys Asp Asn Gly Thr Leu Ala Met Gly
        435                 440                 445

Trp Gly Ser Gly Thr Ala Asn Phe Pro Tyr Leu Val Thr Pro Glu Gln
    450                 455                 460

Ala Ile Ser Asn Glu Val Leu Lys His Lys Asn Gly Val Phe Thr Ala
465                 470                 475                 480

Thr Asp Asn Trp Ala Ile Asp Gln Ile Glu Ala Leu Ala Lys Thr Ala
                485                 490                 495

Ser Val Ser Leu Val Phe Val Asn Ala Asp Ser Gly Glu Gly Tyr Ile
            500                 505                 510

Asn Val Asp Gly Asn Leu Gly Asp Arg Arg Asn Leu Thr Leu Trp Arg
        515                 520                 525

Asn Gly Asp Asn Val Ile Lys Ala Ala Ala Ser Asn Cys Asn Asn Thr
    530                 535                 540

Ile Val Val Ile His Ser Val Gly Pro Val Leu Val Asn Glu Trp Tyr
545                 550                 555                 560

Asp Asn Pro Asn Val Thr Ala Ile Leu Trp Gly Gly Leu Pro Gly Gln
                565                 570                 575

Glu Ser Gly Asn Ser Leu Ala Asp Val Leu Tyr Gly Arg Val Asn Pro
            580                 585                 590

Gly Ala Lys Ser Pro Phe Thr Trp Gly Lys Thr Arg Glu Ala Tyr Gln
        595                 600                 605

Asp Tyr Leu Val Thr Glu Pro Asn Asn Gly Asn Gly Ala Pro Gln Glu
    610                 615                 620

Asp Phe Val Glu Gly Val Phe Ile Asp Tyr Arg Gly Phe Asp Lys Arg
625                 630                 635                 640
```

```
Asn Glu Thr Pro Ile Tyr Glu Phe Gly Tyr Gly Leu Ser Tyr Thr Thr
                645                 650                 655

Phe Asn Tyr Ser Asn Leu Glu Val Gln Val Leu Ser Ala Pro Ala Tyr
            660                 665                 670

Glu Pro Ala Ser Gly Glu Thr Glu Ala Ala Pro Thr Phe Gly Glu Val
        675                 680                 685

Gly Asn Ala Ser Asp Tyr Leu Tyr Pro Ser Gly Leu Gln Arg Ile Thr
    690                 695                 700

Lys Phe Ile Tyr Pro Trp Leu Asn Gly Thr Asp Leu Glu Ala Ser Ser
705                 710                 715                 720

Gly Asp Ala Ser Tyr Gly Gln Asp Ser Ser Asp Tyr Leu Pro Glu Gly
                725                 730                 735

Ala Thr Asp Gly Ser Ala Gln Pro Ile Leu Pro Ala Gly Gly Gly Pro
            740                 745                 750

Gly Gly Asn Pro Arg Leu Tyr Asp Glu Leu Ile Arg Val Ser Val Thr
        755                 760                 765

Ile Lys Asn Thr Gly Lys Val Ala Gly Asp Glu Val Pro Gln Leu Tyr
    770                 775                 780

Val Ser Leu Gly Gly Pro Asn Glu Pro Lys Ile Val Leu Arg Gln Phe
785                 790                 795                 800

Glu Arg Ile Thr Leu Gln Pro Ser Glu Glu Thr Lys Trp Ser Thr Thr
                805                 810                 815

Leu Thr Arg Arg Asp Leu Ala Asn Trp Asn Val Glu Lys Gln Asp Trp
            820                 825                 830

Glu Ile Thr Ser Tyr Pro Lys Met Val Phe Val Gly Ser Ser Ser Arg
        835                 840                 845

Lys Leu Pro Leu Arg Ala Ser Leu Pro Thr Val His
    850                 855                 860
```

<210> SEQ ID NO 61
<211> LENGTH: 2583
<212> TYPE: DNA
<213> ORGANISM: Aspergillus aculeatus

<400> SEQUENCE: 61

```
atgaagctca gttggcttga ggcggctgcc ttgacggctg cttcagtcgt cagcgctgat      60

gaactggcgt tctctcctcc tttctacccc tctccgtggg ccaatggcca gggagagtgg     120

gcggaagcct accagcgtgc agtggccatt gtatcccaga tgactctgga tgagaaggtc     180

aacctgacca ccggaactgg atgggagctg gagaagtgcg tcggtcagac tggtggtgtc     240

ccaagactga acatcggtgg catgtgtctt caggacagtc ccttgggaat tcgtgatagt     300

gactacaatt cggctttccc tgctggtgtc aacgttgctg cgacatggga caagaacctt     360

gcttatctac gtggtcaggc tatgggtcaa gagttcagtg acaaaggaat tgatgttcaa     420

ttgggaccgg ccgcgggtcc cctcggcagg agccctgatg gaggtcgcaa ctgggaaggt     480

ttctctccag acccggctct tactggtgtg ctctttgcgg agacgattaa gggtattcaa     540

gacgctggtg tcgtggcgac agccaagcat tacattctca atgagcaaga gcatttccgc     600

caggtcgcag aggctgcggg ctacggattc aatatctccg acacgatcag ctctaacgtt     660

gatgacaaga ccattcatga aatgtacctc tggcccttcg cggatgccgt tcgcgccggc     720

gttggcgcca tcatgtgttc ctacaaccag atcaacaaca gctacggttg ccagaacagt     780

tacactctga acaagcttct gaaggccgag ctcggcttcc agggctttgt gatgtctgac     840

tggggtgctc accacagtgg tgttggctct gctttggccg gcttggatat gtcaatgcct     900
```

```
ggcgatatca ccttcgattc tgccactagt ttctggggta ccaacctgac cattgctgtg    960

ctcaacggta ccgtcccgca gtggcgcgtt gacgacatgg ctgtccgtat catggctgcc   1020

tactacaagg ttggccgcga ccgcctgtac cagccgccta acttcagctc ctggactcgc   1080

gatgaatacg gcttcaagta tttctacccc caggaagggc cctatgagaa ggtcaatcac   1140

tttgtcaatg tgcagcgcaa ccacagcgag gttattcgca agttgggagc agacagtact   1200

gttctactga agaacaacaa tgccctgccg ctgaccggaa aggagcgcaa agttgcgatc   1260

ctgggtgaag atgctggatc caactcgtac ggtgccaatg gctgctctga ccgtggctgt   1320

gacaacggta ctcttgctat ggcttggggt agcggcactg ccgaattccc atatctcgtg   1380

acccctgagc aggctattca agccgaggtg ctcaagcata agggcagcgt ctacgccatc   1440

acggacaact gggcgctgag ccaggtggag accctcgcta aacaagccag tgtctctctt   1500

gtatttgtca actcggacgc gggagagggc tatatctccg tggacggaaa cgagggcgac   1560

cgcaacaacc tcaccctctg gaagaacggc gacaacctca tcaaggctgc tgcaaacaac   1620

tgcaacaaca ccatcgttgt catccactcc gttggacctg ttttggttga cgagtggtat   1680

gaccacccca acgttactgc catcctctgg gcgggcttgc ctggccagga gtctggcaac   1740

tccttggctg acgtgctcta cggccgcgtc aacccgggcg ccaaatctcc attcacctgg   1800

ggcaagacga gggaggcgta cggggattac cttgtccgtg agctcaacaa cggcaacgga   1860

gctccccaag atgatttctc ggaaggtgtt ttcattgact accgcggatt cgacaagcgc   1920

aatgagaccc cgatctacga gttcggacat ggtctgagct acaccacttt caactactct   1980

ggccttcaca tccaggttct caacgcttcc tccaacgctc aagtagccac tgagactggc   2040

gccgctccca ccttcggaca agtcggcaat gcctctgact acgtgtaccc tgagggattg   2100

accagaatca gcaagttcat ctatccctgg cttaattcca cagacctgaa ggcctcatct   2160

ggcgacccgt actatggagt cgacaccgcg gagcacgtgc ccgagggtgc tactgatggc   2220

tctccgcagc ccgttctgcc tgccggtggt ggctctggtg gtaacccgcg cctctacgat   2280

gagttgatcc gtgtttcggt gacagtcaag aacactggtc gtgttgccgg tgatgctgtg   2340

cctcaattgt atgtttccct tggtggaccc aatgagccca aggttgtgtt gcgcaaattc   2400

gaccgcctca ccctcaagcc ctccgaggag acggtgtgga cgactaccct gacccgccgc   2460

gatctgtcta actgggacgt tgcggctcag gactgggtca tcacttctta cccgaagaag   2520

gtccatgttg gtagctcttc gcgtcagctg ccccttcacg cggcgctccc gaaggtgcaa   2580

tga                                                                 2583
```

```
<210> SEQ ID NO 62
<211> LENGTH: 860
<212> TYPE: PRT
<213> ORGANISM: Aspergillus aculeatus

<400> SEQUENCE: 62

Met Lys Leu Ser Trp Leu Glu Ala Ala Ala Leu Thr Ala Ala Ser Val
1               5                   10                  15

Val Ser Ala Asp Glu Leu Ala Phe Ser Pro Pro Phe Tyr Pro Ser Pro
            20                  25                  30

Trp Ala Asn Gly Gln Gly Glu Trp Ala Glu Ala Tyr Gln Arg Ala Val
        35                  40                  45

Ala Ile Val Ser Gln Met Thr Leu Asp Glu Lys Val Asn Leu Thr Thr
    50                  55                  60
```

-continued

```
Gly Thr Gly Trp Glu Leu Glu Lys Cys Val Gly Gln Thr Gly Gly Val
65                  70                  75                  80

Pro Arg Leu Asn Ile Gly Gly Met Cys Leu Gln Asp Ser Pro Leu Gly
                85                  90                  95

Ile Arg Asp Ser Asp Tyr Asn Ser Ala Phe Pro Ala Gly Val Asn Val
            100                 105                 110

Ala Ala Thr Trp Asp Lys Asn Leu Ala Tyr Leu Arg Gly Gln Ala Met
        115                 120                 125

Gly Gln Glu Phe Ser Asp Lys Gly Ile Asp Val Gln Leu Gly Pro Ala
    130                 135                 140

Ala Gly Pro Leu Gly Arg Ser Pro Asp Gly Gly Arg Asn Trp Glu Gly
145                 150                 155                 160

Phe Ser Pro Asp Pro Ala Leu Thr Gly Val Leu Phe Ala Glu Thr Ile
                165                 170                 175

Lys Gly Ile Gln Asp Ala Gly Val Val Ala Thr Ala Lys His Tyr Ile
            180                 185                 190

Leu Asn Glu Gln Glu His Phe Arg Gln Val Ala Glu Ala Ala Gly Tyr
        195                 200                 205

Gly Phe Asn Ile Ser Asp Thr Ile Ser Ser Asn Val Asp Asp Lys Thr
    210                 215                 220

Ile His Glu Met Tyr Leu Trp Pro Phe Ala Asp Ala Val Arg Ala Gly
225                 230                 235                 240

Val Gly Ala Ile Met Cys Ser Tyr Asn Gln Ile Asn Asn Ser Tyr Gly
                245                 250                 255

Cys Gln Asn Ser Tyr Thr Leu Asn Lys Leu Leu Lys Ala Glu Leu Gly
            260                 265                 270

Phe Gln Gly Phe Val Met Ser Asp Trp Gly Ala His His Ser Gly Val
        275                 280                 285

Gly Ser Ala Leu Ala Gly Leu Asp Met Ser Met Pro Gly Asp Ile Thr
    290                 295                 300

Phe Asp Ser Ala Thr Ser Phe Trp Gly Thr Asn Leu Thr Ile Ala Val
305                 310                 315                 320

Leu Asn Gly Thr Val Pro Gln Trp Arg Val Asp Asp Met Ala Val Arg
                325                 330                 335

Ile Met Ala Ala Tyr Tyr Lys Val Gly Arg Asp Arg Leu Tyr Gln Pro
            340                 345                 350

Pro Asn Phe Ser Ser Trp Thr Arg Asp Glu Tyr Gly Phe Lys Tyr Phe
        355                 360                 365

Tyr Pro Gln Glu Gly Pro Tyr Glu Lys Val Asn His Phe Val Asn Val
    370                 375                 380

Gln Arg Asn His Ser Glu Val Ile Arg Lys Leu Gly Ala Asp Ser Thr
385                 390                 395                 400

Val Leu Leu Lys Asn Asn Asn Ala Leu Pro Leu Thr Gly Lys Glu Arg
                405                 410                 415

Lys Val Ala Ile Leu Gly Glu Asp Ala Gly Ser Asn Ser Tyr Gly Ala
            420                 425                 430

Asn Gly Cys Ser Asp Arg Gly Cys Asp Asn Gly Thr Leu Ala Met Ala
        435                 440                 445

Trp Gly Ser Gly Thr Ala Glu Phe Pro Tyr Leu Val Thr Pro Glu Gln
    450                 455                 460

Ala Ile Gln Ala Glu Val Leu Lys His Lys Gly Ser Val Tyr Ala Ile
465                 470                 475                 480

Thr Asp Asn Trp Ala Leu Ser Gln Val Glu Thr Leu Ala Lys Gln Ala
```

```
                485                 490                 495

Ser Val Ser Leu Val Phe Val Asn Ser Asp Ala Gly Glu Gly Tyr Ile
            500                 505                 510

Ser Val Asp Gly Asn Glu Gly Asp Arg Asn Asn Leu Thr Leu Trp Lys
        515                 520                 525

Asn Gly Asp Asn Leu Ile Lys Ala Ala Ala Asn Asn Cys Asn Asn Thr
    530                 535                 540

Ile Val Val Ile His Ser Val Gly Pro Val Leu Val Asp Glu Trp Tyr
545                 550                 555                 560

Asp His Pro Asn Val Thr Ala Ile Leu Trp Ala Gly Leu Pro Gly Gln
                565                 570                 575

Glu Ser Gly Asn Ser Leu Ala Asp Val Leu Tyr Gly Arg Val Asn Pro
            580                 585                 590

Gly Ala Lys Ser Pro Phe Thr Trp Gly Lys Thr Arg Glu Ala Tyr Gly
        595                 600                 605

Asp Tyr Leu Val Arg Glu Leu Asn Asn Gly Asn Gly Ala Pro Gln Asp
    610                 615                 620

Asp Phe Ser Glu Gly Val Phe Ile Asp Tyr Arg Gly Phe Asp Lys Arg
625                 630                 635                 640

Asn Glu Thr Pro Ile Tyr Glu Phe Gly His Gly Leu Ser Tyr Thr Thr
                645                 650                 655

Phe Asn Tyr Ser Gly Leu His Ile Gln Val Leu Asn Ala Ser Ser Asn
            660                 665                 670

Ala Gln Val Ala Thr Glu Thr Gly Ala Ala Pro Thr Phe Gly Gln Val
        675                 680                 685

Gly Asn Ala Ser Asp Tyr Val Tyr Pro Glu Gly Leu Thr Arg Ile Ser
    690                 695                 700

Lys Phe Ile Tyr Pro Trp Leu Asn Ser Thr Asp Leu Lys Ala Ser Ser
705                 710                 715                 720

Gly Asp Pro Tyr Tyr Gly Val Asp Thr Ala Glu His Val Pro Glu Gly
                725                 730                 735

Ala Thr Asp Gly Ser Pro Gln Pro Val Leu Pro Ala Gly Gly Gly Ser
            740                 745                 750

Gly Gly Asn Pro Arg Leu Tyr Asp Glu Leu Ile Arg Val Ser Val Thr
        755                 760                 765

Val Lys Asn Thr Gly Arg Val Ala Gly Asp Ala Val Pro Gln Leu Tyr
    770                 775                 780

Val Ser Leu Gly Gly Pro Asn Glu Pro Lys Val Val Leu Arg Lys Phe
785                 790                 795                 800

Asp Arg Leu Thr Leu Lys Pro Ser Glu Glu Thr Val Trp Thr Thr Thr
                805                 810                 815

Leu Thr Arg Arg Asp Leu Ser Asn Trp Asp Val Ala Ala Gln Asp Trp
            820                 825                 830

Val Ile Thr Ser Tyr Pro Lys Lys Val His Val Gly Ser Ser Ser Arg
        835                 840                 845

Gln Leu Pro Leu His Ala Ala Leu Pro Lys Val Gln
    850                 855                 860
```

<210> SEQ ID NO 63
<211> LENGTH: 3294
<212> TYPE: DNA
<213> ORGANISM: Aspergillus oryzae

<400> SEQUENCE: 63

```
atgcgttcct ccccccctcct ccgctccgcc gttgtggccg ccctgccggt gttggccctt     60
gccgctgatg gcaggtccac ccgctactgg gactgctgca agccttcgtg cggctgggcc    120
aagaaggctc ccgtgaacca gcctgtcttt tcctgcaacg ccaacttcca gcgtatcacg    180
gacttcgacg ccaagtccgg ctgcgagccg ggcggtgtcg cctactcgtg cgccgaccag    240
accccatggg ctgtgaacga cgacttcgcg ctcggttttg ctgccacctc tattgccggc    300
agcaatgagg cgggctggtg ctgcgcctgc tacgagctca ccttcacatc cggtcctgtt    360
gctggcaaga agatggtcgt ccagtccacc agcactggcg gtgatcttgg cagcaaccac    420
ttcgatctca acatccccgg cggcggcgtc ggcatcttcg acggatgcac tccccagttc    480
ggtggtctgc ccggccagcg ctacggcggc atctcgtccc gcaacgagtg cgatcggttc    540
cccgacgccc tcaagcccgg ctgctactgg cgcttcgact ggttcaagaa cgccgacaat    600
ccgagcttca gcttccgtca ggtccagtgc ccagccgagc tcgtcgctcg caccggatgc    660
cgccgcaacg acgacggcaa cttccctgcc gtccagatcc ccatgcgttc ctccccccctc    720
ctccgctccg ccgttgtggc cgccctgccg gtgttggccc ttgccaagga tgatctcgcg    780
tactcccctc ctttctaccc ttccccatgg gcagatggtc agggtgaatg ggcggaagta    840
tacaaacgcg ctgtagacat agtttcccag atgacgttga cagagaaagt caacttaacg    900
actggaacag gatggcaact agagaggtgt gttggacaaa ctggcagtgt tcccagactc    960
aacatcccca gcttgtgttt gcaggatagt cctcttggta ttcgtttctc ggactacaat   1020
tcagctttcc ctgcgggtgt taatgtcgct gccacctggg acaagacgct cgcctacctt   1080
cgtggtcagg caatgggtga ggagttcagt gataagggta ttgacgttca gctgggtcct   1140
gctgctggcc ctctcggtgc tcatccggat ggcggtagaa actgggaagg tttctcacca   1200
gatccagccc tcaccggtgt actttttgcg gagacgatta agggtattca agatgctggt   1260
gtcattgcga cagctaagca ttatatcatg aacgaacaag agcatttccg ccaacaaccc   1320
gaggctgcgg gttacggatt caacgtaagc gacagtttga gttccaacgt tgatgacaag   1380
actatgcatg aattgtacct ctggcccttc gcggatgcag tacgcgctgg agtcggtgct   1440
gtcatgtgct cttacaacca aatcaacaac agctacggtt gcgagaatag cgaaactctg   1500
aacaagcttt tgaaggcgga gcttggtttc caaggcttcg tcatgagtga ttggaccgct   1560
catcacagcg gcgtaggcgc tgctttagca ggtctggata tgtcgatgcc cggtgatgtt   1620
accttcgata gtggtacgtc tttctggggt gcaaacttga cggtcggtgt ccttaacggt   1680
acaatccccc aatggcgtgt tgatgacatg gctgtccgta tcatggccgc ttattacaag   1740
gttggccgcg acaccaaata caccccctccc aacttcagct cgtggaccag ggacgaatat   1800
ggtttcgcgc ataaccatgt ttcggaaggt gcttacgaga gggtcaacga attcgtggac   1860
gtgcaacgcg atcatgccga cctaatccgt cgcatcggcg cgcagagcac tgttctgctg   1920
aagaacaagg gtgccttgcc cttgagccgc aaggaaaagc tggtcgccct tctgggagag   1980
gatgcgggtt ccaactcgtg gggcgctaac ggctgtgatg accgtggttg cgataacggt   2040
acccttgcca tggcctgggg tagcggtact gcgaatttcc catacctcgt gacaccagag   2100
caggcgattc agaacgaagt tcttcagggc cgtggtaatg tcttcgccgt gaccgacagt   2160
tgggcgctcg acaagatcgc tgcggctgcc cgccaggcca gcgtatctct cgtgttcgtc   2220
aactccgact caggagaagg ctatcttagt gtggatggaa atgagggcga tcgtaacaac   2280
atcactctgt ggaagaacgg cgacaatgtg gtcaagaccg cagcgaataa ctgtaacaac   2340
accgttgtca tcatccactc cgtcggacca gttttgatcg atgaatggta tgaccacccc   2400
```

```
aatgtcactg gtattctctg ggctggtctg ccaggccagg agtctggtaa ctccattgcc   2460

gatgtgctgt acggtcgtgt caaccctggc gccaagtctc ctttcacttg gggcaagacc   2520

cgggagtcgt atggttctcc cttggtcaag gatgccaaca atggcaacgg agcgccccag   2580

tctgatttca cccagggtgt tttcatcgat taccgccatt tcgataagtt caatgagacc   2640

cctatctacg agtttggcta cggcttgagc tacaccacct tcgagctctc cgacctccat   2700

gttcagcccc tgaacgcgtc ccgatacact cccaccagtg gcatgactga agctgcaaag   2760

aactttggtg aaattggcga tgcgtcggag tacgtgtatc cggaggggct ggaaaggatc   2820

catgagttta tctatccctg gatcaactct accgacctga aggcatcgtc tgacgattct   2880

aactacggct gggaagactc caagtatatt cccgaaggcg ccacggatgg gtctgcccag   2940

ccccgtttgc ccgctagtgg tggtgccgga ggaaaccccg gtctgtacga ggatcttttc   3000

cgcgtctctg tgaaggtcaa gaacacgggc aatgtcgccg gtgatgaagt tcctcagctg   3060

tacgtttccc taggcggccc gaatgagccc aaggtggtac tgcgcaagtt tgagcgtatt   3120

cacttggccc cttcgcagga ggccgtgtgg acaacgaccc ttacccgtcg tgaccttgca   3180

aactgggacg tttcggctca ggactggacc gtcactcctt accccaagac gatctacgtt   3240

ggaaactcct cacggaaact gccgctccag gcctcgctgc ctaaggccca gtaa         3294
```

<210> SEQ ID NO 64
<211> LENGTH: 1097
<212> TYPE: PRT
<213> ORGANISM: Aspergillus oryzae

<400> SEQUENCE: 64

```
Met Arg Ser Ser Pro Leu Leu Arg Ser Ala Val Val Ala Ala Leu Pro
1               5                   10                  15

Val Leu Ala Leu Ala Ala Asp Gly Arg Ser Thr Arg Tyr Trp Asp Cys
            20                  25                  30

Cys Lys Pro Ser Cys Gly Trp Ala Lys Lys Ala Pro Val Asn Gln Pro
        35                  40                  45

Val Phe Ser Cys Asn Ala Asn Phe Gln Arg Ile Thr Asp Phe Asp Ala
    50                  55                  60

Lys Ser Gly Cys Glu Pro Gly Gly Val Ala Tyr Ser Cys Ala Asp Gln
65                  70                  75                  80

Thr Pro Trp Ala Val Asn Asp Asp Phe Ala Leu Gly Phe Ala Ala Thr
                85                  90                  95

Ser Ile Ala Gly Ser Asn Glu Ala Gly Trp Cys Cys Ala Cys Tyr Glu
            100                 105                 110

Leu Thr Phe Thr Ser Gly Pro Val Ala Gly Lys Lys Met Val Val Gln
        115                 120                 125

Ser Thr Ser Thr Gly Gly Asp Leu Gly Ser Asn His Phe Asp Leu Asn
    130                 135                 140

Ile Pro Gly Gly Gly Val Gly Ile Phe Asp Gly Cys Thr Pro Gln Phe
145                 150                 155                 160

Gly Gly Leu Pro Gly Gln Arg Tyr Gly Gly Ile Ser Ser Arg Asn Glu
                165                 170                 175

Cys Asp Arg Phe Pro Asp Ala Leu Lys Pro Gly Cys Tyr Trp Arg Phe
            180                 185                 190

Asp Trp Phe Lys Asn Ala Asp Asn Pro Ser Phe Ser Phe Arg Gln Val
        195                 200                 205

Gln Cys Pro Ala Glu Leu Val Ala Arg Thr Gly Cys Arg Arg Asn Asp
```

```
    210                 215                 220

Asp Gly Asn Phe Pro Ala Val Gln Ile Pro Met Arg Ser Ser Pro Leu
225                 230                 235                 240

Leu Arg Ser Ala Val Val Ala Ala Leu Pro Val Leu Ala Leu Ala Lys
                245                 250                 255

Asp Asp Leu Ala Tyr Ser Pro Pro Phe Tyr Pro Ser Pro Trp Ala Asp
            260                 265                 270

Gly Gln Gly Glu Trp Ala Glu Val Tyr Lys Arg Ala Val Asp Ile Val
        275                 280                 285

Ser Gln Met Thr Leu Thr Glu Lys Val Asn Leu Thr Thr Gly Thr Gly
    290                 295                 300

Trp Gln Leu Glu Arg Cys Val Gly Gln Thr Gly Ser Val Pro Arg Leu
305                 310                 315                 320

Asn Ile Pro Ser Leu Cys Leu Gln Asp Ser Pro Leu Gly Ile Arg Phe
                325                 330                 335

Ser Asp Tyr Asn Ser Ala Phe Pro Ala Gly Val Asn Val Ala Ala Thr
            340                 345                 350

Trp Asp Lys Thr Leu Ala Tyr Leu Arg Gly Gln Ala Met Gly Glu Glu
        355                 360                 365

Phe Ser Asp Lys Gly Ile Asp Val Gln Leu Gly Pro Ala Ala Gly Pro
    370                 375                 380

Leu Gly Ala His Pro Asp Gly Gly Arg Asn Trp Glu Gly Phe Ser Pro
385                 390                 395                 400

Asp Pro Ala Leu Thr Gly Val Leu Phe Ala Glu Thr Ile Lys Gly Ile
                405                 410                 415

Gln Asp Ala Gly Val Ile Ala Thr Ala Lys His Tyr Ile Met Asn Glu
            420                 425                 430

Gln Glu His Phe Arg Gln Gln Pro Glu Ala Ala Gly Tyr Gly Phe Asn
        435                 440                 445

Val Ser Asp Ser Leu Ser Ser Asn Val Asp Asp Lys Thr Met His Glu
    450                 455                 460

Leu Tyr Leu Trp Pro Phe Ala Asp Ala Val Arg Ala Gly Val Gly Ala
465                 470                 475                 480

Val Met Cys Ser Tyr Asn Gln Ile Asn Asn Ser Tyr Gly Cys Glu Asn
                485                 490                 495

Ser Glu Thr Leu Asn Lys Leu Leu Lys Ala Glu Leu Gly Phe Gln Gly
            500                 505                 510

Phe Val Met Ser Asp Trp Thr Ala His His Ser Gly Val Gly Ala Ala
        515                 520                 525

Leu Ala Gly Leu Asp Met Ser Met Pro Gly Asp Val Thr Phe Asp Ser
    530                 535                 540

Gly Thr Ser Phe Trp Gly Ala Asn Leu Thr Val Gly Val Leu Asn Gly
545                 550                 555                 560

Thr Ile Pro Gln Trp Arg Val Asp Asp Met Ala Val Arg Ile Met Ala
                565                 570                 575

Ala Tyr Tyr Lys Val Gly Arg Asp Thr Lys Tyr Thr Pro Pro Asn Phe
            580                 585                 590

Ser Ser Trp Thr Arg Asp Glu Tyr Gly Phe Ala His Asn His Val Ser
        595                 600                 605

Glu Gly Ala Tyr Glu Arg Val Asn Glu Phe Val Asp Val Gln Arg Asp
    610                 615                 620

His Ala Asp Leu Ile Arg Arg Ile Gly Ala Gln Ser Thr Val Leu Leu
625                 630                 635                 640
```

```
Lys Asn Lys Gly Ala Leu Pro Leu Ser Arg Lys Glu Lys Leu Val Ala
            645                 650                 655

Leu Leu Gly Glu Asp Ala Gly Ser Asn Ser Trp Gly Ala Asn Gly Cys
        660                 665                 670

Asp Asp Arg Gly Cys Asp Asn Gly Thr Leu Ala Met Ala Trp Gly Ser
    675                 680                 685

Gly Thr Ala Asn Phe Pro Tyr Leu Val Thr Pro Glu Gln Ala Ile Gln
  690                 695                 700

Asn Glu Val Leu Gln Gly Arg Gly Asn Val Phe Ala Val Thr Asp Ser
705                 710                 715                 720

Trp Ala Leu Asp Lys Ile Ala Ala Ala Ala Arg Gln Ala Ser Val Ser
            725                 730                 735

Leu Val Phe Val Asn Ser Asp Ser Gly Glu Gly Tyr Leu Ser Val Asp
        740                 745                 750

Gly Asn Glu Gly Asp Arg Asn Asn Ile Thr Leu Trp Lys Asn Gly Asp
    755                 760                 765

Asn Val Val Lys Thr Ala Ala Asn Asn Cys Asn Asn Thr Val Val Ile
  770                 775                 780

Ile His Ser Val Gly Pro Val Leu Ile Asp Glu Trp Tyr Asp His Pro
785                 790                 795                 800

Asn Val Thr Gly Ile Leu Trp Ala Gly Leu Pro Gly Gln Glu Ser Gly
            805                 810                 815

Asn Ser Ile Ala Asp Val Leu Tyr Gly Arg Val Asn Pro Gly Ala Lys
        820                 825                 830

Ser Pro Phe Thr Trp Gly Lys Thr Arg Glu Ser Tyr Gly Ser Pro Leu
    835                 840                 845

Val Lys Asp Ala Asn Asn Gly Asn Gly Ala Pro Gln Ser Asp Phe Thr
  850                 855                 860

Gln Gly Val Phe Ile Asp Tyr Arg His Phe Asp Lys Phe Asn Glu Thr
865                 870                 875                 880

Pro Ile Tyr Glu Phe Gly Tyr Gly Leu Ser Tyr Thr Thr Phe Glu Leu
            885                 890                 895

Ser Asp Leu His Val Gln Pro Leu Asn Ala Ser Arg Tyr Thr Pro Thr
        900                 905                 910

Ser Gly Met Thr Glu Ala Ala Lys Asn Phe Gly Glu Ile Gly Asp Ala
    915                 920                 925

Ser Glu Tyr Val Tyr Pro Glu Gly Leu Glu Arg Ile His Glu Phe Ile
  930                 935                 940

Tyr Pro Trp Ile Asn Ser Thr Asp Leu Lys Ala Ser Ser Asp Asp Ser
945                 950                 955                 960

Asn Tyr Gly Trp Glu Asp Ser Lys Tyr Ile Pro Glu Gly Ala Thr Asp
            965                 970                 975

Gly Ser Ala Gln Pro Arg Leu Pro Ala Ser Gly Gly Ala Gly Gly Asn
        980                 985                 990

Pro Gly Leu Tyr Glu Asp Leu Phe  Arg Val Ser Val Lys  Val Lys Asn
    995                 1000                1005

Thr Gly  Asn Val Ala Gly Asp  Glu Val Pro Gln Leu  Tyr Val Ser
  1010                1015                1020

Leu Gly  Gly Pro Asn Glu Pro  Lys Val Val Leu Arg  Lys Phe Glu
  1025                1030                1035

Arg Ile  His Leu Ala Pro Ser  Gln Glu Ala Val Trp  Thr Thr Thr
  1040                1045                1050
```

```
Leu Thr Arg Arg Asp Leu Ala Asn Trp Asp Val Ser Ala Gln Asp
    1055                1060                1065

Trp Thr Val Thr Pro Tyr Pro Lys Thr Ile Tyr Val Gly Asn Ser
    1070                1075                1080

Ser Arg Lys Leu Pro Leu Gln Ala Ser Leu Pro Lys Ala Gln
    1085                1090                1095


<210> SEQ ID NO 65
<211> LENGTH: 3294
<212> TYPE: DNA
<213> ORGANISM: Aspergillus oryzae

<400> SEQUENCE: 65

atgcgttcct ccccctcct ccgctccgcc gttgtggccg ccctgccggt gttggccctt      60

gccgctgatg gcaggtccac ccgctactgg gactgctgca agccttcgtg cggctgggcc    120

aagaaggctc ccgtgaacca gcctgtcttt tcctgcaacg ccaacttcca gcgtatcacg    180

gacttcgacg ccaagtccgg ctgcgagccg ggcggtgtcg cctactcgtg cgccgaccag    240

accccatggg ctgtgaacga cgacttcgcg ctcggttttg ctgccacctc tattgccggc    300

agcaatgagg cgggctggtg ctgcgcctgc tacgagctca ccttcacatc cggtcctgtt    360

gctggcaaga agatggtcgt ccagtccacc agcactggcg gtgatcttgg cagcaaccac    420

ttcgatctca acatccccgg cggcggcgtc ggcatcttcg acggatgcac tccccagttc    480

ggtggtctgc ccggccagcg ctacggcggc atctcgtccc gcaacgagtg cgatcggttc    540

cccgacgccc tcaagcccgg ctgctactgg cgcttcgact ggttcaagaa cgccgacaat    600

ccgagcttca gcttccgtca ggtccagtgc ccagccgagc tcgtcgctcg caccggatgc    660

cgccgcaacg acgacggcaa cttccctgcc gtccagatcc ccatgcgttc ctcccccctc    720

ctccgctccg ccgttgtggc cgccctgccg gtgttggccc ttgccaagga tgatctcgcg    780

tactcccctc ctttctaccc ttccccatgg gcagatggtc agggtgaatg ggcggaagta    840

tacaaacgcg ctgtagacat agtttcccag atgacgttga cagagaaagt caacttaacg    900

actggaacag gatggcaact agagaggtgt gttggacaaa ctggcagtgt tcccagactc    960

aacatcccca gcttgtgttt gcaggatagt cctcttggta ttcgtttctc ggactacaat   1020

tcagctttcc ctgcgggtgt taatgtcgct gccacctggg acaagacgct cgcctacctt   1080

cgtggtcagg caatgggtga ggagttcagt gataagggta ttgacgttca gctgggtcct   1140

gctgctggcc ctctcggtgc tcatccggat ggcggtagaa actgggaaag tttctcacca   1200

gatccagccc tcaccggtgt actttttgcg gagacgatta agggtattca agatgctggt   1260

gtcattgcga cagctaagca ttatatcatg aacgaacaag agcatttccg ccaacaaccc   1320

gaggctgcgg gttacggatt caacgtaagc gacagtttga gttccaacgt tgatgacaag   1380

actatgcatg aattgtacct ctggcccttc gcggatgcag tacgcgctgg agtcggtgct   1440

gttatgtgct cttacaacca aatcaacaac agctacggtt gcgagaatag cgaaactctg   1500

aacaagcttt tgaaggcgga gcttggtttc caaggcttcg tcatgagtga ttggaccgct   1560

caacacagcg gcgtaggcgc tgctttagca ggtctggata tgtcgatgcc cggtgatgtt   1620

accttcgata gtggtacgtc tttctggggt gcaaacttga cggtcggtgt ccttaacggt   1680

acaatccccc aatggcgtgt tgatgacatg gctgtccgta tcatggccgc ttattacaag   1740

gttggccgcg acaccaaata cacccctccc aacttcagct cgtggaccag ggacgaatat   1800

ggtttcgcgc ataaccatgt ttcggaaggt gcttacgaga gggtcaacga attcgtggac   1860
```

```
gtgcaacgcg atcatgccga cctaatccgt cgcatcggcg cgcagagcac tgttctgctg   1920

aagaacaagg gtgccttgcc cttgagccgc aaggaaaagc tggtcgccct tctgggagag   1980

gatgcgggtt ccaactcgtg ggcgctaac  ggctgtgatg accgtggttg cgataacggt   2040

acccttgcca tggcctgggg tagcggtact gcgaatttcc catacctcgt gacaccagag   2100

caggcgattc agaacgaagt tcttcagggc cgtggtaatg tcttcgccgt gaccgacagt   2160

tgggcgctcg acaagatcgc tgcggctgcc cgccaggcca gcgtatctct cgtgttcgtc   2220

aactccgact caggagaagg ctatcttagt gtggatggaa atgagggcga tcgtaacaac   2280

atcactctgt ggaagaacgg cgacaatgtg gtcaagaccg cagcgaataa ctgtaacaac   2340

accgttgtca tcatccactc cgtcggacca gttttgatcg atgaatggta tgaccacccc   2400

aatgtcactg gtattctctg ggctggtctg ccaggccagg agtctggtaa ctccattgcc   2460

gatgtgctgt acggtcgtgt caaccctggc gccaagtctc ctttcacttg ggcaagacc    2520

cgggagtcgt atggttctcc cttggtcaag gatgccaaca atggcaacgg agcgccccag   2580

tctgatttca cccagggtgt tttcatcgat taccgccatt tcgataagtt caatgagacc   2640

cctatctacg agtttggcta cggcttgagc tacaccacct tcgagctctc cgacctccat   2700

gttcagcccc tgaacgcgtc ccgatacact cccaccagtg gcatgactga agctgcaaag   2760

aactttggtg aaattggcga tgcgtcggag tacgtgtatc cggaggggct ggaaaggatc   2820

catgagttta tctatccctg gatcaactct accgacctga aggcatcgtc tgacgattct   2880

aactacggct gggaagactc caagtatatt cccgaaggcg ccacggatgg gtctgcccag   2940

ccccgtttgc ccgctagtgg tggtgccgga ggaaaccccg gtctgtacga ggatcttttc   3000

cgcgtctctg tgaaggtcaa gaacacgggc aatgtcgccg gtgatgaagt tcctcagctg   3060

tacgtttccc taggcggccc gaatgagccc aaggtggtac tgcgcaagtt tgagcgtatt   3120

cacttggccc cttcgcagga ggccgtgtgg acaacgaccc ttacccgtcg tgaccttgca   3180

aactgggacg tttcggctca ggactggacc gtcactcctt accccaagac gatctacgtt   3240

ggaaactcct cacggaaact gccgctccag gcctcgctgc ctaaggccca gtaa         3294
```

```
<210> SEQ ID NO 66
<211> LENGTH: 1097
<212> TYPE: PRT
<213> ORGANISM: Aspergillus oryzae

<400> SEQUENCE: 66

Met Arg Ser Ser Pro Leu Leu Arg Ser Ala Val Val Ala Ala Leu Pro
1               5                   10                  15

Val Leu Ala Leu Ala Ala Asp Gly Arg Ser Thr Arg Tyr Trp Asp Cys
            20                  25                  30

Cys Lys Pro Ser Cys Gly Trp Ala Lys Lys Ala Pro Val Asn Gln Pro
        35                  40                  45

Val Phe Ser Cys Asn Ala Asn Phe Gln Arg Ile Thr Asp Phe Asp Ala
    50                  55                  60

Lys Ser Gly Cys Glu Pro Gly Gly Val Ala Tyr Ser Cys Ala Asp Gln
65                  70                  75                  80

Thr Pro Trp Ala Val Asn Asp Asp Phe Ala Leu Gly Phe Ala Ala Thr
                85                  90                  95

Ser Ile Ala Gly Ser Asn Glu Ala Gly Trp Cys Cys Ala Cys Tyr Glu
            100                 105                 110

Leu Thr Phe Thr Ser Gly Pro Val Ala Gly Lys Lys Met Val Val Gln
        115                 120                 125
```

```
Ser Thr Ser Thr Gly Gly Asp Leu Gly Ser Asn His Phe Asp Leu Asn
    130                 135                 140

Ile Pro Gly Gly Gly Val Gly Ile Phe Asp Gly Cys Thr Pro Gln Phe
145                 150                 155                 160

Gly Gly Leu Pro Gly Gln Arg Tyr Gly Gly Ile Ser Ser Arg Asn Glu
                165                 170                 175

Cys Asp Arg Phe Pro Asp Ala Leu Lys Pro Gly Cys Tyr Trp Arg Phe
            180                 185                 190

Asp Trp Phe Lys Asn Ala Asp Asn Pro Ser Phe Ser Phe Arg Gln Val
        195                 200                 205

Gln Cys Pro Ala Glu Leu Val Ala Arg Thr Gly Cys Arg Arg Asn Asp
    210                 215                 220

Asp Gly Asn Phe Pro Ala Val Gln Ile Pro Met Arg Ser Ser Pro Leu
225                 230                 235                 240

Leu Arg Ser Ala Val Val Ala Ala Leu Pro Val Leu Ala Leu Ala Lys
                245                 250                 255

Asp Asp Leu Ala Tyr Ser Pro Pro Phe Tyr Pro Ser Pro Trp Ala Asp
            260                 265                 270

Gly Gln Gly Glu Trp Ala Glu Val Tyr Lys Arg Ala Val Asp Ile Val
        275                 280                 285

Ser Gln Met Thr Leu Thr Glu Lys Val Asn Leu Thr Thr Gly Thr Gly
    290                 295                 300

Trp Gln Leu Glu Arg Cys Val Gly Gln Thr Gly Ser Val Pro Arg Leu
305                 310                 315                 320

Asn Ile Pro Ser Leu Cys Leu Gln Asp Ser Pro Leu Gly Ile Arg Phe
                325                 330                 335

Ser Asp Tyr Asn Ser Ala Phe Pro Ala Gly Val Asn Val Ala Ala Thr
            340                 345                 350

Trp Asp Lys Thr Leu Ala Tyr Leu Arg Gly Gln Ala Met Gly Glu Glu
        355                 360                 365

Phe Ser Asp Lys Gly Ile Asp Val Gln Leu Gly Pro Ala Ala Gly Pro
    370                 375                 380

Leu Gly Ala His Pro Asp Gly Gly Arg Asn Trp Glu Ser Phe Ser Pro
385                 390                 395                 400

Asp Pro Ala Leu Thr Gly Val Leu Phe Ala Glu Thr Ile Lys Gly Ile
                405                 410                 415

Gln Asp Ala Gly Val Ile Ala Thr Ala Lys His Tyr Ile Met Asn Glu
            420                 425                 430

Gln Glu His Phe Arg Gln Gln Pro Glu Ala Ala Gly Tyr Gly Phe Asn
        435                 440                 445

Val Ser Asp Ser Leu Ser Ser Asn Val Asp Asp Lys Thr Met His Glu
    450                 455                 460

Leu Tyr Leu Trp Pro Phe Ala Asp Ala Val Arg Ala Gly Val Gly Ala
465                 470                 475                 480

Val Met Cys Ser Tyr Asn Gln Ile Asn Asn Ser Tyr Gly Cys Glu Asn
                485                 490                 495

Ser Glu Thr Leu Asn Lys Leu Leu Lys Ala Glu Leu Gly Phe Gln Gly
            500                 505                 510

Phe Val Met Ser Asp Trp Thr Ala Gln His Ser Gly Val Gly Ala Ala
        515                 520                 525

Leu Ala Gly Leu Asp Met Ser Met Pro Gly Asp Val Thr Phe Asp Ser
    530                 535                 540
```

```
Gly Thr Ser Phe Trp Gly Ala Asn Leu Thr Val Gly Val Leu Asn Gly
545                 550                 555                 560

Thr Ile Pro Gln Trp Arg Val Asp Asp Met Ala Val Arg Ile Met Ala
                565                 570                 575

Ala Tyr Tyr Lys Val Gly Arg Asp Thr Lys Tyr Thr Pro Pro Asn Phe
            580                 585                 590

Ser Ser Trp Thr Arg Asp Glu Tyr Gly Phe Ala His Asn His Val Ser
        595                 600                 605

Glu Gly Ala Tyr Glu Arg Val Asn Glu Phe Val Asp Val Gln Arg Asp
    610                 615                 620

His Ala Asp Leu Ile Arg Arg Ile Gly Ala Gln Ser Thr Val Leu Leu
625                 630                 635                 640

Lys Asn Lys Gly Ala Leu Pro Leu Ser Arg Lys Glu Lys Leu Val Ala
                645                 650                 655

Leu Leu Gly Glu Asp Ala Gly Ser Asn Ser Trp Gly Ala Asn Gly Cys
            660                 665                 670

Asp Asp Arg Gly Cys Asp Asn Gly Thr Leu Ala Met Ala Trp Gly Ser
        675                 680                 685

Gly Thr Ala Asn Phe Pro Tyr Leu Val Thr Pro Glu Gln Ala Ile Gln
    690                 695                 700

Asn Glu Val Leu Gln Gly Arg Gly Asn Val Phe Ala Val Thr Asp Ser
705                 710                 715                 720

Trp Ala Leu Asp Lys Ile Ala Ala Ala Ala Arg Gln Ala Ser Val Ser
                725                 730                 735

Leu Val Phe Val Asn Ser Asp Ser Gly Glu Gly Tyr Leu Ser Val Asp
            740                 745                 750

Gly Asn Glu Gly Asp Arg Asn Asn Ile Thr Leu Trp Lys Asn Gly Asp
        755                 760                 765

Asn Val Val Lys Thr Ala Ala Asn Asn Cys Asn Asn Thr Val Val Ile
    770                 775                 780

Ile His Ser Val Gly Pro Val Leu Ile Asp Glu Trp Tyr Asp His Pro
785                 790                 795                 800

Asn Val Thr Gly Ile Leu Trp Ala Gly Leu Pro Gly Gln Glu Ser Gly
                805                 810                 815

Asn Ser Ile Ala Asp Val Leu Tyr Gly Arg Val Asn Pro Gly Ala Lys
            820                 825                 830

Ser Pro Phe Thr Trp Gly Lys Thr Arg Glu Ser Tyr Gly Ser Pro Leu
        835                 840                 845

Val Lys Asp Ala Asn Asn Gly Asn Gly Ala Pro Gln Ser Asp Phe Thr
    850                 855                 860

Gln Gly Val Phe Ile Asp Tyr Arg His Phe Asp Lys Phe Asn Glu Thr
865                 870                 875                 880

Pro Ile Tyr Glu Phe Gly Tyr Gly Leu Ser Tyr Thr Thr Phe Glu Leu
                885                 890                 895

Ser Asp Leu His Val Gln Pro Leu Asn Ala Ser Arg Tyr Thr Pro Thr
            900                 905                 910

Ser Gly Met Thr Glu Ala Ala Lys Asn Phe Gly Glu Ile Gly Asp Ala
        915                 920                 925

Ser Glu Tyr Val Tyr Pro Glu Gly Leu Glu Arg Ile His Glu Phe Ile
    930                 935                 940

Tyr Pro Trp Ile Asn Ser Thr Asp Leu Lys Ala Ser Ser Asp Asp Ser
945                 950                 955                 960

Asn Tyr Gly Trp Glu Asp Ser Lys Tyr Ile Pro Glu Gly Ala Thr Asp
```

```
            965                 970                 975

Gly Ser Ala Gln Pro Arg Leu Pro Ala Ser Gly Gly Ala Gly Gly Asn
            980                 985                 990

Pro Gly Leu Tyr Glu Asp Leu Phe  Arg Val Ser Val Lys  Val Lys Asn
        995                 1000                1005

Thr Gly  Asn Val Ala Gly Asp  Glu Val Pro Gln Leu  Tyr Val Ser
    1010                1015                1020

Leu Gly  Gly Pro Asn Glu Pro  Lys Val Val Leu Arg  Lys Phe Glu
    1025                1030                1035

Arg Ile  His Leu Ala Pro Ser  Gln Glu Ala Val Trp  Thr Thr Thr
    1040                1045                1050

Leu Thr  Arg Arg Asp Leu Ala  Asn Trp Asp Val Ser  Ala Gln Asp
    1055                1060                1065

Trp Thr  Val Thr Pro Tyr Pro  Lys Thr Ile Tyr Val  Gly Asn Ser
    1070                1075                1080

Ser Arg  Lys Leu Pro Leu Gln  Ala Ser Leu Pro Lys  Ala Gln
    1085                1090                1095
```

<210> SEQ ID NO 67
<211> LENGTH: 1415
<212> TYPE: DNA
<213> ORGANISM: Aspergillus fumigatus

<400> SEQUENCE: 67

```
atggtccatc tatcttcatt ggcagcagcc ctggctgctc tgcctctgta tgtttaccca     60

ctcacgagag gaggaacagc tttgacattg ctatagtgta tatggagctg gcctgaacac    120

agcagccaaa gccaaaggac taaagtactt tggttccgcc acggacaatc cagagctcac    180

ggactctgcg tatgtcgcgc aactgagcaa caccgatgat tttggtcaaa tcacacccgg    240

aaactccatg aaggtttgct tacgtctgcc tccctggagc attgcctcaa aagctaattg    300

gttgttttgt ttggatagtg ggatgccacc gagccttctc agaattcttt ttcgttcgca    360

aatggagacg ccgtggtcaa tctggcgaac aagaatggcc agctgatgcg atgccatact    420

ctggtctggc acagtcagct accgaactgg ggtatgtaaa cgtcttgtct attctcaaat    480

actctctaac agttgacagt ctctagcggg tcatggacca atgcgaccct tttggcggcc    540

atgaagaatc atatcaccaa tgtggttact cactacaagg ggaagtgcta cgcctgggat    600

gttgtcaatg aaggtttgtt gctccatcta tcctcaatag ttcttttgaa actgacaagc    660

ctgtcaatct agccctgaac gaggacggta ctttccgtaa ctctgtcttc taccagatca    720

tcggcccagc atacattcct attgcgttcg ccacggctgc tgccgcagat cccgacgtga    780

aactctacta caacgactac aacattgaat actcaggcgc caaagcgact gctgcgcaga    840

atatcgtcaa gatgatcaag gcctacggcg cgaagatcga cggcgtcggc ctccaggcac    900

actttatcgt cggcagcact ccgagtcaat cggatctgac gaccgtcttg aagggctaca    960

ctgctctcgg cgttgaggtg gcctataccg aacttgacat ccgcatgcag ctgccctcga   1020

ccgccgcaaa gctggcccag cagtccactg acttccaagg cgtggccgca gcatgcgtta   1080

gcaccactgg ctgcgtgggt gtcactatct gggactggac cgacaagtac tcctgggtcc   1140

ccagcgtgtt ccaaggctac ggcgccccat tgccttggga tgagaactat gtgaagaagc   1200

cagcgtacga tggcctgatg gcgggtcttg gagcaagcgg ctccggcacc acaacgacca   1260

ctactactac ttctactacg acaggaggta cggaccctac tggagtcgct cagaaatggg   1320

gacagtgtgg cggtattggc tggaccgggc caacaacttg tgtcagtggt accacttgcc   1380
```

```
aaaagctgaa tgactggtac tcacagtgcc tgtaa                            1415


<210> SEQ ID NO 68
<211> LENGTH: 397
<212> TYPE: PRT
<213> ORGANISM: Aspergillus fumigatus

<400> SEQUENCE: 68

Met Val His Leu Ser Ser Leu Ala Ala Ala Leu Ala Ala Leu Pro Leu
1               5                   10                  15

Val Tyr Gly Ala Gly Leu Asn Thr Ala Ala Lys Ala Lys Gly Leu Lys
            20                  25                  30

Tyr Phe Gly Ser Ala Thr Asp Asn Pro Glu Leu Thr Asp Ser Ala Tyr
        35                  40                  45

Val Ala Gln Leu Ser Asn Thr Asp Asp Phe Gly Gln Ile Thr Pro Gly
    50                  55                  60

Asn Ser Met Lys Trp Asp Ala Thr Glu Pro Ser Gln Asn Ser Phe Ser
65                  70                  75                  80

Phe Ala Asn Gly Asp Ala Val Val Asn Leu Ala Asn Lys Asn Gly Gln
                85                  90                  95

Leu Met Arg Cys His Thr Leu Val Trp His Ser Gln Leu Pro Asn Trp
            100                 105                 110

Val Ser Ser Gly Ser Trp Thr Asn Ala Thr Leu Leu Ala Ala Met Lys
        115                 120                 125

Asn His Ile Thr Asn Val Val Thr His Tyr Lys Gly Lys Cys Tyr Ala
    130                 135                 140

Trp Asp Val Val Asn Glu Ala Leu Asn Glu Asp Gly Thr Phe Arg Asn
145                 150                 155                 160

Ser Val Phe Tyr Gln Ile Ile Gly Pro Ala Tyr Ile Pro Ile Ala Phe
                165                 170                 175

Ala Thr Ala Ala Ala Ala Asp Pro Asp Val Lys Leu Tyr Tyr Asn Asp
            180                 185                 190

Tyr Asn Ile Glu Tyr Ser Gly Ala Lys Ala Thr Ala Ala Gln Asn Ile
        195                 200                 205

Val Lys Met Ile Lys Ala Tyr Gly Ala Lys Ile Asp Gly Val Gly Leu
    210                 215                 220

Gln Ala His Phe Ile Val Gly Ser Thr Pro Ser Gln Ser Asp Leu Thr
225                 230                 235                 240

Thr Val Leu Lys Gly Tyr Thr Ala Leu Gly Val Glu Val Ala Tyr Thr
                245                 250                 255

Glu Leu Asp Ile Arg Met Gln Leu Pro Ser Thr Ala Ala Lys Leu Ala
            260                 265                 270

Gln Gln Ser Thr Asp Phe Gln Gly Val Ala Ala Ala Cys Val Ser Thr
        275                 280                 285

Thr Gly Cys Val Gly Val Thr Ile Trp Asp Trp Thr Asp Lys Tyr Ser
    290                 295                 300

Trp Val Pro Ser Val Phe Gln Gly Tyr Gly Ala Pro Leu Pro Trp Asp
305                 310                 315                 320

Glu Asn Tyr Val Lys Lys Pro Ala Tyr Asp Gly Leu Met Ala Gly Leu
                325                 330                 335

Gly Ala Ser Gly Ser Gly Thr Thr Thr Thr Thr Thr Thr Thr Ser Thr
            340                 345                 350

Thr Thr Gly Gly Thr Asp Pro Thr Gly Val Ala Gln Lys Trp Gly Gln
        355                 360                 365
```

```
Cys Gly Gly Ile Gly Trp Thr Gly Pro Thr Thr Cys Val Ser Gly Thr
    370                 375                 380

Thr Cys Gln Lys Leu Asn Asp Trp Tyr Ser Gln Cys Leu
385                 390                 395


<210> SEQ ID NO 69
<211> LENGTH: 2564
<212> TYPE: DNA
<213> ORGANISM: Trichoderma reesei

<400> SEQUENCE: 69

ggacagccgg acgcaatggt gaataacgca gctcttctcg ccgccctgtc ggctctcctg      60

cccacggccc tggcgcagaa caatcaaaca tacgccaact actctgctca gggccagcct     120

gatctctacc ccgagacact tgccacgctc acactctcgt tccccgactg cgaacatggc     180

cccctcaaga acaatctcgt ctgtgactca tcggccggct atgtagagcg agcccaggcc     240

ctcatctcgc tcttcaccct cgaggagctc attctcaaca cgcaaaactc gggccccggc     300

gtgcctcgcc tgggtcttcc gaactaccaa gtctggaatg aggctctgca cggcttggac     360

cgcgccaact tcgccaccaa gggcggccag ttcgaatggg cgacctcgtt ccccatgccc     420

atcctcacta cggcggccct caaccgcaca ttgatccacc agattgccga catcatctcg     480

acccaagctc gagcattcag caacagcggc cgttacggtc tcgacgtcta tgcgccaaac     540

gtcaatggct tccgaagccc cctctggggc cgtggccagg agacgcccgg cgaagacgcc     600

tttttcctca gctccgccta tacttacgag tacatcacgg gcatccaggg tggcgtcgac     660

cctgagcacc tcaaggttgc cgccacggtg aagcactttg ccggatacga cctcgagaac     720

tggaacaacc agtcccgtct cggtttcgac gccatcataa ctcagcagga cctctccgaa     780

tactacactc cccagttcct cgctgcggcc cgttatgcaa agtcacgcag cttgatgtgc     840

gcatacaact ccgtcaacgg cgtgcccagc tgtgccaaca gcttcttcct gcagacgctt     900

ttgcgcgaga gctggggctt ccccgaatgg ggatacgtct cgtccgattg cgatgccgtc     960

tacaacgttt tcaaccctca tgactacgcc agcaaccagt cgtcagccgc cgccagctca    1020

ctgcgagccg gcaccgatat cgactgcggt cagacttacc cgtggcacct caacgagtcc    1080

tttgtggccg gcgaagtctc ccgcggcgag atcgagcggt ccgtcacccg tctgtacgcc    1140

aacctcgtcc gtctcggata cttcgacaag aagaaccagt accgctcgct cggttggaag    1200

gatgtcgtca agactgatgc ctggaacatc tcgtacgagg ctgctgttga gggcatcgtc    1260

ctgctcaaga acgatggcac tctccctctg tccaagaagg tgcgcagcat tgctctgatc    1320

ggaccatggg ccaatgccac aacccaaatg caaggcaact actatggccc tgccccatac    1380

ctcatcagcc ctctggaagc tgctaagaag gccggctatc acgtcaactt tgaactcggc    1440

acagagatcg ccggcaacag caccactggc tttgccaagg ccattgctgc cgccaagaag    1500

tcggatgcca tcatctacct cggtggaatt gacaacacca ttgaacagga gggcgctgac    1560

cgcacggaca ttgcttggcc cggtaatcag ctggatctca tcaagcagct cagcgaggtc    1620

ggcaaacccc ttgtcgtcct gcaaatgggc ggtggtcagg tagactcatc ctcgctcaag    1680

agcaacaaga aggtcaactc cctcgtctgg ggcggatatc ccggccagtc gggaggcgtt    1740

gccctcttcg acattctctc tggcaagcgt gctcctgccg gccgactggt caccactcag    1800

tacccggctg agtatgttca ccaattcccc cagaatgaca tgaacctccg acccgatgga    1860

aagtcaaacc ctggacagac ttacatctgg tacaccggca aacccgtcta cgagtttggc    1920
```

```
agtggtctct tctacaccac cttcaaggag actctcgcca gccaccccaa gagcctcaag   1980

ttcaacacct catcgatcct ctctgctcct caccccggat acacttacag cgagcagatt   2040

cccgtcttca ccttcgaggc caacatcaag aactcgggca agacggagtc cccatatacg   2100

gccatgctgt ttgttcgcac aagcaacgct ggcccagccc cgtacccgaa caagtggctc   2160

gtcggattcg accgacttgc cgacatcaag cctggtcact cttccaagct cagcatcccc   2220

atccctgtca gtgctctcgc ccgtgttgat tctcacggaa accggattgt ataccccggc   2280

aagtatgagc tagccttgaa caccgacgag tctgtgaagc ttgagtttga gttggtggga   2340

gaagaggtaa cgattgagaa ctggccgttg gaggagcaac agatcaagga tgctacacct   2400

gacgcataag ggttttaatg atgttgttat gacaaacggg tagagtagtt aatgatggaa   2460

taggaagagg ccatagtttt ctgtttgcaa accatttttg ccattgcgaa aaaaaaaaaa   2520

aaaaaaaaaa aaaaaaaaaa aaaaaaaaaa aaaaaaaaaa aaaa                    2564


<210> SEQ ID NO 70
<211> LENGTH: 780
<212> TYPE: PRT
<213> ORGANISM: Trichoderma reesei

<400> SEQUENCE: 70

Met Val Asn Asn Ala Ala Leu Leu Ala Ala Leu Ser Ala Leu Leu Pro
1               5                   10                  15

Thr Ala Leu Ala Gln Asn Asn Gln Thr Tyr Ala Asn Tyr Ser Ala Gln
            20                  25                  30

Gly Gln Pro Asp Leu Tyr Pro Glu Thr Leu Ala Thr Leu Thr Leu Ser
        35                  40                  45

Phe Pro Asp Cys Glu His Gly Pro Leu Lys Asn Asn Leu Val Cys Asp
    50                  55                  60

Ser Ser Ala Gly Tyr Val Glu Arg Ala Gln Ala Leu Ile Ser Leu Phe
65                  70                  75                  80

Thr Leu Glu Glu Leu Ile Leu Asn Thr Gln Asn Ser Gly Pro Gly Val
                85                  90                  95

Pro Arg Leu Gly Leu Pro Asn Tyr Gln Val Trp Asn Glu Ala Leu His
            100                 105                 110

Gly Leu Asp Arg Ala Asn Phe Ala Thr Lys Gly Gly Gln Phe Glu Trp
        115                 120                 125

Ala Thr Ser Phe Pro Met Pro Ile Leu Thr Thr Ala Ala Leu Asn Arg
    130                 135                 140

Thr Leu Ile His Gln Ile Ala Asp Ile Ile Ser Thr Gln Ala Arg Ala
145                 150                 155                 160

Phe Ser Asn Ser Gly Arg Tyr Gly Leu Asp Val Tyr Ala Pro Asn Val
                165                 170                 175

Asn Gly Phe Arg Ser Pro Leu Trp Gly Arg Gly Gln Glu Thr Pro Gly
            180                 185                 190

Glu Asp Ala Phe Phe Leu Ser Ser Ala Tyr Thr Tyr Glu Tyr Ile Thr
        195                 200                 205

Gly Ile Gln Gly Gly Val Asp Pro Glu His Leu Lys Val Ala Ala Thr
    210                 215                 220

Val Lys His Phe Ala Gly Tyr Asp Leu Glu Asn Trp Asn Asn Gln Ser
225                 230                 235                 240

Arg Leu Gly Phe Asp Ala Ile Ile Thr Gln Gln Asp Leu Ser Glu Tyr
                245                 250                 255

Tyr Thr Pro Gln Phe Leu Ala Ala Ala Arg Tyr Ala Lys Ser Arg Ser
```

```
            260                 265                 270

Leu Met Cys Ala Tyr Asn Ser Val Asn Gly Val Pro Ser Cys Ala Asn
        275                 280                 285

Ser Phe Phe Leu Gln Thr Leu Leu Arg Glu Ser Trp Gly Phe Pro Glu
    290                 295                 300

Trp Gly Tyr Val Ser Ser Asp Cys Asp Ala Val Tyr Asn Val Phe Asn
305                 310                 315                 320

Pro His Asp Tyr Ala Ser Asn Gln Ser Ser Ala Ala Ala Ser Ser Leu
                325                 330                 335

Arg Ala Gly Thr Asp Ile Asp Cys Gly Gln Thr Tyr Pro Trp His Leu
            340                 345                 350

Asn Glu Ser Phe Val Ala Gly Glu Val Ser Arg Gly Glu Ile Glu Arg
        355                 360                 365

Ser Val Thr Arg Leu Tyr Ala Asn Leu Val Arg Leu Gly Tyr Phe Asp
    370                 375                 380

Lys Lys Asn Gln Tyr Arg Ser Leu Gly Trp Lys Asp Val Val Lys Thr
385                 390                 395                 400

Asp Ala Trp Asn Ile Ser Tyr Glu Ala Ala Val Glu Gly Ile Val Leu
                405                 410                 415

Leu Lys Asn Asp Gly Thr Leu Pro Leu Ser Lys Lys Val Arg Ser Ile
            420                 425                 430

Ala Leu Ile Gly Pro Trp Ala Asn Ala Thr Thr Gln Met Gln Gly Asn
        435                 440                 445

Tyr Tyr Gly Pro Ala Pro Tyr Leu Ile Ser Pro Leu Glu Ala Ala Lys
    450                 455                 460

Lys Ala Gly Tyr His Val Asn Phe Glu Leu Gly Thr Glu Ile Ala Gly
465                 470                 475                 480

Asn Ser Thr Thr Gly Phe Ala Lys Ala Ile Ala Ala Ala Lys Lys Ser
                485                 490                 495

Asp Ala Ile Ile Tyr Leu Gly Gly Ile Asp Asn Thr Ile Glu Gln Glu
            500                 505                 510

Gly Ala Asp Arg Thr Asp Ile Ala Trp Pro Gly Asn Gln Leu Asp Leu
        515                 520                 525

Ile Lys Gln Leu Ser Glu Val Gly Lys Pro Leu Val Val Leu Gln Met
    530                 535                 540

Gly Gly Gly Gln Val Asp Ser Ser Ser Leu Lys Ser Asn Lys Lys Val
545                 550                 555                 560

Asn Ser Leu Val Trp Gly Gly Tyr Pro Gly Gln Ser Gly Gly Val Ala
                565                 570                 575

Leu Phe Asp Ile Leu Ser Gly Lys Arg Ala Pro Ala Gly Arg Leu Val
            580                 585                 590

Thr Thr Gln Tyr Pro Ala Glu Tyr Val His Gln Phe Pro Gln Asn Asp
        595                 600                 605

Met Asn Leu Arg Pro Asp Gly Lys Ser Asn Pro Gly Gln Thr Tyr Ile
    610                 615                 620

Trp Tyr Thr Gly Lys Pro Val Tyr Glu Phe Gly Ser Gly Leu Phe Tyr
625                 630                 635                 640

Thr Thr Phe Lys Glu Thr Leu Ala Ser His Pro Lys Ser Leu Lys Phe
                645                 650                 655

Asn Thr Ser Ser Ile Leu Ser Ala Pro His Pro Gly Tyr Thr Tyr Ser
            660                 665                 670

Glu Gln Ile Pro Val Phe Thr Phe Glu Ala Asn Ile Lys Asn Ser Gly
        675                 680                 685
```

```
Lys Thr Glu Ser Pro Tyr Thr Ala Met Leu Phe Val Arg Thr Ser Asn
    690                 695                 700

Ala Gly Pro Ala Pro Tyr Pro Asn Lys Trp Leu Val Gly Phe Asp Arg
705                 710                 715                 720

Leu Ala Asp Ile Lys Pro Gly His Ser Ser Lys Leu Ser Ile Pro Ile
                725                 730                 735

Pro Val Ser Ala Leu Ala Arg Val Asp Ser His Gly Asn Arg Ile Val
            740                 745                 750

Tyr Pro Gly Lys Tyr Glu Leu Ala Leu Asn Thr Asp Glu Ser Val Lys
        755                 760                 765

Leu Glu Phe Glu Leu Val Gly Glu Glu Val Thr Ile
    770                 775                 780


<210> SEQ ID NO 71
<211> LENGTH: 37
<212> TYPE: DNA
<213> ORGANISM: Aspergillus fumigatus

<400> SEQUENCE: 71

actggattta ccatgacttt gtccaagatc acttcca                               37


<210> SEQ ID NO 72
<211> LENGTH: 40
<212> TYPE: DNA
<213> ORGANISM: Aspergillus fumigatus

<400> SEQUENCE: 72

tcacctctag ttaattaagc gttgaacagt gcaggaccag                            40


<210> SEQ ID NO 73
<211> LENGTH: 17
<212> TYPE: DNA
<213> ORGANISM: Aspergillus fumigatus

<400> SEQUENCE: 73

tgtcccttgt cgatgcg                                                     17


<210> SEQ ID NO 74
<211> LENGTH: 17
<212> TYPE: DNA
<213> ORGANISM: Aspergillus fumigatus

<400> SEQUENCE: 74

cacatgactt ggcttcc                                                     17


<210> SEQ ID NO 75
<211> LENGTH: 36
<212> TYPE: DNA
<213> ORGANISM: Aspergillus fumigatus

<400> SEQUENCE: 75

ggctaacata gcataggtga ttacttacct cgctcc                                36


<210> SEQ ID NO 76
<211> LENGTH: 36
<212> TYPE: DNA
<213> ORGANISM: Aspergillus fumigatus

<400> SEQUENCE: 76

ggagcgaggt aagtaatcac ctatgctatg ttagcc                                36
```

<210> SEQ ID NO 77
<211> LENGTH: 45
<212> TYPE: DNA
<213> ORGANISM: Aspergillus fumigatus

<400> SEQUENCE: 77
cctggtgttt gggcttccga tgaactgatc gccaacaaca acacg 45

<210> SEQ ID NO 78
<211> LENGTH: 45
<212> TYPE: DNA
<213> ORGANISM: Aspergillus fumigatus

<400> SEQUENCE: 78
cgtgttgttg ttggcgatca gttcatcgga agcccaaaca ccagg 45

<210> SEQ ID NO 79
<211> LENGTH: 35
<212> TYPE: DNA
<213> ORGANISM: Aspergillus fumigatus

<400> SEQUENCE: 79
gccaacaaca acacgtggac agtgaccatt cctgc 35

<210> SEQ ID NO 80
<211> LENGTH: 35
<212> TYPE: DNA
<213> ORGANISM: Aspergillus fumigatus

<400> SEQUENCE: 80
gcaggaatgg tcactgtcca cgtgttgttg ttggc 35

<210> SEQ ID NO 81
<211> LENGTH: 38
<212> TYPE: DNA
<213> ORGANISM: Trichoderma reesei

<400> SEQUENCE: 81
actggattta ccatgaacaa gtccgtggct ccattgct 38

<210> SEQ ID NO 82
<211> LENGTH: 38
<212> TYPE: DNA
<213> ORGANISM: Trichoderma reesei

<400> SEQUENCE: 82
tcacctctag ttaattaact actttcttgc gagacacg 38

<210> SEQ ID NO 83
<211> LENGTH: 25
<212> TYPE: DNA
<213> ORGANISM: Aspergillus fumigatus

<400> SEQUENCE: 83
gggcatgctg gcctccacct tctcc 25

<210> SEQ ID NO 84
<211> LENGTH: 30
<212> TYPE: DNA
<213> ORGANISM: Aspergillus fumigatus

<400> SEQUENCE: 84
gggttaatta actacaggca ctgagagtaa 30

<210> SEQ ID NO 85
<211> LENGTH: 37
<212> TYPE: DNA
<213> ORGANISM: Aspergillus fumigatus

<400> SEQUENCE: 85
actggattta ccatgaagca ccttgcatct tccatcg 37

<210> SEQ ID NO 86
<211> LENGTH: 34
<212> TYPE: DNA
<213> ORGANISM: Aspergillus fumigatus

<400> SEQUENCE: 86
tcacctctag ttaattaaaa ggacgggtta gcgt 34

<210> SEQ ID NO 87
<211> LENGTH: 22
<212> TYPE: DNA
<213> ORGANISM: Aspergillus fumigatus

<400> SEQUENCE: 87
gtgaataacg cagctcttct cg 22

<210> SEQ ID NO 88
<211> LENGTH: 25
<212> TYPE: DNA
<213> ORGANISM: Aspergillus fumigatus

<400> SEQUENCE: 88
ccttaattaa ttatgcgtca ggtgt 25

<210> SEQ ID NO 89
<211> LENGTH: 33
<212> TYPE: DNA
<213> ORGANISM: Trichoderma reesei

<400> SEQUENCE: 89
cggactgcgc accatggtga ataacgcagc tct 33

<210> SEQ ID NO 90
<211> LENGTH: 35
<212> TYPE: DNA
<213> ORGANISM: Trichoderma reesei

<400> SEQUENCE: 90
tcgccacgga gcttattatg cgtcaggtgt agcat 35

<210> SEQ ID NO 91
<211> LENGTH: 37
<212> TYPE: DNA
<213> ORGANISM: Aspergillus aculeatus

<400> SEQUENCE: 91
tcttggatcc accatggtcg gactgctttc aatcacc 37

<210> SEQ ID NO 92
<211> LENGTH: 34
<212> TYPE: DNA
<213> ORGANISM: Aspergillus aculeatus

<400> SEQUENCE: 92

```
ttaactcgag tcacagacac tgcgagtaat agtc                              34


<210> SEQ ID NO 93
<211> LENGTH: 33
<212> TYPE: DNA
<213> ORGANISM: Aspergillus aculeatus

<400> SEQUENCE: 93

cggactgcgc accatggtcg gactgctttc aat                               33


<210> SEQ ID NO 94
<211> LENGTH: 35
<212> TYPE: DNA
<213> ORGANISM: Aspergillus aculeatus

<400> SEQUENCE: 94

tcgccacgga gcttatcaca gacactgcga gtaat                             35
```